US011883506B2

(12) United States Patent
Herzog et al.

(10) Patent No.: US 11,883,506 B2
(45) Date of Patent: Jan. 30, 2024

(54) PLAKOPHILIN-2 (PKP2) GENE THERAPY USING AAV VECTOR

(71) Applicant: Spacecraft Seven, LLC, Cranbury, NJ (US)

(72) Inventors: Christopher Dean Herzog, Fanwood, NJ (US); Chester Bittencort Sacramento, Cranbury, NJ (US); Raj Prabhakar, Cranbury, NJ (US); David Ricks, Cranbury, NJ (US)

(73) Assignee: Spacecraft Seven, LLC, Cranbury, NJ (US)

( * ) Notice: Subject to any disclaimer, the term of this patent is extended or adjusted under 35 U.S.C. 154(b) by 0 days.

(21) Appl. No.: 17/670,389

(22) Filed: Feb. 11, 2022

(65) Prior Publication Data

US 2022/0168446 A1 Jun. 2, 2022

Related U.S. Application Data

(63) Continuation of application No. PCT/US2021/045220, filed on Aug. 9, 2021.

(60) Provisional application No. 63/063,032, filed on Aug. 7, 2020.

(51) Int. Cl.

| | |
|---|---|
| ***A61K 48/00*** | (2006.01) |
| ***C12N 15/864*** | (2006.01) |
| ***C12N 15/113*** | (2010.01) |
| ***C12N 15/02*** | (2006.01) |
| ***A61P 9/00*** | (2006.01) |
| ***C07K 14/005*** | (2006.01) |
| ***C12N 15/86*** | (2006.01) |
| *A61K 38/00* | (2006.01) |

(52) U.S. Cl.

CPC .......... *A61K 48/005* (2013.01); *C07K 14/005* (2013.01); *C12N 15/113* (2013.01); *C12N 15/86* (2013.01); *A61K 38/00* (2013.01); *C12N 2750/14143* (2013.01)

(58) Field of Classification Search

None

See application file for complete search history.

(56) References Cited

U.S. PATENT DOCUMENTS

| | | | |
|---|---|---|---|
| 4,861,719 | A | 8/1989 | Miller |
| 5,126,260 | A | 6/1992 | Tuan et al. |
| 5,139,941 | A | 8/1992 | Muzyczka et al. |
| 5,173,414 | A | 12/1992 | Lebkowski et al. |
| 5,278,056 | A | 1/1994 | Bank et al. |
| 5,882,877 | A | 3/1999 | Gregory et al. |
| 6,004,797 | A | 12/1999 | Colosi |
| 6,013,516 | A | 1/2000 | Verma et al. |
| 6,027,721 | A | 2/2000 | Hammang et al. |
| 6,136,597 | A | 10/2000 | Hope et al. |
| 7,094,604 | B2 | 8/2006 | Snyder et al. |
| 7,198,950 | B2 | 4/2007 | Trono et al. |
| 7,575,924 | B2 | 8/2009 | Trono et al. |
| 7,588,772 | B2 | 9/2009 | Kay et al. |
| 7,629,153 | B2 | 12/2009 | Trono et al. |
| 8,093,042 | B2 | 1/2012 | Charneau et al. |
| 8,329,462 | B2 | 12/2012 | Trono et al. |
| 8,524,446 | B2 | 9/2013 | Gao et al. |
| 8,748,169 | B2 | 6/2014 | Trono et al. |
| 8,900,858 | B2 | 12/2014 | Trono et al. |
| 9,109,012 | B2 | 8/2015 | Williams |
| 9,175,077 | B2 | 11/2015 | Gallo et al. |
| 9,340,798 | B2 | 5/2016 | Trono et al. |
| 9,434,928 | B2 | 9/2016 | Mendell et al. |
| 9,737,620 | B2 | 8/2017 | Williams |
| 10,363,269 | B2 | 7/2019 | Tareen |
| 2002/0065236 | A1 | 5/2002 | Yew et al. |
| 2004/0053870 | A1 | 3/2004 | Yew et al. |
| 2006/0200869 | A1 | 9/2006 | Naldini et al. |
| 2007/0037165 | A1 | 2/2007 | Venter et al. |
| 2009/0111106 | A1 | 4/2009 | Mitrophanous et al. |
| 2010/0284990 | A1 | 11/2010 | Kaemmerer et al. |
| 2011/0296544 | A1 | 12/2011 | Domon et al. |
| 2012/0071859 | A1 | 3/2012 | Morgan et al. |
| 2012/0172418 | A1 | 7/2012 | Schambach et al. |
| 2014/0220678 | A1 | 8/2014 | Trono et al. |
| 2015/0111955 | A1 | 4/2015 | High et al. |
| 2015/0291966 | A1 | 10/2015 | Zhang et al. |
| 2016/0108430 | A1 | 4/2016 | Carrier et al. |

(Continued)

FOREIGN PATENT DOCUMENTS

| | | | |
|---|---|---|---|
| JP | 2006524051 | A | 10/2006 |
| JP | 2007054069 | A | 3/2007 |

(Continued)

OTHER PUBLICATIONS

Gerull and Brodehl, Genetic Animal Models for Arrhythmogenic Cardiomyopathy, Frontiers in Physiology, 2020, pp. 1-20.*

Inoue et al., Modeling reduced contractility and impaired desmosome assembly due to plakophilin-2 deficiency using isogenic iPS cell-derived cardiomyocytes, 2022, pp. 337-351.*

Elliot et al, 2019, Definition and treatment of arrhythmogenic cardiomyopathy: an updated expert panel report, European J of Hear Hailfure, 2019, pp. 955-964.*

(Continued)

*Primary Examiner* — Maria Marvich

(74) *Attorney, Agent, or Firm* — Cooley LLP

(57) ABSTRACT

Provided herein is a gene therapy for PKP2 (Plakophilin-2), e.g. using an adeno-associated virus (AAV) vector. The promoter of the vector may be a MHCK7 promoter or a cardiac troponin T (HTNNT2) promoter. The capsid may be an AAV9 or AAVrh74 capsid or a functional variant thereof. Other promoters or capsids may be used. Further provided are methods of treatment, such as by intravenous, intracoronary, intracarotid or intracardiac administration of the rAAV vector, and other compositions and methods.

12 Claims, 8 Drawing Sheets

Specification includes a Sequence Listing.

(56) References Cited

U.S. PATENT DOCUMENTS

| | | | | |
|---|---|---|---|---|
| 2017/0218395 | A1 | 8/2017 | Byrne et al. | |
| 2018/0326022 | A1 | 11/2018 | Prosser et al. | |
| 2018/0360992 | A1 | 12/2018 | Patel et al. | |
| 2019/0000998 | A1 | 1/2019 | Mendell et al. | |
| 2019/0038773 | A1 | 2/2019 | Esteves et al. | |
| 2020/0215155 | A1 | 7/2020 | Shiekh et al. | |
| 2020/0308582 | A1* | 10/2020 | Schmidt | C12N 15/1138 |
| 2022/0143215 | A1* | 5/2022 | Keravala | C12N 15/86 |
| 2022/0168447 | A1 | 6/2022 | Herzog et al. | |

FOREIGN PATENT DOCUMENTS

| | | | | |
|---|---|---|---|---|
| RU | 2233333 C2 | 7/2004 | | |
| RU | 2280074 C2 | 7/2006 | | |
| WO | WO-9201070 A1 | 1/1992 | | |
| WO | WO-9303769 A1 | 3/1993 | | |
| WO | WO-94/19478 A1 | 9/1994 | | |
| WO | WO-95/14785 A1 | 6/1995 | | |
| WO | WO-96/22378 A1 | 7/1996 | | |
| WO | WO-01/83692 A2 | 11/2001 | | |
| WO | WO-01/83692 A3 | 11/2001 | | |
| WO | WO-03042397 A2 | 5/2003 | | |
| WO | WO-03092612 A2 | 11/2003 | | |
| WO | WO-2004015106 A1 | 2/2004 | | |
| WO | WO-2009/012176 A2 | 1/2009 | | |
| WO | WO-2009/012176 A3 | 1/2009 | | |
| WO | WO-2013078316 A1 | 5/2013 | | |
| WO | WO-2014170470 A1 | 10/2014 | | |
| WO | WO-2015/038958 A1 | 3/2015 | | |
| WO | WO-2015056014 A1 | 4/2015 | | |
| WO | WO-2015060722 A1 | 4/2015 | | |
| WO | WO-2015/168666 A2 | 11/2015 | | |
| WO | WO-2015/168666 A3 | 11/2015 | | |
| WO | WO-2015168547 A2 | 11/2015 | | |
| WO | WO-2015188191 A1 | 12/2015 | | |
| WO | WO-2016118780 A1 | 7/2016 | | |
| WO | WO-2016145217 A1 | 9/2016 | | |
| WO | WO-2016200543 A2 | 12/2016 | | |
| WO | WO-2017083750 A1 | 5/2017 | | |
| WO | WO-2017/100671 A1 | 6/2017 | | |
| WO | WO-2017127565 A1 | 7/2017 | | |
| WO | WO-2017184903 A1 | 10/2017 | | |
| WO | WO-2018049273 A1 | 3/2018 | | |
| WO | WO-2018060097 A1 | 4/2018 | | |
| WO | WO-2018201065 A1 | 11/2018 | | |
| WO | WO-2018208998 A1 | 11/2018 | | |
| WO | WO-2019060619 A1 | 3/2019 | | |
| WO | WO-2019079338 A1 | 4/2019 | | |
| WO | WO-2019200167 A1 | 10/2019 | | |
| WO | WO-2019207132 A1 | 10/2019 | | |
| WO | WO-2019210325 A1 | 10/2019 | | |
| WO | WO-2020014523 A1 | 1/2020 | | |
| WO | WO-2020028430 A1 | 2/2020 | | |
| WO | WO-2020033842 A1 | 2/2020 | | |
| WO | WO-2020037249 A1 | 2/2020 | | |
| WO | WO-2020/152210 | 7/2020 | | |
| WO | WO-2020167996 A1 | 8/2020 | | |
| WO | WO-2020237219 A1 | 11/2020 | | |
| WO | WO-2021053222 A1 * | 3/2021 | | C07K 14/4716 |
| WO | WO-2021/163357 | 8/2021 | | |
| WO | WO-2021/187380 | 9/2021 | | |
| WO | WO-2021/216456 | 10/2021 | | |
| WO | WO-2021236981 A2 | 11/2021 | | |
| WO | WO-2022017630 A1 | 1/2022 | | |
| WO | WO-2022018171 A1 | 1/2022 | | |
| WO | WO-2022031756 A1 | 2/2022 | | |
| WO | WO-2022031760 A1 | 2/2022 | | |
| WO | WO-2022032226 A1 | 2/2022 | | |
| WO | WO-2022/076648 | 4/2022 | | |
| WO | WO-2022125489 A1 | 6/2022 | | |
| WO | WO-2022/195074 | 9/2022 | | |
| WO | WO-2022/221320 | 10/2022 | | |
| WO | WO-2023/283649 | 1/2023 | | |

OTHER PUBLICATIONS

Bass-Stringer et al, Adeno-Associated Virus Gene Therapy: Translational Progress and Future Prospects in the Treatment of Heart Failure, Heart, Lung and Circulation (2018) 27, 1285-1300.*

Giacomelli et al, Human heart disease: lessons from human pluripotent stem cell-derived cardiomyocytes, Cell. Mol. Life Sci., 2017, pp. 1-29.*

Cerrone et al, Plakophilin-2 is required for transcription of genes that control calcium cycling and cardiac rhythm, Nature Communications, 2017, pp. 1-16.*

Bonne, S. et al. (2000). "Assignment[1] of the plakophilin-2 gene (PKP2) and a plakophilin-2 pseudogene (PKP2P1) to human chromosome bands 12p11 and 12p13, respectively, by in situ hybridization," Cytogenet. Cell Genet. 88:286-287.

Bonne, S. et al. (1998). "Chromosomal mapping of human armadillo genes belonging to the p120$^{ctn}$/plakophilin subfamily," Genomics 51:452-454.

Burger, C. et al. (2004). "Recombinant AAV viral vectors pseudotyped with viral capsids from serotypes 1, 2, and 5 display differential efficiency and cell tropism after delivery to different regions of the central nervous system," Mal. Ther. 10:302-317.

Cruz, F.M. et al. (2015). "Exercise triggers ARVC phenotype in mice expressing a disease-causing mutated version of human plakophilin-2," J. Am. Coll. Cardiol. 65:1438-1450.

Dalal, D. et al. (2006). "Clinical features of arrhythmogenic right ventricular dysplasia/cardiomyopathy associated with mutations in plakophilin-2," Circulation 113:1641-1649.

De, B.P. et al. (2006). "High Levels of Persistent Expression of A1-Antitrypsin Mediated by the Nonhuman Primate Serotype rh.10 Adeno-associated Virus Despite Preexisting Immunity to Common Human Adeno-associated Viruses," Mol. Ther. 13:67-76.

Deyle, D.R. et al. (2009). "Adeno-associated virus vector integration," Curr. Opin. Mal. Ther. 11:442-447.

Duan, D. et al. (2001). "Expanding AAV packaging capacity with trans-splicing or overlapping vectors: a quantitative comparison," Mal. Ther. 4:383-391.

Gao, G. et al. (2004). "Clades of Adeno-Associated Viruses are Widely Disseminated in Human Tissues," J. Virol. 78:6381-6388.

GenBank Accession No. NC_001829.1 (2018). "Adeno-associated virus-4, complete genome," 3 total pages.

GenBank Accession No. NC_002077.1 (2018). "Adeno-associated virus-1, complete genome," 3 total pages.

GenBank Accession No. NC_001401.2 (2018). "Adeno-associated virus-2, complete genome," 5 total pages.

GenBank Accession No. AF085716.1 (1999). "Adeno-associated virus 5 DNA binding trs helicase (Rep22) and capsid protein (VP1) genes,complete cds," 2 total pages.

GenBank Accession No. NC_001862.1 (2004). "Adeno-associated virus-6, complete genome," 3 total pages.

GenBank Accession No. AX753246.1 (2003). "Sequence 1 from patent EP1310571," 2 total pages.

GenBank Accession No. AX753249.1 (2003). "Sequence 4 from patent EP1310571," 2 total pages.

Gerull, B. et al. (2004). "Mutations in the desmosomal protein plakophilin-2 are common in arrhythmogenic right ventricular cardiomyopathy," Nature Genet. 36:1162-1164.

Grimm, D. et al. (2003). "From virus evolution to vector revolution: use of naturally occurring serotypes of adeno-associated virus (AAV) as novel vectors for human gene therapy," Curr. Gene Ther. 3:281-304.

Grossmann, K.S. et al. (2004). "Requirement of plakophilin 2 for heart morphogenesis and cardiac junction formation," J. Cell. Biol. 167:149-160.

Kwon, I. et al. (2008). "Designer gene delivery vectors: molecular engineering and evolution of adeno-associated viral vectors for enhanced gene transfer," Pharm. Res. 25:489-499.

Marcus, F.I. et al. (1982). "Right ventricular dysplasia: a report of 24 adult cases," Circulation 65:384-398.

Marsic, D. et al. (2014). "Vector Design *Tour de Force*: Integrating Combinatorial and Rational Approaches to Derive Novel Adeno-associated Virus Variants," Molecular Therapy 22:1900-1909.

McCarty, D. et al. (2001). "Self-complementary recombinant adeno-associated virus (scAAV) vectors promote efficient transduction

(56) References Cited

OTHER PUBLICATIONS independently of DNA synthesis," Gene Therapy. 8:1248-1254.
Mertens, C. et al. (1996). "Plakophilins 2a and 2b: constitutive proteins of dual location in the karyoplasm and the desmosomal plaque," J. Cell. Biol. 135:1009-1025.
Mori, S. et al. (2004). "Two novel adeno-associated viruses from cynomolgus monkey: Pseudotyping characterization of capsid protein," Virology 330:375-383.
Muzyczka, N. (1992). "Use of adeno-associated virus as a general transduction vector for mammalian cells," Current Topics in Microbiology and Immunology 158:97-129.
Schlabach, M.R. et al. (2010). "Synthetic design of strong promoters," PNAS 107:2538-2543.
Srivastava, A. et al. (1983). "Nucleotide Sequence and Organization of the Adeno-Associated Virus 2 Genome," J. Virol. 45:555-564.
Van Tintelen, J.P. et al. (2006). "Plakophilin-2 mutations are the major determinant of familial arrhythmogenic right ventricular dysplasia/cardiomyopathy," Circulation 113:1650-1658.
Wang, L. et al. (2017). "Single stranded adeno-associated virus achieves efficient gene transfer to anterior segment in the mouse eye," PLoS ONE 12(8): e0182473.
Wu, Z. et al. (2006). "Adeno-associated virus serotypes: vector toolkit for human gene therapy," Mal. Ther. 14:316-327.
Chamberlain, K. et al. "Cardiac gene therapy with adeno-associated virus-based vectors," Current Opinion in Cardiology, 2017, vol. 32, No. 3, May 2017, pp. 275-282.
Wang, Q. et al., "Identification of cis Elements in the Cardiac Troponin T Gene Conferring Specific Expression in Cardiac Muscle of Transgenic Mice," American Heart Association, From the Departments of Biological Sciences (Q.W., J.J.- C.L.) and Internal Medicine (C.D.S.), 2020, University of Iowa, Iowa City, Iowa. pp. 478-484.
Wang, Guoshun et al., "Characterization of cis-Regulating Elements and trans-Activating Factors of the Rat Cardiac Troponin T Gene," The Journal of Biological Chemistry, 1994, vol. 269, No. 48, pp. 30595-30603.
Werfel, S. et al., "Rapid and highly efficient inducible cardiac gene knockout in adult mice using AAV-mediated expression of Cre recombinase," Cardiovascular Research, 104(1):15-23 ( 2014).
Schambach et al., "Biosafety features of lentiviral vectors" Hum Gene Ther. Feb. 2013; 24(2):132-142.
Albert, K et al., "AAV Vector-Mediated Gene Delivery to Substantia Nigra Dopamine Neurons: Implications for Gene Therapy and Disease Models," Genes, Feb. 8, 2017, vol. 8, No. 63, 15 pages.
Albrechtsen, B. et al. (1991). "Transcriptional termination sequence at the end of the *Escherichia coli* ribosomal RNA G operon: Complex terminators and antitermination", Nucl. Acids Res. 19:1845-1852.
Almarza, E. et al. (2011). "Correction of SCID-X1 using an enhancerless Vav promoter," Hum. Gene Ther. 22:263-270.
Berns, K.I., "Parvoviridae and their replication," Virology, 1990, pp. 1743-1763.
Blacklowe, N.R. "Adeno-Associated Viruses of Human," Parvoviruses and Human Disease, Chapter 11, 1988, pp. 165-174.
Bouchard, M.J. et al. (2004). "The Enigmatic X Gene of Hepatitis B Virus", J. Virol. 78:12725-12734.
Brown, H.C. et al. (2018). "Target-cell directed bioengineering approaches for gene therapy of Hemophilia A," Mol. Ther. Methods Clin. Dev. 9:57-69.
Carter, B.J. et al. (1989). Chapter 11 in Handbook of Parvoviruses, vol. I, CRC Press, Inc., pp. 169-226.
Cearley, C.N. et al. (2008). "Expanded repertoire of AAV vector serotypes mediate unique patterns of transduction in mouse brain," Mol. Ther. 16:1710-1718.
Cerrone et al., "Blockade of the Adenosine 2A Receptor Mitigates the Cardiomyopathy Induced by Loss of Plakophilin-2 Expression" Front Physiol. Dec. 5, 2018; 9:1750, 1-10.
Cerrone et al., "Missense Mutations in Plakophilin-2 Cause Sodium Current Deficit and Associate with a Brugada Syndrome Phenotype" Circulation Mar. 11, 2014; 129(10): 1092-1103.
Cerrone et al., "Sodium current deficit and arrhythmogenesis in a murine model of plakophilin-2 haploinsufficiency" Cardiovascular Research (2012) 95: 460-468.
Chandler et al., "Systemic AAV9 gene therapy improves the lifespan of mice with Niemann-Pick disease, type C1," Human Molecular Genetics 26(1):52-64 (2017).
Cid-Arregui, et al., "A Synthetic E7 Gene of Human Papillomavirus Type 16 That Yields Enhanced Expression of the Protein in Mammalian Cells and is Useful for DNA Immunization Studies". J Virol. (Apr. 2003); 77(8): 4928-4937.
Colella et, al., "Emerging Issues in AAV-Mediated In Vivo Gene Therapy" Methods & Clinical Development, Molecular Therapy, Dec. 1, 2017, vol. 8, pp. 87-104.
Donello, J.E. et al (1998). "Woodchuck hepatitis virus contains a tripartite posttranscriptional regulatory element," J. Virol. 72:5085-5092.
Fu, H. et al. (2011). "Correction of neurological disease of Mucopolysaccharidosis IIIB in adult mice by rAAV9 trans-blood-brain barrier gene delivery," Mol. Therapy 19:1025-1033.
Galibert, F et al., "Woodchuck hepatitis virus, complete genome" GenBank: J02442.1, publication date: Aug. 3, 1993. 2 pages.
Gerull and Brodehl, "Genetic Animal Models for Arrhythmogenic Cardiomyopathy" Front Physiol. Jun. 24, 2020; 11:624. doi:10.3389/fphys.2020.00624. eCollection 2020. 20 pages.
Gray, S.J. et al. (2011). "Preclinical differences of intravascular AAV9 delivery to neurons and glia: A comparative study of adult mice and nonhuman primates," Mol. Therapy 19:1058-1069.
Hlavaty, et al., "Effect of posttranscriptional regulatory elements on transgene expression and virus production in the context of retroviral vectors", Virology (2005), 341: 1-11.
Inagaki, K. et al. (2006). "Robust systemic transduction with AAV9 vectors in mice: Efficient global cardiac gene transfer superior to that of AAV8," Mol. Therapy 14:45-53.
Jackson, K.L. et al. (2016). "Corrigendum: Better targeting, better efficiency for wide-scale neuronal transduction with the Synapsin promoter and AAV-PHP.B," Front. Mol. Neurosci. 9:1.
Kim et al., "Disruption of Ca2+ i Homeostasis and Connexin 43 Hemichannel Function in the Right Ventricle Precedes Overt Arrhythmogenic Cardiomyopathy in Plakophilin-2-Deficient Mice" Circulation (2019) 140:1015-1030, and Suppl. pp. 1-65.
Kingsman, S.M. et al. (2005). "Potential oncogene activity of the Woodchuck Hepatitis posttranscriptional regulatory element (WPRE)", Gene Ther. 12:3-4.
Matrai, J. et al. (2010). "Preclinical and clinical progress in hemophilia gene therapy", Curr Opin Hematol. 17:387-392.
Moncayo-Arlandi et al., "Molecular disturbance underlies to arrhythmogenic cardiomyopathy induced by transgene content, age and exercise in a truncated PKP2 mouse model" Hum Mol Genet. Sep. 1, 2016; 25(17):3676-3688.
Naldini, L. (2011). "Ex vivo gene transfer and correction for cell-based therapies", Nature Reviews Genetics 12:301-315.
NCBI Reference Sequence: NM_001005242.3, "*Homo sapiens* plakophilin 2 (PKP2), transcript variant 2a, mRNA" Dec. 27, 2022. 5 pages.
NCBI Reference Sequence: NM_004572.4, "*Homo sapiens* plakophilin 2 (PKP2), transcript variant 2b, mRNA" Dec. 30, 2022. 7 pages.
Pfeifer G.P. et al., "*Homo sapiens* phosphoglycerate kinase 1 (PGK1) gene, partial cds" GenBank: M60581.1, publication date: Jul. 26, 2016. 1 page.
Powell, S.K. et al. (2015). "Viral Expression Cassette Elements to Enhance Transgene Target Specificity and Expression in Gene Therapy," Discov. Med. 19:49-57.
Rose, J.A., "Parvovirus reproduction," Comprehensive Virology, Chapter 1, (1974). Chapter 1, pp. 1-61.
Ruzo, A. et al. (2012). "Correction of pathological accumulation of glycosaminoglycans in central nervous system and peripheral tissues of MPSIIIA mice through systemic AAV9 gene transfer," Human Gene Ther. 23:1237-1246.
Salva et al., "Design of tissue-specific regulatory cassettes for high-level rAAV-mediated expression in skeletal and cardiac muscle" Mol Ther. Feb. 2007; 15(2):320-329.

(56) References Cited

OTHER PUBLICATIONS

Schambach, A. et al. (2006). "Woodchuck hepatitis virus post-transcriptional regulatory element deleted from X protein and promoter sequences enhances retroviral vector titer and expression", Gene Ther. 13:641-645.
Shevtsova, Z. et al., "Promoters and serotypes: targeting of adeno-associated virus vectors for gene transfer in the rat central nervous system in vitro and in vivo," Experimental Physiology, Cambridge University Press, Cambridge, GB, Jan. 1, 2005, vol. 90, No. 1, pp. 53-59.
Takeshita, F. et al. "Muscle creatine kinase/SV40 hybrid promoter for muscle-targeted long-term transgene expression." International Journal of Molecular Medicine, vol. 19.2 (2007): pp. 309-315, 7 pages.
Van Opbergen et al., "Plakophilin-2 Haploinsufficiency Causes Calcium Handling Deficits and Modulates the Cardiac Response Towards Stress" Int. J. Mol. Sci. Aug. 21, 2019; 20(17):4076.
Weismann, C.M. et al. (2015). "Systemic AAV9 gene transfer in adult GM1 gangliosidosis mice reduces lysosomal storage in CNS and extends lifespan," Human Molecular Genetics 24:4353-4364.
Zanta-Boussif, M.A. et al. (2009). "Validation of a mutated PRE sequence allowing high and sustained transgene expression while abrogating WHV-X protein synthesis: Application to the gene therapy of WAS", Gene Ther. 16:605-619.
Zufferey et al., "Woodchuck Hepatitis Virus Posttranscriptional Regulatory Element Enhances Expression of Transgenes Delivered by Retroviral Vectors." J. Virol. (1999); 73(4): 2886-2892.
Zychlinski, D., et al., "Physiological Promoters Reduce the Genotoxic Risk of Integrating Gene Vectors," Molecular Therapy, 2008, vol. 16, pp. 718-725.

* cited by examiner

PLAKOPHILIN-2 (PKP2) GENE THERAPY USING AAV VECTOR

CROSS-REFERENCE TO RELATED APPLICATIONS

This application is a continuation of International Application No. PCT/US2021/045220, filed Aug. 9, 2021, which claims the benefit of U.S. Provisional Application No. 63/063,032, filed Aug. 7, 2020, which is incorporated by reference herein in its entirety.

STATEMENT REGARDING THE SEQUENCE LISTING

The Sequence Listing associated with this application is provided in text format in lieu of a paper copy, and is hereby incorporated by reference into the specification. The name of the text file containing the Sequence Listing is ROPA_021_01WO_ST25.txt. The text file is about 212 KB, created on Aug. 8, 2021, and is being submitted electronically via EFS-Web.

BACKGROUND

Arrhythmogenic right ventricular cardiomyopathy (ARVC) is a form of adult-onset heart disease, which impacts an estimated 1 in 1,000 to 1 in 1,250 people. It manifests as breakdown of the muscular wall of the heart (the myocardium) over time, which leads to increased risk of abnormal heartbeat (arrhythmia) and an increased risk of sudden death when an affected individual exercises strenuously. Individuals may also experience a sensation of fluttering or pounding in the chest (palpitations), light-headedness, fainting (syncope), shortness of breath, and abnormal swelling in the legs or abdomen. Over time, ARVC can lead to heart failure.

At least 13 genes are implicated in ARVC, many of which are involved in the biogenesis of desmosomes, which are intracellular junctions that provide strong adhesion between cells. When desmosomes fail to form properly, myocardial cells may detach from one another and die. The right ventricle in particular may develop weakness, while fatty deposits and scar tissue may replace the damaged myocardium, leading to distension of the right ventricle. These alterations ultimately prevent effective heart pumping and disrupt the electrical signals that control the heartbeat, leading to arrhythmia. Autosomal dominant plakophilin-2 (PKP2) cardiomyopathy is an inherited ARVC in which mutations affecting PKP2 are detected.

There remains, therefore, an unmet need in the art for treatments for PKP2-related diseases and disorders, including ARVC. The compositions and methods disclosed herein address this need.

SUMMARY

The present invention relates generally to gene therapy for a disease or disorder, e.g., a cardiac disease or disorder, using a vector expressing PKP2 or a functional variant thereof.

In one aspect, the disclosure provides polynucleotide, comprising an expression cassette and optionally flanking adeno-associated virus (AAV) inverted terminal repeats (ITRs), wherein the polynucleotide comprises a polynucleotide sequence encoding a Plakophilin-2 (PKP2) or a functional variant thereof, operatively linked to a promoter.

In some embodiments, the promoter is a cardiac-specific promoter.

In some embodiments, the promoter is a muscle-specific promoter.

In some embodiments, the promoter is a cardiomyocyte-specific promoter.

In some embodiments, the promoter is a Myosin Heavy-chain Creatine Kinase 7 (MHCK7) promoter.

In some embodiments, the MHCK7 promoter shares at least 75%, 80%, 85%, 90%, 95%, 96%, 97%, 98%, 99% or 100% identity with SEQ ID NO: 31.

In some embodiments, the promoter is a cardiac troponin T (hTNNT2) promoter.

In some embodiments, the hTNNT2 promoter shares at least 75%, 80%, 85%, 90%, 95%, 96%, 97%, 98%, 99% or 100% identity with SEQ ID NO: 32.

In some embodiments, the expression cassette comprises exon 1 of the cardiac troponin T (hTNNT2) gene, wherein optionally the hTNNT2 promoter and exon 1 together share at least 75%, 80%, 85%, 90%, 95%, 96%, 97%, 98%, 99% or 100% identity with SEQ ID NO: 32.

In some embodiments, the promoter is a ubiquitous promoter, optionally a CMV promoter or a CAG promoter.

In some embodiments, the expression cassette comprises a polyA signal.

In some embodiments, the polyA signal is a human growth hormone (hGH) polyA.

In some embodiments, the expression cassette comprises a Woodchuck Hepatitis Virus Posttranscriptional Regulatory Element (WPRE), optionally a WPRE(x).

In some embodiments, the Plakophilin-2 (PKP2) or functional variant thereof is a PKP2.

In some embodiments, the PKP2 is a functional PKP2.

In some embodiments, the PKP2 is a human PKP2.

In some embodiments, the PKP2 is PKP2 isoform A.

In some embodiments, the PKP2 isoform A shares at least 75%, 80%, 85%, 90%, 95%, 96%, 97%, 98%, 99% or 100% identity with SEQ ID NO: 1.

In some embodiments, the PKP2 is PKP2 isoform B.

In some embodiments, the PKP2 shares at least 75%, 80%, 85%, 90%, 95%, 96%, 97%, 98%, 99% or 100% identity with SEQ ID NO: 2.

In some embodiments, the polynucleotide sequence encoding PKP2 is a human PKP2 polynucleotide.

In some embodiments, the polynucleotide sequence encoding PKP2 shares at least 75%, 80%, 85%, 90%, 95%, 96%, 97%, 98%, 99% or 100% identity with SEQ ID NO: 3.

In some embodiments, the polynucleotide sequence encoding PKP2 shares at least 75%, 80%, 85%, 90%, 95%, 96%, 97%, 98%, 99% or 100% identity with SEQ ID NO: 4.

In some embodiments, the polynucleotide comprises at least about 4.0 kb, at least about 4.1 kb, at least about 4.2 kb, at least about 4.3 kb, at least about 4.4 kb, or at least about 4.5 kb.

In some embodiments, the polynucleotide comprises at most about 4.1 kb, at most about 4.2 kb, at most about 4.3 kb, at most about 4.4 kb, at most about 4.5 kb, or at most about 4.6 kb.

In some embodiments, the polynucleotide comprises 4.0 kb to 4.6 kb, 4.0 kb to 4.5 kb, or 4.0 kb to 4.4 kb or wherein the polynucleotide comprises 4.0 kb to 4.3 kb, 4.0 kb to 4.2 kb, or 4.0 kb to 4.1 kb.

In some embodiments, the PKP2 or functional variant thereof comprises at least 800 or at least 830 amino acids.

In some embodiments, the polynucleotide shares at least 75%, 80%, 85%, 90%, 95%, 96%, 97%, 98%, 99% or 100% identity with any one of SEQ ID NOs: 8-15.

In some embodiments, the expression cassette is flanked by 5' and 3' inverted terminal repeats (ITRs)

In some embodiments, the ITRs are AAV2 ITRs and/or the ITRs share at least 75%, 80%, 85%, 90%, 95%, 96%, 97%, 98%, 99% or 100% identity with any one of SEQ ID NO: 20-26.

In another aspect, the disclosure provides a gene therapy vector, comprising the polynucleotide of any one of the preceding embodiments.

In some embodiments, the gene therapy vector is a recombinant adeno-associated virus (rAAV) vector.

In some embodiments, the rAAV vector is an AAV9 or a functional variant thereof.

In some embodiments, the rAAV vector comprises a capsid protein that shares 90%, 91%, 92%, 93%, 94%, 95%, 96%, 97%, 98%, 99% or 100% identity to any one of SEQ ID NO: 77.

In some embodiments, the rAAV vector is an AAVrh10 or a functional variant thereof.

In some embodiments, the rAAV vector comprises a capsid protein that shares 90%, 91%, 92%, 93%, 94%, 95%, 96%, 97%, 98%, 99% or 100% identity to any one of SEQ ID NO: 79.

In some embodiments, the rAAV vector is an AAV6 or a functional variant thereof.

In some embodiments, the rAAV vector comprises a capsid protein that shares 90%, 91%, 92%, 93%, 94%, 95%, 96%, 97%, 98%, 99% or 100% identity to any one of SEQ ID NO: 78.

In some embodiments, the rAAV vector is an AAVrh74 or a functional variant thereof.

In some embodiments, the rAAV vector comprises a capsid protein that shares 90%, 91%, 92%, 93%, 94%, 95%, 96%, 97%, 98%, 99% or 100% identity to any one of SEQ ID NO: 80.

In another aspect, the disclosure provides a method of treating and/or preventing a disease or disorder in a subject in need thereof, comprising administering the vector of any one of the preceding embodiments to the subject.

In some embodiments, the disease or disorder is a cardiac disorder.

In some embodiments, the disease or disorder is cardiomyopathy.

In some embodiments, the cardiomyopathy is arrhythmogenic right ventricular cardiomyopathy (ARVC).

In some embodiments, the cardiomyopathy is hypertrophic cardiomyopathy or dilated cardiomyopathy.

In some embodiments, the disease or disorder is characterized by fibrofatty infiltration of myocardium.

In some embodiments, the disease or disorder is heart failure.

In some embodiments, the subject is a mammal.

In some embodiments, the subject is a primate.

In some embodiments, the subject is a human.

In some embodiments, the subject has a mutation in a PRP2 gene.

In some embodiments, the vector is administered by intravenous injection, intracardiac injection, intracardiac infusion, and/or cardiac catheterization.

In some embodiments, the administration increases PKP2 expression by at least about 5%.

In some embodiments, the administration increases PKP2 expression by at least about 30%.

In some embodiments, the administration increases PKP2 expression by at least about 70%.

In some embodiments, the administration increases PKP2 expression by about 5% to about 10%.

In some embodiments, the administration increases PKP2 expression by about 30% to about 50%.

In some embodiments, the administration increases PKP2 expression by about 50% to about 70%.

In some embodiments, the administration increases PKP2 expression by about 70% to about 100%.

In some embodiments, the method treats and/or prevents the disease or disorder.

In some embodiments, the method comprises administering an effective amount of the vector.

In some embodiments, the disease or disorder is related to or caused by loss of function in PKP2 in the subject.

In some embodiments, the disease or disorder is related to or caused by gain of function in PKP2 in the subject.

In some embodiments, the subject has a mutation that causes an amino acid substitution selected from p.Arg490Trp, Asp26Asn, Thr50_Val51SerfsX60, Arg79X, Tyr86X, Gln133X, Val406SerfsX3, Tyr616X, Trp676X, Cys796Arg, Cys796E, Tyr807X, Glu62Lys, S688P, Trp848X, Y86X, V406X, Y616X, W848X, and Y807X, relative to a human PKP2 gene encoding a human PKP2 having the sequence of SEQ ID NO: 2.

In some embodiments, the method comprises administering a pharmaceutical composition comprising an effective amount of the vector.

In some embodiments, the method comprises administering between about $1\times10^{11}$ vector genomes and about $1\times10^{13}$ vector genomes of the vector to the subject, administering between about $1\times10^{12}$ vector genomes and about $1\times10^{14}$ vector genomes of the vector to the subject, or administering between about $1\times10^{13}$ vector genomes and about $1\times10^{15}$ vector genomes of the vector to the subject.

In another aspect, the disclosure provides a pharmaceutical composition comprising the vector of any one of the preceding embodiments.

In another aspect, the disclosure provides a kit comprising the vector of any one of the preceding embodiments or the pharmaceutical composition of the preceding embodiment and optionally instructions for use.

In another aspect, the disclosure provides a use of the vector of any one of the preceding embodiments in treating a disease or disorder, optionally according to the method of any one of the preceding embodiments.

In another aspect, the disclosure provides a vector according to any one of the preceding embodiments for use in treating a disease or disorder, optionally according to the method of any one of the preceding embodiments.

In another aspect, the disclosure provides a polynucleotide, comprising a polynucleotide sequences that shares at least 90%, 91%, 92%, 93%, 94%, 95%, 96%, 97%, 98%, 99%, or 100% identity to any one of SEQ ID NOs: 12-15 and 89-92 or to any one of SEQ ID NOs: 8-11 and 93-96.

In some embodiments, the promoter is a MHCK7 promoter.

In some embodiments, the MHCK7 promoter shares at least 75%, 80%, 85%, 90%, 95%, 96%, 97%, 98%, 99% or 100% identity with SEQ ID NO: 31.

In some embodiments, the PKP2 is a human PKP2.

In some embodiments, the PKP2 is PKP2 isoform A.

In some embodiments, the PKP2 isoform A shares at least 80%, 90%, 95%, 99% or 100% identity with SEQ ID NO: 1.

In another aspect, the disclosure provides a gene therapy vector, comprising the polynucleotide of any one of the preceding embodiments.

In some embodiments, the gene therapy vector is a recombinant adeno-associated virus (rAAV) vector.

In some embodiments, the rAAV vector is an AAV9 vector.

In some embodiments, the rAAV vector is an AAVrh74 vector.

In another aspect, the disclosure provides a method of treating and/or preventing a cardiac disorder in a subject identified as having a mutation in the PRP2 gene, comprising administering the vector of any one of the preceding embodiments to the subject.

In some embodiments, the cardiac disorder is cardiomyopathy, optionally arrhythmogenic right ventricular cardiomyopathy (ARVC), hypertrophic cardiomyopathy, or dilated cardiomyopathy.

In some embodiments, the cardiac disorder is heart failure.

In some embodiments, the subject is a mammal.

In some embodiments, the vector is administered by intravenous injection, intracardiac injection, intracardiac infusion, and/or cardiac catheterization.

In some embodiments, the method prevents or reduces a decrease in left ventricle ejection fraction percentage (LVEF %), optionally by about 50%, about 60%, about 70%, about 80%, about 90%, or about 100% compared to the decrease observed in an untreated subject identified as having a mutation in the PRP2 gene.

In some embodiments, the method prevents or reduces a decrease in left ventricle fractional shortening percentage (FS %), optionally by about 50%, about 60%, about 70%, about 80%, about 90%, or about 100% compared to the decrease observed in an untreated subject identified as having a mutation in the PRP2 gene.

In some embodiments, the method prevents or reduces an increase in right ventricle area in millimeters squared (RV Area (mm2), optionally by about 50%, about 60%, about 70%, about 80%, about 90%, or about 100% compared to the increase observed in an untreated subject identified as having a mutation in the PRP2 gene.

In some embodiments, the method prevents or reduces a decrease in right ventricle velocity time integral in millimeters per second (RV VTI (mm/sec), optionally by about 50%, about 60%, about 70%, about 80%, about 90%, or about 100% compared to the decrease observed in an untreated subject identified as having a mutation in the PRP2 gene.

In some embodiments, the method prevents or reduces an increase in left ventricle or right ventricle fibrosis, optionally by about 50%, about 60%, about 70%, about 80%, about 90%, or about 100% compared to the increase observed in an untreated subject identified as having a mutation in the PRP2 gene.

Various other aspects and embodiments are disclosed in the detailed description that follows. The invention is limited solely by the appended claims.

BRIEF DESCRIPTION OF FIGURES

FIG. 5A shows Western Blots (WB) of PKP2 (top panel) or loading control, GAPDH (bottom panel). FIG. 5B show a bar graph of the Western Blot. The AAV vector serotype (AAV9 or rh74) and the promoter (MHCK7 or hTnT) are noted. Controls included a GFP vector (CON-GFP) and no transduction (No Tdxn).

FIG. 6A shows results with the AAV9 vector and MHCK7 promoter (AAV9-MHCK7). FIG. 6B shows results with the AAVrh.74 vector and MHCK7 promoter (AAVrh.74-MHCK7). FIG. 6C shows results with the AAV9 vector and hTnT promoter (AAV9-hTnT). FIG. 6D shows results with the AAVrh.74 vector and hTnT promoter (AAVrh.74-hTnT).

FIG. 7A shows results with the AAV9 vector and MHCK7 promoter (AAV9-MHCK7). FIG. 7B shows results with the AAVrh.74 vector and MHCK7 promoter (AAVrh.74-MHCK7). FIG. 7C shows results with the AAV9 vector and hTnT promoter (AAV9-hTnT). FIG. 7D shows results with the AAVrh.74 vector and the hTnT promoter (AAVrh.74-hTnT).

FIG. 8A shows results with the AAV9 vector and MHCK7 promoter (AAV9-MHCK7). FIG. 8B shows results with the AAVrh.74 vector and MHCK7 promoter (AAVrh.74-MHCK7). FIG. 8C shows results with the AAV9 vector and hTnT promoter (AAV9-hTnT). FIG. 8D shows results with the AAVrh.74 vector and hTnT promoter (AAVrh.74-hTnT).

FIG. 9A shows results with the AAV9 vector and MHCK7 promoter (AAV9-MHCK7). FIG. 9B shows results with the AAVrh.74 vector and MHCK7 promoter (AAVrh.74-MHCK7). FIG. 9C shows results with the AAV9 vector and hTnT promoter (AAV9-hTnT). FIG. 9D shows results with the AAVrh.74 vector and hTnT promoter (AAVrh.74-hTnT).

FIG. 10A is a bar graph of percent collagen in the left ventricle. FIG. 10B is a bar graph of percent collagen in the right ventricle.

DETAILED DESCRIPTION OF THE INVENTION

Figure 1:
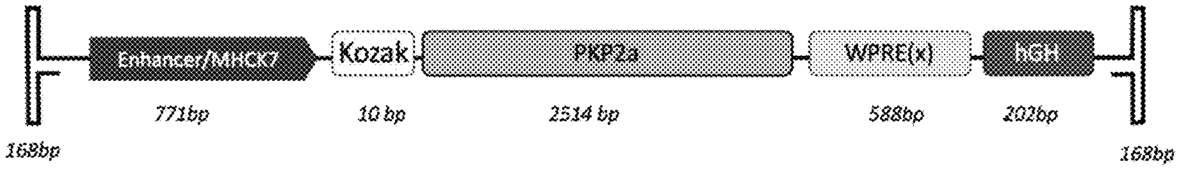
FIG. 1 shows a diagram illustrating a non-limiting example of a vector genome. The full polynucleotide sequence of the vector genome is SEQ ID NO: 12. The expression cassette is SEQ ID NO: 8. The MHCK7 promoter as described herein is labelled "Enhancer/MHCK7" in the diagram.
Figure 2:
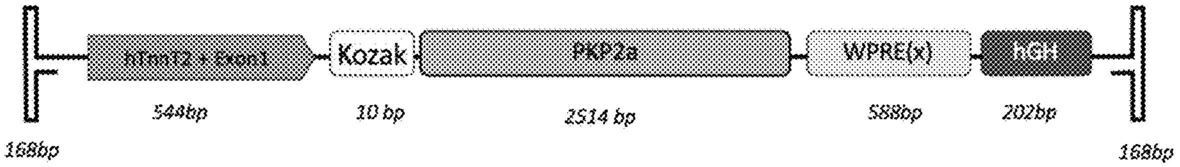
FIG. 2 shows a diagram illustrating a non-limiting example of a vector genome. The full polynucleotide sequence of the vector genome is SEQ ID NO: 13. The expression cassette is SEQ ID NO: 9.
Figure 3:
FIG. 3 shows a diagram illustrating a non-limiting example of a vector genome. The full polynucleotide sequence of the vector genome is SEQ ID NO: 14. The expression cassette is SEQ ID NO: 10. The MHCK7 promoter as described herein is labelled "Enhancer/MHCK7" in the diagram.
Figure 4:
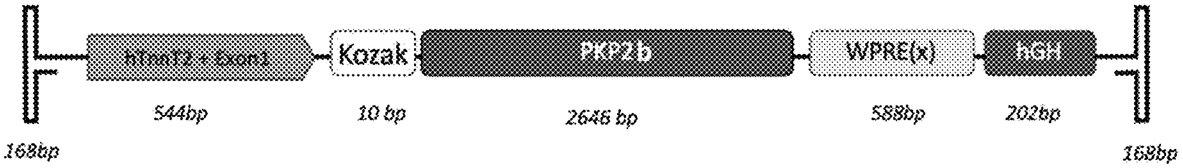
FIG. 4 shows a diagram illustrating a non-limiting example of a vector genome. The full polynucleotide sequence of the vector genome is SEQ ID NO: 15. The expression cassette is SEQ ID NO: 11.

The present disclosure provided gene therapy vectors for PKP2 that deliver a polynucleotide encoding a PKP2 polypeptide or a functional variant thereof, along with methods of use, and other compositions and methods. In particular embodiments, the disclosure relates to a gene therapy vector comprising a promoter sequence operatively linked to a polynucleotide encoding a PKP2 polypeptide or a functional variant thereof. In some embodiments, the promoter is a Myosin Heavy-chain Creatine Kinase 7 (MHCK7) promoter. In some embodiment, the AAV vector is an AAV9 vector. In some embodiments, the promoter is an MHCK7 promoter and the AAV vector is an AAV9 vector. In some embodiments, the promoter is a hTNNT2 promoter. In some embodiment, the promoter is an hTNNT2 promoter and the AAV vector is an AAV9 vector. In some embodiments, the PKP2 is human PKP2a. In some embodiments, the PKP2 is human PKP2b. In some embodiment, the AAV vector is an rh74 vector. In some embodiments, the promoter is an MHCK7 promoter and the AAV vector is an rh74 vector. In some embodiments, the promoter is a hTNNT2 promoter. In some embodiment, the promoter is an hTNNT2 promoter and the AAV vector is an rh74 vector. In some embodiments, the PKP2 is human PKP2a. In some embodiments, the PKP2 is human PKP2b.

This disclosure further provides methods of treating a disorder or disorder in a subject by administering a gene therapy vector of the disclosure to the subject. In a certain embodiment, the disorder or disorder is arrhythmogenic right ventricular cardiomyopathy (ARVC).

In certain embodiments, the subject being treated is an ARVC patient having one or more mutation in a PKP2 gene. More than half of ARVC patients carry mutations in the desmosomal gene PKP2 encoding the protein Plakophilin-2 (PKP2). PKP2 is also associated with Brugada syndrome (BrS) and idiopathic ventricular fibrillation. It is a member of the armadillo repeat and plakophilin protein family. The protein contains nine central, conserved armadillo repeat domains flanked by N-terminal and C-terminal domains. It functions to link cadherins to intermediate filaments in the cytoskeleton Plakophilin 2 localizes to cell desmosomes and nuclei and binds plakoglobin, desmoplakin, and the desmosomal cadherins via an N-terminal head domain. PKP2 provides a lateral stabilizing force with the desmosomal-intermediate filament assembly facilitating cell-to-cell contact. It may also serve roles in intracellular signaling regulation, electrophysiologic and trafficking regulation, and control of transcription processes.

Intravenous injection of an AAV9 vector encoding a C-terminal deletion mutant of PKP2a (R735X) in the heart of wild-type mice accelerates the appearance of ARVC when treated mice are subjected to exercise training. Cruz et al. *J Am Coll Cardiol.* 65(14):1438-50 (2015). Mutant PKP2a causes a disease phenotype; and control AAV9 vector expressing the non-mutant PKP2a causes no phenotypic change in wild type mice. Heterologous expression of wild-type human PKP2a does not induce disease or altered function. These studies demonstrate that mutant PKP2a can cause a disease phenotype. They fail to demonstrate a curative role for PKP2, because heterologous expression of non-mutant PKP2 resulted in no phenotypic change in the wild-type mouse.

In accordance with the present invention, a polynucleotide encoding a PKP2 or functional variant thereof, wherein the PKP2 or functional variant thereof comprises at least 800 or at least 830 amino acids (e.g., no C terminal truncation at Arg-735), may be employed in generating a gene therapy vector. The resulting vector may be employed in treating diseases or disorders, e.g. a PKP2-related disease or disorder, e.g. ARVC, Brugada syndrome (BrS), idiopathic ventricular fibrillation, dilated cardiomyopathy (DCM), and others.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

All publications and patents mentioned herein are hereby incorporated by reference in their entirety as if each individual publication or patent was specifically and individually indicated to be incorporated by reference. In case of conflict, the present application, including any definitions herein, will control. However, mention of any reference, article, publication, patent, patent publication, and patent application cited herein is not, and should not be taken as an acknowledgment, or any form of suggestion, that they constitute valid prior art or form part of the common general knowledge in any country in the world.

In the present description, any concentration range, percentage range, ratio range, or integer range is to be understood to include the value of any integer within the recited range and, when appropriate, fractions thereof (such as one tenth and one hundredth of an integer), unless otherwise indicated. The term "about", when immediately preceding a number or numeral, means that the number or numeral ranges plus or minus 10%. It should be understood that the terms "a" and "an" as used herein refer to "one or more" of the enumerated components unless otherwise indicated. The use of the alternative (e.g., "or") should be understood to mean either one, both, or any combination thereof of the alternatives. The term "and/or" should be understood to mean either one, or both of the alternatives. As used herein, the terms "include" and "comprise" are used synonymously.

As used herein, the terms "identity" and "identical" refer, with respect to a polypeptide or polynucleotide sequence, to the percentage of exact matching residues in an alignment of that "query" sequence to a "subject" sequence, such as an alignment generated by the BLAST algorithm. Identity is calculated, unless specified otherwise, across the full length of the subject sequence. Thus a query sequence "shares at least x % identity to" a subject sequence if, when the query sequence is aligned to the subject sequence, at least x % (rounded down) of the residues in the subject sequence are aligned as an exact match to a corresponding residue in the query sequence. Where the subject sequence has variable positions (e.g., residues denoted X), an alignment to any residue in the query sequence is counted as a match. Sequence alignments may be performed using the NCBI Blast service (BLAST+ version 2.12.0).

As used herein, the term "operatively linked" refers to a functional relationship between two or more nucleic acid (e.g., DNA) segments. Typically, it refers to the functional relationship of a transcriptional regulatory sequence to a transcribed sequence. For example, a promoter sequence is operatively linked to a coding sequence if it stimulates or modulates the transcription of the coding sequence in an appropriate host cell or other expression system. Generally, promoter transcriptional regulatory sequences that are operatively linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

As used herein, an "AAV vector" or "rAAV vector" refers to a recombinant vector comprising one or more polynucleotides of interest (or transgenes) that are flanked by AAV inverted terminal repeat sequences (ITRs). Such AAV vectors can be replicated and packaged into infectious viral particles when present in a host cell that has been transfected with a plasmid encoding and expressing rep and cap gene products. Alternatively, AAV vectors can be packaged into infectious particles using a host cell that has been stably engineered to express rep and cap genes.

As used herein, an "AAV virion" or "AAV viral particle" or "AAV vector particle" refers to a viral particle composed of at least one AAV capsid protein and an encapsidated polynucleotide AAV vector. As used herein, if the particle comprises a heterologous polynucleotide (i.e., a polynucleotide other than a wild-type AAV genome such as a transgene to be delivered to a mammalian cell), it is typically referred to as an "AAV vector particle" or simply an "AAV vector." Thus, production of AAV vector particle necessarily includes production of AAV vector, as such a vector is contained within an AAV vector particle.

As used herein, "promoter" refers to a polynucleotide sequence capable of promoting initiation of RNA transcription from a polynucleotide in a eukaryotic cell.

As used herein, "vector genome" refers to the polynucleotide sequence packaged by the vector (e.g., an rAAV virion), including flanking sequences (in AAV, inverted terminal repeats). The terms "expression cassette" and "polynucleotide cassette" refer to the portion of the vector genome between the flanking ITR sequences. "Expression cassette" implies that the vector genome comprises at least one gene encoding a gene product operatively linked to an element that drives expression (e.g., a promoter).

As used herein, the term "patient in need" or "subject in need" refers to a patient or subject at risk of, or suffering from, a disease, disorder or condition that is amenable to treatment or amelioration with a recombinant gene therapy vector or gene editing system disclosed herein. A patient or subject in need may, for instance, be a patient or subject diagnosed with a disorder associated with heart. A subject may have a mutation in an PKP2 gene or deletion of all or a part of PKP2 gene, or of gene regulatory sequences, that causes aberrant expression of the PKP2 protein. "Subject" and "patient" are used interchangeably herein. The subject treated by the methods described herein may be an adult or a child. Subjects may range in age.

As used herein, the term "variant" refers to a protein that has one or more amino-acid substitution, insertion, or deletion as compared to a parental protein. As used herein, the term "functional variant" refers to a protein that has one or more amino-acid substitution, insertion, or deletion as compared to a parental protein, and which retains one or more desired activities of the parental protein.

As used herein, "treating" refers to ameliorating one or more symptoms of a disease or disorder. The term "preventing" refers to delaying or interrupting the onset of one or more symptoms of a disease or disorder or slowing the progression of PKP2-related disease or disorder, e.g., arrhythmogenic right ventricular cardiomyopathy (ARVC).

Adeno-associated virus (AAV) is a replication-deficient parvovirus, the single-stranded DNA genome of which is about 4.7 kb in length including two ~145-nucleotide inverted terminal repeat (ITRs). There are multiple known variants of AAV, also sometimes called serotypes when classified by antigenic epitopes. The nucleotide sequences of the genomes of the AAV serotypes are known. For example, the complete genome of AAV-1 is provided in GenBank Accession No. NC_002077; the complete genome of AAV-2 is provided in GenBank Accession No. NC_001401 and Srivastava et al., J. Virol., 45: 555-564 (1983); the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_00 1862; at least portions of AAV-7 and AAV-8 genomes are provided in GenBank Accession Nos. AX753246 and AX753249, respectively; the AAV-9 genome is provided in Gao et al., J. Virol., 78: 6381-6388 (2004); the AAV-10 genome is provided in Mol. Ther., 13(1): 67-76 (2006); and the AAV-11 genome is provided in Virology, 330(2): 375-383 (2004). The sequence of the AAVrh.74 genome is provided in U.S. Pat. No. 9,434,928, incorporated herein by reference. Cis-acting sequences directing viral DNA replication (rep), encapsidation/packaging and host cell chromosome integration are contained within the AAV ITRs. Three AAV promoters (named p5, p19, and p40 for their relative map locations) drive the expression of the two AAV internal open reading frames encoding rep and cap genes. The two rep promoters (p5 and p19), coupled with the differential splicing of the single AAV intron (at nucleotides 2107 and 2227), result in the production of four rep proteins (rep78, rep68, rep52, and rep40) from the rep gene. Rep proteins possess multiple enzymatic properties that are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, Current Topics in Microbiology and Immunology, 158: 97-129 (1992).

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). The AAV proviral genome is inserted as cloned DNA in plasmids, which makes construction of recombinant genomes feasible. Furthermore, because the signals directing AAV replication and genome encapsidation are contained within the ITRs of the AAV genome, some or all of the internal approximately 4.3 kb of the genome (encoding replication and structural capsid proteins, rep-cap) may be replaced with foreign DNA. To generate AAV vectors, the rep and cap proteins may be provided in trans. Another significant feature of AAV is that it is an extremely stable and hearty virus. It easily withstands the conditions used to inactivate adenovirus (56° to 65° C. for several hours), making cold preservation of AAV less critical. AAV may even be lyophilized. Finally, AAV-infected cells are not resistant to superinfection.

Gene delivery viral vectors useful in the practice of the present invention can be constructed utilizing methodologies well known in the art of molecular biology. Typically, viral vectors carrying transgenes are assembled from polynucleotides encoding the transgene, suitable regulatory elements and elements necessary for production of viral proteins, which mediate cell transduction. Such recombinant viruses may be produced by techniques known in the art, e.g., by transfecting packaging cells or by transient transfection with helper plasmids or viruses. Typical examples of virus packaging cells include but are not limited to HeLa cells, SF9 cells (optionally with a baculovirus helper vector), 293 cells, etc. A Herpesvirus-based system can be used to produce AAV vectors, as described in US20170218395A1. Detailed protocols for producing such replication-defective recombinant viruses may be found for instance in WO95/14785, WO96/22378, U.S. Pat. Nos. 5,882,877, 6,013,516, 4,861,719, 5,278,056 and WO94/19478, the complete contents of each of which is hereby incorporated by reference.

The present disclosure contemplates compositions and methods of use related to Plakophilin-2 (PKP2) proteins or polypeptides. Various mutations in PKP2 are known to be associated with cardiomyopathy and heart failure, including diseases like those described in van Tintelen et al. *Circulation* 113:1650-58 (2006); Novelli *Front. Cardiovasc. Med.* (2008); and in other sources. Viral vector-mediated delivery of the PKP2 gene may therefore serve as a viable therapeutic for PKP2-related human diseases such as cardiomyopathy and heart failure.

More than 230 mutations in the PKP2 gene have been identified in people with arrhythmogenic right ventricular cardiomyopathy (ARVC). (See "PKP2 gene," MedlinePlus). This condition most commonly affects the myocardium surrounding the right ventricle, one of the two lower chambers of the heart. ARVC increases the risk of an abnormal heartbeat (arrhythmia) and sudden death. Some PKP2 gene mutations lead to the production of an abnormally short version of plakophilin 2. Other mutations alter the structure of plakophilin 2 by adding, deleting, or changing one or more of its protein building blocks (amino acids). Studies suggest that the altered protein impairs the formation and function of desmosomes.

Without normal desmosomes, cells of the myocardium detach from one another and die, particularly when the heart muscle is placed under stress (such as during vigorous exercise). The damaged myocardium is gradually replaced by fat and scar tissue. As this abnormal tissue builds up, the walls of the right ventricle become stretched out, preventing the heart from pumping blood effectively. These changes also disrupt the electrical signals that control the heartbeat, which can lead to arrhythmia. Description of PKP2-related disease may be found in the following references: Bonne et al. *Genomics* 51:452-454 (1998) [PubMed: 9721216]; Bonne et al. *Cytogenet. Cell Genet.* 88:286-287 (2000) [PubMed: 10828611]; Dalal et al., *Circulation* 113:1641-1649 (2006) [PubMed: 16549640]; Gerull et al. *Nature Genet.* 36:1162-1164 (2004 [PubMed: 15489853]; Grossmann et al. *J. Cell Biol.* 167:149-160 (2004) [PubMed: 15479741]; Marcus et al. *Circulation* 65:384-398 (1982) [PubMed: 7053899]; and Mertens et al. *J. Cell Biol.* 135: 1009-1025 (1996) [PubMed: 8922383]. See also OMIM.org entry 602861 ("PLAKOPHILIN 2; PKP2").

The native sequences of human PKP2a and its isoform PKP2b are shown below, with Arg-735 underlined:

```
PKP2a - 837 amino acids
                                    (SEQ ID NO: 1)
  1  MAAPGAPAEY GYIRTVLGQQ ILGQLDSSSL ALPSEAKLKL

 41  AGSSGRGGQT VKSLRIQEQV QQTLARKGRS SVGNGNLHRT

 81  SSVPEYVYNL HLVENDFVGG RSPVPKTYDM LKAGTTATYE

121  GRWGRGTAQY SSQKSVEERS LRHPLRRLEI SPDSSPERAH

161  YTHSDYQYSQ RSQAGHTLHH QESRRAALLV PPRYARSEIV

201  GVSRAGTTSR QRHFDTYHRQ YQHGSVSDTV FDSIPANPAL

241  LTYPRPGTSR SMGNLLEKEN YLTAGLTVGQ VRPLVPLQPV

281  TQNRASRSSW HQSSFHSTRT LREAGPSVAV DSSGRRAHLT

321  VGQAAAGGSG NLLTERSTFT DSQLGNADME MTLERAVSML

361  EADHMLPSRI SAAATFIQHE CFQKSEARKR VNQLRGILKL

401  LQLLKVQNED VQRAVCGALR NLVFEDNDNK LEVAELNGVP

441  RLLQVLKQTR DLETKKQITG LLWNLSSNDK LKNLMITEAL

481  LTLTENIIIP FSGWPEGDYP KANGLLDFDI FYNVTGCLRN

521  MSSAGADGRK AMRRCDGLID SLVHYVRGTI ADYQPDDKAT

561  ENCVCILHNL SYQLEAELPE KYSQNIYIQN RNIQTDNNKS

601  IGCFGSRSRK VKEQYQDVPM PEEKSNPKGV EWLWHSIVIR

641  MYLSLIAKSV RNYTQEASLG ALQNLTAGSG PMPTSVAQTV

681  VQKESGLQHT RKMLHVGDPS VKKTAISLLR NLSRNLSLQN

721  EIAKETLPDL VSIIPDTVPS TDLLIETTAS ACYTLNNIIQ
```

-continued

```
761  NSYQNARDLL NTGGIQKIMA ISAGDAYASN KASKAASVLL

801  YSLWAHTELH HAYKKAQFKK TDFVNSRTAK AYHSLKD
```

PKP2b - 881 amino acids (SEQ ID NO: 2)

```
  1  MAAPGAPAEY GYIRTVLGQQ ILGQLDSSSL ALPSEAKLKL

 41  AGSSGRGGQT VKSLRIQEQV QQTLARKGRS SVGNGNLHRT

 81  SSVPEYVYNL HLVENDFVGG RSPVPKTYDM LKAGTTATYE

121  GRWGRGTAQY SSQKSVEERS LRHPLRRLEI SPDSSPERAH

161  YTHSDYQYSQ RSQAGHTLHH QESRRAALLV PPRYARSEIV

201  GVSRAGTTSR QRHFDTYHRQ YQHGSVSDTV FDSIPANPAL

241  LTYPRPGTSR SMGNLLEKEN YLTAGLTVGQ VRPLVPLQPV

281  TQNRASRSSW HQSSFHSTRT LREAGPSVAV DSSGRRAHLT

321  VGQAAAGGSG NLLTERSTFT DSQLGNADME MTLERAVSML

361  EADHMLPSRI SAAATFIQHE CFQKSEARKR VNQLRGILKL

401  LQLLKVQNED VQRAVCGALR NLVFEDNDNK LEVAELNGVP

441  RLLQVLKQTR DLETKKQITD HTVNLRSRNG WPGAVAHACN

481  PSTLGGQGGR ITRSGVRDQP DQHGLLWNLS SNDKLKNLMI

521  TEALLTLTEN IIIPFSGWPE GDYPKANGLL DFDIFYNVTG

561  CLRNMSSAGA DGRKAMRRCD GLIDSLVHYV RGTIADYQPD

601  DKATENCVCI LHNLSYQLEA ELPEKYSQNI YIQNRNIQTD

641  NNKSIGCFGS RSRKVKEQYQ DVPMPEEKSN PKGVEWLWHS

681  IVIRMYLSLI AKSVRNYTQE ASLGALQNLT AGSGPMPTSV

721  AQTVVQKESG LQHTRKMLHV GDPSVKKTAI SLLRNLSRNL

761  SLQNEIAKET LPDLVSIIPD TVPSTDLLIE TTASACYTLN

801  NIIQNSYQNA RDLLNTGGIQ KIMAISAGDA YASNKASKAA

841  SVLLYSLWAH TELHHAYKKA QFKKTDFVNS RTAKAYHSLK

881  D
```

One experimental model of PKP2-related disease is the R735X model, as described in Cruz et al. *J Am Coll Cardiol* 65:1438-50 (2015). R735X is numbered according to the PKP2b isoform. The R735X mutant of PKP2a is 690 amino acids in length, due to C-terminal truncation at Arg-690, (Arg-735 relative to PKP2b, SEQ ID NO: 2).

In some embodiments, the PKP2 protein comprises a polypeptide sequence at least 75%, 80%, 85%, 90%, 92%, 93%, 94%, 95%, 96%, 97%, 98%, 99%, or 100% identical to any one of SEQ ID NO: 1 or SEQ ID NO: 2. In some embodiments, the PKP2 protein is a wild-type or native PKP2 protein, e.g. human PKP2a or human PKP2b.

In some embodiments, the disclosure provides a recombinant adeno-associated virus (rAAV) virion, comprising a capsid and a vector genome, wherein the vector genome comprises a polynucleotide sequence encoding an PKP2 or a functional variant thereof, operatively linked to a promoter. In some embodiments, the disclosure provides a recombinant adeno-associated virus (rAAV) virion, comprising a capsid and a vector genome, wherein the vector genome comprises a polynucleotide sequence encoding an PKP2, operatively linked to a promoter. The polynucleotide encoding the PKP2a may comprise a polynucleotide sequence at least 75%, 80%, 85%, 90%, 92%, 93%, 94%, 95%, 96%, 97%, 98%, 99%, or 100% identical to SEQ ID NO: 3.

The polynucleotide encoding the PKP2b may comprise a polynucleotide sequence at least 75%, 80%, 85%, 90%, 92%, 93%, 94%, 95%, 96%, 97%, 98%, 99%, or 100% identical to SEQ ID NO: 4.

Optionally, the polynucleotide sequence encoding the vector genome may comprise a Kozak sequence, including but not limited to GCCACCATGG (SEQ ID NO: 5). Kozak sequence may overlap the polynucleotide sequence encoding an PKP2a protein or a functional variant thereof. For example, the vector genome may comprise a polynucleotide sequence (with first ten nucleotides constituting the Kozak sequence) at least 75%, 80%, 85%, 90%, 92%, 93%, 94%, 95%, 96%, 97%, 98%, 99%, or 100% identical to SEQ ID NO: 6.

Kozak sequence may overlap the polynucleotide sequence encoding an PKP2b protein or a functional variant thereof. For example, the vector genome may comprise a polynucleotide sequence (with first ten nucleotides constituting the Kozak sequence) at least 75%, 80%, 85%, 90%, 92%, 93%, 94%, 95%, 96%, 97%, 98%, 99%, or 100% identical to SEQ ID NO: 7.

In some embodiments, the Kozak sequence is an alternative Kozak sequence comprising or consisting of any one of:

(SEQ ID NO: 16)
(gcc)gccRccAUGG;

AGNNAUGN;

ANNAUGG;

ANNAUGC;

ACCAUGG;
and (SEQ ID NO: 18)
GACACCAUGG.

In some embodiments, the vector genome comprises no Kozak sequence.

The polynucleotide sequence may be codon-optimized. For example, the vector genome may comprise a polynucleotide sequence encoding a PKP2a that shares at least 75%, 80%, 85%, 90%, 92%, 93%, 94%, 95%, 96%, 97%, 98%, 99%, or 100% identity to SEQ ID NO: 87.

The vector genome may comprise a polynucleotide sequence encoding a PKP2b that shares at least 75%, 80%, 85%, 90%, 92%, 93%, 94%, 95%, 96%, 97%, 98%, 99%, or 100% identity to SEQ ID NO: 88.

The AAV virions of the disclosure comprise a vector genome. The vector genome may comprise an expression cassette (or a polynucleotide cassette for gene-editing applications not requiring expression of the polynucleotide sequence). Any suitable inverted terminal repeats (ITRs) may be used. The ITRs may be AAV ITRs from the same serotype as the capsid present in the AAV virion, or a different serotype from the capsid (e.g., AAV2 ITRs may be used with an AAV virion having an AAV9 capsid or an AAVrh74 capsid). In each case, the serotype of the capsid determines the name applied to the virion. The ITR are generally the most 5' and most 3' elements of the vector genome. The vector genome will also generally contain, in 5' to 3' order, a promoter, a transgene, 3' untranslated region (UTR) sequences (e.g., a WPRE element), and a polyadenylation sequence. In variations, the vector genome includes an enhancer element (generally 5' to the promoter) and/or an exon (generally 3' to the promoter). In variations, the vector genomes of the disclosure encode a partial or complete transgene sequence used as a repair template in a gene editing system. In such variations, the vector genome may comprise an exogenous promoter, or the gene editing system may insert the transgene into a locus in the genome having an endogenous promoter, such as a cardiac- or myocyte-specific promoter.

In some embodiments, the 5' ITR comprises a polynucleotide sequence at least 75%, 80%, 85%, 90%, 92%, 93%, 94%, 95%, 96%, 97%, 98%, 99%, or 100% identical to SEQ ID NO: 20.

In some embodiments, the 5' ITR comprises a polynucleotide sequence at least 75%, 80%, 85%, 90%, 92%, 93%, 94%, 95%, 96%, 97%, 98%, 99%, or 100% identical to SEQ ID NO: 21.

In some embodiments, the 5' ITR comprises a polynucleotide sequence at least 75%, 80%, 85%, 90%, 92%, 93%, 94%, 95%, 96%, 97%, 98%, 99%, or 100% identical to SEQ ID NO: 22)

In some embodiments, the 5' ITR comprises a polynucleotide sequence at least 75%, 80%, 85%, 90%, 92%, 93%, 94%, 95%, 96%, 97%, 98%, 99%, or 100% identical to SEQ ID NO: 23.

In some embodiments, the 3' ITR comprises a polynucleotide sequence at least 75%, 80%, 85%, 90%, 92%, 93%, 94%, 95%, 96%, 97%, 98%, 99%, or 100% identical to SEQ ID NO: 24.

In some embodiments, the 3' ITR comprises a polynucleotide sequence at least 75%, 80%, 85%, 90%, 92%, 93%, 94%, 95%, 96%, 97%, 98%, 99%, or 100% identical to SEQ ID NO: 25.

In some embodiments, the 3' ITR comprises a polynucleotide sequence at least 75%, 80%, 85%, 90%, 92%, 93%, 94%, 95%, 96%, 97%, 98%, 99%, or 100% identical to SEQ ID NO: 26.

In some embodiments the vector genome comprises one or more filler sequences, e.g., at least 75%, 80%, 85%, 90%, 92%, 93%, 94%, 95%, 96%, 97%, 98%, 99%, or 100% identical to SEQ ID NO: 27; SEQ ID NO: 28; or SEQ ID NO: 29.

In some embodiments, the polynucleotide sequence encoding an PKP2 protein or functional variant thereof is operatively linked to a promoter. In certain embodiments, the promoter is an MHCK7 promoter. In certain embodiments, the promoter is an TNNT2 promoter.

The present disclosure contemplates use of various promoters. Promoters useful in embodiments of the present disclosure include, without limitation, a cytomegalovirus (CMV) promoter, phosphoglycerate kinase (PGK) promoter, or a promoter sequence comprised of the CMV enhancer and portions of the chicken beta-actin promoter and the rabbit beta-globin gene (CAG). In some cases, the promoter may be a synthetic promoter. Exemplary synthetic promoters are provided by Schlabach et al. *PNAS USA.* 107(6):2538-43 (2010). In some embodiments, the promoter comprises a polynucleotide sequence at least 75%, 80%, 85%, 90%, 92%, 93%, 94%, 95%, 96%, 97%, 98%, 99%, or 100% identical to SEQ ID NO: 30.

In some embodiments, a polynucleotide sequence encoding an PKP2 protein or functional variant thereof is operatively linked to an inducible promoter. An inducible promoter may be configured to cause the polynucleotide sequence to be transcriptionally expressed or not transcriptionally expressed in response to addition or accumulation of an agent or in response to removal, degradation, or dilution of an agent. The agent may be a drug. The agent may be tetracycline or one of its derivatives, including, without limitation, doxycycline. In some cases, the inducible promoter is a tet-on promoter, a tet-off promoter, a chemically-regulated promoter, a physically-regulated promoter (i.e., a promoter that responds to presence or absence of light or to low or high temperature). Inducible promoters include heavy metal ion inducible promoters (such as the mouse mammary tumor virus (mMTV) promoter or various growth hormone promoters), and the promoters from T7 phage which are active in the presence of T7 RNA polymerase. This list of inducible promoters is non-limiting.

In some cases, the promoter is a tissue-specific promoter, such as a promoter capable of driving expression in a cardiac cell to a greater extent than in a non-cardiac cell. In some embodiments, tissue-specific promoter is a selected from any various cardiac cell-specific promoters including but not limited to, desmin (Des), alpha-myosin heavy chain (α-MHC), myosin light chain 2 (MLC-2), cardiac troponin C (cTnC), cardiac troponin T (hTNNT2), muscle creatine kinase (CK) and combinations of promoter/enhancer regions thereof, such as MHCK7. In some cases, the promoter is a ubiquitous promoter. A "ubiquitous promoter" refers to a promoter that is not tissue-specific under experimental or clinical conditions. In some cases, the ubiquitous promoter is any one of Cytomegalovirus (CMV), Cytomegalovirus early enhancer element chicken beta-Actin gene intron with the splice acceptor of the rabbit beta-Globin gene (CAG), ubiquitin C (UBC), Phosphoglycerate Kinase (PGK), Eukaryotic translation elongation factor 1 alpha 1 (EF1-alpha), Glyceraldehyde 3-phosphate dehydrogenase (GAPDH), simian virus 40 (SV40), Hepatitis B virus (HBV), chicken beta-actin, and human beta-actin promoters.

In some embodiments, the promoter sequence is selected from Table 3. In some embodiments, the promoter comprises a polynucleotide sequence at least 75%, 80%, 85%, 90%, 92%, 93%, 94%, 95%, 96%, 97%, 98%, 99%, or 100% identical to any one of SEQ ID NOS: 31-51. In some embodiments, the promoter comprises a fragment of a polynucleotide sequence of any one of SEQ ID NOs: 31-51, e.g., a fragment comprising at least 25%, at least 50%, at least 75%, 80%, 85%, 90%, 92%, 93%, 94%, 95%, 96%, 97%, 98%, 99%, or 100% of any one of SEQ ID NOs: 31-51.

TABLE 3

| PROMOTER | SEQUENCE | SEQ ID NO: |
|---|---|---|
| MHCK7 | ACCCTTCAGATTAAAAATAACTGAGGTAAGGGCCTGGGTAG<br>GGGAGGTGGTGTGAGACGCTCCTGTCTCTCCTCTATCTGCCC<br>ATCGGCCCTTTGGGGAGGAGGAATGTGCCCAAGGACTAAAA<br>AAAGGCCATGGAGCCAGAGGGGCGAGGGCAACAGACCTTTC<br>ATGGGCAAACCTTGGGGCCCTGCTGTCTAGCATGCCCCACTA<br>CGGGTCTAGGCTGCCCATGTAAGGAGGCAAGGCCTGGGGAC<br>ACCCGAGATGCCTGGTTATAATTAACCCAGACATGTGGCTGC | 31 |

TABLE 3 -continued

| PROMOTER | SEQUENCE | SEQ ID NO: |
|---|---|---|
| | CCCCCCCCCCCCAACACCTGCTGCCTCTAAAAATAACCCTGT<br>CCCTGGTGGATCCCCTGCATGCGAAGATCTTCGAACAAGGCT<br>GTGGGGGACTGAGGGCAGGCTGTAACAGGCTTGGGGGCCAG<br>GGCTTATACGTGCCTGGGACTCCCAAAGTATTACTGTTCCAT<br>GTTCCCGGCGAAGGGCCAGCTGTCCCCCGCCAGCTAGACTCA<br>GCACTTAGTTTAGGAACCAGTGAGCAAGTCAGCCCTTGGGGC<br>AGCCCATACAAGGCCATGGGGCTGGGCAAGCTGCACGCCTG<br>GGTCCGGGGTGGGCACGGTGCCCGGGCAACGAGCTGAAAGC<br>TCATCTGCTCTCAGGGGCCCCTCCCTGGGGACAGCCCCTCCT<br>GGCTAGTCACACCCTGTAGGCTCCTCTATATAACCCAGGGGC<br>ACAGGGGCTGCCCTCATTCTACCACCACCTCCACAGCACAGA<br>CAGACACTCAGGAGCCAGCCAG | |
| Human cardiac troponin T promoter (without exon 1) hTnnT2/ HTNNT2 | CTCAGTCCATTAGGAGCCAGTAGCCTGGAAGATGTCTTTACC<br>CCCAGCATCAGTTCAAGTGGAGCAGCACATAACTCTTGCCCT<br>CTGCCTTCCAAGATTCTGGTGCTGAGACTTATGGAGTGTCTT<br>GGAGGTTGCCTTCTGCCCCCCAACCCTGCTCCCAGCTGGCCC<br>TCCCAGGCCTGGGTTGCTGGCCTCTGCTTTATCAGGATTCTCA<br>AGAGGGACAGCTGGTTTATGTTGCATGACTGTTCCCTGCATA<br>TCTGCTCTGGTTTTAAATAGCTTATCTGAGCAGCTGGAGGAC<br>CACATGGGCTTATATGGCGTGGGGTACATGTTCCTGTAGCCT<br>TGTCCCTGGCACCTGCCAAAATAGCAGCCAACACCCCCCACC<br>CCCACCGCCATCCCCCTGCCCCACCCGTCCCCTGTCGCACAT<br>TCCTCCCTCCGCAGGGCTGGCTCACCAGGCCCCAGCCCACAT<br>GCCTGCTTAAAGCCCTCTCCATCCTCTGCCTCACCCAGT | 33 |
| Human cardiac troponin T promoter (with exon 1, underlined) hTnnT2/ HTNNT2 | CTCAGTCCATTAGGAGCCAGTAGCCTGGAAGATGTCTTTACC<br>CCCAGCATCAGTTCAAGTGGAGCAGCACATAACTCTTGCCCT<br>CTGCCTTCCAAGATTCTGGTGCTGAGACTTATGGAGTGTCTT<br>GGAGGTTGCCTTCTGCCCCCCAACCCTGCTCCCAGCTGGCCC<br>TCCCAGGCCTGGGTTGCTGGCCTCTGCTTTATCAGGATTCTCA<br>AGAGGGACAGCTGGTTTATGTTGCATGACTGTTCCCTGCATA<br>TCTGCTCTGGTTTTAAATAGCTTATCTGAGCAGCTGGAGGAC<br>CACATGGGCTTATATGGCGTGGGGTACATGTTCCTGTAGCCT<br>TGTCCCTGGCACCTGCCAAAATAGCAGCCAACACCCCCCACC<br>CCCACCGCCATCCCCCTGCCCCACCCGTCCCCTGTCGCACAT<br>TCCTCCCTCCGCAGGGCTGGCTCACCAGGCCCCAGCCCACAT<br>GCCTGCTTAAAGCCCTCTCCATCCTCTGCCTCACCCAGTCCCC<br>GCTGAGACTGAGCAGACGCCTCCAGGATCTGTCGGCAG | 32 |
| Mouse α-cardiac myosin heavy chain promoter (aMHC) | GGTACCGGATCCTGCAAGGTCACACAAGGGTCTCCACCCACC<br>AGGTGCCCTAGTCTCAATTTCAGTTTCCATGCCTTGTTCTCAC<br>AATGCTGGCCTCCCCAGAGCTAATTTGGACTTTGTTTTTATTT<br>CAAAAGGGCCTGAATGAGGAGTAGATCTTGTGCTACCCAGC<br>TCTAAGGGTGCCCGTGAAGCCCTCAGACCTGGAGCCTTTGCA<br>ACAGCCCTTTAGGTGGAAGCAGAATAAAGCAATTTTCCTTAA<br>AGCCAAAATCCTGCCTCTAGACTCTTCTTCTCTGACCTCGGTC<br>CCTGGGCTCTAGGGTGGGGAGGTGGGGCTTGGAAGAAGAAG<br>GTGGGGAAGTGGCAAAAGCCGATCCCTAGGGCCCTGTGAAG<br>TTCGGAGCCTTCCCTGTACAGCACTGGCTCATAGATCCTCCT<br>CCAGCCAAACATAGCAAGAAGTGATACCTCCTTTGTGACTTC<br>CCCAGGCCCAGTACCTGTCAGGTTGAAACAGGATTTAGAGA<br>AGCCTCTGAACTCACCTGAACTCTGAAGCTCATCCACCAAGC<br>AAGCACCTAGGTGCCACTGCTAGTTAGTATCCTACGCTGATA<br>ATATGCAGAGCTGGGCCACAGAAGTCCTGGGGTGTAGGAAC<br>TGACCAGTGACTTTTCAGTCGGCAAAGGTATGACCCCCCTCAG<br>CAGATGTAGTAATGTCCCCTTAGATCCCATCCCAGGCAGGTC<br>TCTAAGAGGACATGGGATGAGAGATGTAGTCATGTGGCATT<br>CCAAACACAGCTATCCACAGTGTCCCTTGCCCCTTCCACTTA<br>GCCAGGAGGACAGTAACCTTAGCCTATCTTTCTTCCTCCCCA<br>TCCTCCCAGGACACACCCCCTGGTCTGCAGTATTCATTTCTTC<br>CTTCACGTCCCCTCTGTGACTTCCATTTGCAAGGCTTTTGACC<br>TCTGCAGCTGCTGGAAGATAGAGTTTGGCCCTAGGTGTGGCA<br>AGCCATCTCAAGAGAAAGCAGACAACAGGGGGACCAGATTT<br>TGGAAGGATCAGGAACTAAATCACTGGCGGGCCTGGGGGTA<br>GAAAAAAGAGTGAGTGAGTCCGCTCCAGCTAAGCCAAGCTA<br>GTCCCCGAGATACTCTGCCACAGCTGGGCTGCTCGGGGTAGC<br>TTTAGGAATGTGGGTCTGAAAGACAATGGGATTGGAAGACA<br>TCTCTTTGAGTCTCCCCTCAACCCCACCTACAGACACACTCGT<br>GTGTGGCCAGACTCCTGTTCAACAGCCCTCTGTGTTCTGACC<br>ACTGAGCTAGGCAACCAGAGCATGGGCCCTGTGCTGAGGAT<br>GAAGAGTTGGTTACCAATAGCAAAAACAGCAGGGGAGGGAG<br>AACAGAGAACGAAATAAGGAAGGAAGAAGGAAAGGCCAGT<br>CAATCAGATGCAGTCAGAAGAGATGGGAAGCCAACACACAG<br>CTTGAGCAGAGGAAACAGAAAAGGGAGAGATTCTGGGCATA<br>AGGAGGCCACAGAAAGAAGAGCCCAGGCCCCCCAAGTCTCC<br>TCTTTATACCCTCATCCCGTCTCCCAATTAAGCCCACTCTTCT | 34 |

TABLE 3 -continued

| PROMOTER | SEQUENCE | SEQ ID NO: |
|---|---|---|
| | TCCTAGATCAGACCTGAGCTGCAGCGAAGAGACCCGTAGGG | |
| | AGGATCACACTGGATGAAGGAGATGTGTGGAGAAGTCCAGG | |
| | GAACCTAAGAGCCAGAGCCTAAAAGAGCAAGAGATAAAGGT | |
| | GCTTCAAAGGTGGCCAGGCTGTGCACACAGAGGGTCGAGGA | |
| | CTGGTGGTAGAGCCTCAAGATAAGGATGATGCTCAGAATGG | |
| | GCGGGGGGGGGATTCTGGGGGGGGAGAGAGAAGGTGAG | |
| | AAGGAGCCTGGAACAGAGAATCTGGAAGCGCTGGAAACGAT | |
| | ACCATAAAGGGAAGAACCCAGGCTACCTTTAGATGTAAATC | |
| | ATGAAAGACAGGGAGAAGGGAAGCTGGAGAGAGTAGAAGG | |
| | ACCCCGGGGCAAGACATTGAAGCAAGGACAAGCCAGGTTGA | |
| | GCGCTCCGTGAAATCAGCCTGCTGAAGGCAGAGCCCTGGTAT | |
| | GAGCACCAGAACAGCAGAGGCTAGGGTTAATGTCGAGACAG | |
| | GGAACAGAAGGTAGACACAGGAACAGACAGAGACGGGGA | |
| | GCCAGGTAACAAAGGAATGGTCCTTCTCACCTGTGGCCAGA | |
| | GCGTCCATCTGTGTCCACATACTCTAGAATGTTCATCAGACT | |
| | GCAGGGCTGGCTTGGGAGGCAGCTGGAAAGAGTATGTGAGA | |
| | GCCAGGGGAGACAAGGGGGCCTAGGAAAGGAAGAAGAGGG | |
| | CAAACCAGGCCACACAAGAGGGCAGAGCCCAGAACTGAGTT | |
| | AACTCCTTCCTTGTTGCATCTTCCATAGGAGGCAGTGGGAAC | |
| | TCTGTGACCACCATCCCCCATGAGCCCCCACTACCCATACCA | |
| | AGTTTGGCCTGAGTGGCATTCTAGGTTCCCTGAGGACAGAGC | |
| | CTGGCCTTTGTCTCTTGGACCTGACCCAAGCTGACCCAATGT | |
| | TCTCAGTACCTTATCATGCCCTCAAGAGCTTGAGAACCAGGC | |
| | AGTGACATATTAGGCCATGGGCTAACCCTGGAGCTTGCACAC | |
| | AGGAGCCTCAAGTGACCTCCAGGGACACAGCTGCAGACAGG | |
| | TGGCCTTTATCCCCAAAGAGCAACCATTTGGCATAGGTGGCT | |
| | GCAAATGGGAATGCAAGGTTGAATCAGGTCCCTTCAAGAAT | |
| | ACTGCATGCAAGACCTAAGACCCCTGGAGAGAGGGGTATGC | |
| | TCCTGCCCCCACCCACCATAAGGGGAGTGAACTATCCTAGGG | |
| | GGCTGGCGACCTTGGGGAGACACCACATTACTGAGAGTGCT | |
| | GAGCCCAGAAAAACTGACCGCCCTGTGTCCTGCCCACCTCCA | |
| | CACTCTAGAGCTATATTGAGAGGTGACAGTAGATAGGGTGG | |
| | GAGCTGGTAGCAGGGAGAGTGTTCCTGGGTGTGAGGGTGTA | |
| | GGGGAAAGCCAGAGCAGGGGAGTCTGGCTTTGTCTCCTGAA | |
| | CACAATGTCTACTTAGTTATAACAGGCATGACCTGCTAAAGA | |
| | CCCAACATCTACGACCTCTGAAAAGACAGCAGCCCTGGAGG | |
| | ACAGGGGTTGTCTCTGAGCCTTGGGTGCTTGATGGTGCCACA | |
| | AAGGAGGGCATGAGTGTGAGTATAAGGCCCCAGGAGCGTTA | |
| | GAGAAGGGCACTTGGGAAGGGGTCAGTCTGCAGAGCCCCTA | |
| | TCCATGGAATCTGGAGCCTGGGGCCAACTGGTGTAAATCTCT | |
| | GGGCCTGCCAGGCATTCAAAGCAGCACCTGCATCCTCTGGCA | |
| | GCCTGGGGAGGCGGAAGGGAGCAACCCCCCACTTATACCCT | |
| | TTCTCCCTCAGCCCCAGGATTAACACCTCTGGCCTTCCCCCTT | |
| | CCCACCTCCCATCAGGAGTGGAGGGTTGCAGAGGGAGGGTA | |
| | AAAACCTACATGTCCAAACATCATGGTGCACGATATATGGAT | |
| | CAGTATGTGTAGAGGCAAGAAAGGAAATCTGCAGGCTTAAC | |
| | TGGGTTAATGTGTAAAGTCTGTGTGCATGTGTGTGTGTCTGA | |
| | CTGAAAACGGGCATGGCTGTGCAGCTGTTCAGTTCTGTGCGT | |
| | GAGGTTACCAGACTGCAGGTTTGTGTGTAAATTGCCCAAGGC | |
| | AAAGTGGGTGAATCCCTTCCATGGTTTAAAGAGATTGGATGA | |
| | TGGCCTGCATCTCAAGGACCATGGAAAATAGAATGGACACT | |
| | CTATATGTGTCTCTAAGCTAAGGTAGCAAGGTCTTTGGAGGA | |
| | CACCTGTCTAGAGATGTGGGCAACAGAGACTACAGACAGTA | |
| | TCTGTACAGAGTAAGGAGAGAGAGGAGGGGGTGTAGAATTC | |
| | TCTTACTATCAAAGGGAAACTGAGTCGTGCACCTGCAAAGTG | |
| | GATGCTCTCCCTAGACATCATGACTTTGTCTCTGGGGAGCCA | |
| | GCACTGTGGAACTTCAGGTCTGAGAGAGTAGGAGGCTCCCCT | |
| | CAGCCTGAAGCTATGCAGATAGCCAGGGTTGAAAGGGGGAA | |
| | GGGAGAGCCTGGGATGGGAGCTTGTGTGTTGGAGGCAGGGG | |
| | ACAGATATTAAGCCTGGAAGAGAAGGTGACCCTTACCCAGT | |
| | TGTTCAACTCACCCTTCAGATTAAAAATAACTGAGGTAAGGG | |
| | CCTGGGTAGGGGAGGTGGTGTGAGACGCTCCTGTCTCTCCTC | |
| | TATCTGCCCATCGGCCCTTTGGGGAGGAGGAATGTGCCCAAG | |
| | GACTAAAAAAAGGCCATGGAGCCAGAGGGGCGAGGGCAAC | |
| | AGACCTTTCATGGGCAAACCTTGGGGCCCTGCTGTCCTCCTG | |
| | TCACCTCCAGAGCCAAGGGATCAAAGGAGGAGGAGCCAGGA | |
| | CAGGAGGGAAGTGGGAGGGAGGGTCCCAGCAGAGGACTCC | |
| | AAATTTAGGCAGCAGGCATATGGGATGGGATATAAAGGGGC | |
| | TGGAGCACTGAGAGCTGTCAGAGATTTCTCCAACCCAGGTAA | |
| | GAGGGAGTTTCGGGTGGGGGCTCTTCACCCACACCAGACCTC | |
| | TCCCCACCTAGAAGGAAACTGCCTTTCCTGGAAGTGGGGTTC | |
| | AGGCCGGTCAGAGATCTGACAGGGTGGCCTTCCACCAGCCT | |
| | GGGAAGTTCTCAGTGGCAGGAGGTTTCCACAAGAAACACTG | |
| | GATGCCCCTTCCCTTACGCTGTCTTCTCCATCTTCCTCCTGGG | |
| | GATGCTCCTCCCCGTCTTGGTTTATCTTGGCTCTTCGTCTTCA | |
| | GCAAGATTTGCCCTGTGCTGTCCACTCCATCTTTCTCTACTGT | |
| | CTCCGTGCCTTGCCTTGCCTTCTTGCGTGTCCTTCCTTTCCAC | |

TABLE 3 -continued

| PROMOTER | SEQUENCE | SEQ ID NO: |
|---|---|---|
| | CCATTTCTCACTTCACCTTTTCTCCCCTTCTCATTTGTATTCAT<br>CCTTCCTTCCTTCCTTCCTTCCTTCCTTCCTTCCTTCCTTCCTTC<br>CTTTCTCCCTTCCTTCCTTCCTTCCTTCCTTCCTTCCTTCCTTCC<br>TTCCTGTGTCAGAGTGCTGAGAATCACACCTGGGGTTCCCAC<br>CCTTATGTAAACAATCTTCCAGTGAGCCACAGCTTCAGTGCT<br>GCTGGGTGCTCTCTTACCTTCCTCACCCCCTGGCTTGTCCTGT<br>TCCATCCTGGTCAGGATCTCTAGATTGGTCTCCCAGCCTCTGC<br>TACTCCTCTTCCTGCCTGTTCCTCTCTCTGTCCAGCTGCGCCA<br>CTGTGGTGCCTCGTTCCAGCTGTGGTCCACATTCTTCAGGATT<br>CTCTGAAAAGTTAACCAGGTGAGAATGTTTCCCCTGTAGACA<br>GCAGATCACGATTCTCCCGGAAGTCAGGCTTCCAGCCCTCTC<br>TTTCTCTGCCCAGCTGCCCGGCACTCTTAGCAAACCTCAGGC<br>ACCCTTACCCCACATAGACCTCTGACAGAGAAGCAGGCACTT<br>TACATGGAGTCCTGGTGGGAGAGCCATAGGCTACGGTGTAA<br>AAGAGGCAGGGAAGTGGTGGTGTAGGAAAGTCAGGACTTCA<br>CATAGAAGCCTAGCCCACACCAGAAATGACAGACAGATCCC<br>TCCTATCTCCCCCATAAGAGTTTGAGTCGACCCGCGGCCCCG<br>AATTG | |
| Chicken cardiac troponin T promoter (cTnT) | GGGATAAAAGCAGTCTGGGCTTTCACATGACAGCATCTGGG<br>GCTGCGGCAGAGGGTCGGGTCCGAAGCGCTGCCTTATCAGC<br>GTCCCCAGCCCTGGGAGGTGACAGCTGGCTGGCTTGTGTCAG<br>CCCCTCGGGCACTCACGTATCTCCGTCCGACGGGTTTAAAAT<br>AGCAAAACTCTGAGGCCACACAATAGCTTGGGCTTATATGG<br>GCTCCTGTGGGGGAAGGGGGAGCACGGAGGGGGCCGGGGCC<br>GCTGCTGCCAAAATAGCAGCTCACAAGTGTTGCATTCCTCTC<br>TGGGCGCCGGGCACATTCCTGCTGGCTCTGCCCGCCCCGGGG<br>TGGGCGCCGGGGGGACCTTAAAGCCTCTGCCCCCCAAGGAG<br>CCCTTCCCAGACAGCCGCCGGCACCCACCGCTCCGTGGGA | 35 |
| Human Creatine Kinase M (hCKM) | CTCTCAGCCCTGGAAGTCCTTGCTCACAGCCGAGGCGCCGAG<br>AGCGCTTGCTCTGCCCAGATCTGCGCGAGTCTGGCGCCCGCG<br>CTCTGAACGGCGTCGCTGCCCAGCCCCCTTCCCCGGGAGGTG<br>GGAGCGGCCACCCAGGGCCCCGTGGCTGCCCTTGTAAGGAG<br>GCGAGGCCCGAGGACACCCGAGACGCCCGGTTATAATTAAC<br>CAGGACACGTGGCGAACCCCCCTCCAACACCTGCCCCCGAA<br>CCCCCCCATACCCAGCGCCTCGGGTCTCGGCCTTTGCGGCAG<br>AGGAGACAGCAAAGCGCCCTCTAAAAATAACTCCTTTCCCG<br>GCGACCGAGACCCTCCCTGTCCCCCGCACAGCGGAAATCTCC<br>CAGTGGCACCGAGGGGGCGAGGGTTAAGTGGGGGGGAGGGT<br>GACCACCGCCTCCCACCCTTGCCCTGAGTTTGAATCTCTCCA<br>ACTCAGCCAGCCTCAGTTTCCCCTCCACTCAGTCCCTAGGAG<br>GAAGGGGCGCCCAAGCGCGGGTTTCTGGGGTTAGACTGCCC<br>TCCATTGCAATTGGTCCTTCTCCCGGCCTCTGCTTCCTCCAGC<br>TCACAGGGTATCTGCTCCTCCTGGAGCCACACCTTGGTTCCC<br>CGAGGTGCCGCTGGGACTCGGGTAGGGGTGAGGGCCCAGGG<br>GGCACAGGGGGAGCCGAGGGCCACAGGAAGGGCTGGTGGCT<br>GAAGGAGACTCAGGGGCCAGGGGACGGTGGCTTCTACGTGC<br>TTGGGACGTTCCCAGCCACCGTCCCATGTTCCCGGCGGGGGG<br>CCAGCTGTCCCCACCGCCAGCCCAACTCAGCACTTGGTCAGG<br>GTATCAGCTTGGTGGGGGGGCGTGAGCCCAGCCCCTGGGGC<br>GGCTCAGCCCATACAAGGCCATGGGGCTGGGCGCAAAGCAT<br>GCCTGGGTTCAGGGTGGGTATGGTGCGGGAGCAGGGAGGTG<br>AGAGGCTCAGCTGCCCTCCAGAACTCCTCCCTGGGGACAACC<br>CCTCCCAGCCAATAGCACAGCCTAGGTCCCCCTATATAAGGC<br>CACGGCTGCTGGCCCTTCCTTTGGGTCAGTGTCACCTCCAGG<br>ATACAGACA | 36 |
| Human beta-actin (HuBa) | GCCCAGCACCCCAAGGCGGCCAACGCCAAAACTCTCCCTCCT<br>CCTCTTCCTCAATCTCGCTCTCGCTCTTTTTTTTTTTCGCAAAA<br>GGAGGGGAGAGGGGGTAAAAAAATGCTGCACTGTGCGGCGA<br>AGCCGGTGAGTGAGCGGCGCGGGGCCAATCAGCGTGCGCCG<br>TTCCGAAAGTTGCCTTTTATGGCTCGAGCGGCCGCGGCGGCG<br>CCCTATAAAACCCAGCGGCGCGACGCGCCACCACCGCCGAG<br>TC | 37 |
| Chicken beta-actin (CBA) | GGTCGAGGTGAGCCCCACGTTCTGCTTCACTCTCCCCATCTC<br>CCCCCCCTCCCCACCCCCAATTTTGTATTTATTTATTTTTTAAT<br>TATTTTGTGCAGCGATGGGGGCGGGGGGGGGGGGGGCGCGC<br>GCCAGGCGGGGCGGGGCGGGGCGAGGGGCGGGGCGGGGCG<br>AGGCGGAGAGGTGCGGCGGCAGCCAATCAGAGCGGCGCGCT<br>CCGAAAGTTTCCTTTTATGGCGAGGCGGCGGCGGCGGCGGCC<br>CTATAAAAAGCGAAGCGCGCGGCGGGCGGGA | 38 |

TABLE 3 -continued

| PROMOTER | SEQUENCE | SEQ ID NO: |
|---|---|---|
| Cytomegalovirus (CMV) | TGGTGATGCGGTTTTGGCAGTACACCAATGGGCGTGGATAGC<br>GGTTTGACTCACGGGGATTTCCAAGTCTCCACCCCATTGACG<br>TCAATGGGAGTTTGTTTTGGCACCAAAATCAACGGGACTTTC<br>CAAAATGTCGTAATAACCCCGCCCCGTTGACGCAAATGGGC<br>GGTAGGCGTGTACGGTGGGAGGTCTATATAAGCAGAGCTCG<br>TTTAGTGAACCG | 39 |
| Cytomegalovirus (CMV) (second version) | TAGTTATTAATAGTAATCAATTACGGGGTCATTAGTTCATAG<br>CCCATATATGGAGTTCCGCGTTACATAACTTACGGTAAATGG<br>CCCGCCTGGCTGACCGCCCAACGACCCCCGCCCATTGACGTC<br>AATAATGACGTATGTTCCCATAGTAACGCCAATAGGGACTTT<br>CCATTGACGTCAATGGGTGGAGTATTTACGGTAAACTGCCCA<br>CTTGGCAGTACATCAAGTGTATCATATGCCAAGTACGCCCCC<br>TATTGACGTCAATGACGGTAAATGGCCCGCCTGGCATTATGC<br>CCAGTACATGACCTTATGGGACTTTCCTACTTGGCAGTACAT<br>CTACGTATTAGTCATCGCTATTACCATGGTGATGCGGTTTTG<br>GCAGTACATCAATGGGCGTGGATAGCGGTTTGACTCACGGG<br>GATTTCCAAGTCTCCACCCCATTGACGTCAATGGGAGTTTGT<br>TTTGGCACCAAAATCAACGGGACTTTCCAAAATGTCGTAACA<br>ACTCCGCCCCATTGACGCAAATGGGCGGTAGGCGTGTACGGT<br>GGGAGGTCTATATAAGCAGAGCTGGTTTAGTGAACCGT | 40 |
| Cytomegalovirus (CMV) (third version) | CGTTACATAACTTACGGTAAATGGCCCGCCTGGCTGACCGCC<br>CAACGACCCCCGCCCATTGACGTCAATAATGACGTATGTTCC<br>CATAGTAACGCCAATAGGGACTTTCCATTGACGTCAATGGGT<br>GGAGTATTTACGGTAAACTGCCCACTTGGCAGTACATCAAGT<br>GTATCATATGCCAAGTACGCCCCCTATTGACGTCAATGACGG<br>TAAATGGCCCGCCTGGCATTATGCCCAGTACATGACCTTATG<br>GGACTTTCCTACTTGGCAGTACATCTACGTATTAGTCATCGCT<br>ATTACCATGGTGATGCGGTTTTGGCAGTACATCAATGGGCGT<br>GGATAGCGGTTTGACTCACGGGGATTTCCAAGTCTCCACCCC<br>ATTGACGTCAATGGGAGTTTGTTTTGGCACCAAAATCAACGG<br>GACTTTCCAAAATGTCGTAACAACTCCGCCCCATTGACGCAA<br>ATGGGCGGTAGGCGTGTACGGTGGGAGGTCTATATAAGCAG<br>AGCT | 41 |
| CAG promoter (first version) | ACTTACGGTAAATGGCCCGCCTGGCTGACCGCCCAACGACCC<br>CCGCCCATTGACGTCAATAATGACGTATGTTCCCATAGTAAC<br>GCCAATAGGGACTTTCCATTGACGTCAATGGGTGGAGTATTT<br>ACGGTAAACTGCCCACTTGGCAGTACATCAAGTGTATCATAT<br>GCCAAGTACGCCCCCTATTGACGTCAATGACGGTAAATGGCC<br>CGCCTGGCATTATGCCCAGTACATGACCTTATGGGACTTTCC<br>TACTTGGCAGTACATCTACGTATTAGTCATCGCTATTACCAT<br>GGTCGAGGTGAGCCCCACGTTCTGCTTCACTCTCCCCATCTC<br>CCCCCCCTCCCCACCCCCAATTTTGTATTTATTTATTTTTTAAT<br>TATTTTGTGCAGCGATGGGGGCGGGGGGGGGGGGGGCGCGC<br>GCCAGGCGGGGCGGGGCGGGGCGAGGGGCGGGGCGGGGCG<br>AGGCGGAGAGGTGCGGCGGCAGCCAATCAGAGCGGCGCGCT<br>CCGAAAGTTTCCTTTTATGGCGAGGCGGCGGCGGCGGCC<br>CTATAAAAAGCGAAGCGCGCGGCGGGCGG | 42 |
| CAG promoter (second version) | CGTTACATAACTTACGGTAAATGGCCCGCCTGGCTGACCGCC<br>CAACGACCCCCGCCCATTGACGTCAATAATGACGTATGTTCC<br>CATAGTAACGCCAATAGGGACTTTCCATTGACGTCAATGGGT<br>GGAGTATTTACGGTAAACTGCCCACTTGGCAGTACATCAAGT<br>GTATCATATGCCAAGTACGCCCCCTATTGACGTCAATGACGG<br>TAAATGGCCCGCCTGGCATTATGCCCAGTACATGACCTTATG<br>GGACTTTCCTACTTGGCAGTACATCTACGTATTAGTCATCGCT<br>ATTACCATGTCGAGGTGAGCCCCACGTTCTGCTTCACTCTCC<br>CCATCTCCCCCCCCTCCCCACCCCCAATTTTGTATTTATTTAT<br>TTTTTAATTATTTTGTGCAGCGATGGGGGCGGGGGGGGGGGG<br>GGCGCGCGCCAGGCGGGGCGGGGCGGGGCGAGGGGCGGGG<br>CGGGGCGAGGCGGAGAGGTGCGGCGGCAGCCAATCAGAGC<br>GGCGCGCTCCGAAAGTTTCCTTTTATGGCGAGGCGGCGGCGG<br>CGGCGGCCCTATAAAAAGCGAAGCGCGCGGCGGGCG | 43 |
| Human EF1-alpha (EF1-α) | CAACCTTTGGAGCTAAGCCAGCAATGGTAGAGGGAAGATTC<br>TGCACGTCCCTTCCAGGCGGCCTCCCCGTCACCACCCCCCCC<br>AACCCGCCCCGACCGGAGCTGAGAGTAATTCATACAAAAGG<br>ACTCGCCCCTGCCTTGGGGAATCCCAGGGACCGTCGTTAAAC<br>TCCCACTAACGTAGAACCCAGAGATCGCTGCGTTCCCGCCCC<br>CTCACCCGCCCGCTCTCGTCATCACTGAGGTGGAGAATAGCA<br>TGCGTGAGGCTCCGGTGCCCGTCAGTGGGCAGAGCGCACAT<br>CGCCCACAGTCCCCGAGAAGTTGGGGGGAGGGGTCGGCAAT | 44 |

TABLE 3 -continued

| PROMOTER | SEQUENCE | SEQ ID NO: |
|---|---|---|
| | TGAACGGGTGCCTAGAGAAGGTGGCGCGGGGTAAACTGGGA AAGTGATGTCGTGTACTGGCTCCGCCTTTTTCCCGAGGGTGG GGGAGAACCGTATATAAGTGCAGTAGTCGCCGTGAACGTT | |
| Human CamKIIa (CaMKIIa) | ACTTGTGGACAAAGTTTGCTCTATTCCACCTCCTCCAGGCCCT CCTTGGGTCCATCACCCCAGGGGTGCTGGGTCCATCCCACCC CCAGGCCCACACAGGCTTGCAGTATTGTGTGCGGTATGGTCA GGGCGTCCGAGAGCAGGTTTCGCAGTGGAAGGCAGGCAGGT GTTGGGGAGGCAGTTACCGGGGCAACGGGAACAGGGCGTTT TGGAGGTGGTTGCCATGGGGACCTGGATGCTGACGAAGGCT CGCGAGGCTGTGAGCAGCCACAGTGCCCTGC | 48 |

In a certain embodiment, the vector genome comprises a polynucleotide sequence at least 75%, 80%, 85%, 90%, 92%, 93%, 94%, 95%, 96%, 97%, 98%, 99%, or 100% identical to SEQ ID NO: 31. In a certain embodiment, the vector genome comprises a polynucleotide sequence at least 75%, 80%, 85%, 90%, 92%, 93%, 94%, 95%, 96%, 97%, 98%, 99%, or 100% identical to SEQ ID NO: 32. In a certain embodiment, the vector genome comprises a polynucleotide sequence at least 75%, 80%, 85%, 90%, 92%, 93%, 94%, 95%, 96%, 97%, 98%, 99%, or 100% identical to SEQ ID NO: 33.

Further illustrative examples of promoters are the SV40 late promoter from simian virus 40, the Baculovirus polyhedron enhancer/promoter element, Herpes Simplex Virus thymidine kinase (HSV tk), the immediate early promoter from cytomegalovirus (CMV) and various retroviral promoters including LTR elements. A large variety of other promoters are known and generally available in the art, and the sequences of many such promoters are available in sequence databases such as the GenBank database.

In some cases, vectors of the present disclosure further comprise one or more regulatory elements selected from the group consisting of an enhancer, an intron, a poly-A signal, a 2A peptide encoding sequence, a WPRE (Woodchuck hepatitis virus posttranscriptional regulatory element), and a HPRE (Hepatitis B posttranscriptional regulatory element).

In some embodiments, the vector comprises a CMV enhancer.

In certain embodiments, the vectors comprise one or more enhancers. In particular embodiments, the enhancer is a CMV enhancer sequence, a GAPDH enhancer sequence, a 0-actin enhancer sequence, or an EF1-α enhancer sequence. Sequences of the foregoing are known in the art. For example, the sequence of the CMV immediate early (IE) enhancer is SEQ ID NO: 50.

In certain embodiments, the vectors comprise one or more introns. In particular embodiments, the intron is a rabbit globin intron sequence, a chicken j-actin intron sequence, a synthetic intron sequence, an SV40 intron, or an EF1-α intron sequence.

In certain embodiments, the vectors comprise a polyA sequence. In particular embodiments, the polyA sequence is a rabbit globin polyA sequence, a human growth hormone polyA sequence, a bovine growth hormone polyA sequence, a PGK polyA sequence, an SV40 polyA sequence, or a TK polyA sequence. In some embodiments, the poly-A signal may be a bovine growth hormone polyadenylation signal (bGHpA).

In certain embodiments, the vectors comprise one or more transcript stabilizing element. In particular embodiments, the transcript stabilizing element is a WPRE sequence, a HPRE sequence, a scaffold-attachment region, a 3' UTR, or a 5' UTR. In particular embodiments, the vectors comprise both a 5' UTR and a 3' UTR.

In some embodiments, the vector comprises a 5' untranslated region (UTR) selected from Table 4. In some embodiments, the vector genome comprises a polynucleotide sequence at least 75%, 80%, 85%, 90%, 92%, 93%, 94%, 95%, 96%, 97%, 98%, 99%, or 100% identical to any one of SEQ ID NOS 51-61.

TABLE 4

| 5' UNTRANSLATED REGION | SEQUENCE | SEQ ID NO: |
|---|---|---|
| Human beta-actin exon/intron | CGCGTCCGCCCGCGAGCACAGAGCCTCGCCTTTGCCGATC CGCCGCCCGTCCACACCCGCCGCCAGGTAAGCCCGGCCAG CCGACCGGGGCATGCGGCCGCGGCCCCTTCGCCCGTGCAGA GCCGCCGTCTGGGCCGCAGCGGGGGGCGCATGGGGCGGA ACCGGACCGCCGTGGGGGGCGCGGGAGAAGCCCCTGGGC CTCCGGAGATGGGGGACACCCCACGCCAGTTCGCAGGCG CGAGGCCGCGCTCGGGCGGGCGCGCTCCGGGGGTGCCGC TCTCGGGGCGGGGGCAACCGGCGGGGTCTTTGTCTGAGCC GGGCTCTTGCCAATGGGGATCGCACGGTGGGCGCGGCGTA GCCCCCGTCAGGCCCGGTGGGGGCTGGGGCGCCATGCGC GTGCGCGCTGGTCCTTTGGGCGCTAACTGCGTGCGCGCTG GGAATTGGCGCTAATTGCGCGTGCGCGCTGGGACTCAATG GCGCTAATCGCGCGTGCGTTCTGGGGCCCGGGCGCTTGCG CCACTTCCTGCCCGAGCCGCTGGCGCCCGAGGGTGTGGCC GCTGCGTGCGCGCGCGCGACCCGGTCGCTGTTTGAACCGG GCGGAGGCGGGGCTGGCGCCCGGTTGGGAGGGGGTTGGG GCCTGGCTTCCTGCCGCGCGCCGCGGGGACGCCTCCGACC AGTGTTTGCCTTTTATGGTAATAACGCGGCCGGCCCGGCT | 51 |

TABLE 4 -continued

Figure 14:
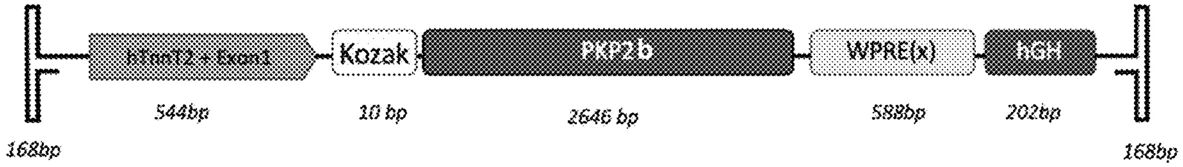
FIG. 14 shows a diagram illustrating a non-limiting example of a vector genome. The full polynucleotide sequence of the vector genome is SEQ ID NO: 92. The expression cassette is SEQ ID NO: 96.

| 5' UNTRANSLATED REGION | SEQUENCE | SEQ ID NO: |
|---|---|---|
| | TCCTTTGTCCCCAATCTGGGCGCGCGCCGGCGCCCCCTGG<br>CGGCCTAAGGACTCGGCGCGCCGGAAGTGGCCAGGGCGG<br>CAGCGGCTGCTCTTGGCGGCCCCGAGGTGACTATAGCCTT<br>CTTTTGTGTCTTGATAGTTCGCCAGCCTCTGCTAACCATGT<br>TCATGCCTTCTTCTTTTTCCTACAGCTCCTGGGCAACGTGC<br>TGGTTATTGTGCTGTCTCATCATTTTGGCAAAGAATTC | |
| Chicken beta-actin exon/intron + rabbit globin intron | GTCGCTGCGCGCTGCCTTCGCCCCGTGCCCCGCTCCGCCG<br>CCGCCTCGCGCCGCCCGCCCCGGCTCTGACTGACCGCGTT<br>ACTCCCACAGGTGAGCGGGCGGGACGGCCCTTCTCCTCCG<br>GGCTGTAATTAGCGCTTGGTTTAATGACGGCTTGTTTCTTT<br>TCTGTGGCTGCGTGAAAGCCTTGAGGGGCTCCGGGAGGGC<br>CCTTTGTGCGGGGGGAGCGGCTCGGGGGGTGCGTGCGTGT<br>GTGTGTGCGTGGGGAGCGCCGCGTGCGGCTCCGCGCTGCC<br>CGGCGGCTGTGAGCGCTGCGGGCGCGGCGCGGGGCTTTGT<br>GCGCTCCGCAGTGTGCGCGAGGGGAGCGCGGCCGGGGGC<br>GGTGCCCCGCGGTGCGGGGGGGGCTGCGAGGGGAACAAA<br>GGCTGCGTGCGGGGTGTGTGCGTGGGGGGGTGAGCAGGG<br>GGTGTGGGCGCGTCGGTCGGGCTGCAACCCCCCCTGCACC<br>CCCCTCCCCGAGTTGCTGAGCACGGCCCGGCTTCGGGTGC<br>GGGGCTCCGTACGGGGCGTGGCGCGGGGCTCGCCGTGCC<br>GGGCGGGGGGTGGCGGCAGGTGGGGGTGCCGGGCGGGGC<br>GGGGCCGCCTCGGGCCGGGGAGGGCTCGGGGGAGGGGCG<br>CGGCGGCCCCCGGAGCGCCGGCGGCTGTCGAGGCGCGGC<br>GAGCCGCAGCCATTGCCTTTTATGGTAATCGTGCGAGAGG<br>GCGCAGGGACTTCCTTTGTCCCAAATCTGTGCGGAGCCGA<br>AATCTGGGAGGCGCCGCCGCACCCCCTCTAGCGGGCGCGG<br>GGCGAAGCGGTGCGGCGCCGGCAGGAAGGAAATGGGCGG<br>GGAGGGCCTTCGTGCGTCGCCGCGCCGCCGTCCCCTTCTC<br>CCTCTCCAGCCTCGGGGCTGTCCGCGGGGGGACGGCTGCC<br>TTCGGGGGGGACGGGGCAGGGCGGGGTTCGGCTTCTGGC<br>GTGTGACCGGCGGCTCTAGAGCCTCTGCTAACCATGTTCA<br>TGCCTTCTTCTTTTTCCTACAGCTCCTGGGCAACGTGCTGG<br>TTATTGTGCTGTCTCATCATTTTGGCAAAGAATTC | 52 |
| SV40 intron (Chimeric intron sequence) Shown in FIG. 14 | GGTAAGTTTAGTCTTTTTGTCTTTTATTTCAGGTCCCGGAT<br>CCGGTGGTGGTGCAAATCAAAGAACTGCTCCTCAGTGGAT<br>GTTGCCTTTACTTCTAGGCCTGTACGGAAGTGTTACTTCTG<br>CTCTAAAAGCTGCGGAATTGTACCCGC | 53 |
| 5' UTR-Syn1 Hs | AGTCTGCGGTGGGCAGCGGAGGAGTCGTGTCGTGCCTGAG<br>AGCGCAGCTGTGCTCCTGGGCACCGCGCAGTCCGCCCCCG<br>CGGCTCCTGGCCAGACCACCCCTAGGACCCCCTGCCCCAA<br>GTCGCA | 54 |
| CMV IE exon | TCAGATCGCCTGGAGAGGCCATCCACGCTGTTTTGACCTC<br>CATAGTGGACACCGGGACCGATCCAGCCTCCGCGGCCGG<br>GAACGGTGCATTGGAACGCGGATTCCCCGTGCCAAGAGTG<br>AC | 55 |
| TPL-ePKP2 (adenovirus derived enhancer element) | CTCACTCTCTTCCGCATCGCTGTCTGCGAGGGCCAGCTGTT<br>GGGCTCGCGGTTGAGGACAAACTCTTCGCGGTCTTTCCAG<br>TACTCTTGGATCGGAAACCCGTCGGCCTCCGAACGGTACT<br>CCGCCACCGAGGGACCTGAGCGAGTCCGCATCGACCGGA<br>TCGGAAAACCTCTCGAGAAAGGCGTCTAACCAGTCACAGT<br>CGCAAGGTAGGCTGAGCACCGTGGCGGGCGGCAGCGGGT<br>GGCGGTCGGGGTTGTTTCTGGCGGAGGTGCTGCTGATGAT<br>GTAATTAAAGTAGGCGGTCTTGAGACGGCGGATGGTCGA<br>GGTGAGGTGTGGCAGGCTTGAGATCCAGCTGTTGGGGTGA<br>GTACTCCCTCTCAAAAGCGGGCATTACTTCTGCGCTAAGA<br>TTGTCAGTTTCCAAAAACGAGGAGGATTTGATATTCACCT<br>GGCCCGATCTGGCCATACACTTGAGTGACAATGACATCCA<br>CTTTGCCTTTCTCTCCACAGGTGTCCACTCCCAG | 56 |
| Human EF1-α intron/exon | CTTTTTCGCAACGGGTTTGCCGCCAGAACACAGGTAAGTG<br>CCGTGTGTGGTTCCCGCGGGCCTGGCCTCTTTACGGGTTAT<br>GGCCCTTGCGTGCCTTGAATTACTTCCACCTGGCTCCAGTA<br>CGTGATTCTTGATCCCGAGCTGGAGCCAGGGGCGGGCCTT<br>GCGCTTTAGGAGCCCCTTCGCCTCGTGCTTGAGTTGAGGC<br>CTGGCCTGGGCGCTGGGGCCGCCGCGTGCGAATCTGGTGG<br>CACCTTCGCGCCTGTCTCGCTGCTTTCGATAAGTCTCTAGC<br>CATTTAAAATTTTTGATGACGTGCTGCGACGCTTTTTTTCT<br>GGCAAGATAGTCTTGTAAATGCGGGCCAGGATCTGCACAC<br>TGGTATTTCGGTTTTTGGGCCCGCGGCCGGCGACGGGGCC<br>CGTGCGTCCCAGCGCACATGTTCGGCGAGGCGGGGCCTGC<br>GAGCGCGGCCACCGAGAATCGGACGGGGGTAGTCTCAAG | 57 |

TABLE 4 -continued

| 5' UNTRANSLATED REGION | SEQUENCE | SEQ ID NO: |
|---|---|---|
| | CTGGCCGGCCTGCTCTGGTGCCTGGCCTCGCGCCGCCGTG<br>TATCGCCCCGCCCTGGGCGGCAAGGCTGGCCCGGTCGGCA<br>CCAGTTGCGTGAGCGGAAAGATGGCCGCTTCCCGGCCCTG<br>CTCCAGGGGGCTCAAAATGGAGGACGCGGCGCTCGGGAG<br>AGCGGGCGGGTGAGTCACCCACACAAAGGAAAAGGGCCT<br>TTCCGTCCTCAGCCGTCGCTTCATGTGACTCCACGGAGTAC<br>CGGGCGCCGTCCAGGCACCTCGATTAGTTCTGGAGCTTTT<br>GGAGTACGTCGTCTTTAGGTTGGGGGGAGGGGTTTTATGC<br>GATGGAGTTTCCCCACACTGAGTGGGTGGAGACTGAAGTT<br>AGGCCAGCTTGGCACTTGATGTAATTCTCCTTGGAATTTG<br>GCCTTTTTGAGTTTGGATCTTGGTTCATTCTCAAGCCTCAG<br>ACAGTGGTTCAAAGTTTTTTTCTTCCATTTCAG | |
| Human EF1-α, intron A | GTAAGTGCCGTGTGTGGTTCCCGCGGGCCTGGCCTCTTTA<br>CGGGTTATGGCCCTTGCGTGCCTTGAATTACTTCCACCTGG<br>CTGCAGTACGTGATTCTTGATCCCGAGCTTCGGGTTGGAA<br>GTGGGTGGGAGAGTTCGAGGCCTTGCGCTTAAGGAGCCCC<br>TTCGCCTCGTGCTTGAGTTGAGGCCTGGCCTGGGCGCTGG<br>GGCCGCCGCGTGCGAATCTGGTGGCACCTTCGCGCCTGTC<br>TCGCTGCTTTCGATAAGTCTCTAGCCATTTAAAATTTTTGA<br>TGACCTGCTGCGACGCTTTTTTTCTGGCAAGATAGTCTTGT<br>AAATGCGGGCCAAGATCTGCACACTGGTATTTCGGTTTTT<br>GGGGCCGCGGGCGGCGACGGGGCCCGTGCGTCCCAGCGC<br>ACATGTTCGGCGAGGCGGGGCCTGCGAGCGCGGCCACCG<br>AGAATCGGACGGGGGTAGTCTCAAGCTGGCCGGCCTGCTC<br>TGGTGCCTGGCCTCGCGCCGCCGTGTATCGCCCCGCCCTG<br>GGCGGCAAGGCTGGCCCGGTCGGCACCAGTTGCGTGAGC<br>GGAAAGATGGCCGCTTCCCGGCCCTGCTGCAGGGAGCTCA<br>AAATGGAGGACGCGGCGCTCGGGAGAGCGGGCGGGTGAG<br>TCACCCACACAAAGGAAAAGGGCCTTTCCGTCCTCAGCCG<br>TCGCTTCATGTGACTCCACGGAGTACCGGGCGCCGTCCAG<br>GCACCTCGATTAGTTCTCGAGCTTTTGGAGTACGTCGTCTT<br>TAGGTTGGGGGGAGGGGTTTTATGCGATGGAGTTTCCCCA<br>CACTGAGTGGGTGGAGACTGAAGTTAGGCCAGCTTGGCAC<br>TTGATGTAATTCTCCTTGGAATTTGCCCTTTTTGAGTTTGG<br>ATCTTGGTTCATTCTCAAGCCTCAGACAGTGGTTCAAAGTT<br>TTTTTCTTCCATTTCAG | 58 |
| 5' UTR human CamKIIa | TCAGAAGCCCCGGGCTCGTCAGTCAAACCGGTTCTCTGTT<br>TGCACTCGGCAGCACGGGCAGGCAAGTGGTCCCTAGGTTC<br>GGG | 59 |
| B-globin intron | GTGAGTCTATGGGACCCTTGATGTTTTCTTTCCCCTTCTTTT<br>CTATGGTTAAGTTCATGTCATAGGAAGGGGAGAAGTAACA<br>GGGTACACATATTGACCAAATCAGGGTAATTTTGCATTTG<br>TAATTTTAAAAAATGCTTTCTTCTTTTAATATACTTTTTTGT<br>TTATCTTATTTCTAATACTTTCCCTAATCTCTTTCTTTCAGG<br>GCAATAATGATACAATGTATCATGCCTCTTTGCACCATTCT<br>AAAGAATAACAGTGATAATTTCTGGGTTAAGGCAATAGCA<br>ATATTTCTGCATATAAATATTTCTGCATATAAATTGTAACT<br>GATGTAAGAGGTTTCATATTGCTAATAGCAGCTACAATCC<br>AGCTACCATTCTGCTTTTATTTTATGGTTGGGATAAGGCTG<br>GATTATTCTGAGTCCAAGCTAGGCCCTTTTGCTAATCATGT<br>TCATACCTCTTATCTTCCTCCCACAG | 60 |
| SV40 intron (long form; underlined 5' and 3' extensions) | TCTAGAGGATCCGGTACTCGAGGAACTGAAAAACCAGAA<br>AGTTAACTGGTAAGTTTAGTCTTTTTGTCTTTTATTTCAGG<br>TCCCGGATCCGGTGGTGGTGCAAATCAAAGAACTGCTCCT<br>CAGTGGATGTTGCCTTTACTTCTAGGCCTGTACGGAAGTG<br>TTACTTCTGCTCTAAAAGCTGCGGAATTGTACCCGC | 61 |

In some embodiments, the vector comprises a 3' untranslated region selected from Table 5. In some embodiments, the vector genome comprises a polynucleotide sequence at least 75%, 80%, 85%, 90%, 92%, 93%, 94%, 95%, 96%, 97%, 98%, 99%, or 10000 identical to any one of SEQ TD NOS 62-70.

TABLE 5

| 3' UNTRANSLATED REGION | SEQUENCE | SEQ ID NO: |
|---|---|---|
| WPRE(x) (mutated woodchuck hepatitis regulatory element-version 1) | AATCAACCTCTGGATTACAAAATTTGTGAAAGATTGACT GGTATTCTTAACTATGTTGCTCCTTTTACGCTATGTGGAT ACGCTGCTTTAATGCCTTTGTATCATGCTATTGCTTCCCGT ATGGCTTTCATTTTCTCCTCCTTGTATAAATCCTGGTTGCT GTCTCTTTATGAGGAGTTGTGGCCCGTTGTCAGGCAACGT GGCGTGGTGTGCACTGTGTTTGCTGACGCAACCCCCACTG GTTGGGGCATTGCCACCACCTGTCAGCTCCTTTCCGGGAC TTTCGCTTTCCCCCTCCCTATTGCCACGGCGGAACTCATC GCCGCCTGCCTTGCCCGCTGCTGGACAGGGGCTCGGCTGT TGGGCACTGACAATTCCGTGGTGTTGTCGGGGAAATCAT CGTCCTTTCCTTGGCTGCTCGCCTGTGTTGCCACCTGGATT CTGCGCGGGACGTCCTTCTGCTACGTCCCTTCGGCCCTCA ATCCAGCGGACCTTCCTTCCCGCGGCCTGCTGCCGGCTCT GCGGCCTCTTCCGCGTCTTCGCCTTCGCCCTCAGACGAGT CGGATCTCCCTTTGGGCCGCCTCCCCGC | 62 |
| WPRE(x) (mutated woodchuck hepatitis regulatory element-version 2) | TCAACCTCTGGATTACAAAATTTGTGAAAGATTGACTGGT ATTCTTAACTATGTTGCTCCTTTTACGCTATGTGGATACG CTGCTTTAATGCCTTTGTATCATGCTATTGCTTCCCGTATG GCTTTCATTTTCTCCTCCTTGTATAAATCCTGGTTGCTGTC TCTTTATGAGGAGTTGTGGCCCGTTGTCAGGCAACGTGGC GTGGTGTGCACTGTGTTTGCTGACGCAACCCCCACTGGTT GGGGCATTGCCACCACCTGTCAGCTCCTTTCCGGGACTTT CGCTTTCCCCCTCCCTATTGCCACGGCGGAACTCATCGCC GCCTGCCTTGCCCGCTGCTGGACAGGGGCTCGGCTGTTGG GCACTGACAATTCCGTGGTGTTGTCGGGGAAATCATCGTC CTTTCCTTGGCTGCTCGCCTGTGTTGCCACCTGGATTCTGC GCGGGACGTCCTTCTGCTACGTCCCTTCGGCCCTCAATCC AGCGGACCTTCCTTCCCGCGGCCTGCTGCCGGCTCTGCGG CCTCTTCCGCGTCTTCGCCTTCGCCCTCAGACGAGTCGGA TCTCCCTTTGGGCCGCCTCCCCGCA | 63 |
| WPRE(x) (mutated woodchuck hepatitis regulatory element-version 3) | TTCCTGTTAATCAACCTCTGGATTACAAAATTTGTGAAAG ATTGACTGGTATTCTTAACTATGTTGCTCCTTTTACGCTAT GTGGATACGCTGCTTTAATGCCTTTGTATCATGCTATTGC TTCCCGTATGGCTTTCATTTTCTCCTCCTTGTATAAATCCT GGTTGCTGTCTCTTTATGAGGAGTTGTGGCCCGTTGTCAG GCAACGTGGCGTGGTGTGCACTGTGTTTGCTGACGCAAC CCCCACTGGTTGGGGCATTGCCACCACCTGTCAGCTCCTT TCCGGGACTTTCGCTTTCCCCCTCCCTATTGCCACGGCGG AACTCATCGCCGCCTGCCTTGCCCGCTGCTGGACAGGGG CTCGGCTGTTGGGCACTGACAATTCCGTGGTGTTGTCGGG GAAGCTGACGTCCTTTCCGCGGCTGCTCGCCTGTGTTGCC ACCTGGATTCTGCGCGGGACGTCCTTCTGCTACGTCCCTT CGGCCCTCAATCCAGCGGACCTTCCTTCCCGCGGCCTGCT GCCGGCTCTGCGGCCTCTTCCGCCTCTTCGCCTTCGCCCT CAGACGAGTCGGATCTCCCTTTGGGCCGCCTCCCCGCCCA TGTATCTTTTTCACCTGTGCCTTGTTTTGCCTGTGTTCCG CGTCCTACTTTTCAAGCCTCCAAGCTGTGCCTTGGGCGGC TTTGGGGCATGGACATAGATCCCTATAAAGAATTTGGTTC ATCTTATCAGTTGTTGAATTTTCTTCCTTTGGAC | 64 |
| CAAX | TGTGTGATAATG | 65 |
| EES | CTGTTCTCATCACATCATATCAAGGTTATATACCATCAAT ATTGCCACAGATGTTACTTAGCCTTTTAATATTTCTCTAAT TTAGTGTATATGCAATGATAGTTCTCTGATTTCTGAGATT GAGTTTCTCATGTGTAATGATTATTTAGAGTTTCTCTTTCA TCTGTTCAAATTTTTGTCTAGTTTTATTTTTTACTGATTTG TAAGACTTCTTTTTATAATCTGCATATTACAATTCTCTTTA CTGGGGTGTTGCAAATATTTTCTGTCATTCTATGGCCTGA CTTTTCTTAATGGTTTTTTAATTTTAAAAATAAGTCTTAAT ATTCATGCAATCTAATTAACAATCTTTTCTTTGTGGTTAG GACTTTGAGTCATAAGAAATTTTTCTCTACACTGAAGTCA TGATGGCATGCTTCTATATTATTTTCTAAAAGATTTAAAG TTTTGCCTTCTCCATTTAGACTTATAATTCACTGGAATTTT TTTGTGTGTATGGTATGACATATGGGTTCCCTTTTATTTTT TACATATAAATATATTTCCCTGTTTTTCTAAAAAAGAAAA AGATCATCATTTTCCCATTGTAAAATGCCATATTTTTTTCA TAGGTCACTTACATATATCAATGGGTCTGTTTCTGAGCTC TACTCTATTTTATCAGCCTCACTGTCTATCCCCACACATCT CATGCTTTGCTCTAAATCTTGATATTTAGTGGAACATTCT TTCCCATTTTGTTCTACAAGAATATTTTTGTTATTGTCTTT GGGCTTTCTATATACATTTTGAAATGAGGTTGACAAGTTA | 66 |

TABLE 5 -continued

| 3' UNTRANSLATED REGION | SEQUENCE | SEQ ID NO: |
|---|---|---|
| HPRE | ATAACAGGCCTATTGATTGGAAAGTTTGTCAACGAATTGT<br>GGGTCTTTTGGGGTTTGCTGCCCCTTTTACGCAATGTGGA<br>TATCCTGCTTTAATGCCTTTATATGCATGTATACAAGCAA<br>AACAGGCTTTTACTTTCTCGCCAACTTACAAGGCCTTTCT<br>CAGTAAACAGTATATGACCCTTTACCCCGTTGCTCGGCAA<br>CGGCCTGGTCTGTGCCAAGTGTTTGCTGACGCAACCCCCA<br>CTGGTTGGGGCTTGGCCATAGGCCATCAGCGCATGCGTG<br>GAACCTTTGTGTCTCCTCTGCCGATCCATACTGCGGAACT<br>CCTAGCCGCTTGTTTTGCTCGCAGCAGGTCTGGAGCAAAC<br>CTCATCGGGACCGACAATTCTGTCGTACTCTCCCGCAAGT<br>ATACATCGTTTCCATGGCTGCTAGGCTGTGCTGCCAACTG<br>GATCCTGCGCGGGACGTCCTTTGTTTACGTCCCGTCGGCG<br>CTGAATCCCGCGGACGACCCCTCCCGGGGCCGCTTGGGG<br>CTCTACCGCCCGCTTCTCCGTCTGCCGTACCGTCCGACCA<br>CGGGGCGCACCTCTCTTTACGCGGACTCCCCGTCTGTGCC<br>TTCTCATCTGCCGGACCGTGTGCACTTCGCTTCACCTCTG<br>CACGTCGCATGGAGGCCACCGTGAACGCCCACCGGAACC<br>TGCCCAAGGTCTTGCATAAGAGGACTCTTGGACTTTCAGC<br>AATGTCATC | 67 |
| R2V17 (HepB derived enhancer element) | TTCCTGTAAACAGGCCTATTGATTGGAAAGTTTGTCAACG<br>AATTGTGGGTCTTTTGGGGTTTGCTGCCCCTTTTACGCAA<br>TGTGGATATCCTGCTTTAATGCCTTTATATGCATGTATAC<br>AAGCAAAACAGGCTTTTACTTTCTCGCCAACTTACAAGGC<br>CTTTCTCAGTAAACAGTATATGACCCTTTACCCCGTTGCT<br>CGGCAACGGCCTGGTCTGTGCCAAGTGTTTGCTGACGCA<br>ACCCCCACTGGTTGGGGCTTGGCCATAGGCCATCAGCGC<br>ATGCGTGGAACCTTTGTGTCTCCTCTGCCGATCCATACTG<br>CGGAACTCCTAGCCGCTTGTTTTGCTCGCAGCTGGACTGG<br>AGCAAACCTCATCGGGACCGACAATTCTGTCGTACTCTCC<br>CGCAAGCACTCACCGTTTCCGCGGCTGCTCGCCTGTGTTG<br>CCACCTGGATTCTGCGCGGGACGTCCTTCTGCTACGTCCC<br>TTCGGCCCTCAATCCAGCGGACCTTCCTTCCCGCGGCCTG<br>CTGCCGGCTCTGCGGCCTCTTCCGCCTCTTCGCCTTCGCC<br>CTCAGACGAGTCGGATCTCCCTTTGGGCCGCCTCCCCGCC<br>CATGTATCTTTTTCACCTGTGCCTTGTTTTTGCCTGTGTTC<br>CGCGTCCTACTTTTCAAGCCTCCAAGCTGTGCCTTGGGCG<br>GCTTTGGGGCATGGACATAGATCCCTATAAAGAATTTGG<br>TTCATCTTATCAGTTGTTGAATTTTCTTCCTTTGGAC | 68 |
| 3' UTR(globin) | GCTGGAGCCTCGGTAGCCGTTCCTCCTGCCCGCTGGGCCT<br>CCCAACGGGCCCTCCTCCCCTCCTTGCACCGGCCCTTCCT<br>GGTCTTTGAATAAA | 69 |
| WPRE(r) | ATTCGAGCATCTTACCGCCATTTATTCCCATATTTGTTCTG<br>TTTTTCTTGATTTGGGTATACATTTAAATGTTAATAAAAC<br>AAAATGGTGGGGCAATCATTTACATTTTTAGGGATATGTA<br>ATTACTAGTTCAGGTGTATTGCCACAAGACAAACATGTTA<br>AGAAACTTTCCCGTTATTTACGCTCTGTTCCTGTTAATCA<br>ACCTCTGGATTACAAAATTTGTGAAAGATTGACTGATATT<br>CTTAACTATGTTGCTCCTTTTACGCTGTGTGGATATGCTG<br>CTTTAATGCCTCTGTATCATGCTATTGCTTCCCGTACGGCT<br>TTCGTTTTCTCCTCCTTGTATAAATCCTGGTTGCTGTCTCT<br>TTATGAGGAGTTGTGGCCCGTTGTCCGTCAACGTGGCGTG<br>GTGTGCTCTGTGTTTGCTGACGCAACCCCCACTGGCTGGG<br>GCATTGCCACCACCTGTCAACTCCTTTCTGGGACTTTCGC<br>TTTCCCCCTCCCGATCGCCACGGCAGAACTCATCGCCGCC<br>TGCCTTGCCCGCTGCTGGACAGGGGCTAGGTTGCTGGGC<br>ACTGATAATTCCGTGGTGTTGTCGGGGAAGGGCC | 70 |

In some embodiments, the vector comprises a polyadenylation (polyA) signal selected from Table 6. In some embodiments, the polyA signal comprises a polynucleotide sequence at least 75%, 80%, 85%, 90%, 92%, 93%, 94%, 95%, 96%, 97%, 98%, 99%, or 100% identical to any one of SEQ ID NOS 71-75.

TABLE 6

| POLY-ADENYLATION SITE | SEQUENCE | SEQ ID NO: |
|---|---|---|
| Rabbit globin (pAGlobin-Oc) | TGGCTAATAAAGGAAATTTATTTTCATTGCAATAGTGTG TTGGAATTTTTTGTGTCTCTCACTCGGAAGAACATATGG GAGGGCAAATCATTTAAAACATCAGAATGAGTATTTGGT TTAGAGTTTGGCAACATATGCCCATATGCTGGCTGCCAT GAACAAAGGTTGGCTATAAAGAGGTCATCAGTATATGA AACAGCCCCCTGCTGTCCATTCCTTATTCCATAGAAAAG CCTTGACTTGAGGTTAGATTTTTTTTATATTTTGTTTTGTG TTATTTTTTTCTTTAACATCCCTAAAATTTTCCTTACATGT TTTACTAGCCAGATTTTTCCTCCTCTCCTGACTACTCCCA GTCATAGCTGTCCCTCTTCTCTTATGGAGATC | 71 |
| Bovine growth hormone (pAGH-Bt-version 1) | TTGCCAGCCATCTGTTGTTTGCCCCTCCCCCGTGCCTTCC TTGACCCTGGAAGGTGCCACTCCCACTGTCCTTTCCTAA TAAAATGAGGAAATTGCATCGCATTGTCTGAGTAGGTGT CATTCTATTCTGGGGGGTGGGGTGGGGCAGGACAGCAA GGGGGAGGATTGGGAATACAATAGCAGGCATGCTGGGG ATGCGGTGGGCTCTATGGGTACCCAGGTGCTGAAGAATT GACCCGGTTCCTCCTGGG | 72 |
| Bovine growth hormone (pAGH-Bt-version 2) | TTGCCAGCCATCTGTTGTTTGCCCCTCCCCCGTGCCTTCC TTGACCCTGGAAGGTGCCACTCCCACTGTCCTTTCCTAA TAAAATGAGGAAATTGCATCGCATTGTCTGAGTAGGTGT CATTCTATTCTGGGGGGTGGGGTGGGGCAGGACAGCAA GGGGGAGGATTGGGAAGACAATAGCAGGCATGCTGGGG ATGCGGTGGGCTCTATGGGTACCCAGGTGCTGAAGAATT GACCCGGTTCCTCCTGGG | 73 |
| Bovine growth hormone (pAGH-Bt-version 3) | CTGTGCCTTCTAGTTGCCAGCCATCTGTTGTTTGCCCCTC CCCCGTGCCTTCCTTGACCCTGGAAGGTGCCACTCCCAC TGTCCTTTCCTAATAAAATGAGGAAATTGCATCGCATTG TCTGAGTAGGTGTCATTCTATTCTGGGGGGTGGGGTGGG GCAGGACAGCAAGGGGGAGGATTGGGAAGACAATAGC AGGCATGCTGGGGATGCGGTGGGCTCTATGG | 74 |
| Human growth hormone (pAGH-Hs) | CTGCCCGGGTGGCATCCCTGTGACCCCTCCCCAGTGCCT CTCCTGGCCCTGGAAGTTGCCACTCCAGTGCCCACCAGC CTTGTCCTAATAAAATTAAGTTGCATCATTTTGTCTGACT AGGTGTCCTTCTATAATATTATGGGGTGGAGGGGGGTGG TATGGAGCAAGGGGCCCAAGTTGGGAAGAAACCTGTAG GGCCTGC | 75 |

Illustrative vector genomes are depicted in FIGS. 1-4 and 11-14; and provided as SEQ ID NOs: 12-15 and 89-92. The expression cassette of each sequence is SEQ TD NOs: 8-11 or 93-96. In some embodiments, the vector genome comprises, consists essentially of, or consists of a polynucleotide sequence that shares at least 90%, 91%, 92%, 93%, 94%, 95%, 96%, 97%, 98%, 99%, or 100% identity to any one of SEQ ID NOs: 12-15 and 89-92, optionally with or without the ITR sequences. In some embodiments, the vector genome comprises, consists essentially of, or consists of a polynucleotide sequence that shares at least 90%, 91%, 92%, 93%, 94%, 95%, 96%, 97%, 98%, 99%, or 100% identity to any one of SEQ ID NOs: 8-11 and 93-96.

In a certain embodiment, the vector genome comprises, in 5' to 3' order, a 5' ITR; an MHCK7 promoter; a PKPa transgene; an WPRE(x) element; an pAGH-HS sequence; and a 3' ITR. The vector genome may comprise, in 5' to 3' order, the polynucleotide sequences SEQ ID NO: 31; any one of SEQ ID NOs: 3, 6, and 87; SEQ ID NO: 63; and SEQ ID NO: 75; or polynucleotide sequences sharing 90%, 91%, 92%, 93%, 94%, 95%, 96%, 97%, 98%, 99%, or 100% identity to each of the foregoing. In certain embodiments, this vector genome is packaged in an AAV9 or AAVrh74 vector. The PKP2a transgene of this embodiment is a full length transgene, i.e. a transgene encoding a PKP of at least 800 or at least 830 amino acids.

In a certain embodiment, the vector genome comprises, in 5' to 3' order, a 5' ITR; a hTnnT2 promoter; a PKPa transgene; an WPRE(x) element; an pAGH-HS sequence; and a 3' ITR. The vector genome may comprise, in 5' to 3' order, the polynucleotide sequences SEQ ID NO: 32 or 33; any one of SEQ ID NOs: 3, 6, and 87; SEQ ID NO: 63; and SEQ ID NO: 75; or polynucleotide sequences sharing 90%, 91%, 92%, 93%, 94%, 95%, 96%, 97%, 98%, 99%, or 100% identity to each of the foregoing. In certain embodiments, this vector genome is packaged in an AAV9 or AAVrh74 vector. The PKP2a transgene of this embodiment is a full length transgene, i.e. a transgene encoding a PKP of at least 800 or at least 830 amino acids.

In a certain embodiment, the vector genome comprises, in 5' to 3' order, a 5' ITR; an MHCK7 promoter; a PKPb transgene; an WPRE(x) element; an pAGH-HS sequence; and a 3' ITR. The vector genome may comprise, in 5' to 3' order, the polynucleotide sequences SEQ ID NO: 31; any one of SEQ ID NOs: 4, 7, and 88; SEQ ID NO: 63; and SEQ ID NO: 75; or polynucleotide sequences sharing 90%, 91%, 92%, 93%, 94%, 95%, 96%, 97%, 98%, 99%, or 100% identity to each of the foregoing. In certain embodiments, this vector genome is packaged in an AAV9 or AAVrh74 vector. The PKP2b transgene of this embodiment is a full length transgene, i.e. a transgene encoding a PKP of at least 800 or at least 830 amino acids.

In a certain embodiment, the vector genome comprises, in 5' to 3' order, a 5' ITR; a hTnnT2 promoter; a PKPb transgene; an WPRE(x) element; an pAGH-HS sequence;

and a 3' ITR. The vector genome may comprise, in 5' to 3' order, the polynucleotide sequences SEQ ID NO: 32 or 33; any one of SEQ ID NOs: 4, 7, and 88; SEQ ID NO: 63; and SEQ ID NO: 75; or polynucleotide sequences sharing 90%, 91%, 92%, 93%, 94%, 95%, 96%, 97%, 98%, 99%, or 100% identity to each of the foregoing. In certain embodiments, this vector genome is packaged in an AAV9 or AAVrh74 vector. The PKP2b transgene of this embodiment is a full length transgene, i.e. a transgene encoding a PKP of at least 800 or at least 830 amino acids.

In a certain embodiment, the vector genome comprises, in 5' to 3' order, a 5' ITR; an MHCK7 promoter; a PKPa transgene; optionally a WPRE element; a polyadenylation sequence; and a 3' ITR. The vector genome may comprise, in 5' to 3' order, the polynucleotide sequences SEQ ID NO: 31; any one of SEQ ID NOs: 3, 6, and 87; or polynucleotide sequences sharing 90%, 91%, 92%, 93%, 94%, 95%, 96%, 97%, 98%, 99%, or 100% identity to each of the foregoing. In certain embodiments, this vector genome is packaged in an AAV9 or AAVrh74 vector. The PKP2a transgene of this embodiment is a full length transgene, i.e. a transgene encoding a PKP of at least 800 or at least 830 amino acids.

In a certain embodiment, the vector genome comprises, in 5' to 3' order, a 5' ITR; a hTnnT2 promoter; a PKPa transgene; optionally a WPRE element; a polyadenylation sequence; and a 3' ITR. The vector genome may comprise, in 5' to 3' order, the polynucleotide sequences SEQ ID NO: 32 or 33; any one of SEQ ID NOs: 3, 6, and 87; or polynucleotide sequences sharing 90%, 91%, 92%, 93%, 94%, 95%, 96%, 97%, 98%, 99%, or 100% identity to each of the foregoing. In certain embodiments, this vector genome is packaged in an AAV9 or AAVrh74 vector. The PKP2a transgene of this embodiment is a full length transgene, i.e. a transgene encoding a PKP of at least 800 or at least 830 amino acids.

In a certain embodiment, the vector genome comprises, in 5' to 3' order, a 5' ITR; an MHCK7 promoter; a PKPb transgene; optionally a WPRE element; a polyadenylation sequence; and a 3' ITR. The vector genome may comprise, in 5' to 3' order, the polynucleotide sequences SEQ ID NO: 31; any one of SEQ ID NOs: 4, 7, and 88; or polynucleotide sequences sharing 90%, 91%, 92%, 93%, 94%, 95%, 96%, 97%, 98%, 99%, or 100% identity to each of the foregoing. In certain embodiments, this vector genome is packaged in an AAV9 or AAVrh74 vector. The PKP2b transgene of this embodiment is a full length transgene, i.e. a transgene encoding a PKP of at least 800 or at least 830 amino acids.

In a certain embodiment, the vector genome comprises, in 5' to 3' order, a 5' ITR; a hTnnT2 promoter; a PKPb transgene; optionally a WPRE element; a polyadenylation sequence; and a 3' ITR. The vector genome may comprise, in 5' to 3' order, the polynucleotide sequences SEQ ID NO: 32 or 33; any one of SEQ ID NOs: 4, 7, and 88; or polynucleotide sequences sharing 90%, 91%, 92%, 93%, 94%, 95%, 96%, 97%, 98%, 99%, or 100% identity to each of the foregoing. In certain embodiments, this vector genome is packaged in an AAV9 or AAVrh74 vector. The PKP2b transgene of this embodiment is a full length transgene, i.e. a transgene encoding a PKP of at least 800 or at least 830 amino acids.

In a certain embodiment, the vector genome comprises, in 5' to 3' order, a 5' ITR; an MHCK7 promoter; SV40 intron; a PKPa transgene; optionally a WPRE element; a polyadenylation sequence; and a 3' ITR. The vector genome may comprise, in 5' to 3' order, the polynucleotide sequences SEQ ID NO: 31; SEQ ID NO: 53 or 61; any one of SEQ ID NOs: 3, 6, and 87; or polynucleotide sequences sharing 90%, 91%, 92%, 93%, 94%, 95%, 96%, 97%, 98%, 99%, or 100% identity to each of the foregoing. In certain embodiments, this vector genome is packaged in an AAV9 or AAVrh74 vector. The PKP2a transgene of this embodiment is a full length transgene, i.e. a transgene encoding a PKP of at least 800 or at least 830 amino acids.

In a certain embodiment, the vector genome comprises, in 5' to 3' order, a 5' ITR; a hTnnT2 promoter; SV40 intron; a PKPa transgene; optionally a WPRE element; a polyadenylation sequence; and a 3' ITR. The vector genome may comprise, in 5' to 3' order, the polynucleotide sequences SEQ ID NO: 32 or 33; SEQ ID NO: 53 or 61; any one of SEQ ID NOs: 3, 6, and 87; or polynucleotide sequences sharing 90%, 91%, 92%, 93%, 94%, 95%, 96%, 97%, 98%, 99%, or 100% identity to each of the foregoing. In certain embodiments, this vector genome is packaged in an AAV9 or AAVrh74 vector. The PKP2a transgene of this embodiment is a full length transgene, i.e. a transgene encoding a PKP of at least 800 or at least 830 amino acids.

In a certain embodiment, the vector genome comprises, in 5' to 3' order, a 5' ITR; an MHCK7 promoter; SV40 intron; a PKPb transgene; optionally a WPRE element; a polyadenylation sequence; and a 3' ITR. The vector genome may comprise, in 5' to 3' order, the polynucleotide sequences SEQ ID NO: 31; SEQ ID NO: 53 or 61; any one of SEQ ID NOs: 4, 7, and 88; or polynucleotide sequences sharing 90%, 91%, 92%, 93%, 94%, 95%, 96%, 97%, 98%, 99%, or 100% identity to each of the foregoing. In certain embodiments, this vector genome is packaged in an AAV9 or AAVrh74 vector. The PKP2b transgene of this embodiment is a full length transgene, i.e. a transgene encoding a PKP of at least 800 or at least 830 amino acids.

In a certain embodiment, the vector genome comprises, in 5' to 3' order, a 5' ITR; a hTnnT2 promoter; SV40 intron; a PKPb transgene; optionally a WPRE element; a polyadenylation sequence; and a 3' ITR. The vector genome may comprise, in 5' to 3' order, the polynucleotide sequences SEQ ID NO: 32 or 33; SEQ ID NO: 53 or 61; any one of SEQ ID NOs: 4, 7, and 88; or polynucleotide sequences sharing 90%, 91%, 92%, 93%, 94%, 95%, 96%, 97%, 98%, 99%, or 100% identity to each of the foregoing. In certain embodiments, this vector genome is packaged in an AAV9 or AAVrh74 vector. The PKP2b transgene of this embodiment is a full length transgene, i.e. a transgene encoding a PKP of at least 800 or at least 830 amino acids.

In each case the optionally WPRE element may be present or absent.

Adeno-Associated Virus Vector

AAV vectors useful in the practice of the present invention can be packaged into AAV virions (viral particles) using various systems including adenovirus-based and helper-free systems. Standard methods in AAV biology include those described in Kwon and Schaffer. *Pharm Res*. (2008) 25(3): 489-99; Wu et al. *Mol. Ther*. (2006) 14(3):316-27. Burger et al. *Mol. Ther*. (2004) 10(2):302-17; Grimm et al. *Curr Gene Ther*. (2003) 3(4):281-304; Deyle D R, Russell D W. *Curr Opin Mol Ther*. (2009) 11(4):442-447; McCarty et al. *Gene Ther*. (2001) 8(16):1248-54; and Duan et al. *Mol Ther*. (2001) 4(4):383-91. Helper-free systems included those described in U.S. Pat. Nos. 6,004,797; 7,588,772; and 7,094, 604;

AAV DNA in the rAAV genomes may be from any AAV variant or serotype for which a recombinant virus can be derived including, but not limited to, AAV variants or serotypes AAV-1, AAV-2, AAV-3, AAV-4, AAV-5, AAV-6, AAV-7, AAV-8, AAV-9, AAV-10, AAV-11, AAV-12, AAV-13 and AAVrh10. Production of pseudotyped rAAV is disclosed in, for example, WO 01/83692. Other types of rAAV variants, for example rAAV with capsid mutations, are also contemplated. See, for example, Marsic et al., Molecular Therapy, 22(11): 1900-1909 (2014). The nucleotide sequences of the genomes of various AAV serotypes are known in the art.

In some cases, the rAAV comprises a self-complementary genome. As defined herein, an rAAV comprising a "self-complementary" or "double stranded" genome refers to an rAAV which has been engineered such that the coding region of the rAAV is configured to form an intra-molecular double-stranded DNA template, as described in McCarty et al. Self-complementary recombinant adeno-associated virus (scAAV) vectors promoter efficient transduction independently of DNA synthesis. Gene Therapy. 8 (16): 1248-54 (2001). The present disclosure contemplates the use, in some cases, of an rAAV comprising a self-complementary genome because upon infection (such transduction), rather than waiting for cell mediated synthesis of the second strand of the rAAV genome, the two complementary halves of scAAV will associate to form one double stranded DNA (dsDNA) unit that is ready for immediate replication and transcription. It will be understood that instead of the full coding capacity found in rAAV (4.7-6 kb), rAAV comprising a self-complementary genome can only hold about half of that amount (≈2.4 kb).

In other cases, the rAAV vector comprises a single stranded genome. As defined herein, a "single standard" genome refers to a genome that is not self-complementary. In most cases, non-recombinant AAVs have singled stranded DNA genomes. There have been some indications that rAAVs should be scAAVs to achieve efficient transduction of cells. The present disclosure contemplates, however, rAAV vectors that maybe have singled stranded genomes, rather than self-complementary genomes, with the understanding that other genetic modifications of the rAAV vector may be beneficial to obtain optimal gene transcription in target cells. In some cases, the present disclosure relates to single-stranded rAAV vectors capable of achieving efficient gene transfer to anterior segment in the mouse eye. See Wang et al. Single stranded adeno-associated virus achieves efficient gene transfer to anterior segment in the mouse eye. PLoS ONE 12(8): e0182473 (2017).

In some cases, the rAAV vector is of the serotype AAV1, AAV2, AAV4, AAV5, AAV6, AAV7, AAV8, AAV9, AAV10, AAV 11, AAV12, AAV13, AAVrh10, or AAVrh74. Production of pseudotyped rAAV is disclosed in, for example, WO 01/83692. Other types of rAAV variants, for example rAAV with capsid mutations, are also contemplated. See, for example, Marsic et al., Molecular Therapy, 22(11): 1900-1909 (2014). In some cases, the rAAV vector is of the serotype AAV9. In some embodiments, said rAAV vector is of serotype AAV9 and comprises a single stranded genome. In some embodiments, said rAAV vector is of serotype AAV9 and comprises a self-complementary genome. In some embodiments, a rAAV vector comprises the inverted terminal repeat (ITR) sequences of AAV2. In some embodiments, the rAAV vector comprises an AAV2 genome, such that the rAAV vector is an AAV-2/9 vector, an AAV-2/6 vector, or an AAV-2/8 vector.

Full-length sequences and sequences for capsid genes for most known AAVs are provided in U.S. Pat. No. 8,524,446, which is incorporated herein in its entirety.

AAV vectors may comprise wild-type AAV sequence or they may comprise one or more modifications to a wild-type AAV sequence. In certain embodiments, an AAV vector comprises one or more amino acid modifications, optionally substitutions, deletions, or insertions, within a capsid protein, optionally VP1, VP2 and/or VP3. In particular embodiments, the modification provides for reduced immunogenicity when the AAV vector is provided to a subject.

Capsid proteins of a rAAV may be modified so that the rAAV is targeted to a particular target tissue of interest such as endothelial cells or more particularly endothelial tip cells. In some embodiments, the rAAV is directly injected into the intracerebroventricular space of the subject.

In some embodiments, the rAAV virion is an AAV2 rAAV virion. The capsid many be an AAV2 capsid or functional variant thereof. In some embodiments, the AAV2 capsid shares at least 98%, 99%, or 100% identity to a reference AAV2 capsid, e.g., SEQ ID NO: 76.

In some embodiments, the rAAV virion is an AAV9 rAAV virion. The capsid many be an AAV9 capsid or functional variant thereof. In some embodiments, the AAV9 capsid shares at least 98%, 99%, or 100% identity to a reference AAV9 capsid, e.g., SEQ ID NO: 77.

In some embodiments, the rAAV virion is an AAV6 rAAV virion. The capsid many be an AAV9 capsid or functional variant thereof. In some embodiments, the AAV6 capsid shares at least 98%, 99%, or 100% identity to a reference AAV6 capsid, e.g., SEQ ID NO: 78.

In some embodiments, the rAAV virion is an AAVrh.10 rAAV virion. The capsid many be an AAV9 capsid or functional variant thereof. In some embodiments, the AAVrh.10 capsid shares at least 98%, 99%, or 100% identity to a reference AAVrh.10 capsid, e.g., SEQ ID NO: 79.

In some embodiments, the capsid protein is encoded by a polynucleotide supplied on a plasmid in trans to the transfer plasmid. The polynucleotide sequence of wild-type AAVrh74 cap is provided as SEQ ID NO: 80.

The disclosure further provides protein sequences for AAVrh74 VP3, including SEQ ID NO: 81, and homologs or functional variants thereof.

In certain cases, the AAVrh74 capsid comprises the amino acid sequence set forth in SEQ ID NO: 81. In some embodiments, the rAAV vector comprises a polypeptide that comprises, or consists essentially of, or yet further consists of a sequence, e.g., at least 65%, at least 70%, at least 75%, at least 80%, 81%, 82%, 83%, 84%, 85%, 86%, 87%, 88%, or 89% more typically 90%, 91%, 92%, 93%, 94%, 95%, 96%, 97%, 98%, 99% or more identical to amino acid sequence of AAVrh74 VP3 which is set forth in SEQ ID NO: 81. In some embodiments, the rAAV vector comprises a polypeptide that comprises, or consists essentially of, or yet further consists of a sequence, e.g., at least 65%, at least 70%, at least 75%, at least 80%, 81%, 82%, 83%, 84%, 85%, 86%, 87%, 88%, or 89%, more typically 90%, 91%, 92%, 93%, 94%, 95%, 96%, 97%, 98%, 99% or more identical to amino acid sequence set forth in SEQ ID NO: 82. In some embodiments, the rAAV vector comprises a polypeptide that comprises, or consists essentially of, or yet further consists of a sequence, e.g., at least 65%, at least 70%, at least 75%, at least 80%, 81%, 82%, 83%, 84%, 85%, 86%, 87%, 88%, or 89%, more typically 90%, 91%, 92%, 93%, 94%, 95%, 96%, 97%, 98%, 99% or more identical to amino acid sequence set forth in SEQ ID NO: 83.

In some embodiments, the rAAV virion is an AAV-PHP.B rAAV virion or a neutrotrophic variant thereof, such as, without limitation, those disclosed in Int'l Pat. Pub. Nos. WO 2015/038958 A1 and WO 2017/100671 A1. For example, the AAV capsid may comprise at least 4 contiguous amino acids from the sequence TLAVPFK (SEQ ID NO:85) or KFPVALT (SEQ ID NO:86), e.g., inserted between a sequence encoding for amino acids 588 and 589 of AAV9.

The capsid many be an AAV-PHP.B capsid or functional variant thereof. In some embodiments, the AAV-PHP.B capsid shares at least 98%, 99%, or 100% identity to a reference AAV-PHP.B capsid, e.g., SEQ ID NO: 84.

Further AAV capsids used in the rAAV virions of the disclosure include those disclosed in Pat. Pub. Nos. WO 2009/012176 A2 and WO 2015/168666 A2.

Without being bound by theory, the present inventors have determined that an AAV9 vector, AAVrh.74, or an AAVrh.10 vector will confer desirable cardiac tropism on the vector. Without being bound by theory, the present inventors have further determined that an AAV9 vector, AAVrh.74, or an AAVrh.10 vector may provide desired specificity to cardiac cells.

In an aspect, the disclosure provides pharmaceutical compositions comprising the rAAV virion of the disclosure and one or more pharmaceutically acceptable carriers, diluents, or excipients.

For purposes of administration, optionally by injection, various solutions can be employed, such as sterile aqueous solutions. Such aqueous solutions can be buffered, if desired, and the liquid diluent first rendered isotonic with saline or glucose. Solutions of rAAV as a free acid (DNA contains acidic phosphate groups) or a pharmacologically acceptable salt can be prepared in water suitably mixed with a surfactant such as Poloxamer 188, e.g., at 0.001% or 0.01%. A dispersion of rAAV can also be prepared in glycerol, liquid polyethylene glycols and mixtures thereof and in oils. Under ordinary conditions of storage and use, these preparations contain a preservative to prevent the growth of microorganisms. In this connection, the sterile aqueous media employed are all readily obtainable by standard techniques well-known to those skilled in the art.

The pharmaceutical forms suitable for injectable use include but are not limited to sterile aqueous solutions or dispersions and sterile powders for the extemporaneous preparation of sterile injectable solutions or dispersions. In all cases the form is sterile and must be fluid to the extent that easy syringability exists. It must be stable under the conditions of manufacture and storage and must be preserved against the contaminating actions of microorganisms such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions may be prepared by incorporating rAAV in the required amount in the appropriate solvent with various other ingredients enumerated above, as required, followed by filter sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the certain methods of preparation are vacuum drying and the freeze-drying technique that yield a powder of the active ingredient plus any additional desired ingredient from the previously sterile-filtered solution thereof.

In another aspect, the disclosure comprises a kit comprising an rAAV virion of the disclosure and instructions for use.

In an aspect, the disclosure provides a method of increasing PKP2 activity in a cell, comprising contacting the cell with an rAAV of the disclosure. In another aspect, the disclosure provides a method of increasing PKP2 activity in a subject, comprising administering to the subject an rAAV of the disclosure. In some embodiments, the cell and/or subject is deficient in PKP2 messenger RNA or PKP2 protein expression levels and/or activity and/or comprises a loss-of-function mutation in PKP2. The cell may be a cardiac cell, e.g. a cardiomyocyte cell. In particular embodiments, the subject is a mammal, e.g., a human.

In some embodiments, the method promotes survival of cardiac cell, e.g. a cardiomyocyte cell, in cell culture and/or in vivo. In some embodiments, the method promotes and/or restores function of the heart.

In another aspect, the disclosure provides a method of treating a disease or disorder in a subject in need thereof, comprising administering to the subject an effective amount of an rAAV virion of the disclosure. In some embodiments, the disease or disorder is a cardiac disease or disorder. Illustrative cardiac disorders include heart failure, arrhythmogenic right ventricular cardiomyopathy (ARVC), Brugada syndrome (BrS) and idiopathic ventricular fibrillation. In certain embodiments, the subject suffers from or is at risk for arrhythmogenic right ventricular cardiomyopathy (ARVC). In particular embodiments, the subject is a mammal, e.g., a human, having a loss-of-function mutation in a PKP2 gene. In particular methods, treatment with the rAAV virion results in expression of the PKP2 protein encoded by the rAAV virion in the subject, e.g., in the subject's heart or cardiac tissue. In certain embodiments, treatment with the rAAV virion results in at least two-fold, at least five-fold, at least ten-fold, or more PKP2 protein levels detectable in the subject's heart.

The AAV-mediated delivery of PKP2 protein to the heart may increase life span, prevent or attenuate cardiac cell degeneration, heart failure, scarring, reduced ejection fraction, arrythmia, angina, exercise intolerance, angina (chest pain), sudden cardiac death, exertional myalgias and cramps. The AAV-mediated delivery of PKP2 protein to the heart may show improvement from, or prevent normal disease course detected by use of pathological electrocardiogram, cardiac MRI, heart biopsy, decrease in paroxysmal ventricular arrhythmias, decrease in sudden cardiac death, and/or decrease in or lack of further development of fibrofatty deposits in right ventricular myocardium. The methods of the disclosure may prevent a decrease in, restore, and/or increase right ventricular ejection fraction (RVEF).

The methods disclosed herein may provide efficient biodistribution in the heart. They may result in sustained in expression in all, or a substantial fraction of, cardiac cells, e.g., cardiomyocytes. Notably, the methods disclosed herein may provide long-lasting expression of PKP2 protein throughout the life of the subject following AAV vector administration. In some embodiments, PKP2 protein expression in response to treatment lasts at least 1, 2, 3, 4, 5, 6, 7, 8, 9, 10, 15, 20, 25, 30, 35, or 40 years.

Combination therapies are also contemplated by the invention. Combinations of methods of the invention with standard medical treatments (e.g., corticosteroids or topical pressure reducing medications) are specifically contemplated, as are combinations with novel therapies. In some cases, a subject may be treated with a steroid and/or combination of immune suppressing agents to prevent or to reduce an immune response to administration of a rAAV described herein.

In some embodiments, the AAV vector is administered at a dose of between about $1\times10^{12}$ and $5\times10^{14}$ vector genomes (vg) or between about $1\times10^{12}$ and $6\times10^{14}$ vg of the AAV vector per kilogram (vg) of total body mass of the subject (vg/kg). In some embodiments, the AAV vector is administered at a dose of between about $1\times10^{13}$ and $5\times10^{14}$ vg/kg. In some embodiments, the AAV vector is administered at a dose of between about $5\times10^{13}$ and $3\times10^{14}$ vg/kg. In some embodiments, the AAV vector is administered at a dose of between about $5\times10^{13}$ and $1\times10^{14}$ vg/kg. In some embodiments, the AAV vector is administered at a dose of less than about $1\times10^{12}$ vg/kg, less than about $3\times10^{12}$ vg/kg, less than about $5\times10^{12}$ vg/kg, less than about $7\times10^{12}$ vg/kg, less than about $1\times10^{13}$ vg/kg, less than about $3\times10^{13}$ vg/kg, less than about $5\times10^{13}$ vg/kg, less than about $7\times10^{13}$ vg/kg, less than about $1\times10^{14}$ vg/kg, less than about $3\times10^{14}$ vg/kg, less than about $5\times10^{14}$ vg/kg, less than about $7\times10^{14}$ vg/kg, less than about $1\times10^{15}$ vg/kg, less than about $3\times10^{15}$ vg/kg, less than about $5\times10^{15}$ vg/kg, or less than about $7\times10^{15}$ vg/kg. In certain embodiments, the AAV vector delivered at any of these doses is an AAV9 vector or an AAV rh74 vector. In some cases, it may be advantageous to use a higher dose for an AAV rh74 vector than for an AAV9 vector.

In some embodiments, the AAV vector is administered at a dose of about $1\times10^{12}$ vg/kg, about $3\times10^{12}$ vg/kg, about $5\times10^{12}$ vg/kg, about $7\times10^{12}$ vg/kg, about $1\times10^{13}$ vg/kg, about $3\times10^{13}$ vg/kg, about $5\times10^{13}$ vg/kg, about $7\times10^{13}$ vg/kg, about $1\times10^{14}$ vg/kg, about $3\times10^{14}$ vg/kg, about $5\times10^{14}$ vg/kg, about $7\times10^{14}$ vg/kg, about $1\times10^{15}$ vg/kg, about $3\times10^{15}$ vg/kg, about $5\times10^{15}$ vg/kg, or about $7\times10^{15}$ vg/kg. In certain embodiments, the AAV vector delivered at any of these doses is an AAV9 vector or an AAV rh74 vector.

In some embodiments, the AAV vector is administered at a dose of $1\times10^{12}$ vg/kg, $3\times10^{12}$ vg/kg, $5\times10^{12}$ vg/kg, $7\times10^{12}$ vg/kg, $1\times10^{13}$ vg/kg, $3\times10^{13}$ vg/kg, $5\times10^{13}$ vg/kg, $7\times10^{13}$ vg/kg, $1\times10^{14}$ vg/kg, $3\times10^{14}$ vg/kg, $5\times10^{14}$ vg/kg, $7\times10^{14}$ vg/kg, $1\times10^{15}$ vg/kg, $3\times10^{15}$ vg/kg, $5\times10^{15}$ vg/kg, or $7\times10^{15}$ vg/kg. In certain embodiments, the AAV vector delivered at any of these doses is an AAV9 vector or an AAV rh74 vector.

In some embodiments, the AAV vector is administered systemically at a dose of between about $1\times10^{12}$ and $5\times10^{14}$ vector genomes (vg) of the AAV vector per kilogram (vg) of total body mass of the subject (vg/kg). In some embodiments, the AAV vector is administered systemically at a dose of between about $1\times10^{13}$ and $5\times10^{14}$ vg/kg. In some embodiments, the AAV vector is administered systemically at a dose of between about $5\times10^{13}$ and $3\times10^{14}$ vg/kg. In some embodiments, the AAV vector is administered systemically at a dose of between about $5\times10^{13}$ and $1\times10^{14}$ vg/kg. In some embodiments, the AAV vector is administered systemically at a dose of less than about $1\times10^{12}$ vg/kg, less than about $3\times10^{12}$ vg/kg, less than about $5\times10^{12}$ vg/kg, less than about $7\times10^{12}$ vg/kg, less than about $1\times10^{13}$ vg/kg, less than about $3\times10^{13}$ vg/kg, less than about $5\times10^{13}$ vg/kg, less than about $7\times10^{13}$ vg/kg, less than about $1\times10^{14}$ vg/kg, less than about $3\times10^{14}$ vg/kg, less than about $5\times10^{14}$ vg/kg, less than about $7\times10^{14}$ vg/kg, less than about $1\times10^{15}$ vg/kg, less than about $3\times10^{15}$ vg/kg, less than about $5\times10^{15}$ vg/kg, or less than about $7\times10^{15}$ vg/kg. In certain embodiments, the AAV vector delivered at any of these doses is an AAV9 vector or an AAV rh74 vector.

In some embodiments, the AAV vector is administered systemically at a dose of about $1\times10^{12}$ vg/kg, about $3\times10^{12}$ vg/kg, about $5\times10^{12}$ vg/kg, about $7\times10^{12}$ vg/kg, about $1\times10^{13}$ vg/kg, about $3\times10^{13}$ vg/kg, about $5\times10^{13}$ vg/kg, about $7\times10^{13}$ vg/kg, about $1\times10^{14}$ vg/kg, about $3\times10^{14}$ vg/kg, about $5\times10^{14}$ vg/kg, about $7\times10^{14}$ vg/kg, about $1\times10^{15}$ vg/kg, about $3\times10^{15}$ vg/kg, about $5\times10^{15}$ vg/kg, or about $7\times10^{15}$ vg/kg. In certain embodiments, the AAV vector delivered at any of these doses is an AAV9 vector or an AAV rh74 vector.

In some embodiments, the AAV vector is administered systemically at a dose of $1\times10^{12}$ vg/kg, $3\times10^{12}$ vg/kg, $5\times10^{12}$ vg/kg, $7\times10^{12}$ vg/kg, $1\times10^{13}$ vg/kg, $3\times10^{13}$ vg/kg, $5\times10^{13}$ vg/kg, $7\times10^{13}$ vg/kg, $1\times10^{14}$ vg/kg, $3\times10^{14}$ vg/kg, $5\times10^{14}$ vg/kg, $7\times10^{14}$ vg/kg, $1\times10^{15}$ vg/kg, $3\times10^{15}$ vg/kg, $5\times10^{15}$ vg/kg, or $7\times10^{15}$ vg/kg. In certain embodiments, the AAV vector delivered at any of these doses is an AAV9 vector or an AAV rh74 vector.

In some embodiments, the AAV vector is administered intravenously at a dose of between about $1\times10^{12}$ and $5\times10^{14}$ vector genomes (vg) of the AAV vector per kilogram (vg) of total body mass of the subject (vg/kg). In some embodiments, the AAV vector is administered intravenously at a dose of between about $1\times10^{13}$ and $5\times10^{14}$ vg/kg. In some embodiments, the AAV vector is administered intravenously at a dose of between about $5\times10^{13}$ and $3\times10^{14}$ vg/kg. In some embodiments, the AAV vector is administered intravenously at a dose of between about $5\times10^{13}$ and $1\times10^{14}$ vg/kg. In some embodiments, the AAV vector is administered intravenously at a dose of less than about $1\times10^{12}$ vg/kg, less than about $3\times10^{12}$ vg/kg, less than about $5\times10^{12}$ vg/kg, less than about $7\times10^{12}$ vg/kg, less than about $1\times10^{13}$ vg/kg, less than about $3\times10^{13}$ vg/kg, less than about $5\times10^{13}$ vg/kg, less than about $7\times10^{13}$ vg/kg, less than about $1\times10^{14}$ vg/kg, less than about $3\times10^{14}$ vg/kg, less than about $5\times10^{14}$ vg/kg, less than about $7\times10^{14}$ vg/kg, less than about $1\times10^{15}$ vg/kg, less than about $3\times10^{15}$ vg/kg, less than about $5\times10^{15}$ vg/kg, or less than about $7\times10^{15}$ vg/kg. In certain embodiments, the AAV vector delivered at any of these doses is an AAV9 vector or an AAV rh74 vector.

In some embodiments, the AAV vector is administered intravenously at a dose of about $1\times10^{12}$ vg/kg, about $3\times10^{12}$ vg/kg, about $5\times10^{12}$ vg/kg, about $7\times10^{12}$ vg/kg, about $1\times10^{13}$ vg/kg, about $3\times10^{13}$ vg/kg, about $5\times10^{13}$ vg/kg, about $7\times10^{13}$ vg/kg, about $1\times10^{14}$ vg/kg, about $3\times10^{14}$ vg/kg, about $5\times10^{14}$ vg/kg, about $7\times10^{14}$ vg/kg, about $1\times10^{15}$ vg/kg, about $3\times10^{15}$ vg/kg, about $5\times10^{15}$ vg/kg, or about $7\times10^{15}$ vg/kg.

In some embodiments, the AAV vector is administered intravenously at a dose of $1\times10^{12}$ vg/kg, $3\times10^{12}$ vg/kg, $5\times10^{12}$ vg/kg, $7\times10^{12}$ vg/kg, $1\times10^{13}$ vg/kg, $3\times10^{13}$ vg/kg, $5\times10^{13}$ vg/kg, $7\times10^{13}$ vg/kg, $1\times10^{14}$ vg/kg, $3\times10^{14}$ vg/kg, $5\times10^{14}$ vg/kg, $7\times10^{14}$ vg/kg, IX $10^{15}$ vg/kg, $3\times10^{15}$ vg/kg, $5\times10^{15}$ vg/kg, or $7\times10^{15}$ vg/kg. In certain embodiments, the AAV vector delivered at any of these doses is an AAV9 vector or an AAV rh74 vector.

Evidence of functional improvement, clinical benefit or efficacy in patients may be revealed by change in New York Heart Association functional classification (NYHA Class), pathological electrocardiogram, cardiac MRI, heart biopsy, decrease in paroxysmal ventricular arrhythmias, decrease in sudden cardiac death, and/or decrease in or lack of further development of fibro-fatty deposits in right ventricular myocardium. Benefit may be observed in electrocardiographic features normally associated with arrhythmogenic right ventricular cardiomyopathy such as T wave inversion, prolonged S-wave upstroke, localized QRS widening, and/or paroxysmal episodes of ventricular tachycardia.

In some embodiments, the method prevents or reduces a decrease in left ventricle ejection fraction percentage (LVEF %), optionally by about 50%, about 60%, about 70%, about 80%, about 90%, or about 100% compared to the decrease observed in an untreated subject suffering from or at risk for disease or disorder related to or caused by loss of function in PKP2.

In some embodiments, the method prevents or reduces a decrease in left ventricle fractional shortening percentage (FS %), optionally by about 50%, about 60%, about 70%, about 80%, about 90%, or about 100% compared to the decrease observed in an untreated subject suffering from or at risk for disease or disorder related to or caused by loss of function in PKP2.

In some embodiments, the method prevents or reduces an increase in right ventricle area in millimeters squared (RV Area (mm2), optionally by about 50%, about 60%, about 70%, about 80%, about 90%, or about 100% compared to the increase observed in an untreated subject suffering from or at risk for disease or disorder related to or caused by loss of function in PKP2.

In some embodiments, the method prevents or reduces a decrease in right ventricle velocity time integral in millimeters per second (RV VTI (mm/sec), optionally by about 50%, about 60%, about 70%, about 80%, about 90%, or about 100% compared to the decrease observed in an untreated subject suffering from or at risk for disease or disorder related to or caused by loss of function in PKP2.

In some embodiments, the method prevents or reduces an increase in left ventricle or right ventricle fibrosis, optionally by about 50%, about 60%, about 70%, about 80%, about 90%, or about 100% compared to the increase observed in an untreated subject suffering from or at risk for disease or disorder related to or caused by loss of function in PKP2.

Administration of an effective dose of the compositions may be by routes standard in the art including, but not limited to, systemic, local, direct injection, intravenous, intracardiac administration. In some cases, administration comprises systemic, local, direct injection, intravenous, intracardiac injection. Administration may be performed by cardiac catheterization.

In some embodiments, the disclosure provides for local administration and systemic administration of an effective dose of rAAV and compositions of the invention. For example, systemic administration may be administration into the circulatory system so that the entire body is affected. Systemic administration includes parental administration through injection, infusion or implantation. Routes of administration for the compositions disclosed herein include intravenous ("IV") administration, intraperitoneal ("IP") administration, intramuscular ("IM") administration, intralesional administration, or subcutaneous ("SC") administration, or the implantation of a slow-release device, e.g., a mini-osmotic pump, a depot formulation, etc. In some embodiments, the methods of the disclosure comprise administering an AAV vector of the disclosure, or pharmaceutical composition thereof by intravenous, intramuscular, intraarterial, intrarenal, intraurethral, intracardiac, intracoronary, intramyocardial, intradermal, epidural, subcutaneous, intraperitoneal, intraventricular, ionophoretic or intracranial administration.

In particular, administration of rAAV of the present invention may be accomplished by using any physical method that will transport the rAAV recombinant vector into the target tissue of an animal. Administration includes, but is not limited to, injection into the heart.

In some embodiments, the methods of the disclosure comprise intracardiac delivery. Infusion may be performed using specialized cannula, catheter, syringe/needle using an infusion pump. Administration may comprise delivery of an effective amount of the rAAV virion, or a pharmaceutical composition comprising the rAAV virion, to the heart. These may be achieved, e.g., via intravenous, intramuscular, intraarterial, intrarenal, intraurethral, intracardiac, intracoronary, intramyocardial, intradermal, epidural, subcutaneous, intraperitoneal, intraventricular, ionophoretic or intracranial administration. The compositions of the disclosure may further be administered intravenously.

The method of treatment disclosed herein may reduce and/or prevent one or more symptoms including but not limited to ventricular hypertrophy, ventricular tachycardia, exercise intolerance, angina, and reduced RVEF.

EXAMPLES

Example 1: Pre-Clinical Bioactivity and Efficacy

Vectors illustrated in FIGS. 1-4 are tested. AAV vectors or respective expression cassettes are tested in vitro using cultured cardiomyocytes (e.g., induced pluripotent stem cell cardiomyocytes, iPSC-CMs) or other cells amenable to transfection or transduction with these constructs. Expression of PKP2 is assessed by immunofluorescence and Western blot. Cell-based studies employing patient iPSC-derived cardiomyocytes will reveal benefit of overexpression of PKP2 transgene (either following AAV vector transduction and/or transfection with vector plasmids) by a decreased adipogenic potential (e.g. less lipid accumulation), decreased upregulation or abnormal peroxisome proliferator-activated receptor gamma activation, associated with increased density of PKP2.

Selected vectors are tested in vivo using mutant mouse models of cardiomyopathy (e.g., PKP2-cKO, among others). Evidence of benefit of AAV mediated overexpression of PKP2 may be revealed using a cardiomyocyte-specific, tamoxifen-activated, PKP2 knockout murine line, referred to as "PKP2-cKO". This mouse model allows control of the onset of PKP2 loss of expression, limits loss of PKP2 to adult myocytes, and initiates a progression of molecular and functional events leading to an arrhythmogenic cardiomyopathy, with right ventricular predominance in this mouse. Additional mouse models that result in similar course of pathology may also be utilized to reveal benefit of AAV-mediated overexpression of PKP2 in cardiomyocytes. Benefit of AAV-mediated PKP2 overexpression would be evidenced by increase in survival, mitigation of the normal progression of cardiomyopathy observed on echocardiograms from left and/or right ventricle (e.g. greater left ventricular ejection fraction, greater left ventricle fractional shortening, and greater right ventricle velocity time interval, compared to PKP cKO formulation buffer control animals).

Electrophysiological evidence of functional benefit of AAV-mediated delivery of PKP2 protein is demonstrated by mitigation of disease-related disrupted calcium dynamics in affected cardiomyocytes, most notably on measures of L-type calcium current, sarcoplasmic reticulum calcium leak, diastolic calcium leak, as well as standard measures of calcium transients in affected (e.g., PKP2-deficient) cardiomyocytes such as time to peak amplitude and relaxation time constants. Histological analyses will reveal benefit of AAV-mediated PKP2 overexpression by diminished appearance of disease-related collagen deposition (e.g., via trichrome stain) in various regions of the heart including ventricles, compared to cKO formulation buffer injected controls. Additional benefit will also be revealed by evaluating cardiomyocyte ventricular proteins involved in calcium signaling pathways, measured by increased (i.e., normalized) relative levels of Casq2, and/or Trdn, and/or Cav 1.2, and/or AnkB and/or RyR2, relative to non AAV-PKP2 treated, PKP2-cKO diseased controls.

Example 2: In Vitro Testing of Adeno-Associated Virus Vectors

Figure 5A:
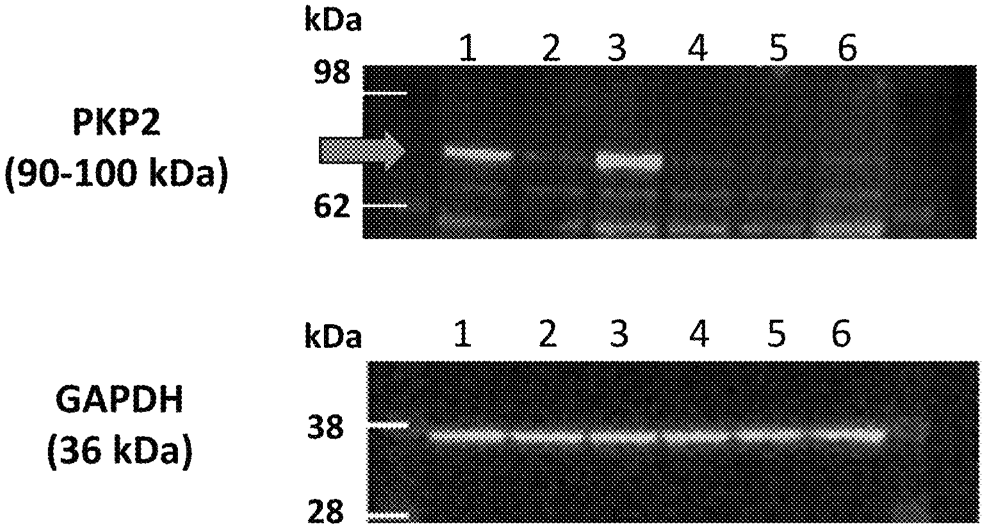
FIGS. 5A-5B show PKP2 protein expression in transduced differentiated AC16 cells.
Figure 5B:
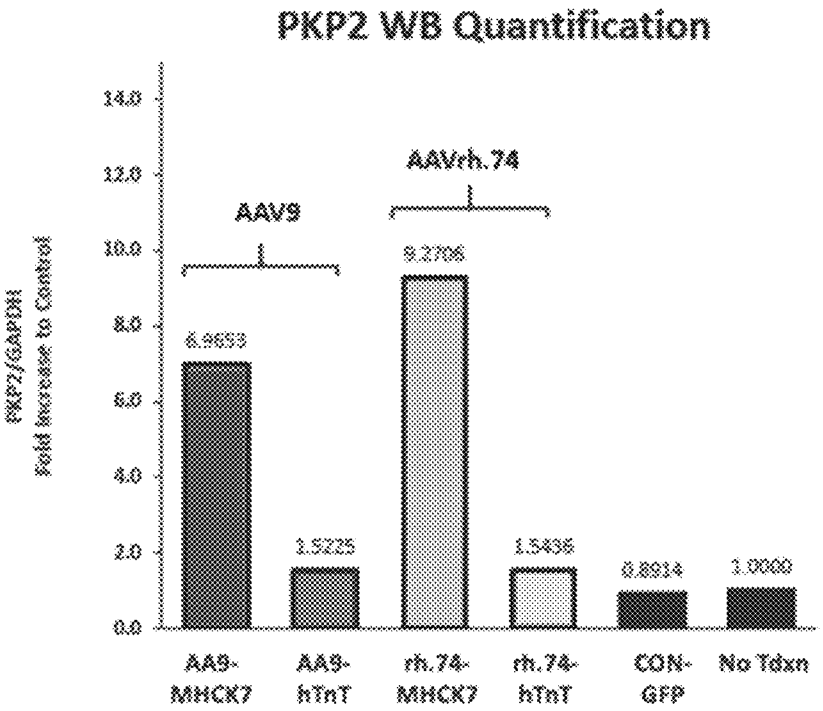
Figures 6A, 6B, 6C, 6D:
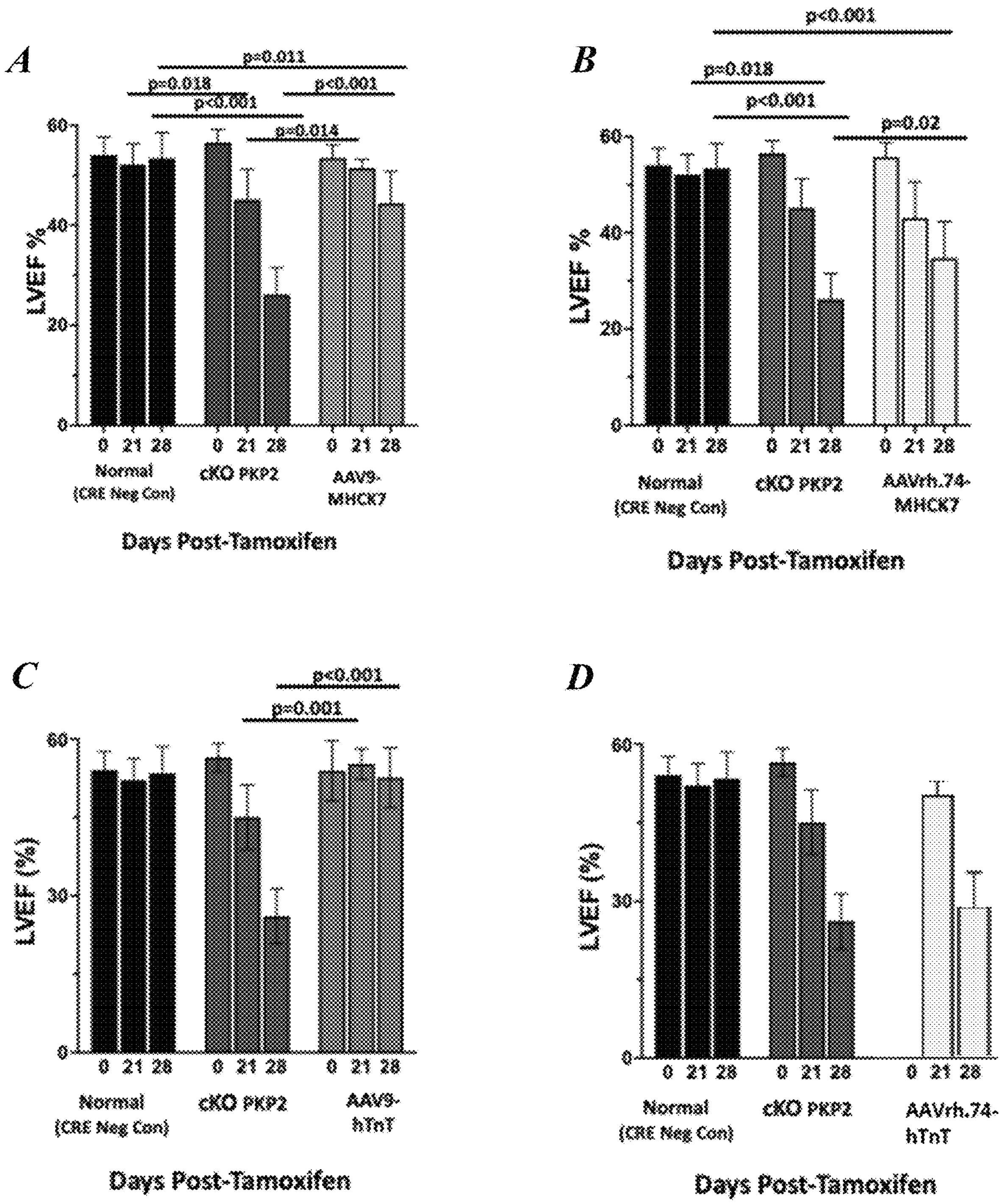
FIGS. 6A-6D show left ventricle ejection fraction percentage (LVEF %) for normal mice (left bars), untreated PKP2 knockout mice (middle bars, cKO PKP2), or treated mice (right bars).
Figures 7A, 7B, 7C, 7D:
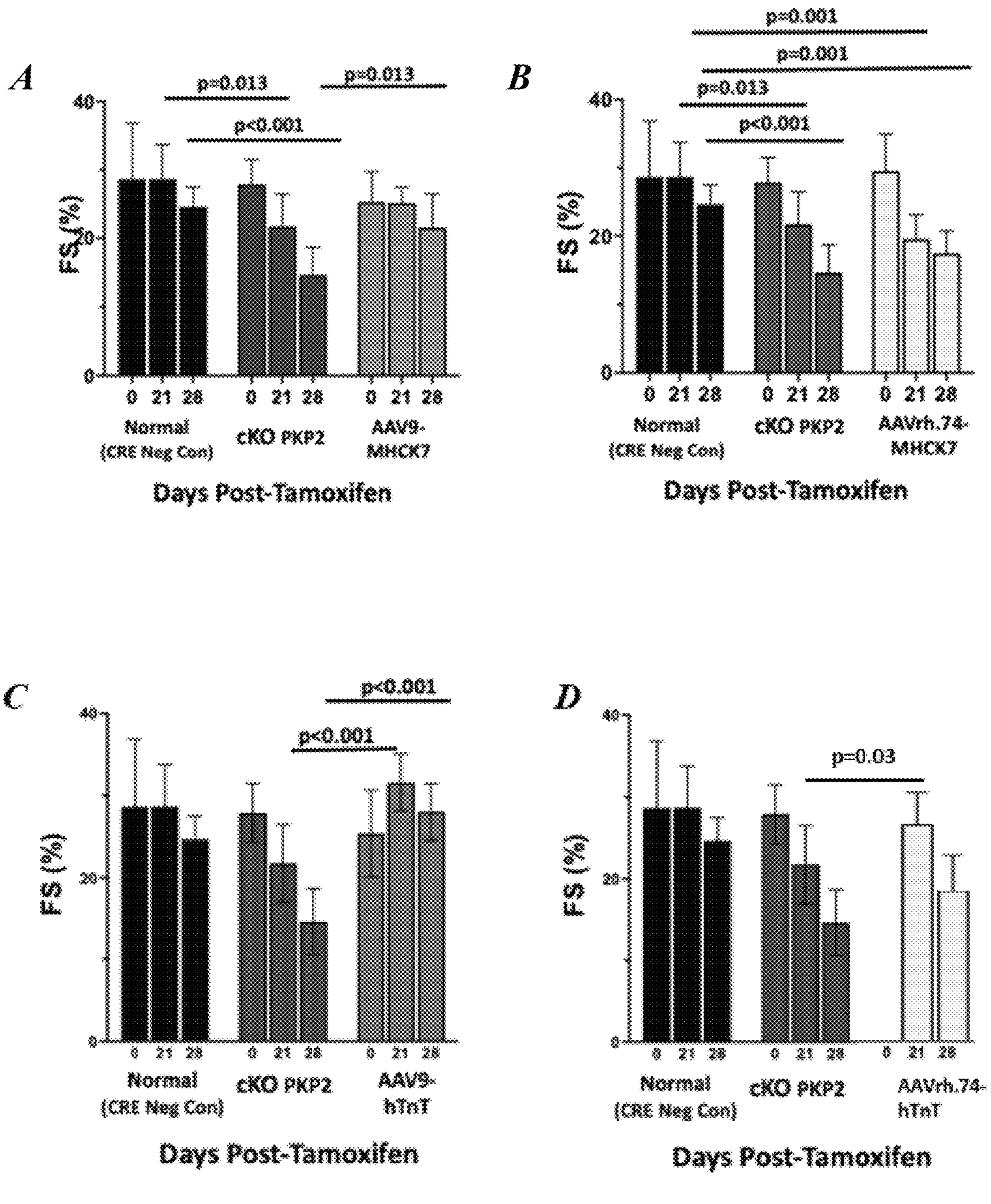
FIGS. 7A-7D show left ventricle fractional shortening percentage (FS %) for normal mice (left bars), untreated PKP2 knockout mice (middle bars, cKO PKP2), or treated mice (right bars).
Figures 8A, 8B, 8C, 8D:
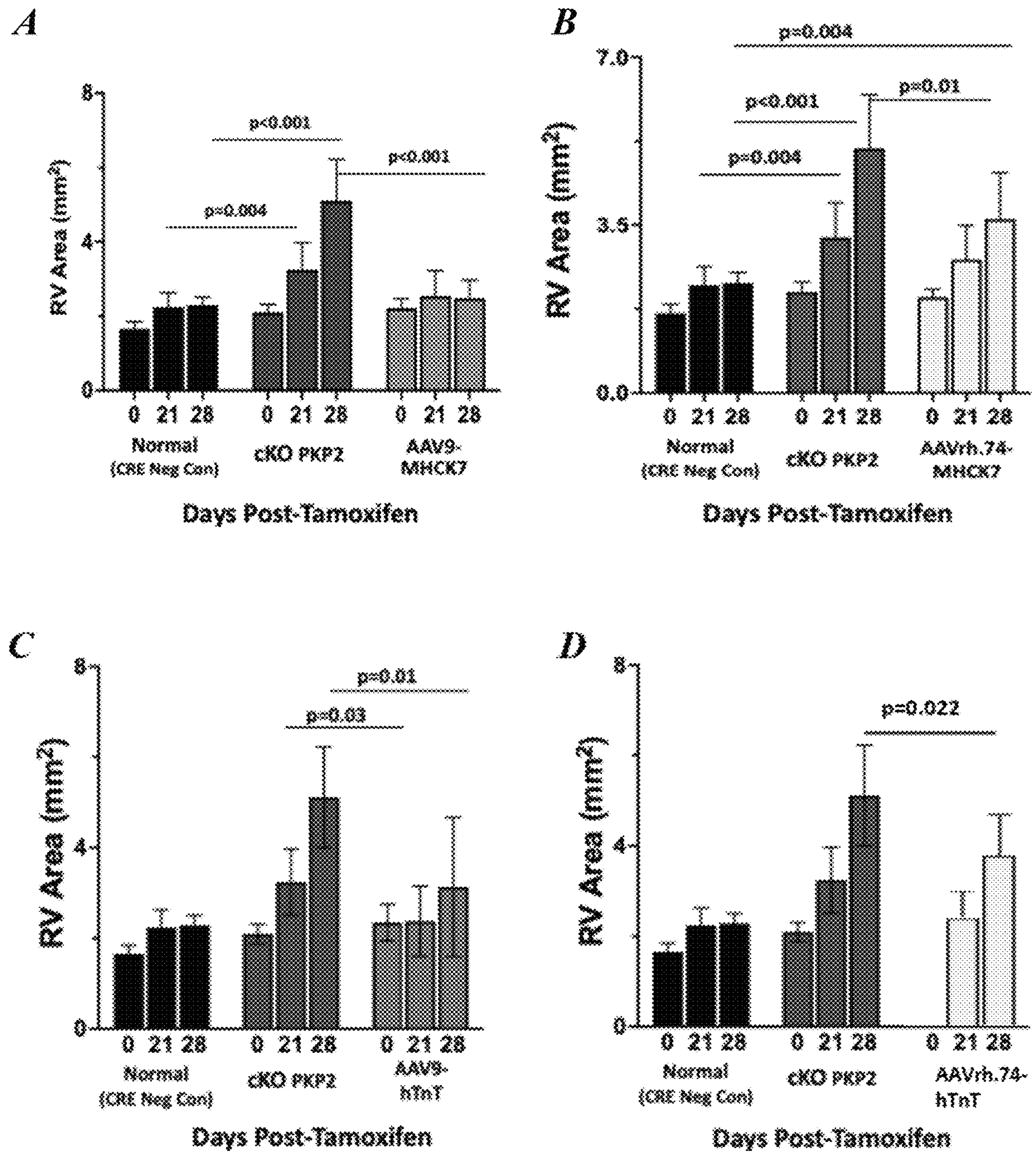
FIGS. 8A-8D show right ventricle area in millimeters squared (RV Area ($mm^2$)) for normal mice (left bars), untreated PKP2 knockout mice (middle bars, cKO PKP2), or treated mice (right bars).
Figures 9A, 9B, 9C, 9D:
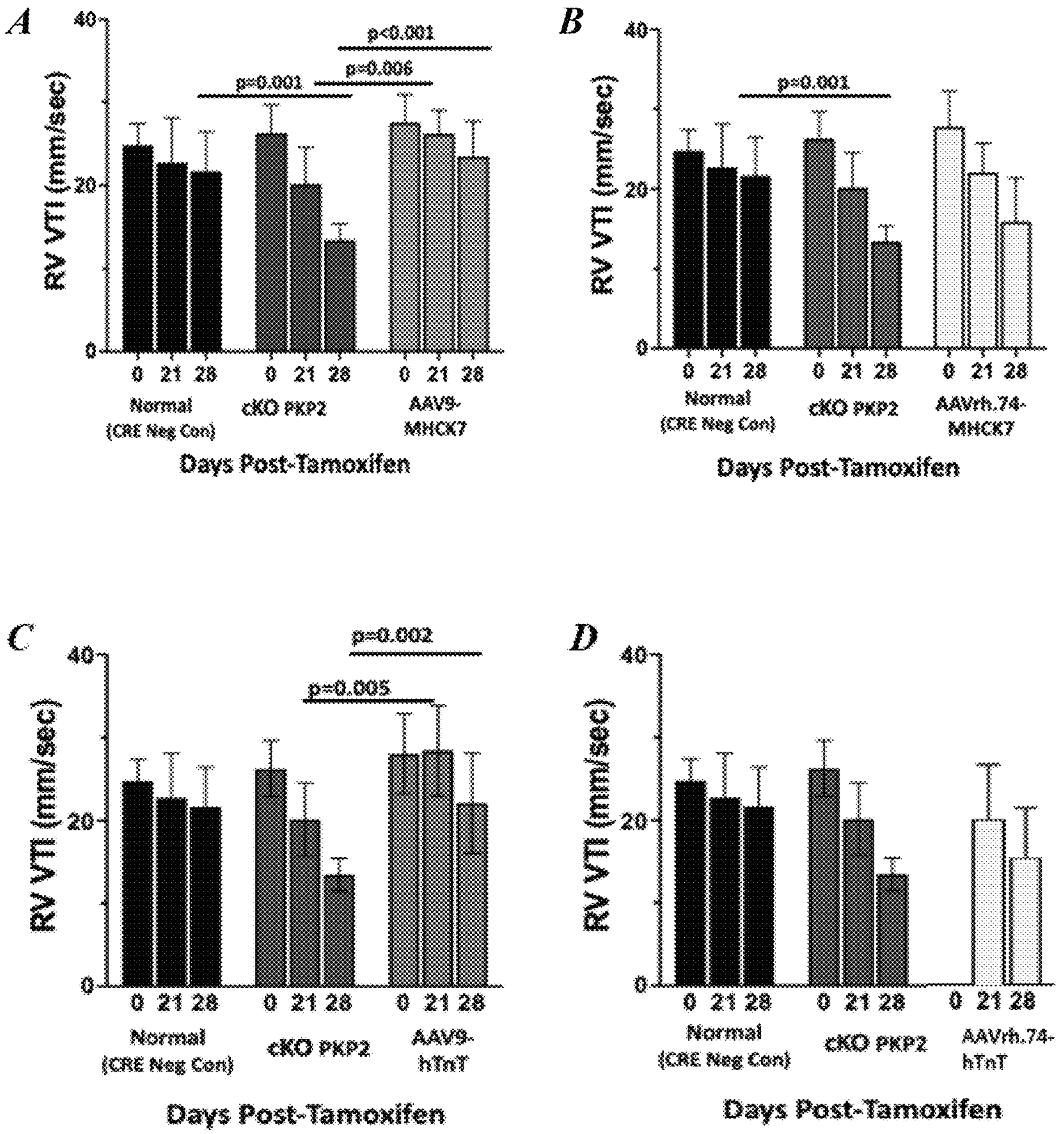
FIGS. 9A-9D show right ventricle velocity time integral in millimeters per second (RV VTI (mm/sec)) for normal mice (left bars), untreated PKP2 knockout mice (middle bars, cKO PKP2), or treated mice (right bars).

AAV vectors are described herein (see FIGS. 11-12) were prepared and used to transduce differentiated AC16 cells, a human cardiomyocyte cell line. Expression levels of PKP2 (PKP2a isoform) were assessed by Western Blot (FIGS. 5A-5B). Surprisingly, the MHCK7 promoter causes robust expression of PKP2 in cardiomyocytes, whereas the hTnnT2 promoter ("hTnT") generates marginal PKP2 levels above background under the current testing conditions. The AAVrh.74 serotype induced higher expression of PKP2 than the AAV9 serotype vector.

Based on these results, we conclude that AAV9 vectors or AAVrh74 vectors can effectively be used to express PKP2 in cardiomyocytes, and that the MHCK7 promoter is superior to the hTnnT2 promoter when solely evaluating the relative levels of PKP2 expression.

Example 3: In Vivo Efficacy of Adeno-Associated Virus Vectors

A "PKP2-cKO" mouse model of PKP2-deficiency, as described in Cerrone et al., Nat Comm., 2017 was obtained. This cardiomyocyte-specific, tamoxifen-activated PKP2 knockout murine line (aMHC-Cre-ER(T2)/Pkp2 fl/fl; referred to as "PKP2-cKO") was utilized to control the onset of PKP2 loss of expression (see Cerrone et al., Nat Comm, 2017). The conditional loss of PKP2 expression in this mouse model is limited to adult myocytes and the temporal progression of the molecular, structural and functional events as a consequence of PKP2-cKO have been established (Cerrone et al., Nat Comm, 2017). PKP2 deficiency in adult ventricular myocytes is sufficient to cause an arrhythmogenic cardiomyopathy of RV predominance, which includes the 'hallmark' functional, molecular, and structural indices consistent with the disease phenotype of ARVC.

PKP2-Cko mice were injected with tamoxifen, causing myocyte-specific knockout of PKP2. Mice were injected with AAV vectors (as described below) at $3\times10^{13}$ vg/kg by intravenous (tail vein) injection. Four weeks later, myocyte-specific knockout of PKP2 was induced by treatment of the mice with tamoxifen. The vector genomes used were:

5' ITR; MHCK7 promoter (with its enhancer element); SV40 intron; Kozak sequence; PKPa transgene; WPRE(x); hGH polyadenylation sequence); 3' ITR—shown in FIG. 11

5' ITR; hTnnT2 promoter (with exon 1); Kozak sequence; PKPa transgene; WPRE(x); hGH polyadenylation sequence); 3' ITR—shown in FIG. 12.

Each vector genome was tested in a AAV9 serotype or AAVrh74 serotype vector.

Figure 10A:
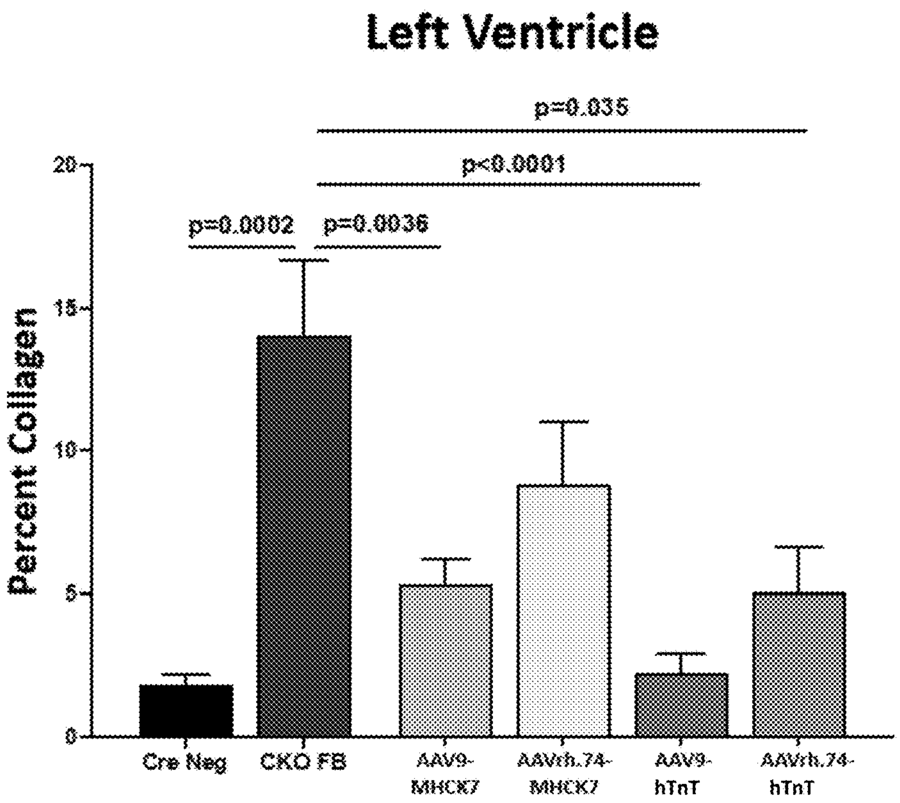
FIGS. 10A-10B illustrate the degree of fibrosis in left and right ventricles based on quantitation of the Percent Collagen following trichrome histological staining of the heart. Control animals without the conditional PKP2 gene knock-out (Cre Neg group) were found to have very little collagen, while control PKP2 knock-out animals receiving Formulation Buffer (CKO FB group) were found to have substantially greater proportion of collagen in both left and right ventricles. AAV-mediated overexpression of PKP2 resulted in robust attenuation of collagen, to varying degrees, in all AAV-injected groups [n=4 for all groups; p-values reflect results from One-way ANOVA with Bonferroni post-hoc analyses].
Figure 10B:
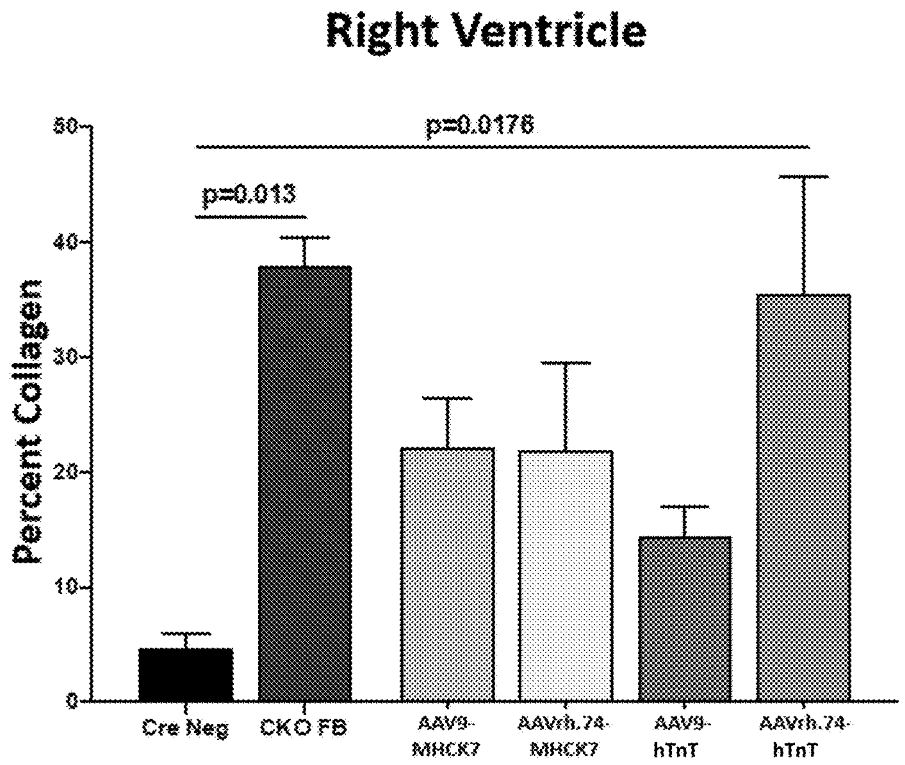
Figure 11:
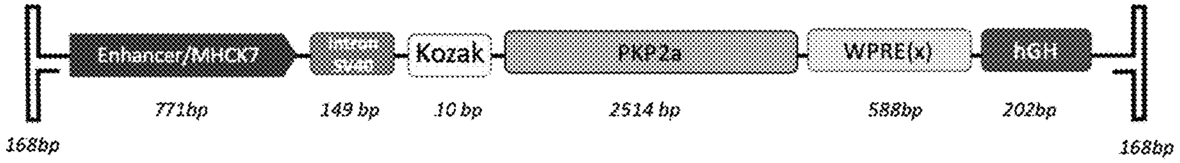
FIG. 11 shows a diagram illustrating a non-limiting example of a vector genome. The full polynucleotide sequence of the vector genome is SEQ ID NO: 89. The expression cassette is SEQ ID NO: 93. The MHCK7 promoter as described herein is labelled "Enhancer/MHCK7" in the diagram.
Figure 12:
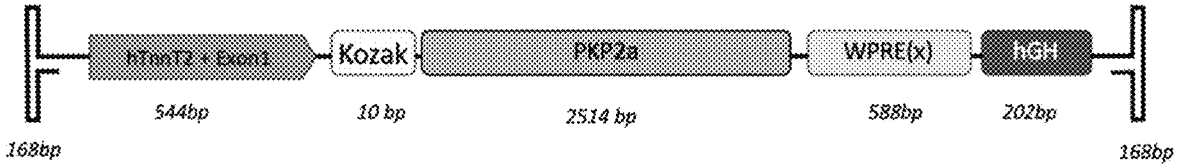
FIG. 12 shows a diagram illustrating a non-limiting example of a vector genome. The full polynucleotide sequence of the vector genome is SEQ ID NO: 90. The expression cassette is SEQ ID NO: 94.
Figure 13:
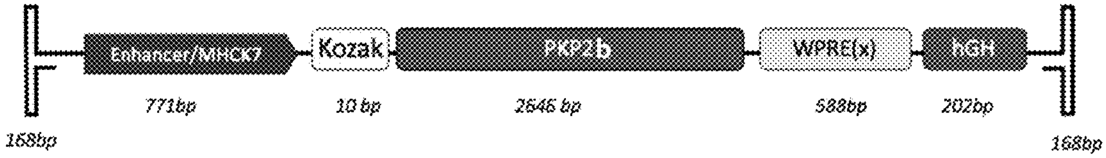
FIG. 13 shows a diagram illustrating a non-limiting example of a vector genome. The full polynucleotide sequence of the vector genome is SEQ ID NO: 91. The expression cassette is SEQ ID NO: 95. The MHCK7 promoter as described herein is labelled "Enhancer/MHCK7" in the diagram.

At 21 or 28 days after tamoxifen treatment, which is 25 or 32 weeks after AAV treatment, mice were evaluated for various physiology parameters, essentially as described in Cerrone et al., Nat Comm, 2017 or using standard methodologies known in the art. Efficacy in treating disease was assessed by left ventricle ejection fraction percentage (LVEF %) (FIGS. 6A-6D), left ventricle fractional shortening percentage (FS %) (FIGS. 7A-7D), right ventricle area in millimeters squared (RV Area ($mm^2$)) (FIGS. 8A-8D), right ventricle velocity time integral in millimeters per second (RV VTI (mm/sec)) (FIGS. 9A-9D), and degree of fibrosis (FIGS. 10A-10B). These measures are appropriate functional and morphological indices to evaluate potential efficacy of AAV-mediated PKP2 overexpression in cardiomyocytes as they are among key parameters indicative of ARVC in human disease. Generally, a right ventricle normally has slightly greater amount of fibrosis (irrespective of disease); and this is further exacerbated with lack of PKP2 in the cKO model. Progressive deterioration of these parameters was observed within 21 days of tamoxifen injection, because tamoxifen injection causes myocyte-specific knockout of the PKP gene.

Evidence for mitigation of the disease phenotype was observed following both AAV9- and AAVrh.74-mediated PKP expression, to varying degrees. With the dose studied to date ($3\times10^{13}$ vg/kg) using a pre-treatment paradigm (AAV 4 weeks prior to tamoxifen-induced PKP cKO), AAV9 surprisingly produced the most robust effects on all parameters. Nevertheless, given the cardiotropism of AAVrh74 and given that biological effects were observed with AAVrh.74-mediated overexpression of PKP2 in this model (e.g. LVEF %, FS %, and right ventricular area), optimization of the dose of AAVrh.74 in combination with the appropriate promoter (i.e., either MHCK7 or hTnnT2) could enable robust therapeutic potential for this vector.

These results demonstrate both AAV9 and AAVrh.74 can be used to treat PKP2-related diseases, such as Arrhythmogenic right ventricular cardiomyopathy (ARVC) [also known as Arrhythmogenic Right Ventricular Dysplasia (ARVD) or Arrhythmogenic Cardiomyopathy (ACM)] for which the PKP-cKO mouse is considered an appropriate model. Additionally, vectors with either MHCK7 promoter or hTnnT2 promoter have been demonstrated to be effective in treating PKP2-related disease.

The invention claimed is:

1. A method of treating arrhythmogenic cardiomyopathy (ACM) in a subject having a mutation in a Plakophilin-2 (PKP2) gene, comprising:

administering to the subject by intravenous administration, intracoronary administration, intracardiac administration, or cardiac catheterization, a recombinant adeno-associated virus (rAAV) vector comprising a vector genome, wherein the vector genome comprises an expression cassette and flanking AAV inverted terminal repeats (ITRs), the expression cassette comprising a polynucleotide comprising:

a polynucleotide sequence encoding a PKP2;

a promoter sequence, wherein the promoter sequence is operatively linked to the polynucleotide sequence encoding the PKP2; and a polyA sequence, wherein the rAAV vector is a recombinant AAVrh74 vector, wherein the promoter sequence comprises a human cardiac troponin T (hTNNT2) promoter and exon 1 of the hTNNT2 gene, wherein the promoter sequence shares at least 98% polynucleotide sequence identity with SEQ ID NO: 32; and wherein the PKP2 is PKP2 isoform A and shares at least 90% polypeptide sequence identity with SEQ ID NO: 1.

2. The method of claim 1, wherein the rAAV vector comprises a capsid protein that shares at least 95% polypeptide sequence identity to SEQ ID NO: 81.

3. The method of claim 1, wherein the rAAV vector comprises a capsid protein that shares 99% polypeptide sequence identity to SEQ ID NO: 81.

4. The method of claim 1, wherein the rAAV vector comprises a capsid protein that shares 100% polypeptide sequence identity to SEQ ID NO: 81.

5. The method of claim 1, wherein the polyA sequence is a human growth hormone (hGH) polyA.

6. The method of claim 1, wherein the rAAV vector is administered by injection or infusion.

7. The method of claim 1, wherein the rAAV vector is administered at a dose of between about $1\times10^{13}$ and $5\times10^{14}$ vg/kg.

8. The method of claim 1, wherein the rAAV vector is administered at a dose of between about $5\times10^{13}$ and $3\times10^{14}$ vg/kg.

9. The method of claim 1, wherein the rAAV vector is administered at a dose of about $2\times10^{14}$ vg/kg.

10. The method of claim 1, wherein the ACM is arrhythmogenic right ventricular cardiomyopathy (ARVC).

11. The method of claim 1, wherein the recombinant adeno-associated virus (rAAV) vector is administered intravenously.

12. The method of claim 1, wherein the recombinant adeno-associated virus (rAAV) vector is administered by intracoronary administration, intracardiac administration, or cardiac catheterization.

* * * * *

SEQUENCE LISTING

```
<160> NUMBER OF SEQ ID NOS: 96

<210> SEQ ID NO 1
<211> LENGTH: 837
<212> TYPE: PRT
<213> ORGANISM: Homo sapiens

<400> SEQUENCE: 1

Met Ala Ala Pro Gly Ala Pro Ala Glu Tyr Gly Tyr Ile Arg Thr Val
```

-continued

```
1               5                   10                  15

Leu Gly Gln Gln Ile Leu Gly Gln Leu Asp Ser Ser Ser Leu Ala Leu
            20                  25                  30

Pro Ser Glu Ala Lys Leu Lys Leu Ala Gly Ser Ser Gly Arg Gly Gly
        35                  40                  45

Gln Thr Val Lys Ser Leu Arg Ile Gln Glu Gln Val Gln Gln Thr Leu
    50                  55                  60

Ala Arg Lys Gly Arg Ser Ser Val Gly Asn Gly Asn Leu His Arg Thr
65                  70                  75                  80

Ser Ser Val Pro Glu Tyr Val Tyr Asn Leu His Leu Val Glu Asn Asp
                85                  90                  95

Phe Val Gly Gly Arg Ser Pro Val Pro Lys Thr Tyr Asp Met Leu Lys
            100                 105                 110

Ala Gly Thr Thr Ala Thr Tyr Glu Gly Arg Trp Gly Arg Gly Thr Ala
        115                 120                 125

Gln Tyr Ser Ser Gln Lys Ser Val Glu Glu Arg Ser Leu Arg His Pro
    130                 135                 140

Leu Arg Arg Leu Glu Ile Ser Pro Asp Ser Ser Pro Glu Arg Ala His
145                 150                 155                 160

Tyr Thr His Ser Asp Tyr Gln Tyr Ser Gln Arg Ser Gln Ala Gly His
                165                 170                 175

Thr Leu His His Gln Glu Ser Arg Arg Ala Ala Leu Leu Val Pro Pro
            180                 185                 190

Arg Tyr Ala Arg Ser Glu Ile Val Gly Val Ser Arg Ala Gly Thr Thr
        195                 200                 205

Ser Arg Gln Arg His Phe Asp Thr Tyr His Arg Gln Tyr Gln His Gly
    210                 215                 220

Ser Val Ser Asp Thr Val Phe Asp Ser Ile Pro Ala Asn Pro Ala Leu
225                 230                 235                 240

Leu Thr Tyr Pro Arg Pro Gly Thr Ser Arg Ser Met Gly Asn Leu Leu
                245                 250                 255

Glu Lys Glu Asn Tyr Leu Thr Ala Gly Leu Thr Val Gly Gln Val Arg
            260                 265                 270

Pro Leu Val Pro Leu Gln Pro Val Thr Gln Asn Arg Ala Ser Arg Ser
        275                 280                 285

Ser Trp His Gln Ser Ser Phe His Ser Thr Arg Thr Leu Arg Glu Ala
    290                 295                 300

Gly Pro Ser Val Ala Val Asp Ser Ser Gly Arg Arg Ala His Leu Thr
305                 310                 315                 320

Val Gly Gln Ala Ala Ala Gly Gly Ser Gly Asn Leu Leu Thr Glu Arg
                325                 330                 335

Ser Thr Phe Thr Asp Ser Gln Leu Gly Asn Ala Asp Met Glu Met Thr
            340                 345                 350

Leu Glu Arg Ala Val Ser Met Leu Glu Ala Asp His Met Leu Pro Ser
        355                 360                 365

Arg Ile Ser Ala Ala Ala Thr Phe Ile Gln His Glu Cys Phe Gln Lys
    370                 375                 380

Ser Glu Ala Arg Lys Arg Val Asn Gln Leu Arg Gly Ile Leu Lys Leu
385                 390                 395                 400

Leu Gln Leu Leu Lys Val Gln Asn Glu Asp Val Gln Arg Ala Val Cys
                405                 410                 415

Gly Ala Leu Arg Asn Leu Val Phe Glu Asp Asn Asp Asn Lys Leu Glu
            420                 425                 430
```

-continued

```
Val Ala Glu Leu Asn Gly Val Pro Arg Leu Leu Gln Val Leu Lys Gln
        435                 440                 445

Thr Arg Asp Leu Glu Thr Lys Lys Gln Ile Thr Gly Leu Leu Trp Asn
    450                 455                 460

Leu Ser Ser Asn Asp Lys Leu Lys Asn Leu Met Ile Thr Glu Ala Leu
465                 470                 475                 480

Leu Thr Leu Thr Glu Asn Ile Ile Ile Pro Phe Ser Gly Trp Pro Glu
                485                 490                 495

Gly Asp Tyr Pro Lys Ala Asn Gly Leu Leu Asp Phe Asp Ile Phe Tyr
            500                 505                 510

Asn Val Thr Gly Cys Leu Arg Asn Met Ser Ser Ala Gly Ala Asp Gly
        515                 520                 525

Arg Lys Ala Met Arg Arg Cys Asp Gly Leu Ile Asp Ser Leu Val His
    530                 535                 540

Tyr Val Arg Gly Thr Ile Ala Asp Tyr Gln Pro Asp Asp Lys Ala Thr
545                 550                 555                 560

Glu Asn Cys Val Cys Ile Leu His Asn Leu Ser Tyr Gln Leu Glu Ala
                565                 570                 575

Glu Leu Pro Glu Lys Tyr Ser Gln Asn Ile Tyr Ile Gln Asn Arg Asn
            580                 585                 590

Ile Gln Thr Asp Asn Asn Lys Ser Ile Gly Cys Phe Gly Ser Arg Ser
        595                 600                 605

Arg Lys Val Lys Glu Gln Tyr Gln Asp Val Pro Met Pro Glu Glu Lys
    610                 615                 620

Ser Asn Pro Lys Gly Val Glu Trp Leu Trp His Ser Ile Val Ile Arg
625                 630                 635                 640

Met Tyr Leu Ser Leu Ile Ala Lys Ser Val Arg Asn Tyr Thr Gln Glu
                645                 650                 655

Ala Ser Leu Gly Ala Leu Gln Asn Leu Thr Ala Gly Ser Gly Pro Met
            660                 665                 670

Pro Thr Ser Val Ala Gln Thr Val Val Gln Lys Glu Ser Gly Leu Gln
        675                 680                 685

His Thr Arg Lys Met Leu His Val Gly Asp Pro Ser Val Lys Lys Thr
    690                 695                 700

Ala Ile Ser Leu Leu Arg Asn Leu Ser Arg Asn Leu Ser Leu Gln Asn
705                 710                 715                 720

Glu Ile Ala Lys Glu Thr Leu Pro Asp Leu Val Ser Ile Ile Pro Asp
                725                 730                 735

Thr Val Pro Ser Thr Asp Leu Leu Ile Glu Thr Thr Ala Ser Ala Cys
            740                 745                 750

Tyr Thr Leu Asn Asn Ile Ile Gln Asn Ser Tyr Gln Asn Ala Arg Asp
        755                 760                 765

Leu Leu Asn Thr Gly Gly Ile Gln Lys Ile Met Ala Ile Ser Ala Gly
    770                 775                 780

Asp Ala Tyr Ala Ser Asn Lys Ala Ser Lys Ala Ala Ser Val Leu Leu
785                 790                 795                 800

Tyr Ser Leu Trp Ala His Thr Glu Leu His His Ala Tyr Lys Lys Ala
                805                 810                 815

Gln Phe Lys Lys Thr Asp Phe Val Asn Ser Arg Thr Ala Lys Ala Tyr
            820                 825                 830

His Ser Leu Lys Asp
        835
```

<210> SEQ ID NO 2
<211> LENGTH: 881
<212> TYPE: PRT
<213> ORGANISM: Homo sapiens

<400> SEQUENCE: 2

Met Ala Ala Pro Gly Ala Pro Ala Glu Tyr Gly Tyr Ile Arg Thr Val
1 5 10 15

Leu Gly Gln Gln Ile Leu Gly Gln Leu Asp Ser Ser Ser Leu Ala Leu
20 25 30

Pro Ser Glu Ala Lys Leu Lys Leu Ala Gly Ser Ser Gly Arg Gly Gly
35 40 45

Gln Thr Val Lys Ser Leu Arg Ile Gln Glu Gln Val Gln Gln Thr Leu
50 55 60

Ala Arg Lys Gly Arg Ser Ser Val Gly Asn Gly Asn Leu His Arg Thr
65 70 75 80

Ser Ser Val Pro Glu Tyr Val Tyr Asn Leu His Leu Val Glu Asn Asp
85 90 95

Phe Val Gly Gly Arg Ser Pro Val Pro Lys Thr Tyr Asp Met Leu Lys
100 105 110

Ala Gly Thr Thr Ala Thr Tyr Glu Gly Arg Trp Gly Arg Gly Thr Ala
115 120 125

Gln Tyr Ser Ser Gln Lys Ser Val Glu Glu Arg Ser Leu Arg His Pro
130 135 140

Leu Arg Arg Leu Glu Ile Ser Pro Asp Ser Ser Pro Glu Arg Ala His
145 150 155 160

Tyr Thr His Ser Asp Tyr Gln Tyr Ser Gln Arg Ser Gln Ala Gly His
165 170 175

Thr Leu His His Gln Glu Ser Arg Arg Ala Ala Leu Leu Val Pro Pro
180 185 190

Arg Tyr Ala Arg Ser Glu Ile Val Gly Val Ser Arg Ala Gly Thr Thr
195 200 205

Ser Arg Gln Arg His Phe Asp Thr Tyr His Arg Gln Tyr Gln His Gly
210 215 220

Ser Val Ser Asp Thr Val Phe Asp Ser Ile Pro Ala Asn Pro Ala Leu
225 230 235 240

Leu Thr Tyr Pro Arg Pro Gly Thr Ser Arg Ser Met Gly Asn Leu Leu
245 250 255

Glu Lys Glu Asn Tyr Leu Thr Ala Gly Leu Thr Val Gly Gln Val Arg
260 265 270

Pro Leu Val Pro Leu Gln Pro Val Thr Gln Asn Arg Ala Ser Arg Ser
275 280 285

Ser Trp His Gln Ser Ser Phe His Ser Thr Arg Thr Leu Arg Glu Ala
290 295 300

Gly Pro Ser Val Ala Val Asp Ser Ser Gly Arg Arg Ala His Leu Thr
305 310 315 320

Val Gly Gln Ala Ala Ala Gly Gly Ser Gly Asn Leu Leu Thr Glu Arg
325 330 335

Ser Thr Phe Thr Asp Ser Gln Leu Gly Asn Ala Asp Met Glu Met Thr
340 345 350

Leu Glu Arg Ala Val Ser Met Leu Glu Ala Asp His Met Leu Pro Ser
355 360 365

Arg Ile Ser Ala Ala Ala Thr Phe Ile Gln His Glu Cys Phe Gln Lys
370 375 380

-continued

```
Ser Glu Ala Arg Lys Arg Val Asn Gln Leu Arg Gly Ile Leu Lys Leu
385                 390                 395                 400

Leu Gln Leu Leu Lys Val Gln Asn Glu Asp Val Gln Arg Ala Val Cys
                405                 410                 415

Gly Ala Leu Arg Asn Leu Val Phe Glu Asp Asn Asp Asn Lys Leu Glu
            420                 425                 430

Val Ala Glu Leu Asn Gly Val Pro Arg Leu Leu Gln Val Leu Lys Gln
        435                 440                 445

Thr Arg Asp Leu Glu Thr Lys Lys Gln Ile Thr Asp His Thr Val Asn
    450                 455                 460

Leu Arg Ser Arg Asn Gly Trp Pro Gly Ala Val Ala His Ala Cys Asn
465                 470                 475                 480

Pro Ser Thr Leu Gly Gly Gln Gly Gly Arg Ile Thr Arg Ser Gly Val
                485                 490                 495

Arg Asp Gln Pro Asp Gln His Gly Leu Leu Trp Asn Leu Ser Ser Asn
            500                 505                 510

Asp Lys Leu Lys Asn Leu Met Ile Thr Glu Ala Leu Leu Thr Leu Thr
        515                 520                 525

Glu Asn Ile Ile Ile Pro Phe Ser Gly Trp Pro Glu Gly Asp Tyr Pro
    530                 535                 540

Lys Ala Asn Gly Leu Leu Asp Phe Asp Ile Phe Tyr Asn Val Thr Gly
545                 550                 555                 560

Cys Leu Arg Asn Met Ser Ser Ala Gly Ala Asp Gly Arg Lys Ala Met
                565                 570                 575

Arg Arg Cys Asp Gly Leu Ile Asp Ser Leu Val His Tyr Val Arg Gly
            580                 585                 590

Thr Ile Ala Asp Tyr Gln Pro Asp Asp Lys Ala Thr Glu Asn Cys Val
        595                 600                 605

Cys Ile Leu His Asn Leu Ser Tyr Gln Leu Glu Ala Glu Leu Pro Glu
    610                 615                 620

Lys Tyr Ser Gln Asn Ile Tyr Ile Gln Asn Arg Asn Ile Gln Thr Asp
625                 630                 635                 640

Asn Asn Lys Ser Ile Gly Cys Phe Gly Ser Arg Ser Arg Lys Val Lys
                645                 650                 655

Glu Gln Tyr Gln Asp Val Pro Met Pro Glu Glu Lys Ser Asn Pro Lys
            660                 665                 670

Gly Val Glu Trp Leu Trp His Ser Ile Val Ile Arg Met Tyr Leu Ser
        675                 680                 685

Leu Ile Ala Lys Ser Val Arg Asn Tyr Thr Gln Glu Ala Ser Leu Gly
    690                 695                 700

Ala Leu Gln Asn Leu Thr Ala Gly Ser Gly Pro Met Pro Thr Ser Val
705                 710                 715                 720

Ala Gln Thr Val Val Gln Lys Glu Ser Gly Leu Gln His Thr Arg Lys
                725                 730                 735

Met Leu His Val Gly Asp Pro Ser Val Lys Lys Thr Ala Ile Ser Leu
            740                 745                 750

Leu Arg Asn Leu Ser Arg Asn Leu Ser Leu Gln Asn Glu Ile Ala Lys
        755                 760                 765

Glu Thr Leu Pro Asp Leu Val Ser Ile Ile Pro Asp Thr Val Pro Ser
    770                 775                 780

Thr Asp Leu Leu Ile Glu Thr Thr Ala Ser Ala Cys Tyr Thr Leu Asn
785                 790                 795                 800
```

-continued

```
Asn Ile Ile Gln Asn Ser Tyr Gln Asn Ala Arg Asp Leu Leu Asn Thr
                805                 810                 815

Gly Gly Ile Gln Lys Ile Met Ala Ile Ser Ala Gly Asp Ala Tyr Ala
            820                 825                 830

Ser Asn Lys Ala Ser Lys Ala Ala Ser Val Leu Leu Tyr Ser Leu Trp
        835                 840                 845

Ala His Thr Glu Leu His His Ala Tyr Lys Lys Ala Gln Phe Lys Lys
    850                 855                 860

Thr Asp Phe Val Asn Ser Arg Thr Ala Lys Ala Tyr His Ser Leu Lys
865                 870                 875                 880

Asp


<210> SEQ ID NO 3
<211> LENGTH: 2511
<212> TYPE: DNA
<213> ORGANISM: Homo sapiens

<400> SEQUENCE: 3

atggcagccc ccggcgcccc agctgagtac ggctacatcc ggaccgtcct gggccagcag     60

atcctgggac aactggacag ctccagcctg gcgctgccct ccgaggccaa gctgaagctg    120

gcggggagca gcggccgcgg cggccagaca gtcaagagcc tgcggatcca ggagcaggtg    180

cagcagaccc tcgcccggaa gggccgcagc tccgtgggca acggaaatct tcaccgaacc    240

agcagtgttc ctgagtatgt ctacaaccta cacttggttg aaaatgattt tgttggaggc    300

cgttcccctg ttcctaaaac ctatgacatg ctaaaggctg gcacaactgc cacttatgaa    360

ggtcgctggg gaagaggaac agcacagtac agctcccaga agtccgtgga agaaaggtcc    420

ttgaggcatc ctctgaggag actggagatt tctcctgaca gcagcccgga gagggctcac    480

tacacgcaca gcgattacca gtacagccag agaagccagg ctgggcacac cctgcaccac    540

caagaaagca ggcgggccgc cctcctagtg ccaccgagat atgctcgttc cgagatcgtg    600

ggggtcagcc gtgctggcac cacaagcagg cagcgccact ttgacacata ccacagacag    660

taccagcatg gctctgttag cgacaccgtt tttgacagca tccctgccaa cccggccctg    720

ctcacgtacc ccaggccagg gaccagccgc agcatgggca acctcttgga gaaggagaac    780

tacctgacgg cagggctcac tgtcgggcag gtcaggccgc tggtgcccct gcagcccgtc    840

actcagaaca gggcttccag gtcctcctgg catcagagct ccttccacag cacccgcacg    900

ctgagggaag ctgggcccag tgtcgccgtg gattccagcg ggaggagagc gcacttgact    960

gtcggccagg cggccgcagg gggaagtggg aatctgctca ctgagagaag cactttcact   1020

gactcccagc tggggaatgc agacatggag atgactctgg agcgagcagt gagtatgctc   1080

gaggcagacc acatgctgcc atccaggatt tctgctgcag ctactttcat acagcacgag   1140

tgcttccaga aatctgaagc tcggaagagg gttaaccagc ttcgtggcat cctcaagctt   1200

ctgcagctcc taaaagttca gaatgaagac gttcagcgag ctgtgtgtgg ggccttgaga   1260

aacttagtat ttgaagacaa tgacaacaaa ttggaggtgg ctgaactaaa tggggtacct   1320

cggctgctcc aggtgctgaa gcaaaccaga gacttggaga ctaaaaaaca aataacaggt   1380

ttgctgtgga atttgtcatc taatgacaaa ctcaagaatc tcatgataac agaagcattg   1440

cttacgctga cggagaatat catcatcccc ttttctgggt ggcctgaagg agactaccca   1500

aaagcaaatg gtttgctcga ttttgacata ttctacaacg tcactggatg cctaagaaac   1560

atgagttctg ctggcgctga tgggagaaaa gcgatgagaa gatgtgacgg actcattgac   1620
```

```
tcactggtcc attatgtcag aggaaccatt gcagattacc agccagatga caaggccacg   1680
gagaattgtg tgtgcattct tcataacctc tcctaccagc tggaggcaga gctcccagag   1740
aaatattccc agaatatcta tattcaaaac cggaatatcc agactgacaa caacaaaagt   1800
attggatgtt ttggcagtcg aagcaggaaa gtaaaagagc aataccagga cgtgccgatg   1860
ccggaggaaa agagcaaccc caagggcgtg gagtggctgt ggcattccat tgttataagg   1920
atgtatctgt ccttgatcgc caaaagtgtc cgcaactaca cacaagaagc atccttagga   1980
gctctgcaga acctcacggc cggaagtgga ccaatgccga catcagtggc tcagacagtt   2040
gtccagaagg aaagtggcct gcagcacacc cgaaagatgc tgcatgttgg tgacccaagt   2100
gtgaaaaaga cagccatctc gctgctgagg aatctgtccc ggaatctttc tctgcagaat   2160
gaaattgcca aagaaactct ccctgatttg gtttccatca ttcctgacac agtcccgagt   2220
actgaccttc tcattgaaac tacagcctct gcctgttaca cattgaacaa cataatccaa   2280
aacagttacc agaatgcacg cgaccttcta aacaccgggg gcatccagaa aattatggcc   2340
attagtgcag gcgatgccta tgcctccaac aaagcaagta aagctgcttc cgtccttctg   2400
tattctctgt gggcacacac ggaactgcat catgcctaca agaaggctca gtttaagaag   2460
acagattttg tcaacagccg gactgccaaa gcctaccact cccttaaaga c            2511
```

<210> SEQ ID NO 4
<211> LENGTH: 2643
<212> TYPE: DNA
<213> ORGANISM: Homo sapiens

<400> SEQUENCE: 4

```
atggcagccc ccggcgcccc agctgagtac ggctacatcc ggaccgtcct gggccagcag     60
atcctgggac aactggacag ctccagcctg gcgctgccct ccgaggccaa gctgaagctg    120
gcggggagca gcggccgcgg cggccagaca gtcaagagcc tgcggatcca ggagcaggtg    180
cagcagaccc tcgcccggaa gggccgcagc tccgtgggca acggaaatct tcaccgaacc    240
agcagtgttc ctgagtatgt ctacaaccta cacttggttg aaaatgattt tgttggaggc    300
cgttcccctg ttcctaaaac ctatgacatg ctaaaggctg gcacaactgc cacttatgaa    360
ggtcgctggg gaagaggaac agcacagtac agctcccaga agtccgtgga agaaaggtcc    420
ttgaggcatc ctctgaggag actggagatt tctcctgaca gcagcccgga gagggctcac    480
tacacgcaca gcgattacca gtacagccag agaagccagg ctgggcacac cctgcaccac    540
caagaaagca ggcgggccgc cctcctagtg ccaccgagat atgctcgttc cgagatcgtg    600
ggggtcagcc gtgctggcac cacaagcagg cagcgccact ttgacacata ccacagacag    660
taccagcatg gctctgttag cgacaccgtt tttgacagca tccctgccaa cccggccctg    720
ctcacgtacc ccaggccagg gaccagccgc agcatgggca acctcttgga gaaggagaac    780
tacctgacgg cagggctcac tgtcgggcag gtcaggccgc tggtgcccct gcagcccgtc    840
actcagaaca gggcttccag gtcctcctgg catcagagct ccttccacag cacccgcacg    900
ctgagggaag ctgggcccag tgtcgccgtg gattccagcg ggaggagagc gcacttgact    960
gtcggccagg cggccgcagg gggaagtggg aatctgctca ctgagagaag cactttcact   1020
gactcccagc tggggaatgc agacatggag atgactctgg agcgagcagt gagtatgctc   1080
gaggcagacc acatgctgcc atccaggatt tctgctgcag ctactttcat acagcacgag   1140
tgcttccaga aatctgaagc tcggaagagg gttaaccagc ttcgtggcat cctcaagctt   1200
ctgcagctcc taaaagttca gaatgaagac gttcagcgag ctgtgtgtgg ggccttgaga   1260
```

aacttagtat ttgaagacaa tgacaacaaa ttggaggtgg ctgaactaaa tggggtacct 1320
cggctgctcc aggtgctgaa gcaaaccaga gacttggaga ctaaaaaaca aataacagac 1380
catacagtca atttaagaag taggaatggc tggccgggcg cggtggctca cgcctgtaat 1440
cccagcactt tgggaggcca aggcgggcgg atcacgaggt caggagttcg agaccagcct 1500
gaccaacatg gtttgctgtg gaatttgtca tctaatgaca aactcaagaa tctcatgata 1560
acagaagcat tgcttacgct gacggagaat atcatcatcc ccttttctgg gtggcctgaa 1620
ggagactacc caaaagcaaa tggtttgctc gattttgaca tattctacaa cgtcactgga 1680
tgcctaagaa acatgagttc tgctggcgct gatgggagaa aagcgatgag aagatgtgac 1740
ggactcattg actcactggt ccattatgtc agaggaacca ttgcagatta ccagccagat 1800
gacaaggcca cggagaattg tgtgtgcatt cttcataacc tctcctacca gctggaggca 1860
gagctcccag agaaatattc ccagaatatc tatattcaaa accggaatat ccagactgac 1920
aacaacaaaa gtattggatg ttttggcagt cgaagcagga aagtaaaaga gcaataccag 1980
gacgtgccga tgccggagga aaagagcaac cccaagggcg tggagtggct gtggcattcc 2040
attgttataa ggatgtatct gtccttgatc gccaaaagtg tccgcaacta cacacaagaa 2100
gcatccttag gagctctgca gaacctcacg gccggaagtg gaccaatgcc gacatcagtg 2160
gctcagacag ttgtccagaa ggaaagtggc ctgcagcaca cccgaaagat gctgcatgtt 2220
ggtgacccaa gtgtgaaaaa gacagccatc tcgctgctga ggaatctgtc ccggaatctt 2280
tctctgcaga atgaaattgc caaagaaact ctccctgatt tggtttccat cattcctgac 2340
acagtcccga gtactgacct tctcattgaa actacagcct ctgcctgtta cacattgaac 2400
aacataatcc aaaacagtta ccagaatgca cgcgaccttc taaacaccgg gggcatccag 2460
aaaattatgg ccattagtgc aggcgatgcc tatgcctcca acaaagcaag taaagctgct 2520
tccgtccttc tgtattctct gtgggcacac acggaactgc atcatgccta caagaaggct 2580
cagtttaaga agacagattt tgtcaacagc cggactgcca aagcctacca ctcccttaaa 2640
gac 2643

<210> SEQ ID NO 5
<211> LENGTH: 10
<212> TYPE: DNA
<213> ORGANISM: Artificial Sequence
<220> FEATURE:
<223> OTHER INFORMATION: Kozak sequence motif

<400> SEQUENCE: 5
gccaccatgg 10

<210> SEQ ID NO 6
<211> LENGTH: 2517
<212> TYPE: DNA
<213> ORGANISM: Artificial Sequence
<220> FEATURE:
<223> OTHER INFORMATION: Polynucleotide encoding an PKP2a with Kozak sequence

<400> SEQUENCE: 6
gccaccatgg cagcccccgg cgccccagct gagtacggct acatccggac cgtcctgggc 60
cagcagatcc tgggacaact ggacagctcc agcctggcgc tgccctccga ggccaagctg 120
aagctggcgg ggagcagcgg ccgcggcggc cagacagtca agagcctgcg gatccaggag 180
caggtgcagc agaccctcgc ccggaagggc cgcagctccg tgggcaacgg aaatcttcac 240
cgaaccagca gtgttcctga gtatgtctac aacctacact tggttgaaaa tgattttgtt 300
ggaggccgtt cccctgttcc taaaacctat gacatgctaa aggctggcac aactgccact 360
tatgaaggtc gctggggaag aggaacagca cagtacagct cccagaagtc cgtggaagaa 420
aggtccttga ggcatcctct gaggagactg gagatttctc ctgacagcag cccggagagg 480
gctcactaca cgcacagcga ttaccagtac agccagagaa gccaggctgg gcacaccctg 540
caccaccaag aaagcaggcg ggccgccctc ctagtgccac cgagatatgc tcgttccgag 600
atcgtggggg tcagccgtgc tggcaccaca agcaggcagc gccactttga cacataccac 660
agacagtacc agcatggctc tgttagcgac accgtttttg acagcatccc tgccaacccg 720
gccctgctca cgtaccccag gccagggacc agccgcagca tgggcaacct cttggagaag 780
gagaactacc tgacggcagg gctcactgtc gggcaggtca ggccgctggt gcccctgcag 840
cccgtcactc agaacagggc ttccaggtcc tcctggcatc agagctcctt ccacagcacc 900
cgcacgctga gggaagctgg gcccagtgtc gccgtggatt ccagcgggag gagagcgcac 960
ttgactgtcg gccaggcggc cgcagggggga agtgggaatc tgctcactga gagaagcact 1020
ttcactgact cccagctggg gaatgcagac atggagatga ctctggagcg agcagtgagt 1080
atgctcgagg cagaccacat gctgccatcc aggatttctg ctgcagctac tttcatacag 1140
cacgagtgct tccagaaatc tgaagctcgg aagagggtta accagcttcg tggcatcctc 1200
aagcttctgc agctcctaaa agttcagaat gaagacgttc agcgagctgt gtgtggggcc 1260
ttgagaaact tagtatttga agacaatgac aacaaattgg aggtggctga actaaatggg 1320
gtacctcggc tgctccaggt gctgaagcaa accagagact tggagactaa aaaacaaata 1380
acaggtttgc tgtggaattt gtcatctaat gacaaactca agaatctcat gataacagaa 1440
gcattgctta cgctgacgga gaatatcatc atccccttt ctgggtggcc tgaaggagac 1500
tacccaaaag caaatggttt gctcgatttt gacatattct acaacgtcac tggatgccta 1560
agaaacatga gttctgctgg cgctgatggg agaaaagcga tgagaagatg tgacggactc 1620
attgactcac tggtccatta tgtcagagga accattgcag attaccagcc agatgacaag 1680
gccacggaga attgtgtgtg cattcttcat aacctctcct accagctgga ggcagagctc 1740
ccagagaaat attcccagaa tatctatatt caaaaccgga atatccagac tgacaacaac 1800
aaaagtattg gatgttttgg cagtcgaagc aggaaagtaa aagagcaata ccaggacgtg 1860
ccgatgccgg aggaaaagag caaccccaag ggcgtggagt ggctgtggca ttccattgtt 1920
ataaggatgt atctgtcctt gatcgccaaa agtgtccgca actacacaca agaagcatcc 1980
ttaggagctc tgcagaacct cacggccgga agtggaccaa tgccgacatc agtggctcag 2040
acagttgtcc agaaggaaag tggcctgcag cacacccgaa agatgctgca tgttggtgac 2100
ccaagtgtga aaaagacagc catctcgctg ctgaggaatc tgtcccggaa tctttctctg 2160
cagaatgaaa ttgccaaaga aactctccct gatttggttt ccatcattcc tgacacagtc 2220
ccgagtactg accttctcat tgaaactaca gcctctgcct gttacacatt gaacaacata 2280
atccaaaaca gttaccagaa tgcacgcgac cttctaaaca ccgggggcat ccagaaaatt 2340
atggccatta gtgcaggcga tgcctatgcc tccaacaaag caagtaaagc tgcttccgtc 2400
cttctgtatt ctctgtgggc acacacggaa ctgcatcatg cctacaagaa ggctcagttt 2460
aagaagacag attttgtcaa cagccggact gccaaagcct accactccct taaagac 2517

<210> SEQ ID NO 7

```
<211> LENGTH: 2649
<212> TYPE: DNA
<213> ORGANISM: Artificial Sequence
<220> FEATURE:
<223> OTHER INFORMATION: Polynucleotide encoding an PKP2b with Kozak
      sequence

<400> SEQUENCE: 7

gccaccatgg cagcccccgg cgccccagct gagtacggct acatccggac cgtcctgggc     60

cagcagatcc tgggacaact ggacagctcc agcctggcgc tgccctccga ggccaagctg    120

aagctggcgg ggagcagcgg ccgcggcggc cagacagtca agagcctgcg gatccaggag    180

caggtgcagc agaccctcgc ccggaagggc cgcagctccg tgggcaacgg aaatcttcac    240

cgaaccagca gtgttcctga gtatgtctac aacctacact tggttgaaaa tgattttgtt    300

ggaggccgtt cccctgttcc taaaacctat gacatgctaa aggctggcac aactgccact    360

tatgaaggtc gctggggaag aggaacagca cagtacagct cccagaagtc cgtggaagaa    420

aggtccttga ggcatcctct gaggagactg gagatttctc ctgacagcag cccggagagg    480

gctcactaca cgcacagcga ttaccagtac agccagagaa gccaggctgg gcacaccctg    540

caccaccaag aaagcaggcg ggccgccctc ctagtgccac cgagatatgc tcgttccgag    600

atcgtggggg tcagccgtgc tggcaccaca agcaggcagc gccactttga cacataccac    660

agacagtacc agcatggctc tgttagcgac accgtttttg acagcatccc tgccaacccg    720

gccctgctca cgtaccccag gccagggacc agccgcagca tgggcaacct cttggagaag    780

gagaactacc tgacggcagg gctcactgtc gggcaggtca ggccgctggt gcccctgcag    840

cccgtcactc agaacagggc ttccaggtcc tcctggcatc agagctcctt ccacagcacc    900

cgcacgctga gggaagctgg gcccagtgtc gccgtggatt ccagcgggag gagagcgcac    960

ttgactgtcg gccaggcggc cgcaggggga agtgggaatc tgctcactga gagaagcact   1020

ttcactgact cccagctggg gaatgcagac atggagatga ctctggagcg agcagtgagt   1080

atgctcgagg cagaccacat gctgccatcc aggatttctg ctgcagctac tttcatacag   1140

cacgagtgct tccagaaatc tgaagctcgg aagagggtta accagcttcg tggcatcctc   1200

aagcttctgc agctcctaaa agttcagaat gaagacgttc agcgagctgt gtgtggggcc   1260

ttgagaaact tagtatttga agacaatgac aacaaattgg aggtggctga actaaatggg   1320

gtacctcggc tgctccaggt gctgaagcaa accagagact tggagactaa aaaacaaata   1380

acagaccata cagtcaattt aagaagtagg aatggctggc cgggcgcggt ggctcacgcc   1440

tgtaatccca gcactttggg aggccaaggc gggcggatca cgaggtcagg agttcgagac   1500

cagcctgacc aacatggttt gctgtggaat ttgtcatcta atgacaaact caagaatctc   1560

atgataacag aagcattgct tacgctgacg gagaatatca tcatcccctt ttctgggtgg   1620

cctgaaggag actacccaaa agcaaatggt ttgctcgatt ttgacatatt ctacaacgtc   1680

actggatgcc taagaaacat gagttctgct ggcgctgatg ggagaaaagc gatgagaaga   1740

tgtgacggac tcattgactc actggtccat tatgtcagag gaaccattgc agattaccag   1800

ccagatgaca aggccacgga gaattgtgtg tgcattcttc ataacctctc ctaccagctg   1860

gaggcagagc tcccagagaa atattcccag aatatctata ttcaaaaccg gaatatccag   1920

actgacaaca acaaaagtat tggatgtttt ggcagtcgaa gcaggaaagt aaaagagcaa   1980

taccaggacg tgccgatgcc ggaggaaaag agcaacccca agggcgtgga gtggctgtgg   2040

cattccattg ttataaggat gtatctgtcc ttgatcgcca aaagtgtccg caactacaca   2100
```

```
caagaagcat ccttaggagc tctgcagaac ctcacggccg gaagtggacc aatgccgaca   2160

tcagtggctc agacagttgt ccagaaggaa agtggcctgc agcacacccg aaagatgctg   2220

catgttggtg acccaagtgt gaaaaagaca gccatctcgc tgctgaggaa tctgtcccgg   2280

aatctttctc tgcagaatga aattgccaaa gaaactctcc ctgatttggt ttccatcatt   2340

cctgacacag tcccgagtac tgaccttctc attgaaacta cagcctctgc ctgttacaca   2400

ttgaacaaca taatccaaaa cagttaccag aatgcacgcg accttctaaa caccgggggc   2460

atccagaaaa ttatggccat tagtgcaggc gatgcctatg cctccaacaa agcaagtaaa   2520

gctgcttccg tccttctgta ttctctgtgg gcacacacgg aactgcatca tgcctacaag   2580

aaggctcagt ttaagaagac agattttgtc aacagccgga ctgccaaagc ctaccactcc   2640

cttaaagac                                                          2649
```

```
<210> SEQ ID NO 8
<211> LENGTH: 4081
<212> TYPE: DNA
<213> ORGANISM: Artificial Sequence
<220> FEATURE:
<223> OTHER INFORMATION: Made in Lab - MHCK7-PKP2a expression cassette

<400> SEQUENCE: 8

acccttcaga ttaaaaataa ctgaggtaag ggcctgggta ggggaggtgg tgtgagacgc     60

tcctgtctct cctctatctg cccatcggcc ctttggggag gaggaatgtg cccaaggact    120

aaaaaaaggc catggagcca gaggggcgag ggcaacagac ctttcatggg caaaccttgg    180

ggccctgctg tctagcatgc cccactacgg gtctaggctg cccatgtaag gaggcaaggc    240

ctggggacac ccgagatgcc tggttataat taacccagac atgtggctgc cccccccccc    300

ccaacacctg ctgcctctaa aaataaccct gtccctggtg gatcccctgc atgcgaagat    360

cttcgaacaa ggctgtgggg gactgagggc aggctgtaac aggcttgggg gccagggctt    420

atacgtgcct gggactccca aagtattact gttccatgtt cccggcgaag ggccagctgt    480

cccccgccag ctagactcag cacttagttt aggaaccagt gagcaagtca gcccttgggg    540

cagcccatac aaggccatgg ggctgggcaa gctgcacgcc tgggtccggg gtgggcacgg    600

tgcccgggca acgagctgaa agctcatctg ctctcagggg cccctccctg ggacagcccc    660

ctcctggcta gtcacaccct gtaggctcct ctatataacc caggggcaca ggggctgccc    720

tcattctacc accacctcca cagcacagac agacactcag gagccagcca ggccaccatg    780

gcagcccccg gcgccccagc tgagtacggc tacatccgga ccgtcctggg ccagcagatc    840

ctgggacaac tggacagctc cagcctggcg ctgccctccg aggccaagct gaagctggcg    900

gggagcagcg gccgcggcgg ccagacagtc aagagcctgc ggatccagga gcaggtgcag    960

cagaccctcg cccggaaggg ccgcagctcc gtgggcaacg gaaatcttca ccgaaccagc   1020

agtgttcctg agtatgtcta caacctacac ttggttgaaa atgattttgt tggaggccgt   1080

tcccctgttc ctaaaaccta tgacatgcta aaggctggca caactgccac ttatgaaggt   1140

cgctggggaa gaggaacagc acagtacagc tcccagaagt ccgtggaaga aaggtccttg   1200

aggcatcctc tgaggagact ggagatttct cctgacagca gcccggagag ggctcactac   1260

acgcacagcg attaccagta cagccagaga agccaggctg ggcacaccct gcaccaccaa   1320

gaaagcaggc gggccgccct cctagtgcca ccgagatatg ctcgttccga gatcgtgggg   1380

gtcagccgtg ctggcaccac aagcaggcag cgccactttg acacatacca cagacagtac   1440

cagcatggct ctgttagcga caccgttttt gacagcatcc ctgccaaccc ggccctgctc   1500
```

-continued

```
acgtacccca ggccagggac cagccgcagc atgggcaacc tcttggagaa ggagaactac   1560
ctgacggcag ggctcactgt cgggcaggtc aggccgctgg tgcccctgca gcccgtcact   1620
cagaacaggg cttccaggtc ctcctggcat cagagctcct tccacagcac ccgcacgctg   1680
agggaagctg ggcccagtgt cgccgtggat tccagcggga ggagagcgca cttgactgtc   1740
ggccaggcgg ccgcaggggg aagtgggaat ctgctcactg agagaagcac tttcactgac   1800
tcccagctgg ggaatgcaga catggagatg actctggagc gagcagtgag tatgctcgag   1860
gcagaccaca tgctgccatc caggatttct gctgcagcta ctttcataca gcacgagtgc   1920
ttccagaaat ctgaagctcg gaagagggtt aaccagcttc gtggcatcct caagcttctg   1980
cagctcctaa aagttcagaa tgaagacgtt cagcgagctg tgtgtggggc cttgagaaac   2040
ttagtatttg aagacaatga caacaaattg gaggtggctg aactaaatgg ggtacctcgg   2100
ctgctccagg tgctgaagca aaccagagac ttggagacta aaaaacaaat aacaggtttg   2160
ctgtggaatt tgtcatctaa tgacaaactc aagaatctca tgataacaga agcattgctt   2220
acgctgacgg agaatatcat catccccttt tctgggtggc ctgaaggaga ctacccaaaa   2280
gcaaatggtt tgctcgattt tgacatattc tacaacgtca ctggatgcct aagaaacatg   2340
agttctgctg gcgctgatgg gagaaaagcg atgagaagat gtgacggact cattgactca   2400
ctggtccatt atgtcagagg aaccattgca gattaccagc cagatgacaa ggccacggag   2460
aattgtgtgt gcattcttca taacctctcc taccagctgg aggcagagct cccagagaaa   2520
tattcccaga atatctatat tcaaaaccgg aatatccaga ctgacaacaa caaaagtatt   2580
ggatgttttg gcagtcgaag caggaaagta aaagagcaat accaggacgt gccgatgccg   2640
gaggaaaaga gcaaccccaa gggcgtggag tggctgtggc attccattgt tataaggatg   2700
tatctgtcct tgatcgccaa aagtgtccgc aactacacac aagaagcatc cttaggagct   2760
ctgcagaacc tcacggccgg aagtggacca atgccgacat cagtggctca gacagttgtc   2820
cagaaggaaa gtggcctgca gcacacccga aagatgctgc atgttggtga cccaagtgtg   2880
aaaaagacag ccatctcgct gctgaggaat ctgtcccgga atctttctct gcagaatgaa   2940
attgccaaag aaactctccc tgatttggtt tccatcattc ctgacacagt cccgagtact   3000
gaccttctca ttgaaactac agcctctgcc tgttacacat tgaacaacat aatccaaaac   3060
agttaccaga atgcacgcga ccttctaaac accgggggca tccagaaaat tatggccatt   3120
agtgcaggcg atgcctatgc ctccaacaaa gcaagtaaag ctgcttccgt ccttctgtat   3180
tctctgtggg cacacacgga actgcatcat gcctacaaga aggctcagtt taagaagaca   3240
gattttgtca acagccggac tgccaaagcc taccactccc ttaaagactg atcaacctct   3300
ggattacaaa atttgtgaaa gattgactgg tattcttaac tatgttgctc cttttacgct   3360
atgtggatac gctgctttaa tgcctttgta tcatgctatt gcttcccgta tggctttcat   3420
tttctcctcc ttgtataaat cctggttgct gtctctttat gaggagttgt ggcccgttgt   3480
caggcaacgt ggcgtggtgt gcactgtgtt tgctgacgca acccccactg gttggggcat   3540
tgccaccacc tgtcagctcc tttccgggac tttcgctttc cccctcccta ttgccacggc   3600
ggaactcatc gccgcctgcc ttgcccgctg ctggacaggg gctcggctgt tgggcactga   3660
caattccgtg gtgttgtcgg ggaaatcatc gtcctttcct tggctgctcg cctgtgttgc   3720
cacctggatt ctgcgcggga cgtccttctg ctacgtccct tcggccctca atccagcgga   3780
ccttccttcc cgcggcctgc tgccggctct gcggcctctt ccgcgtcttc gccttcgccc   3840
```

-continued

```
tcagacgagt cggatctccc tttgggccgc ctccccgcac tgcccgggtg gcatccctgt   3900

gacccctccc cagtgcctct cctggccctg gaagttgcca ctccagtgcc caccagcctt   3960

gtcctaataa aattaagttg catcattttg tctgactagg tgtccttcta taatattatg   4020

gggtggaggg gggtggtatg gagcaagggg cccaagttgg gaagaaacct gtagggcctg   4080

c                                                                    4081
```

<210> SEQ ID NO 9
<211> LENGTH: 3854
<212> TYPE: DNA
<213> ORGANISM: Artificial Sequence
<220> FEATURE:
<223> OTHER INFORMATION: Made in lab - hTnT-PKP2a expression cassette

<400> SEQUENCE: 9

```
ctcagtccat taggagccag tagcctggaa gatgtcttta cccccagcat cagttcaagt     60

ggagcagcac ataactcttg ccctctgcct tccaagattc tggtgctgag acttatggag    120

tgtcttggag gttgccttct gccccccaac cctgctccca gctggccctc ccaggcctgg    180

gttgctggcc tctgctttat caggattctc aagagggaca gctggtttat gttgcatgac    240

tgttccctgc atatctgctc tggttttaaa tagcttatct gagcagctgg aggaccacat    300

gggcttatat ggcgtggggt acatgttcct gtagccttgt ccctggcacc tgccaaaata    360

gcagccaaca ccccccaccc ccaccgccat cccccctgccc cacccgtccc ctgtcgcaca    420

ttcctccctc cgcagggctg gctcaccagg ccccagccca catgcctgct taaagccctc    480

tccatcctct gcctcaccca gtccccgctg agactgagca gacgcctcca ggatctgtcg    540

gcaggccacc atggcagccc ccggcgcccc agctgagtac ggctacatcc ggaccgtcct    600

gggccagcag atcctgggac aactggacag ctccagcctg gcgctgccct ccgaggccaa    660

gctgaagctg gcggggagca gcggccgcgg cggccagaca gtcaagagcc tgcggatcca    720

ggagcaggtg cagcagaccc tcgcccggaa gggccgcagc tccgtgggca acggaaatct    780

tcaccgaacc agcagtgttc ctgagtatgt ctacaaccta cacttggttg aaaatgattt    840

tgttggaggc cgttcccctg ttcctaaaac ctatgacatg ctaaaggctg gcacaactgc    900

cacttatgaa ggtcgctggg gaagaggaac agcacagtac agctcccaga agtccgtgga    960

agaaaggtcc ttgaggcatc ctctgaggag actggagatt tctcctgaca gcagcccgga   1020

gagggctcac tacacgcaca gcgattacca gtacagccag agaagccagg ctgggcacac   1080

cctgcaccac caagaaagca ggcgggccgc cctcctagtg ccaccgagat atgctcgttc   1140

cgagatcgtg gggggtcagcc gtgctggcac cacaagcagg cagcgccact ttgacacata   1200

ccacagacag taccagcatg gctctgttag cgacaccgtt tttgacagca tccctgccaa   1260

cccggccctg ctcacgtacc ccaggccagg gaccagccgc agcatgggca acctcttgga   1320

gaaggagaac tacctgacgg cagggctcac tgtcgggcag gtcaggccgc tggtgcccct   1380

gcagcccgtc actcagaaca gggcttccag gtcctcctgg catcagagct ccttccacag   1440

cacccgcacg ctgagggaag ctgggcccag tgtcgccgtg gattccagcg ggaggagagc   1500

gcacttgact gtcggccagg cggccgcagg gggaagtggg aatctgctca ctgagagaag   1560

cactttcact gactcccagc tggggaatgc agacatggag atgactctgg agcgagcagt   1620

gagtatgctc gaggcagacc acatgctgcc atccaggatt tctgctgcag ctactttcat   1680

acagcacgag tgcttccaga aatctgaagc tcggaagagg gttaaccagc ttcgtggcat   1740

cctcaagctt ctgcagctcc taaaagttca gaatgaagac gttcagcgag ctgtgtgtgg   1800
```

```
ggccttgaga aacttagtat ttgaagacaa tgacaacaaa ttggaggtgg ctgaactaaa   1860

tggggtacct cggctgctcc aggtgctgaa gcaaaccaga gacttggaga ctaaaaaaca   1920

aataacaggt ttgctgtgga atttgtcatc taatgacaaa ctcaagaatc tcatgataac   1980

agaagcattg cttacgctga cggagaatat catcatcccc ttttctgggt ggcctgaagg   2040

agactaccca aaagcaaatg gtttgctcga ttttgacata ttctacaacg tcactggatg   2100

cctaagaaac atgagttctg ctggcgctga tgggagaaaa gcgatgagaa gatgtgacgg   2160

actcattgac tcactggtcc attatgtcag aggaaccatt gcagattacc agccagatga   2220

caaggccacg gagaattgtg tgtgcattct tcataacctc tcctaccagc tggaggcaga   2280

gctcccagag aaatattccc agaatatcta tattcaaaac cggaatatcc agactgacaa   2340

caacaaaagt attggatgtt ttggcagtcg aagcaggaaa gtaaaagagc aataccagga   2400

cgtgccgatg ccggaggaaa agagcaaccc caagggcgtg gagtggctgt ggcattccat   2460

tgttataagg atgtatctgt ccttgatcgc caaaagtgtc cgcaactaca cacaagaagc   2520

atccttagga gctctgcaga acctcacggc cggaagtgga ccaatgccga catcagtggc   2580

tcagacagtt gtccagaagg aaagtggcct gcagcacacc cgaaagatgc tgcatgttgg   2640

tgacccaagt gtgaaaaaga cagccatctc gctgctgagg aatctgtccc ggaatctttc   2700

tctgcagaat gaaattgcca aagaaactct ccctgatttg gtttccatca ttcctgacac   2760

agtcccgagt actgaccttc tcattgaaac tacagcctct gcctgttaca cattgaacaa   2820

cataatccaa aacagttacc agaatgcacg cgaccttcta aacaccgggg gcatccagaa   2880

aattatggcc attagtgcag gcgatgccta tgcctccaac aaagcaagta aagctgcttc   2940

cgtccttctg tattctctgt gggcacacac ggaactgcat catgcctaca agaaggctca   3000

gtttaagaag acagattttg tcaacagccg gactgccaaa gcctaccact cccttaaaga   3060

ctgatcaacc tctggattac aaaatttgtg aaagattgac tggtattctt aactatgttg   3120

ctccttttac gctatgtgga tacgctgctt taatgccttt gtatcatgct attgcttccc   3180

gtatggcttt cattttctcc tccttgtata aatcctggtt gctgtctctt tatgaggagt   3240

tgtggcccgt tgtcaggcaa cgtggcgtgg tgtgcactgt gtttgctgac gcaaccccca   3300

ctggttgggg cattgccacc acctgtcagc tcctttccgg gactttcgct ttccccctcc   3360

ctattgccac ggcggaactc atcgccgcct gccttgcccg ctgctggaca ggggctcggc   3420

tgttgggcac tgacaattcc gtggtgttgt cggggaaatc atcgtccttt ccttggctgc   3480

tcgcctgtgt tgccacctgg attctgcgcg ggacgtcctt ctgctacgtc ccttcggccc   3540

tcaatccagc ggaccttcct tcccgcggcc tgctgccggc tctgcggcct cttccgcgtc   3600

ttcgccttcg ccctcagacg agtcggatct ccctttgggc cgcctccccg cactgcccgg   3660

gtggcatccc tgtgacccct ccccagtgcc tctcctggcc ctggaagttg ccactccagt   3720

gcccaccagc cttgtcctaa taaaattaag ttgcatcatt ttgtctgact aggtgtcctt   3780

ctataatatt atggggtgga ggggggtggt atggagcaag ggcccaagt tgggaagaaa   3840

cctgtagggc ctgc                                                      3854
```

<210> SEQ ID NO 10
<211> LENGTH: 4213
<212> TYPE: DNA
<213> ORGANISM: Artificial Sequence
<220> FEATURE:
<223> OTHER INFORMATION: Made in Lab - MHCK7-PKP2b expression cassette

<400> SEQUENCE: 10

```
acccttcaga ttaaaaataa ctgaggtaag ggcctgggta ggggaggtgg tgtgagacgc     60
tcctgtctct cctctatctg cccatcggcc ctttggggag gaggaatgtg cccaaggact    120
aaaaaaaggc catggagcca gaggggcgag ggcaacagac ctttcatggg caaaccttgg    180
ggccctgctg tctagcatgc cccactacgg gtctaggctg cccatgtaag gaggcaaggc    240
ctggggacac ccgagatgcc tggttataat taacccagac atgtggctgc cccccccccc    300
ccaacacctg ctgcctctaa aaataaccct gtccctggtg gatcccctgc atgcgaagat    360
cttcgaacaa ggctgtgggg gactgagggc aggctgtaac aggcttgggg gccagggctt    420
atacgtgcct gggactccca aagtattact gttccatgtt cccggcgaag ggccagctgt    480
cccccgccag ctagactcag cacttagttt aggaaccagt gagcaagtca gcccttgggg    540
cagcccatac aaggccatgg ggctgggcaa gctgcacgcc tgggtccggg gtgggcacgg    600
tgcccgggca acgagctgaa agctcatctg ctctcagggg cccctccctg gggacagccc    660
ctcctggcta gtcacaccct gtaggctcct ctatataacc caggggcaca ggggctgccc    720
tcattctacc accacctcca cagcacagac agacactcag gagccagcca ggccaccatg    780
gcagcccccg gcgccccagc tgagtacggc tacatccgga ccgtcctggg ccagcagatc    840
ctgggacaac tggacagctc cagcctggcg ctgccctccg aggccaagct gaagctggcg    900
gggagcagcg gccgcggcgg ccagacagtc aagagcctgc ggatccagga gcaggtgcag    960
cagaccctcg cccggaaggg ccgcagctcc gtgggcaacg gaaatcttca ccgaaccagc   1020
agtgttcctg agtatgtcta caacctacac ttggttgaaa atgattttgt tggaggccgt   1080
tcccctgttc ctaaaaccta tgacatgcta aaggctggca caactgccac ttatgaaggt   1140
cgctggggaa gaggaacagc acagtacagc tcccagaagt ccgtggaaga aaggtccttg   1200
aggcatcctc tgaggagact ggagatttct cctgacagca gcccggagag ggctcactac   1260
acgcacagcg attaccagta cagccagaga agccaggctg ggcacaccct gcaccaccaa   1320
gaaagcaggc gggccgccct cctagtgcca ccgagatatg ctcgttccga gatcgtgggg   1380
gtcagccgtg ctggcaccac aagcaggcag cgccactttg acacatacca cagacagtac   1440
cagcatggct ctgttagcga caccgttttt gacagcatcc ctgccaaccc ggccctgctc   1500
acgtacccca ggccagggac cagccgcagc atgggcaacc tcttggagaa ggagaactac   1560
ctgacggcag ggctcactgt cgggcaggtc aggccgctgg tgcccctgca gcccgtcact   1620
cagaacaggg cttccaggtc ctcctggcat cagagctcct tccacagcac ccgcacgctg   1680
agggaagctg ggcccagtgt cgccgtggat tccagcggga ggagagcgca cttgactgtc   1740
ggccaggcgg ccgcaggggg aagtgggaat ctgctcactg agagaagcac tttcactgac   1800
tcccagctgg ggaatgcaga catggagatg actctggagc gagcagtgag tatgctcgag   1860
gcagaccaca tgctgccatc caggatttct gctgcagcta ctttcataca gcacgagtgc   1920
ttccagaaat ctgaagctcg gaagagggtt aaccagcttc gtggcatcct caagcttctg   1980
cagctcctaa aagttcagaa tgaagacgtt cagcgagctg tgtgtggggc cttgagaaac   2040
ttagtatttg aagacaatga caacaaattg gaggtggctg aactaaatgg ggtacctcgg   2100
ctgctccagg tgctgaagca aaccagagac ttggagacta aaaaacaaat aacagaccat   2160
acagtcaatt taagaagtag gaatggctgg ccgggcgcgg tggctcacgc ctgtaatccc   2220
agcactttgg gaggccaagg cgggcggatc acgaggtcag gagttcgaga ccagcctgac   2280
caacatggtt tgctgtggaa tttgtcatct aatgacaaac tcaagaatct catgataaca   2340
```

gaagcattgc ttacgctgac ggagaatatc atcatcccct tttctgggtg gcctgaagga 2400
gactacccaa aagcaaatgg tttgctcgat tttgacatat tctacaacgt cactggatgc 2460
ctaagaaaca tgagttctgc tggcgctgat gggagaaaag cgatgagaag atgtgacgga 2520
ctcattgact cactggtcca ttatgtcaga ggaaccattg cagattacca gccagatgac 2580
aaggccacgg agaattgtgt gtgcattctt cataacctct cctaccagct ggaggcagag 2640
ctcccagaga aatattccca gaatatctat attcaaaacc ggaatatcca gactgacaac 2700
aacaaaagta ttggatgttt tggcagtcga agcaggaaag taaaagagca ataccaggac 2760
gtgccgatgc cggaggaaaa gagcaacccc aagggcgtgg agtggctgtg gcattccatt 2820
gttataagga tgtatctgtc cttgatcgcc aaaagtgtcc gcaactacac acaagaagca 2880
tccttaggag ctctgcagaa cctcacggcc ggaagtggac caatgccgac atcagtggct 2940
cagacagttg tccagaagga aagtggcctg cagcacaccc gaaagatgct gcatgttggt 3000
gacccaagtg tgaaaaagac agccatctcg ctgctgagga atctgtcccg gaatctttct 3060
ctgcagaatg aaattgccaa agaaactctc cctgatttgg tttccatcat tcctgacaca 3120
gtcccgagta ctgaccttct cattgaaact acagcctctg cctgttacac attgaacaac 3180
ataatccaaa acagttacca gaatgcacgc gaccttctaa acaccggggg catccagaaa 3240
attatggcca ttagtgcagg cgatgcctat gcctccaaca aagcaagtaa agctgcttcc 3300
gtccttctgt attctctgtg ggcacacacg gaactgcatc atgcctacaa gaaggctcag 3360
tttaagaaga cagattttgt caacagccgg actgccaaag cctaccactc ccttaaagac 3420
tgatcaacct ctggattaca aaatttgtga aagattgact ggtattctta actatgttgc 3480
tccttttacg ctatgtggat acgctgcttt aatgcctttg tatcatgcta ttgcttcccg 3540
tatggctttc attttctcct ccttgtataa atcctggttg ctgtctcttt atgaggagtt 3600
gtggcccgtt gtcaggcaac gtggcgtggt gtgcactgtg tttgctgacg caacccccac 3660
tggttggggc attgccacca cctgtcagct cctttccggg actttcgctt tccccctccc 3720
tattgccacg gcggaactca tcgccgcctg ccttgcccgc tgctggacag gggctcggct 3780
gttgggcact gacaattccg tggtgttgtc ggggaaatca tcgtcctttc cttggctgct 3840
cgcctgtgtt gccacctgga ttctgcgcgg gacgtccttc tgctacgtcc cttcggccct 3900
caatccagcg gaccttcctt cccgcggcct gctgccggct ctgcggcctc ttccgcgtct 3960
tcgccttcgc cctcagacga gtcggatctc cctttgggcc gcctccccgc actgcccggg 4020
tggcatccct gtgacccctc cccagtgcct ctcctggccc tggaagttgc cactccagtg 4080
cccaccagcc ttgtcctaat aaaattaagt tgcatcattt tgtctgacta ggtgtccttc 4140
tataatatta tggggtggag gggggtggta tggagcaagg ggcccaagtt gggaagaaac 4200
ctgtagggcc tgc 4213

<210> SEQ ID NO 11
<211> LENGTH: 3986
<212> TYPE: DNA
<213> ORGANISM: Artificial Sequence
<220> FEATURE:
<223> OTHER INFORMATION: Made in Lab - hTnT-PKP2b express cassette

<400> SEQUENCE: 11
ctcagtccat taggagccag tagcctggaa gatgtcttta cccccagcat cagttcaagt 60
ggagcagcac ataactcttg ccctctgcct tccaagattc tggtgctgag acttatggag 120

-continued

```
tgtcttggag gttgccttct gccccccaac cctgctccca gctggccctc ccaggcctgg    180
gttgctggcc tctgctttat caggattctc aagagggaca gctggtttat gttgcatgac    240
tgttccctgc atatctgctc tggttttaaa tagcttatct gagcagctgg aggaccacat    300
gggcttatat ggcgtggggt acatgttcct gtagccttgt ccctggcacc tgccaaaata    360
gcagccaaca ccccccaccc ccaccgccat cccccctgccc cacccgtccc ctgtcgcaca    420
ttcctccctc cgcagggctg gctcaccagg ccccagccca catgcctgct taaagccctc    480
tccatcctct gcctcaccca gtccccgctg agactgagca gacgcctcca ggatctgtcg    540
gcaggccacc atggcagccc ccggcgcccc agctgagtac ggctacatcc ggaccgtcct    600
gggccagcag atcctgggac aactggacag ctccagcctg gcgctgccct ccgaggccaa    660
gctgaagctg gcggggagca gcggccgcgg cggccagaca gtcaagagcc tgcggatcca    720
ggagcaggtg cagcagaccc tcgcccggaa gggccgcagc tccgtgggca acggaaatct    780
tcaccgaacc agcagtgttc ctgagtatgt ctacaaccta cacttggttg aaaatgattt    840
tgttggaggc cgttcccctg ttcctaaaac ctatgacatg ctaaaggctg gcacaactgc    900
cacttatgaa ggtcgctggg gaagaggaac agcacagtac agctcccaga agtccgtgga    960
agaaaggtcc ttgaggcatc ctctgaggag actggagatt tctcctgaca gcagcccgga   1020
gagggctcac tacacgcaca gcgattacca gtacagccag agaagccagg ctgggcacac   1080
cctgcaccac caagaaagca ggcgggccgc cctcctagtg ccaccgagat atgctcgttc   1140
cgagatcgtg ggggtcagcc gtgctggcac cacaagcagg cagcgccact ttgacacata   1200
ccacagacag taccagcatg gctctgttag cgacaccgtt tttgacagca tccctgccaa   1260
cccggccctg ctcacgtacc ccaggccagg gaccagccgc agcatgggca acctcttgga   1320
gaaggagaac tacctgacgg cagggctcac tgtcgggcag gtcaggccgc tggtgcccct   1380
gcagcccgtc actcagaaca gggcttccag gtcctcctgg catcagagct ccttccacag   1440
cacccgcacg ctgagggaag ctgggcccag tgtcgccgtg gattccagcg ggaggagagc   1500
gcacttgact gtcggccagg cggccgcagg gggaagtggg aatctgctca ctgagagaag   1560
cactttcact gactcccagc tggggaatgc agacatggag atgactctgg agcgagcagt   1620
gagtatgctc gaggcagacc acatgctgcc atccaggatt tctgctgcag ctactttcat   1680
acagcacgag tgcttccaga aatctgaagc tcggaagagg gttaaccagc ttcgtggcat   1740
cctcaagctt ctgcagctcc taaaagttca gaatgaagac gttcagcgag ctgtgtgtgg   1800
ggccttgaga aacttagtat ttgaagacaa tgacaacaaa ttggaggtgg ctgaactaaa   1860
tggggtacct cggctgctcc aggtgctgaa gcaaaccaga gacttggaga ctaaaaaaca   1920
aataacagac catacagtca atttaagaag taggaatggc tggccgggcg cggtggctca   1980
cgcctgtaat cccagcactt tgggaggcca aggcgggcgg atcacgaggt caggagttcg   2040
agaccagcct gaccaacatg gtttgctgtg gaatttgtca tctaatgaca aactcaagaa   2100
tctcatgata acagaagcat tgcttacgct gacggagaat atcatcatcc ccttttctgg   2160
gtggcctgaa ggagactacc caaaagcaaa tggtttgctc gattttgaca tattctacaa   2220
cgtcactgga tgcctaagaa acatgagttc tgctggcgct gatgggagaa aagcgatgag   2280
aagatgtgac ggactcattg actcactggt ccattatgtc agaggaacca ttgcagatta   2340
ccagccagat gacaaggcca cggagaattg tgtgtgcatt cttcataacc tctcctacca   2400
gctggaggca gagctcccag agaaatattc ccagaatatc tatattcaaa accggaatat   2460
ccagactgac aacaacaaaa gtattggatg ttttggcagt cgaagcagga aagtaaaaga   2520
```

```
gcaataccag gacgtgccga tgccggagga aaagagcaac cccaagggcg tggagtggct   2580
gtggcattcc attgttataa ggatgtatct gtccttgatc gccaaaagtg tccgcaacta   2640
cacacaagaa gcatccttag gagctctgca gaacctcacg gccggaagtg gaccaatgcc   2700
gacatcagtg gctcagacag ttgtccagaa ggaaagtggc ctgcagcaca cccgaaagat   2760
gctgcatgtt ggtgacccaa gtgtgaaaaa gacagccatc tcgctgctga ggaatctgtc   2820
ccggaatctt tctctgcaga atgaaattgc caaagaaact ctccctgatt tggtttccat   2880
cattcctgac acagtcccga gtactgacct tctcattgaa actacagcct ctgcctgtta   2940
cacattgaac aacataatcc aaaacagtta ccagaatgca cgcgaccttc taaacaccgg   3000
gggcatccag aaaattatgg ccattagtgc aggcgatgcc tatgcctcca acaaagcaag   3060
taaagctgct tccgtccttc tgtattctct gtgggcacac acggaactgc atcatgccta   3120
caagaaggct cagtttaaga agacagattt tgtcaacagc cggactgcca aagcctacca   3180
ctcccttaaa gactgatcaa cctctggatt acaaaatttg tgaaagattg actggtattc   3240
ttaactatgt tgctcctttt acgctatgtg gatacgctgc tttaatgcct ttgtatcatg   3300
ctattgcttc ccgtatggct ttcattttct cctccttgta taaatcctgg ttgctgtctc   3360
tttatgagga gttgtggccc gttgtcaggc aacgtggcgt ggtgtgcact gtgtttgctg   3420
acgcaacccc cactggttgg ggcattgcca ccacctgtca gctcctttcc gggactttcg   3480
ctttccccct ccctattgcc acggcggaac tcatcgccgc ctgccttgcc cgctgctgga   3540
caggggctcg gctgttgggc actgacaatt ccgtggtgtt gtcggggaaa tcatcgtcct   3600
ttccttggct gctcgcctgt gttgccacct ggattctgcg cgggacgtcc ttctgctacg   3660
tcccttcggc cctcaatcca gcggaccttc cttcccgcgg cctgctgccg gctctgcggc   3720
ctcttccgcg tcttcgcctt cgccctcaga cgagtcggat ctccctttgg gccgcctccc   3780
cgcactgccc gggtggcatc cctgtgaccc ctccccagtg cctctcctgg ccctggaagt   3840
tgccactcca gtgcccacca gccttgtcct aataaaatta agttgcatca ttttgtctga   3900
ctaggtgtcc ttctataata ttatggggtg gagggggtg gtatggagca aggggcccaa   3960
gttgggaaga aacctgtagg gcctgc                                         3986
```

<210> SEQ ID NO 12
<211> LENGTH: 4417
<212> TYPE: DNA
<213> ORGANISM: Artificial Sequence
<220> FEATURE:
<223> OTHER INFORMATION: Made in Labe - full polynucleotide sequence of vector genome

<400> SEQUENCE: 12

```
gcgcgctcgc tcgctcactg aggccgcccg ggcaaagccc gggcgtcggg cgacctttgg     60
tcgcccggcc tcagtgagcg agcgagcgcg cagagaggga gtggccaact ccatcactag    120
gggttccttg tagttaatga ttaacccgcc atgctactta tctacgtaac ccttcagatt    180
aaaaataact gaggtaaggg cctgggtagg ggaggtggtg tgagacgctc ctgtctctcc    240
tctatctgcc catcggccct ttggggagga ggaatgtgcc caaggactaa aaaaaggcca    300
tggagccaga ggggcgaggg caacagacct ttcatgggca aaccttgggg ccctgctgtc    360
tagcatgccc cactacgggt ctaggctgcc catgtaagga ggcaaggcct ggggacaccc    420
gagatgcctg gttataatta acccagacat gtggctgccc cccccccccc aacacctgct    480
gcctctaaaa ataaccctgt ccctggtgga tcccctgcat gcgaagatct tcgaacaagg    540
```

```
ctgtggggga ctgagggcag gctgtaacag gcttgggggc cagggcttat acgtgcctgg    600
gactcccaaa gtattactgt tccatgttcc cggcgaaggg ccagctgtcc cccgccagct    660
agactcagca cttagtttag gaaccagtga gcaagtcagc ccttggggca gcccatacaa    720
ggccatgggg ctgggcaagc tgcacgcctg ggtccggggt gggcacggtg cccgggcaac    780
gagctgaaag ctcatctgct ctcaggggcc cctccctggg gacagcccct cctggctagt    840
cacaccctgt aggctcctct atataaccca ggggcacagg ggctgccctc attctaccac    900
cacctccaca gcacagacag acactcagga gccagccagg ccaccatggc agcccccggc    960
gccccagctg agtacggcta catccggacc gtcctgggcc agcagatcct gggacaactg   1020
gacagctcca gcctggcgct gccctccgag gccaagctga agctggcggg gagcagcggc   1080
cgcggcggcc agacagtcaa gagcctgcgg atccaggagc aggtgcagca gaccctcgcc   1140
cggaagggcc gcagctccgt gggcaacgga aatcttcacc gaaccagcag tgttcctgag   1200
tatgtctaca acctacactt ggttgaaaat gattttgttg gaggccgttc ccctgttcct   1260
aaaacctatg acatgctaaa ggctggcaca actgccactt atgaaggtcg ctggggaaga   1320
ggaacagcac agtacagctc ccagaagtcc gtggaagaaa ggtccttgag gcatcctctg   1380
aggagactgg agatttctcc tgacagcagc ccggagaggg ctcactacac gcacagcgat   1440
taccagtaca gccagagaag ccaggctggg cacaccctgc accaccaaga aagcaggcgg   1500
gccgccctcc tagtgccacc gagatatgct cgttccgaga tcgtgggggt cagccgtgct   1560
ggcaccacaa gcaggcagcg ccactttgac acataccaca gacagtacca gcatggctct   1620
gttagcgaca ccgtttttga cagcatccct gccaacccgg ccctgctcac gtaccccagg   1680
ccagggacca gccgcagcat gggcaacctc ttggagaagg agaactacct gacggcaggg   1740
ctcactgtcg ggcaggtcag gccgctggtg cccctgcagc ccgtcactca gaacagggct   1800
tccaggtcct cctggcatca gagctccttc cacagcaccc gcacgctgag ggaagctggg   1860
cccagtgtcg ccgtggattc cagcgggagg agagcgcact tgactgtcgg ccaggcggcc   1920
gcagggggaa gtgggaatct gctcactgag agaagcactt tcactgactc ccagctgggg   1980
aatgcagaca tggagatgac tctggagcga gcagtgagta tgctcgaggc agaccacatg   2040
ctgccatcca ggatttctgc tgcagctact ttcatacagc acgagtgctt ccagaaatct   2100
gaagctcgga agagggttaa ccagcttcgt ggcatcctca agcttctgca gctcctaaaa   2160
gttcagaatg aagacgttca gcgagctgtg tgtggggcct tgagaaactt agtatttgaa   2220
gacaatgaca acaaattgga ggtggctgaa ctaaatgggg tacctcggct gctccaggtg   2280
ctgaagcaaa ccagagactt ggagactaaa aaacaaataa caggtttgct gtggaatttg   2340
tcatctaatg acaaactcaa gaatctcatg ataacagaag cattgcttac gctgacggag   2400
aatatcatca tccccttttc tgggtggcct gaaggagact acccaaaagc aaatggtttg   2460
ctcgattttg acatattcta caacgtcact ggatgcctaa gaaacatgag ttctgctggc   2520
gctgatggga gaaaagcgat gagaagatgt gacggactca ttgactcact ggtccattat   2580
gtcagaggaa ccattgcaga ttaccagcca gatgacaagg ccacggagaa ttgtgtgtgc   2640
attcttcata acctctccta ccagctggag gcagagctcc cagagaaata ttcccagaat   2700
atctatattc aaaaccggaa tatccagact gacaacaaca aaagtattgg atgttttggc   2760
agtcgaagca ggaaagtaaa agagcaatac caggacgtgc cgatgccgga ggaaaagagc   2820
aaccccaagg gcgtggagtg gctgtggcat tccattgtta taaggatgta tctgtccttg   2880
```

-continued

```
atcgccaaaa gtgtccgcaa ctacacacaa gaagcatcct taggagctct gcagaacctc   2940

acggccggaa gtggaccaat gccgacatca gtggctcaga cagttgtcca gaaggaaagt   3000

ggcctgcagc acacccgaaa gatgctgcat gttggtgacc caagtgtgaa aaagacagcc   3060

atctcgctgc tgaggaatct gtcccggaat ctttctctgc agaatgaaat tgccaaagaa   3120

actctccctg atttggtttc catcattcct gacacagtcc cgagtactga ccttctcatt   3180

gaaactacag cctctgcctg ttacacattg aacaacataa tccaaaacag ttaccagaat   3240

gcacgcgacc ttctaaacac cgggggcatc cagaaaatta tggccattag tgcaggcgat   3300

gcctatgcct ccaacaaagc aagtaaagct gcttccgtcc ttctgtattc tctgtgggca   3360

cacacggaac tgcatcatgc ctacaagaag gctcagttta agaagacaga ttttgtcaac   3420

agccggactg ccaaagccta ccactccctt aaagactgat caacctctgg attacaaaat   3480

ttgtgaaaga ttgactggta ttcttaacta tgttgctcct tttacgctat gtggatacgc   3540

tgctttaatg cctttgtatc atgctattgc ttcccgtatg gctttcattt tctcctcctt   3600

gtataaatcc tggttgctgt ctctttatga ggagttgtgg cccgttgtca ggcaacgtgg   3660

cgtggtgtgc actgtgtttg ctgacgcaac ccccactggt tggggcattg ccaccacctg   3720

tcagctcctt tccgggactt tcgctttccc cctccctatt gccacggcgg aactcatcgc   3780

cgcctgcctt gcccgctgct ggacaggggc tcggctgttg ggcactgaca attccgtggt   3840

gttgtcgggg aaatcatcgt cctttccttg gctgctcgcc tgtgttgcca cctggattct   3900

gcgcgggacg tccttctgct acgtcccttc ggccctcaat ccagcggacc ttccttcccg   3960

cggcctgctg ccggctctgc ggcctcttcc gcgtcttcgc cttcgccctc agacgagtcg   4020

gatctccctt tgggccgcct ccccgcactg cccgggtggc atccctgtga cccctcccca   4080

gtgcctctcc tggccctgga agttgccact ccagtgccca ccagccttgt cctaataaaa   4140

ttaagttgca tcattttgtc tgactaggtg tccttctata atattatggg gtggaggggg   4200

gtggtatgga gcaaggggcc caagttggga agaaacctgt agggcctgct acgtagataa   4260

gtagcatggc gggttaatca ttaactacaa ggaaccccta gtgatggagt tggccactcc   4320

ctctctgcgc gctcgctcgc tcactgaggc cgggcgacca aaggtcgccc gacgcccggg   4380

ctttgcccgg gcggcctcag tgagcgagcg agcgcgc                            4417
```

```
<210> SEQ ID NO 13
<211> LENGTH: 4190
<212> TYPE: DNA
<213> ORGANISM: Artificial Sequence
<220> FEATURE:
<223> OTHER INFORMATION: Made in Labe - full polynucleotide sequence of
      vector genome

<400> SEQUENCE: 13
```

```
gcgcgctcgc tcgctcactg aggccgcccg ggcaaagccc gggcgtcggg cgacctttgg     60

tcgcccggcc tcagtgagcg agcgagcgcg cagagaggga gtggccaact ccatcactag    120

gggttccttg tagttaatga ttaacccgcc atgctactta tctacgtact cagtccatta    180

ggagccagta gcctggaaga tgtctttacc cccagcatca gttcaagtgg agcagcacat    240

aactcttgcc ctctgccttc caagattctg gtgctgagac ttatggagtg tcttggaggt    300

tgccttctgc cccccaaccc tgctcccagc tggccctccc aggcctgggt tgctggcctc    360

tgctttatca ggattctcaa gagggacagc tggtttatgt tgcatgactg ttccctgcat    420

atctgctctg gttttaaata gcttatctga gcagctggag gaccacatgg gcttatatgg    480
```

-continued

```
cgtggggtac atgttcctgt agccttgtcc ctggcacctg ccaaaatagc agccaacacc    540
ccccaccccc accgccatcc ccctgcccca cccgtcccct gtcgcacatt cctccctccg    600
cagggctggc tcaccaggcc ccagcccaca tgcctgctta aagccctctc catcctctgc    660
ctcacccagt ccccgctgag actgagcaga cgcctccagg atctgtcggc aggccaccat    720
ggcagccccc ggcgccccag ctgagtacgg ctacatccgg accgtcctgg gccagcagat    780
cctgggacaa ctggacagct ccagcctggc gctgccctcc gaggccaagc tgaagctggc    840
ggggagcagc ggccgcggcg gccagacagt caagagcctg cggatccagg agcaggtgca    900
gcagaccctc gcccggaagg gccgcagctc cgtgggcaac ggaaatcttc accgaaccag    960
cagtgttcct gagtatgtct acaacctaca cttggttgaa aatgattttg ttggaggccg   1020
ttcccctgtt cctaaaacct atgacatgct aaaggctggc acaactgcca cttatgaagg   1080
tcgctgggga agaggaacag cacagtacag ctcccagaag tccgtggaag aaaggtcctt   1140
gaggcatcct ctgaggagac tggagatttc tcctgacagc agcccggaga gggctcacta   1200
cacgcacagc gattaccagt acagccagag aagccaggct gggcacaccc tgcaccacca   1260
agaaagcagg cgggccgccc tcctagtgcc accgagatat gctcgttccg agatcgtggg   1320
ggtcagccgt gctggcacca caagcaggca gcgccacttt gacacatacc acagacagta   1380
ccagcatggc tctgttagcg acaccgtttt tgacagcatc cctgccaacc cggccctgct   1440
cacgtacccc aggccaggga ccagccgcag catgggcaac ctcttggaga aggagaacta   1500
cctgacggca gggctcactg tcgggcaggt caggccgctg gtgcccctgc agcccgtcac   1560
tcagaacagg gcttccaggt cctcctggca tcagagctcc ttccacagca cccgcacgct   1620
gagggaagct gggcccagtg tcgccgtgga ttccagcggg aggagagcgc acttgactgt   1680
cggccaggcg gccgcagggg gaagtgggaa tctgctcact gagagaagca ctttcactga   1740
ctcccagctg gggaatgcag acatggagat gactctggag cgagcagtga gtatgctcga   1800
ggcagaccac atgctgccat ccaggatttc tgctgcagct actttcatac agcacgagtg   1860
cttccagaaa tctgaagctc ggaagagggt taaccagctt cgtggcatcc tcaagcttct   1920
gcagctccta aaagttcaga atgaagacgt tcagcgagct gtgtgtgggg ccttgagaaa   1980
cttagtattt gaagacaatg acaacaaatt ggaggtggct gaactaaatg gggtacctcg   2040
gctgctccag gtgctgaagc aaaccagaga cttggagact aaaaaacaaa taacaggttt   2100
gctgtggaat ttgtcatcta atgacaaact caagaatctc atgataacag aagcattgct   2160
tacgctgacg gagaatatca tcatcccctt ttctgggtgg cctgaaggag actacccaaa   2220
agcaaatggt ttgctcgatt ttgacatatt ctacaacgtc actggatgcc taagaaacat   2280
gagttctgct ggcgctgatg ggagaaaagc gatgagaaga tgtgacggac tcattgactc   2340
actggtccat tatgtcagag gaaccattgc agattaccag ccagatgaca aggccacgga   2400
gaattgtgtg tgcattcttc ataacctctc ctaccagctg gaggcagagc tcccagagaa   2460
atattcccag aatatctata ttcaaaaccg gaatatccag actgacaaca acaaaaagtat   2520
tggatgtttt ggcagtcgaa gcaggaaagt aaaagagcaa taccaggacg tgccgatgcc   2580
ggaggaaaag agcaacccca agggcgtgga gtggctgtgg cattccattg ttataaggat   2640
gtatctgtcc ttgatcgcca aaagtgtccg caactacaca caagaagcat ccttaggagc   2700
tctgcagaac ctcacggccg gaagtggacc aatgccgaca tcagtggctc agacagttgt   2760
ccagaaggaa agtggcctgc agcacacccg aaagatgctg catgttggtg acccaagtgt   2820
gaaaaagaca gccatctcgc tgctgaggaa tctgtcccgg aatctttctc tgcagaatga   2880
```

```
aattgccaaa gaaactctcc ctgatttggt ttccatcatt cctgacacag tcccgagtac   2940

tgaccttctc attgaaacta cagcctctgc ctgttacaca ttgaacaaca taatccaaaa   3000

cagttaccag aatgcacgcg accttctaaa caccgggggc atccagaaaa ttatggccat   3060

tagtgcaggc gatgcctatg cctccaacaa agcaagtaaa gctgcttccg tccttctgta   3120

ttctctgtgg gcacacacgg aactgcatca tgcctacaag aaggctcagt ttaagaagac   3180

agattttgtc aacagccgga ctgccaaagc ctaccactcc cttaaagact gatcaacctc   3240

tggattacaa aatttgtgaa agattgactg gtattcttaa ctatgttgct ccttttacgc   3300

tatgtggata cgctgcttta atgcctttgt atcatgctat tgcttcccgt atggctttca   3360

ttttctcctc cttgtataaa tcctggttgc tgtctcttta tgaggagttg tggcccgttg   3420

tcaggcaacg tggcgtggtg tgcactgtgt ttgctgacgc aacccccact ggttggggca   3480

ttgccaccac ctgtcagctc ctttccggga ctttcgcttt ccccctccct attgccacgg   3540

cggaactcat cgccgcctgc cttgcccgct gctggacagg ggctcggctg ttgggcactg   3600

acaattccgt ggtgttgtcg gggaaatcat cgtcctttcc ttggctgctc gcctgtgttg   3660

ccacctggat tctgcgcggg acgtccttct gctacgtccc ttcggccctc aatccagcgg   3720

accttccttc ccgcggcctg ctgccggctc tgcggcctct tccgcgtctt cgccttcgcc   3780

ctcagacgag tcggatctcc ctttgggccg cctccccgca ctgcccgggt ggcatccctg   3840

tgacccctcc ccagtgcctc tcctggccct ggaagttgcc actccagtgc ccaccagcct   3900

tgtcctaata aaattaagtt gcatcatttt gtctgactag gtgtccttct ataatattat   3960

ggggtggagg ggggtggtat ggagcaaggg gcccaagttg ggaagaaacc tgtagggcct   4020

gctacgtaga taagtagcat ggcgggttaa tcattaacta caaggaaccc ctagtgatgg   4080

agttggccac tccctctctg cgcgctcgct cgctcactga ggccgggcga ccaaaggtcg   4140

cccgacgccc gggctttgcc cgggcggcct cagtgagcga gcgagcgcgc              4190
```

<210> SEQ ID NO 14
<211> LENGTH: 4549
<212> TYPE: DNA
<213> ORGANISM: Artificial Sequence
<220> FEATURE:
<223> OTHER INFORMATION: Made in Labe - full polynucleotide sequence of vector genome

<400> SEQUENCE: 14

```
gcgcgctcgc tcgctcactg aggccgcccg ggcaaagccc gggcgtcggg cgacctttgg     60

tcgcccggcc tcagtgagcg agcgagcgcg cagagaggga gtggccaact ccatcactag    120

gggttccttg tagttaatga ttaacccgcc atgctactta tctacgtaac ccttcagatt    180

aaaaataact gaggtaaggg cctgggtagg ggaggtggtg tgagacgctc ctgtctctcc    240

tctatctgcc catcggccct ttggggagga ggaatgtgcc caaggactaa aaaaaggcca    300

tggagccaga ggggcgaggg caacagacct ttcatgggca aaccttgggg ccctgctgtc    360

tagcatgccc cactacgggt ctaggctgcc catgtaagga ggcaaggcct ggggacaccc    420

gagatgcctg gttataatta acccagacat gtggctgccc cccccccccc aacacctgct    480

gcctctaaaa ataaccctgt ccctggtgga tcccctgcat gcgaagatct tcgaacaagg    540

ctgtggggga ctgagggcag gctgtaacag gcttgggggc cagggcttat acgtgcctgg    600

gactcccaaa gtattactgt tccatgttcc cggcgaaggg ccagctgtcc cccgccagct    660

agactcagca cttagtttag gaaccagtga gcaagtcagc ccttggggca gcccatacaa    720
```

-continued

```
ggccatgggg ctgggcaagc tgcacgcctg ggtccggggt gggcacggtg cccgggcaac    780
gagctgaaag ctcatctgct ctcaggggcc cctccctggg gacagcccct cctggctagt    840
cacaccctgt aggctcctct atataaccca ggggcacagg ggctgccctc attctaccac    900
cacctccaca gcacagacag acactcagga gccagccagg ccaccatggc agcccccggc    960
gccccagctg agtacggcta catccggacc gtcctgggcc agcagatcct gggacaactg   1020
gacagctcca gcctggcgct gccctccgag gccaagctga agctggcggg gagcagcggc   1080
cgcggcggcc agacagtcaa gagcctgcgg atccaggagc aggtgcagca gaccctcgcc   1140
cggaagggcc gcagctccgt gggcaacgga aatcttcacc gaaccagcag tgttcctgag   1200
tatgtctaca acctacactt ggttgaaaat gattttgttg gaggccgttc ccctgttcct   1260
aaaacctatg acatgctaaa ggctggcaca actgccactt atgaaggtcg ctggggaaga   1320
ggaacagcac agtacagctc ccagaagtcc gtggaagaaa ggtccttgag gcatcctctg   1380
aggagactgg agatttctcc tgacagcagc ccggagaggg ctcactacac gcacagcgat   1440
taccagtaca gccagagaag ccaggctggg cacaccctgc accaccaaga aagcaggcgg   1500
gccgccctcc tagtgccacc gagatatgct cgttccgaga tcgtgggggt cagccgtgct   1560
ggcaccacaa gcaggcagcg ccactttgac acataccaca gacagtacca gcatggctct   1620
gttagcgaca ccgtttttga cagcatccct gccaacccgg ccctgctcac gtaccccagg   1680
ccagggacca gccgcagcat gggcaacctc ttggagaagg agaactacct gacggcaggg   1740
ctcactgtcg ggcaggtcag gccgctggtg cccctgcagc ccgtcactca gaacagggct   1800
tccaggtcct cctggcatca gagctccttc cacagcaccc gcacgctgag ggaagctggg   1860
cccagtgtcg ccgtggattc cagcgggagg agagcgcact tgactgtcgg ccaggcggcc   1920
gcagggggaa gtgggaatct gctcactgag agaagcactt tcactgactc ccagctgggg   1980
aatgcagaca tggagatgac tctggagcga gcagtgagta tgctcgaggc agaccacatg   2040
ctgccatcca ggatttctgc tgcagctact ttcatacagc acgagtgctt ccagaaatct   2100
gaagctcgga agagggttaa ccagcttcgt ggcatcctca agcttctgca gctcctaaaa   2160
gttcagaatg aagacgttca gcgagctgtg tgtggggcct tgagaaactt agtatttgaa   2220
gacaatgaca acaaattgga ggtggctgaa ctaaatgggg tacctcggct gctccaggtg   2280
ctgaagcaaa ccagagactt ggagactaaa aaacaaataa cagaccatac agtcaattta   2340
agaagtagga atggctggcc gggcgcggtg gctcacgcct gtaatcccag cactttggga   2400
ggccaaggcg ggcggatcac gaggtcagga gttcgagacc agcctgacca acatggtttg   2460
ctgtggaatt tgtcatctaa tgacaaactc aagaatctca tgataacaga agcattgctt   2520
acgctgacgg agaatatcat catccccttt tctgggtggc ctgaaggaga ctacccaaaa   2580
gcaaatggtt tgctcgattt tgacatattc tacaacgtca ctggatgcct aagaaacatg   2640
agttctgctg gcgctgatgg gagaaaagcg atgagaagat gtgacggact cattgactca   2700
ctggtccatt atgtcagagg aaccattgca gattaccagc cagatgacaa ggccacggag   2760
aattgtgtgt gcattcttca taacctctcc taccagctgg aggcagagct cccagagaaa   2820
tattcccaga atatctatat tcaaaaccgg aatatccaga ctgacaacaa caaaagtatt   2880
ggatgttttg gcagtcgaag caggaaagta aaagagcaat accaggacgt gccgatgccg   2940
gaggaaaaga gcaaccccaa gggcgtggag tggctgtggc attccattgt tataaggatg   3000
tatctgtcct tgatcgccaa aagtgtccgc aactacacac aagaagcatc cttaggagct   3060
```

ctgcagaacc tcacggccgg aagtggacca atgccgacat cagtggctca gacagttgtc 3120
cagaaggaaa gtggcctgca gcacacccga aagatgctgc atgttggtga cccaagtgtg 3180
aaaaagacag ccatctcgct gctgaggaat ctgtcccgga atctttctct gcagaatgaa 3240
attgccaaag aaactctccc tgatttggtt tccatcattc ctgacacagt cccgagtact 3300
gaccttctca ttgaaactac agcctctgcc tgttacacat tgaacaacat aatccaaaac 3360
agttaccaga atgcacgcga ccttctaaac accgggggca tccagaaaat tatggccatt 3420
agtgcaggcg atgcctatgc ctccaacaaa gcaagtaaag ctgcttccgt ccttctgtat 3480
tctctgtggg cacacacgga actgcatcat gcctacaaga aggctcagtt taagaagaca 3540
gattttgtca acagccggac tgccaaagcc taccactccc ttaaagactg atcaacctct 3600
ggattacaaa atttgtgaaa gattgactgg tattcttaac tatgttgctc cttttacgct 3660
atgtggatac gctgctttaa tgcctttgta tcatgctatt gcttcccgta tggctttcat 3720
tttctcctcc ttgtataaat cctggttgct gtctctttat gaggagttgt ggcccgttgt 3780
caggcaacgt ggcgtggtgt gcactgtgtt tgctgacgca acccccactg gttggggcat 3840
tgccaccacc tgtcagctcc tttccgggac tttcgctttc cccctcccta ttgccacggc 3900
ggaactcatc gccgcctgcc ttgcccgctg ctggacaggg gctcggctgt tgggcactga 3960
caattccgtg gtgttgtcgg ggaaatcatc gtcctttcct tggctgctcg cctgtgttgc 4020
cacctggatt ctgcgcggga cgtccttctg ctacgtccct tcggccctca atccagcgga 4080
ccttccttcc cgcggcctgc tgccggctct gcggcctctt ccgcgtcttc gccttcgccc 4140
tcagacgagt cggatctccc tttgggccgc ctccccgcac tgcccgggtg gcatccctgt 4200
gacccctccc cagtgcctct cctggccctg gaagttgcca ctccagtgcc caccagcctt 4260
gtcctaataa aattaagttg catcattttg tctgactagg tgtccttcta taatattatg 4320
gggtggaggg gggtggtatg gagcaagggg cccaagttgg gaagaaacct gtagggcctg 4380
ctacgtagat aagtagcatg gcgggttaat cattaactac aaggaacccc tagtgatgga 4440
gttggccact ccctctctgc gcgctcgctc gctcactgag gccgggcgac caaaggtcgc 4500
ccgacgcccg ggctttgccc gggcggcctc agtgagcgag cgagcgcgc 4549

<210> SEQ ID NO 15
<211> LENGTH: 4322
<212> TYPE: DNA
<213> ORGANISM: Artificial Sequence
<220> FEATURE:
<223> OTHER INFORMATION: Made in Labe - full polynucleotide sequence of vector genome

<400> SEQUENCE: 15
gcgcgctcgc tcgctcactg aggccgcccg ggcaaagccc gggcgtcggg cgacctttgg 60
tcgcccggcc tcagtgagcg agcgagcgcg cagagaggga gtggccaact ccatcactag 120
gggttccttg tagttaatga ttaacccgcc atgctactta tctacgtact cagtccatta 180
ggagccagta gcctggaaga tgtctttacc cccagcatca gttcaagtgg agcagcacat 240
aactcttgcc ctctgccttc caagattctg gtgctgagac ttatggagtg tcttggaggt 300
tgccttctgc cccccaaccc tgctcccagc tggccctccc aggcctgggt tgctggcctc 360
tgctttatca ggattctcaa gagggacagc tggtttatgt tgcatgactg ttccctgcat 420
atctgctctg gttttaaata gcttatctga gcagctggag gaccacatgg gcttatatgg 480
cgtggggtac atgttcctgt agccttgtcc ctggcacctg ccaaaatagc agccaacacc 540

```
ccccaccccc accgccatcc ccctgcccca cccgtcccct gtcgcacatt cctccctccg    600
cagggctggc tcaccaggcc ccagcccaca tgcctgctta aagccctctc catcctctgc    660
ctcacccagt ccccgctgag actgagcaga cgcctccagg atctgtcggc aggccaccat    720
ggcagccccc ggcgccccag ctgagtacgg ctacatccgg accgtcctgg gccagcagat    780
cctgggacaa ctggacagct ccagcctggc gctgccctcc gaggccaagc tgaagctggc    840
ggggagcagc ggccgcggcg gccagacagt caagagcctg cggatccagg agcaggtgca    900
gcagaccctc gcccggaagg gccgcagctc cgtgggcaac ggaaatcttc accgaaccag    960
cagtgttcct gagtatgtct acaacctaca cttggttgaa aatgattttg ttggaggccg   1020
ttcccctgtt cctaaaacct atgacatgct aaaggctggc acaactgcca cttatgaagg   1080
tcgctgggga agaggaacag cacagtacag ctcccagaag tccgtggaag aaaggtcctt   1140
gaggcatcct ctgaggagac tggagatttc tcctgacagc agcccggaga gggctcacta   1200
cacgcacagc gattaccagt acagccagag aagccaggct gggcacaccc tgcaccacca   1260
agaaagcagg cgggccgccc tcctagtgcc accgagatat gctcgttccg agatcgtggg   1320
ggtcagccgt gctggcacca caagcaggca gcgccacttt gacacatacc acagacagta   1380
ccagcatggc tctgttagcg acaccgtttt tgacagcatc cctgccaacc cggccctgct   1440
cacgtacccc aggccaggga ccagccgcag catgggcaac ctcttggaga aggagaacta   1500
cctgacggca gggctcactg tcgggcaggt caggccgctg gtgcccctgc agcccgtcac   1560
tcagaacagg gcttccaggt cctcctggca tcagagctcc ttccacagca cccgcacgct   1620
gagggaagct gggcccagtg tcgccgtgga ttccagcggg aggagagcgc acttgactgt   1680
cggccaggcg gccgcagggg gaagtgggaa tctgctcact gagagaagca ctttcactga   1740
ctcccagctg gggaatgcag acatggagat gactctggag cgagcagtga gtatgctcga   1800
ggcagaccac atgctgccat ccaggatttc tgctgcagct actttcatac agcacgagtg   1860
cttccagaaa tctgaagctc ggaagagggt taaccagctt cgtggcatcc tcaagcttct   1920
gcagctccta aaagttcaga atgaagacgt tcagcgagct gtgtgtgggg ccttgagaaa   1980
cttagtattt gaagacaatg acaacaaatt ggaggtggct gaactaaatg ggtacctcg    2040
gctgctccag gtgctgaagc aaaccagaga cttggagact aaaaaacaaa taacagacca   2100
tacagtcaat ttaagaagta ggaatggctg gccgggcgcg gtggctcacg cctgtaatcc   2160
cagcactttg ggaggccaag gcgggcggat cacgaggtca ggagttcgag accagcctga   2220
ccaacatggt ttgctgtgga atttgtcatc taatgacaaa ctcaagaatc tcatgataac   2280
agaagcattg cttacgctga cggagaatat catcatcccc ttttctgggt ggcctgaagg   2340
agactaccca aaagcaaatg gtttgctcga ttttgacata ttctacaacg tcactggatg   2400
cctaagaaac atgagttctg ctggcgctga tgggagaaaa gcgatgagaa gatgtgacgg   2460
actcattgac tcactggtcc attatgtcag aggaaccatt gcagattacc agccagatga   2520
caaggccacg gagaattgtg tgtgcattct tcataacctc tcctaccagc tggaggcaga   2580
gctcccagag aaatattccc agaatatcta tattcaaaac cggaatatcc agactgacaa   2640
caacaaaagt attggatgtt ttggcagtcg aagcaggaaa gtaaaagagc aataccagga   2700
cgtgccgatg ccggaggaaa agagcaaccc caagggcgtg gagtggctgt ggcattccat   2760
tgttataagg atgtatctgt ccttgatcgc caaaagtgtc cgcaactaca cacaagaagc   2820
atccttagga gctctgcaga acctcacggc cggaagtgga ccaatgccga catcagtggc   2880
tcagacagtt gtccagaagg aaagtggcct gcagcacacc cgaaagatgc tgcatgttgg   2940
```

tgacccaagt gtgaaaaaga cagccatctc gctgctgagg aatctgtccc ggaatctttc 3000
tctgcagaat gaaattgcca aagaaactct ccctgatttg gtttccatca ttcctgacac 3060
agtcccgagt actgaccttc tcattgaaac tacagcctct gcctgttaca cattgaacaa 3120
cataatccaa aacagttacc agaatgcacg cgaccttcta aacaccgggg gcatccagaa 3180
aattatggcc attagtgcag gcgatgccta tgcctccaac aaagcaagta aagctgcttc 3240
cgtccttctg tattctctgt gggcacacac ggaactgcat catgcctaca agaaggctca 3300
gtttaagaag acagattttg tcaacagccg gactgccaaa gcctaccact cccttaaaga 3360
ctgatcaacc tctggattac aaaatttgtg aaagattgac tggtattctt aactatgttg 3420
ctccttttac gctatgtgga tacgctgctt taatgccttt gtatcatgct attgcttccc 3480
gtatggcttt cattttctcc tccttgtata aatcctggtt gctgtctctt tatgaggagt 3540
tgtggcccgt tgtcaggcaa cgtggcgtgg tgtgcactgt gtttgctgac gcaaccccca 3600
ctggttgggg cattgccacc acctgtcagc tcctttccgg gactttcgct ttccccctcc 3660
ctattgccac ggcggaactc atcgccgcct gccttgcccg ctgctggaca ggggctcggc 3720
tgttgggcac tgacaattcc gtggtgttgt cggggaaatc atcgtccttt ccttggctgc 3780
tcgcctgtgt tgccacctgg attctgcgcg ggacgtcctt ctgctacgtc ccttcggccc 3840
tcaatccagc ggaccttcct tcccgcggcc tgctgccggc tctgcggcct cttccgcgtc 3900
ttcgccttcg ccctcagacg agtcggatct ccctttgggc cgcctccccg cactgcccgg 3960
gtggcatccc tgtgacccct ccccagtgcc tctcctggcc ctggaagttg ccactccagt 4020
gcccaccagc cttgtcctaa taaaattaag ttgcatcatt ttgtctgact aggtgtcctt 4080
ctataatatt atggggtgga ggggggtggt atggagcaag gggcccaagt tgggaagaaa 4140
cctgtagggc ctgctacgta gataagtagc atggcgggtt aatcattaac tacaaggaac 4200
ccctagtgat ggagttggcc actccctctc tgcgcgctcg ctcgctcact gaggccgggc 4260
gaccaaaggt cgcccgacgc ccgggctttg cccgggcggc ctcagtgagc gagcgagcgc 4320
gc 4322

<210> SEQ ID NO 16
<211> LENGTH: 13
<212> TYPE: DNA
<213> ORGANISM: Artificial Sequence
<220> FEATURE:
<223> OTHER INFORMATION: Kozak sequence motif

<400> SEQUENCE: 16
gccgccrcca ugg 13

<210> SEQ ID NO 17

<400> SEQUENCE: 17

000

<210> SEQ ID NO 18
<211> LENGTH: 10
<212> TYPE: DNA
<213> ORGANISM: Artificial Sequence
<220> FEATURE:
<223> OTHER INFORMATION: Kozak sequence motif

<400> SEQUENCE: 18
gacaccaugg 10

<210> SEQ ID NO 19

<400> SEQUENCE: 19

000

<210> SEQ ID NO 20
<211> LENGTH: 141
<212> TYPE: DNA
<213> ORGANISM: Adeno-associated virus

<400> SEQUENCE: 20
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc t 141

<210> SEQ ID NO 21
<211> LENGTH: 168
<212> TYPE: DNA
<213> ORGANISM: Adeno-associated virus 2

<400> SEQUENCE: 21
gcgcgctcgc tcgctcactg aggccgcccg ggcaaagccc gggcgtcggg cgacctttgg 60
tcgcccggcc tcagtgagcg agcgagcgcg cagagaggga gtggccaact ccatcactag 120
gggttccttg tagttaatga ttaacccgcc atgctactta tctacgta 168

<210> SEQ ID NO 22
<211> LENGTH: 170
<212> TYPE: DNA
<213> ORGANISM: Adeno-associated virus

<400> SEQUENCE: 22
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctacgta 170

<210> SEQ ID NO 23
<211> LENGTH: 145
<212> TYPE: DNA
<213> ORGANISM: Adeno-associated virus

<400> SEQUENCE: 23
ttggccactc cctctctgcg cgctcgctcg ctcactgagg ccgcccgggc aaagcccggg 60
cgtcgggcga cctttggtcg cccggcctca gtgagcgagc gagcgcgcag agagggagtg 120
gccaactcca tcactagggg ttcct 145

<210> SEQ ID NO 24
<211> LENGTH: 141
<212> TYPE: DNA
<213> ORGANISM: Adeno-associated viurs

<400> SEQUENCE: 24
aggaacccct agtgatggag ttggccactc cctctctgcg cgctcgctcg ctcactgagg 60
ccgggcgacc aaaggtcgcc cgacgcccgg gctttgcccg ggcggcctca gtgagcgagc 120
gagcgcgcag ctgcctgcag g 141

<210> SEQ ID NO 25
<211> LENGTH: 168
<212> TYPE: DNA
<213> ORGANISM: Adeno-associated virus 2

<400> SEQUENCE: 25
tacgtagata agtagcatgg cgggttaatc attaactaca aggaacccct agtgatggag 60
ttggccactc cctctctgcg cgctcgctcg ctcactgagg ccgggcgacc aaaggtcgcc 120
cgacgcccgg gctttgcccg ggcggcctca gtgagcgagc gagcgcgc 168

<210> SEQ ID NO 26
<211> LENGTH: 133
<212> TYPE: DNA
<213> ORGANISM: Adeno-associated virus 2

<400> SEQUENCE: 26
aggaacccct agtgatggag actccctctc tgcgcgctcg ctcgctcact gaggccgggc 60
gaccaaaggt cgcccgacgc ccgggctttg cccgggcggc ctcagtgagc gagcgagcgc 120
gcagagaggg agt 133

<210> SEQ ID NO 27
<211> LENGTH: 124
<212> TYPE: DNA
<213> ORGANISM: Artificial Sequence
<220> FEATURE:
<223> OTHER INFORMATION: Made in Lab - vector filler sequence

<400> SEQUENCE: 27
gcggcaattc agtcgataac tataacggtc ctaaggtagc gatttaaata cgcgctctct 60
taaggtagcc ccgggacgcg tcaattgact acaaaccgag tatctgcaga gggccctgcg 120
tatg 124

<210> SEQ ID NO 28
<211> LENGTH: 84
<212> TYPE: DNA
<213> ORGANISM: Artificial Sequence
<220> FEATURE:
<223> OTHER INFORMATION: Made in Lab - vector filler sequence

<400> SEQUENCE: 28
cttctgaggc ggaaagaacc agatcctctc ttaaggtagc atcgagattt aaattaggga 60
taacagggta atggcgcggg ccgc 84

<210> SEQ ID NO 29
<211> LENGTH: 63
<212> TYPE: DNA
<213> ORGANISM: Artificial Sequence
<220> FEATURE:
<223> OTHER INFORMATION: Made in Lab - vector filler sequence

<400> SEQUENCE: 29
gttacccagg ctggagtgca gtggcacatt tctgctcact gcaacctcct cctccctggg 60
ttc 63

<210> SEQ ID NO 30
<211> LENGTH: 573
<212> TYPE: DNA
<213> ORGANISM: Artificial Sequence
<220> FEATURE:
<223> OTHER INFORMATION: Made in lab - CAG promoter in part Human
betaherpesvirus 5

<400> SEQUENCE: 30
acttacggta aatggcccgc ctggctgacc gcccaacgac ccccgcccat tgacgtcaat 60
aatgacgtat gttcccatag taacgccaat agggactttc cattgacgtc aatgggtgga 120
gtatttacgg taaactgccc acttggcagt acatcaagtg tatcatatgc caagtacgcc 180
ccctattgac gtcaatgacg gtaaatggcc cgcctggcat tatgcccagt acatgacctt 240
atgggacttt cctacttggc agtacatcta cgtattagtc atcgctatta ccatggtcga 300
ggtgagcccc acgttctgct tcactctccc catctccccc ccctccccac ccccaatttt 360
gtatttattt atttttaat tattttgtgc agcgatgggg gcgggggggg ggggggcgcg 420
cgccaggcgg ggcggggcgg ggcgaggggc ggggcggggc gaggcggaga ggtgcggcgg 480
cagccaatca gagcggcgcg ctccgaaagt ttccttttat ggcgaggcgg cggcggcggc 540
ggccctataa aaagcgaagc gcgcggcggg cgg 573

<210> SEQ ID NO 31
<211> LENGTH: 771
<212> TYPE: DNA
<213> ORGANISM: Artificial Sequence
<220> FEATURE:
<223> OTHER INFORMATION: Made in Lab - MHCK7 promoter

<400> SEQUENCE: 31
acccttcaga ttaaaaataa ctgaggtaag ggcctgggta ggggaggtgg tgtgagacgc 60
tcctgtctct cctctatctg cccatcggcc ctttggggag gaggaatgtg cccaaggact 120
aaaaaaaggc catggagcca gaggggcgag ggcaacagac ctttcatggg caaaccttgg 180
ggccctgctg tctagcatgc cccactacgg gtctaggctg cccatgtaag gaggcaaggc 240
ctggggacac ccgagatgcc tggttataat taacccagac atgtggctgc cccccccccc 300
ccaacacctg ctgcctctaa aaataaccct gtccctggtg gatcccctgc atgcgaagat 360
cttcgaacaa ggctgtgggg gactgagggc aggctgtaac aggcttgggg gccagggctt 420
atacgtgcct gggactccca aagtattact gttccatgtt cccggcgaag ggccagctgt 480
cccccgccag ctagactcag cacttagttt aggaaccagt gagcaagtca gcccttgggg 540
cagcccatac aaggccatgg ggctgggcaa gctgcacgcc tgggtccggg gtgggcacgg 600
tgcccgggca acgagctgaa agctcatctg ctctcagggg cccctccctg gggacagccc 660
ctcctggcta gtcacaccct gtaggctcct ctatataacc caggggcaca ggggctgccc 720
tcattctacc accacctcca cagcacagac agacactcag gagccagcca g 771

<210> SEQ ID NO 32
<211> LENGTH: 544
<212> TYPE: DNA
<213> ORGANISM: Homo sapiens

<400> SEQUENCE: 32
ctcagtccat taggagccag tagcctggaa gatgtcttta cccccagcat cagttcaagt 60
ggagcagcac ataactcttg ccctctgcct tccaagattc tggtgctgag acttatggag 120
tgtcttggag gttgccttct gccccccaac cctgctccca gctggccctc ccaggcctgg 180
gttgctggcc tctgctttat caggattctc aagagggaca gctggtttat gttgcatgac 240
tgttccctgc atatctgctc tggttttaaa tagcttatct gagcagctgg aggaccacat 300
gggcttatat ggcgtggggt acatgttcct gtagccttgt ccctggcacc tgccaaaata 360

```
gcagccaaca ccccccaccc ccaccgccat ccccctgccc cacccgtccc ctgtcgcaca    420

ttcctccctc cgcagggctg gctcaccagg ccccagccca catgcctgct taaagccctc    480

tccatcctct gcctcaccca gtccccgctg agactgagca gacgcctcca ggatctgtcg    540

gcag                                                                 544
```

<210> SEQ ID NO 33
<211> LENGTH: 502
<212> TYPE: DNA
<213> ORGANISM: Homo sapiens

<400> SEQUENCE: 33

```
ctcagtccat taggagccag tagcctggaa gatgtcttta cccccagcat cagttcaagt     60

ggagcagcac ataactcttg ccctctgcct tccaagattc tggtgctgag acttatggag    120

tgtcttggag gttgccttct gccccccaac cctgctccca gctggccctc ccaggcctgg    180

gttgctggcc tctgctttat caggattctc aagagggaca gctggtttat gttgcatgac    240

tgttccctgc atatctgctc tggttttaaa tagcttatct gagcagctgg aggaccacat    300

gggcttatat ggcgtggggt acatgttcct gtagccttgt ccctggcacc tgccaaaata    360

gcagccaaca ccccccaccc ccaccgccat ccccctgccc cacccgtccc ctgtcgcaca    420

ttcctccctc cgcagggctg gctcaccagg ccccagccca catgcctgct taaagccctc    480

tccatcctct gcctcaccca gt                                             502
```

<210> SEQ ID NO 34
<211> LENGTH: 5464
<212> TYPE: DNA
<213> ORGANISM: Mus musculus

<400> SEQUENCE: 34

```
ggtaccggat cctgcaaggt cacacaaggg tctccaccca ccaggtgccc tagtctcaat     60

ttcagtttcc atgccttgtt ctcacaatgc tggcctcccc agagctaatt tggactttgt    120

ttttatttca aaagggcctg aatgaggagt agatcttgtg ctacccagct ctaagggtgc    180

ccgtgaagcc ctcagacctg gagcctttgc aacagccctt taggtggaag cagaataaag    240

caattttcct taaagccaaa atcctgcctc tagactcttc ttctctgacc tcggtccctg    300

ggctctaggg tggggaggtg gggcttggaa gaagaaggtg gggaagtggc aaaagccgat    360

ccctagggcc ctgtgaagtt cggagccttc cctgtacagc actggctcat agatcctcct    420

ccagccaaac atagcaagaa gtgatacctc ctttgtgact tccccaggcc cagtacctgt    480

caggttgaaa caggatttag agaagcctct gaactcacct gaactctgaa gctcatccac    540

caagcaagca cctaggtgcc actgctagtt agtatcctac gctgataata tgcagagctg    600

ggccacagaa gtcctggggt gtaggaactg accagtgact tttcagtcgg caaaggtatg    660

accccctcag cagatgtagt aatgtcccct tagatcccat cccaggcagg tctctaagag    720

gacatgggat gagagatgta gtcatgtggc attccaaaca cagctatcca cagtgtccct    780

tgccccttcc acttagccag gaggacagta accttagcct atctttcttc ctccccatcc    840

tcccaggaca cacccccctgg tctgcagtat tcatttcttc cttcacgtcc cctctgtgac    900

ttccatttgc aaggcttttg acctctgcag ctgctggaag atagagtttg gccctaggtg    960

tggcaagcca tctcaagaga aagcagacaa caggggggacc agattttgga aggatcagga   1020

actaaatcac tggcgggcct gggggtagaa aaaagagtga gtgagtccgc tccagctaag   1080

ccaagctagt ccccgagata ctctgccaca gctgggctgc tcggggtagc tttaggaatg   1140
```

-continued

```
tgggtctgaa agacaatggg attggaagac atctctttga gtctcccctc aaccccacct   1200
acagacacac tcgtgtgtgg ccagactcct gttcaacagc cctctgtgtt ctgaccactg   1260
agctaggcaa ccagagcatg ggccctgtgc tgaggatgaa gagttggtta ccaatagcaa   1320
aaacagcagg ggagggagaa cagagaacga aataaggaag gaagaaggaa aggccagtca   1380
atcagatgca gtcagaagag atgggaagcc aacacacagc ttgagcagag gaaacagaaa   1440
agggagagat tctgggcata aggaggccac agaaagaaga gcccaggccc cccaagtctc   1500
ctctttatac cctcatcccg tctcccaatt aagcccactc ttcttcctag atcagacctg   1560
agctgcagcg aagagacccg tagggaggat cacactggat gaaggagatg tgtggagaag   1620
tccagggaac ctaagagcca gagcctaaaa gagcaagaga taaaggtgct tcaaaggtgg   1680
ccaggctgtg cacacagagg gtcgaggact ggtggtagag cctcaagata aggatgatgc   1740
tcagaatggg cggggggggg gattctgggg gggggagaga gaaggtgaga aggagcctgg   1800
aacagagaat ctggaagcgc tggaaacgat accataaagg gaagaaccca ggctaccttt   1860
agatgtaaat catgaaagac agggagaagg gaagctggag agagtagaag gaccccgggg   1920
caagacattg aagcaaggac aagccaggtt gagcgctccg tgaaatcagc ctgctgaagg   1980
cagagccctg gtatgagcac cagaacagca gaggctaggg ttaatgtcga gacagggaac   2040
agaaggtaga cacaggaaca gacagagacg ggggagccag gtaacaaagg aatggtcctt   2100
ctcacctgtg gccagagcgt ccatctgtgt ccacatactc tagaatgttc atcagactgc   2160
agggctggct tgggaggcag ctggaaagag tatgtgagag ccaggggaga caagggggcc   2220
taggaaagga agaagagggc aaaccaggcc acacaagagg gcagagccca gaactgagtt   2280
aactccttcc ttgttgcatc ttccatagga ggcagtggga actctgtgac caccatcccc   2340
catgagcccc cactacccat accaagtttg gcctgagtgg cattctaggt tccctgagga   2400
cagagcctgg cctttgtctc ttggacctga cccaagctga cccaatgttc tcagtacctt   2460
atcatgccct caagagcttg agaaccaggc agtgacatat taggccatgg gctaaccctg   2520
gagcttgcac acaggagcct caagtgacct ccagggacac agctgcagac aggtggcctt   2580
tatccccaaa gagcaaccat ttggcatagg tggctgcaaa tgggaatgca aggttgaatc   2640
aggtcccttc aagaatactg catgcaagac ctaagacccc tggagagagg ggtatgctcc   2700
tgcccccacc caccataagg ggagtgaact atcctagggg gctggcgacc ttggggagac   2760
accacattac tgagagtgct gagcccagaa aaactgaccg ccctgtgtcc tgcccacctc   2820
cacactctag agctatattg agaggtgaca gtagataggg tgggagctgg tagcagggag   2880
agtgttcctg ggtgtgaggg tgtaggggaa agccagagca ggggagtctg gctttgtctc   2940
ctgaacacaa tgtctactta gttataacag gcatgacctg ctaaagaccc aacatctacg   3000
acctctgaaa agacagcagc cctggaggac aggggttgtc tctgagcctt gggtgcttga   3060
tggtgccaca aaggagggca tgagtgtgag tataaggccc caggagcgtt agagaagggc   3120
acttgggaag gggtcagtct gcagagcccc tatccatgga atctggagcc tggggccaac   3180
tggtgtaaat ctctgggcct gccaggcatt caaagcagca cctgcatcct ctggcagcct   3240
ggggaggcgg aagggagcaa ccccccactt ataccctttc tccctcagcc ccaggattaa   3300
cacctctggc cttccccctt cccacctccc atcaggagtg gagggttgca gagggagggt   3360
aaaaacctac atgtccaaac atcatggtgc acgatatatg gatcagtatg tgtagaggca   3420
agaaaggaaa tctgcaggct taactgggtt aatgtgtaaa gtctgtgtgc atgtgtgtgt   3480
```

-continued

```
gtctgactga aaacgggcat ggctgtgcag ctgttcagtt ctgtgcgtga ggttaccaga   3540

ctgcaggttt gtgtgtaaat tgcccaaggc aaagtgggtg aatcccttcc atggtttaaa   3600

gagattggat gatggcctgc atctcaagga ccatggaaaa tagaatggac actctatatg   3660

tgtctctaag ctaaggtagc aaggtctttg gaggacacct gtctagagat gtgggcaaca   3720

gagactacag acagtatctg tacagagtaa ggagagagag gagggggtgt agaattctct   3780

tactatcaaa gggaaactga gtcgtgcacc tgcaaagtgg atgctctccc tagacatcat   3840

gactttgtct ctggggagcc agcactgtgg aacttcaggt ctgagagagt aggaggctcc   3900

cctcagcctg aagctatgca gatagccagg gttgaaaggg ggaagggaga gcctgggatg   3960

ggagcttgtg tgttggaggc aggggacaga tattaagcct ggaagagaag gtgaccctta   4020

cccagttgtt caactcaccc ttcagattaa aaataactga ggtaagggcc tgggtagggg   4080

aggtggtgtg agacgctcct gtctctcctc tatctgccca tcggcccttt ggggaggagg   4140

aatgtgccca aggactaaaa aaaggccatg gagccagagg ggcgagggca acagaccttt   4200

catgggcaaa ccttggggcc ctgctgtcct cctgtcacct ccagagccaa gggatcaaag   4260

gaggaggagc caggacagga gggaagtggg agggagggtc ccagcagagg actccaaatt   4320

taggcagcag gcatatggga tgggatataa aggggctgga gcactgagag ctgtcagaga   4380

tttctccaac ccaggtaaga gggagtttcg ggtgggggct cttcacccac accagacctc   4440

tccccaccta gaaggaaact gcctttcctg gaagtggggt tcaggccggt cagagatctg   4500

acagggtggc cttccaccag cctgggaagt tctcagtggc aggaggtttc cacaagaaac   4560

actggatgcc ccttccctta cgctgtcttc tccatcttcc tcctggggat gctcctcccc   4620

gtcttggttt atcttggctc ttcgtcttca gcaagatttg ccctgtgctg tccactccat   4680

ctttctctac tgtctccgtg ccttgccttg ccttcttgcg tgtccttcct ttccacccat   4740

ttctcacttc accttttctc cccttctcat ttgtattcat ccttccttcc ttccttcctt   4800

ccttccttcc ttccttcctt ccttcctttc tcccttcctt ccttccttcc ttccttcctt   4860

ccttccttcc ttcctgtgtc agagtgctga gaatcacacc tggggttccc acccttatgt   4920

aaacaatctt ccagtgagcc acagcttcag tgctgctggg tgctctctta ccttcctcac   4980

cccctggctt gtcctgttcc atcctggtca ggatctctag attggtctcc cagcctctgc   5040

tactcctctt cctgcctgtt cctctctctg tccagctgcg ccactgtggt gcctcgttcc   5100

agctgtggtc cacattcttc aggattctct gaaaagttaa ccaggtgaga atgtttcccc   5160

tgtagacagc agatcacgat tctcccggaa gtcaggcttc cagccctctc tttctctgcc   5220

cagctgcccg gcactcttag caaacctcag gcacccttac cccacataga cctctgacag   5280

agaagcaggc actttacatg gagtcctggt gggagagcca taggctacgg tgtaaaagag   5340

gcagggaagt ggtggtgtag gaaagtcagg acttcacata gaagcctagc ccacaccaga   5400

aatgacagac agatccctcc tatctccccc ataagagttt gagtcgaccc gcggccccga   5460

attg                                                                5464
```

<210> SEQ ID NO 35
<211> LENGTH: 413
<212> TYPE: DNA
<213> ORGANISM: Gallus gallus

<400> SEQUENCE: 35

```
gggataaaag cagtctgggc tttcacatga cagcatctgg ggctgcggca gagggtcggg     60

tccgaagcgc tgccttatca gcgtccccag ccctgggagg tgacagctgg ctggcttgtg    120
```

tcagcccctc gggcactcac gtatctccgt ccgacgggtt taaaatagca aaactctgag 180
gccacacaat agcttgggct tatatgggct cctgtggggg aagggggagc acggaggggg 240
ccggggccgc tgctgccaaa atagcagctc acaagtgttg cattcctctc tgggcgccgg 300
gcacattcct gctggctctg cccgccccgg ggtgggcgcc ggggggacct taaagcctct 360
gccccccaag gagcccttcc cagacagccg ccggcaccca ccgctccgtg gga 413

<210> SEQ ID NO 36
<211> LENGTH: 1090
<212> TYPE: DNA
<213> ORGANISM: Homo sapiens

<400> SEQUENCE: 36
ctctcagccc tggaagtcct tgctcacagc cgaggcgccg agagcgcttg ctctgcccag 60
atctgcgcga gtctggcgcc cgcgctctga acggcgtcgc tgcccagccc ccttccccgg 120
gaggtgggag cggccaccca gggccccgtg gctgcccttg taaggaggcg aggcccgagg 180
acacccgaga cgcccggtta taattaacca ggacacgtgg cgaacccccc tccaacacct 240
gcccccgaac ccccccatac ccagcgcctc gggtctcggc ctttgcggca gaggagacag 300
caaagcgccc tctaaaaata actcctttcc cggcgaccga gaccctccct gtcccccgca 360
cagcggaaat ctcccagtgg caccgagggg gcgagggtta agtggggggg agggtgacca 420
ccgcctccca cccttgccct gagtttgaat ctctccaact cagccagcct cagtttcccc 480
tccactcagt ccctaggagg aaggggcgcc caagcgcggg tttctggggt tagactgccc 540
tccattgcaa ttggtccttc tcccggcctc tgcttcctcc agctcacagg gtatctgctc 600
ctcctggagc cacaccttgg ttccccgagg tgccgctggg actcgggtag gggtgagggc 660
ccagggggca caggggggagc cgagggccac aggaagggct ggtggctgaa ggagactcag 720
gggccagggg acggtggctt ctacgtgctt gggacgttcc cagccaccgt cccatgttcc 780
cggcgggggg ccagctgtcc ccaccgccag cccaactcag cacttggtca gggtatcagc 840
ttggtggggg ggcgtgagcc cagcccctgg ggcggctcag cccatacaag gccatggggc 900
tgggcgcaaa gcatgcctgg gttcagggtg ggtatggtgc gggagcaggg aggtgagagg 960
ctcagctgcc ctccagaact cctccctggg gacaacccct cccagccaat agcacagcct 1020
aggtccccct atataaggcc acggctgctg gcccttcctt tgggtcagtg tcacctccag 1080
gatacagaca 1090

<210> SEQ ID NO 37
<211> LENGTH: 253
<212> TYPE: DNA
<213> ORGANISM: Homo sapiens

<400> SEQUENCE: 37
gcccagcacc ccaaggcggc caacgccaaa actctccctc ctcctcttcc tcaatctcgc 60
tctcgctctt tttttttttc gcaaaaggag gggagagggg gtaaaaaaat gctgcactgt 120
gcggcgaagc cggtgagtga gcggcgcggg gccaatcagc gtgcgccgtt ccgaaagttg 180
ccttttatgg ctcgagcggc cgcggcggcg ccctataaaa cccagcggcg cgacgcgcca 240
ccaccgccga gtc 253

<210> SEQ ID NO 38
<211> LENGTH: 281
<212> TYPE: DNA

<213> ORGANISM: Gallus gallus

<400> SEQUENCE: 38

```
ggtcgaggtg agccccacgt tctgcttcac tctccccatc tcccccccct ccccaccccc     60

aattttgtat ttatttattt tttaattatt ttgtgcagcg atgggggcgg gggggggggg    120

ggcgcgcgcc aggcggggcg gggcggggcg aggggcgggg cggggcgagg cggagaggtg    180

cggcggcagc caatcagagc ggcgcgctcc gaaagtttcc ttttatggcg aggcggcggc    240

ggcggcggcc ctataaaaag cgaagcgcgc ggcgggcggg a                        281
```

<210> SEQ ID NO 39
<211> LENGTH: 220
<212> TYPE: DNA
<213> ORGANISM: Human betaherpesvirus 5

<400> SEQUENCE: 39

```
tggtgatgcg gttttggcag tacaccaatg ggcgtggata gcggtttgac tcacggggat     60

ttccaagtct ccaccccatt gacgtcaatg ggagtttgtt ttggcaccaa aatcaacggg    120

actttccaaa atgtcgtaat aaccccgccc cgttgacgca aatgggcggt aggcgtgtac    180

ggtgggaggt ctatataagc agagctcgtt tagtgaaccg                          220
```

<210> SEQ ID NO 40
<211> LENGTH: 583
<212> TYPE: DNA
<213> ORGANISM: Human betaherpesvirus 5

<400> SEQUENCE: 40

```
tagttattaa tagtaatcaa ttacggggtc attagttcat agcccatata tggagttccg     60

cgttacataa cttacggtaa atggcccgcc tggctgaccg cccaacgacc cccgcccatt    120

gacgtcaata atgacgtatg ttcccatagt aacgccaata gggactttcc attgacgtca    180

atgggtggag tatttacggt aaactgccca cttggcagta catcaagtgt atcatatgcc    240

aagtacgccc cctattgacg tcaatgacgg taaatggccc gcctggcatt atgcccagta    300

catgacctta tgggactttc ctacttggca gtacatctac gtattagtca tcgctattac    360

catggtgatg cggttttggc agtacatcaa tgggcgtgga tagcggtttg actcacgggg    420

atttccaagt ctccacccca ttgacgtcaa tgggagtttg ttttggcacc aaaatcaacg    480

ggactttcca aaatgtcgta acaactccgc cccattgacg caaatgggcg gtaggcgtgt    540

acggtgggag gtctatataa gcagagctgg tttagtgaac cgt                      583
```

<210> SEQ ID NO 41
<211> LENGTH: 508
<212> TYPE: DNA
<213> ORGANISM: Human betaherpesvirus 5

<400> SEQUENCE: 41

```
cgttacataa cttacggtaa atggcccgcc tggctgaccg cccaacgacc cccgcccatt     60

gacgtcaata atgacgtatg ttcccatagt aacgccaata gggactttcc attgacgtca    120

atgggtggag tatttacggt aaactgccca cttggcagta catcaagtgt atcatatgcc    180

aagtacgccc cctattgacg tcaatgacgg taaatggccc gcctggcatt atgcccagta    240

catgacctta tgggactttc ctacttggca gtacatctac gtattagtca tcgctattac    300

catggtgatg cggttttggc agtacatcaa tgggcgtgga tagcggtttg actcacgggg    360

atttccaagt ctccacccca ttgacgtcaa tgggagtttg ttttggcacc aaaatcaacg    420
```

ggactttcca aaatgtcgta acaactccgc cccattgacg caaatgggcg gtaggcgtgt 480
acggtgggag gtctatataa gcagagct 508

<210> SEQ ID NO 42
<211> LENGTH: 573
<212> TYPE: DNA
<213> ORGANISM: Artificial Sequence
<220> FEATURE:
<223> OTHER INFORMATION: Made in lab - CAG promoter in part Human betaherpesvirus 5

<400> SEQUENCE: 42
acttacggta aatggcccgc ctggctgacc gcccaacgac ccccgcccat tgacgtcaat 60
aatgacgtat gttcccatag taacgccaat agggactttc cattgacgtc aatgggtgga 120
gtatttacgg taaactgccc acttggcagt acatcaagtg tatcatatgc caagtacgcc 180
ccctattgac gtcaatgacg gtaaatggcc cgcctggcat tatgcccagt acatgacctt 240
atgggacttt cctacttggc agtacatcta cgtattagtc atcgctatta ccatggtcga 300
ggtgagcccc acgttctgct tcactctccc catctccccc ccctccccac ccccaatttt 360
gtatttattt atttttaat tattttgtgc agcgatgggg gcgggggggg ggggggcgcg 420
cgccaggcgg ggcggggcgg ggcgaggggc ggggcggggc gaggcggaga ggtgcggcgg 480
cagccaatca gagcggcgcg ctccgaaagt ttccttttat ggcgaggcgg cggcggcggc 540
ggccctataa aaagcgaagc gcgcggcggg cgg 573

<210> SEQ ID NO 43
<211> LENGTH: 580
<212> TYPE: DNA
<213> ORGANISM: Artificial Sequence
<220> FEATURE:
<223> OTHER INFORMATION: Made in lab - CAG promoter in part Human betaherpesvirus 5

<400> SEQUENCE: 43
cgttacataa cttacggtaa atggcccgcc tggctgaccg cccaacgacc cccgcccatt 60
gacgtcaata atgacgtatg ttcccatagt aacgccaata gggactttcc attgacgtca 120
atgggtggag tatttacggt aaactgccca cttggcagta catcaagtgt atcatatgcc 180
aagtacgccc cctattgacg tcaatgacgg taaatggccc gcctggcatt atgcccagta 240
catgacctta tgggactttc ctacttggca gtacatctac gtattagtca tcgctattac 300
catgtcgagg tgagccccac gttctgcttc actctcccca tctccccccc ctccccaccc 360
ccaattttgt atttatttat tttttaatta ttttgtgcag cgatgggggc gggggggggg 420
ggggcgcgcg ccaggcgggg cggggcgggg cgaggggcgg ggcggggcga ggcggagagg 480
tgcggcggca gccaatcaga gcggcgcgct ccgaaagttt ccttttatgg cgaggcggcg 540
gcggcggcgg ccctataaaa agcgaagcgc gcggcgggcg 580

<210> SEQ ID NO 44
<211> LENGTH: 455
<212> TYPE: DNA
<213> ORGANISM: Homo sapiens

<400> SEQUENCE: 44
caacctttgg agctaagcca gcaatggtag agggaagatt ctgcacgtcc cttccaggcg 60
gcctccccgt caccaccccc cccaacccgc cccgaccgga gctgagagta attcatacaa 120
aaggactcgc ccctgccttg gggaatccca gggaccgtcg ttaaactccc actaacgtag 180
aacccagaga tcgctgcgtt cccgccccct cacccgcccg ctctcgtcat cactgaggtg 240
gagaatagca tgcgtgaggc tccggtgccc gtcagtgggc agagcgcaca tcgcccacag 300
tccccgagaa gttgggggga ggggtcggca attgaacggg tgcctagaga aggtggcgcg 360
gggtaaactg ggaaagtgat gtcgtgtact ggctccgcct ttttcccgag ggtgggggag 420
aaccgtatat aagtgcagta gtcgccgtga acgtt 455

<210> SEQ ID NO 45

<400> SEQUENCE: 45

000

<210> SEQ ID NO 46

<400> SEQUENCE: 46

000

<210> SEQ ID NO 47

<400> SEQUENCE: 47

000

<210> SEQ ID NO 48
<211> LENGTH: 281
<212> TYPE: DNA
<213> ORGANISM: Homo sapiens

<400> SEQUENCE: 48
acttgtggac aaagtttgct ctattccacc tcctccaggc cctccttggg tccatcaccc 60
caggggtgct gggtccatcc cacccccagg cccacacagg cttgcagtat tgtgtgcggt 120
atggtcaggg cgtccgagag caggtttcgc agtggaaggc aggcaggtgt tggggaggca 180
gttaccgggg caacgggaac agggcgtttt ggaggtggtt gccatgggga cctggatgct 240
gacgaaggct cgcgaggctg tgagcagcca cagtgccctg c 281

<210> SEQ ID NO 49

<400> SEQUENCE: 49

000

<210> SEQ ID NO 50
<211> LENGTH: 293
<212> TYPE: DNA
<213> ORGANISM: Human betaherpesvirus 5

<400> SEQUENCE: 50
acttacggta aatggcccgc ctggctgacc gcccaacgac ccccgcccat tgacgtcaat 60
aatgacgtat gttcccatag taacgccaat agggactttc cattgacgtc aatgggtgga 120
gtatttacgg taaactgccc acttggcagt acatcaagtg tatcatatgc caagtacgcc 180
ccctattgac gtcaatgacg gtaaatggcc cgcctggcat tatgcccagt acatgacctt 240
atgggacttt cctacttggc agtacatcta cgtattagtc atcgctatta cca 293

<210> SEQ ID NO 51
<211> LENGTH: 953

<212> TYPE: DNA
<213> ORGANISM: Homo sapiens

<400> SEQUENCE: 51
cgcgtccgcc cgcgagcaca gagcctcgcc tttgccgatc cgccgcccgt ccacacccgc 60
cgccaggtaa gcccggccag ccgaccgggg catgcggccg cggcccttcg cccgtgcaga 120
gccgccgtct gggccgcagc gggggcgca tggggcggaa ccggaccgcc gtgggggcg 180 cgggagaagc ccctgggcct ccggagatgg gggacacccc acgccagttc gcaggcgcga 240
ggccgcgctc gggcgggcgc gctccggggg tgccgctctc ggggcggggg caaccggcgg 300
ggtctttgtc tgagccgggc tcttgccaat ggggatcgca cggtgggcgc ggcgtagccc 360
ccgtcaggcc cggtgggggc tggggcgcca tgcgcgtgcg cgctggtcct ttgggcgcta 420
actgcgtgcg cgctgggaat tggcgctaat tgcgcgtgcg cgctgggact caatggcgct 480
aatcgcgcgt gcgttctggg gcccgggcgc ttgcgccact tcctgcccga gccgctggcg 540
cccgagggtg tggccgctgc gtgcgcgcgc gcgacccggt cgctgtttga accgggcgga 600
ggcggggctg gcgcccggtt gggagggggt tggggcctgg cttcctgccg cgcgccgcgg 660
ggacgcctcc gaccagtgtt tgccttttat ggtaataacg cggccggccc ggcttccttt 720
gtccccaatc tgggcgcgcg ccggcgcccc ctggcggcct aaggactcgg cgcgccggaa 780
gtggccaggg cggcagcggc tgctcttggc ggccccgagg tgactatagc cttcttttgt 840
gtcttgatag ttcgccagcc tctgctaacc atgttcatgc cttcttcttt ttcctacagc 900
tcctgggcaa cgtgctggtt attgtgctgt ctcatcattt tggcaaagaa ttc 953

<210> SEQ ID NO 52
<211> LENGTH: 1068
<212> TYPE: DNA
<213> ORGANISM: Artificial Sequence
<220> FEATURE:
<223> OTHER INFORMATION: Made in Lab - Chicken beta-actin exon/intron plus rabbit globin intron

<400> SEQUENCE: 52
gtcgctgcgc gctgccttcg ccccgtgccc cgctccgccg ccgcctcgcg ccgcccgccc 60
cggctctgac tgaccgcgtt actcccacag gtgagcgggc gggacggccc ttctcctccg 120
ggctgtaatt agcgcttggt ttaatgacgg cttgtttctt ttctgtggct gcgtgaaagc 180
cttgaggggc tccgggaggg ccctttgtgc gggggggagcg gctcgggggg tgcgtgcgtg 240
tgtgtgtgcg tggggagcgc cgcgtgcggc tccgcgctgc ccggcggctg tgagcgctgc 300
gggcgcggcg cggggctttg tgcgctccgc agtgtgcgcg aggggagcgc ggccgggggc 360
ggtgccccgc ggtgcggggg gggctgcgag gggaacaaag gctgcgtgcg gggtgtgtgc 420
gtgggggggt gagcaggggg tgtgggcgcg tcggtcgggc tgcaaccccc cctgcacccc 480
cctccccgag ttgctgagca cggcccggct tcgggtgcgg ggctccgtac ggggcgtggc 540
gcggggctcg ccgtgccggg cgggggggtgg cggcaggtgg gggtgccggg cggggcgggg 600
ccgcctcggg ccggggaggg ctcgggggag gggcgcggcg gcccccggag cgccggcggc 660
tgtcgaggcg cggcgagccg cagccattgc cttttatggt aatcgtgcga gagggcgcag 720
ggacttcctt tgtcccaaat ctgtgcggag ccgaaatctg ggaggcgccg ccgcaccccc 780
tctagcgggc gcggggcgaa gcggtgcggc gccggcagga aggaaatggg cggggagggc 840
cttcgtgcgt cgccgcgccg ccgtcccctt ctccctctcc agcctcgggg ctgtccgcgg 900
ggggacggct gccttcgggg gggacggggc agggcggggt tcggcttctg gcgtgtgacc 960
ggcggctcta gagcctctgc taaccatgtt catgccttct tctttttcct acagctcctg 1020
ggcaacgtgc tggttattgt gctgtctcat cattttggca aagaattc 1068

<210> SEQ ID NO 53
<211> LENGTH: 149
<212> TYPE: DNA
<213> ORGANISM: Artificial Sequence
<220> FEATURE:
<223> OTHER INFORMATION: Made in Lab - chimeric intron sequence

<400> SEQUENCE: 53
ggtaagttta gtctttttgt cttttatttc aggtcccgga tccggtggtg gtgcaaatca 60
aagaactgct cctcagtgga tgttgccttt acttctaggc ctgtacggaa gtgttacttc 120
tgctctaaaa gctgcggaat tgtacccgc 149

<210> SEQ ID NO 54
<211> LENGTH: 126
<212> TYPE: DNA
<213> ORGANISM: Homo sapiens

<400> SEQUENCE: 54
agtctgcggt gggcagcgga ggagtcgtgt cgtgcctgag agcgcagctg tgctcctggg 60
caccgcgcag tccgcccccg cggctcctgg ccagaccacc cctaggaccc cctgccccaa 120
gtcgca 126

<210> SEQ ID NO 55
<211> LENGTH: 121
<212> TYPE: DNA
<213> ORGANISM: Human betaherpesvirus 5

<400> SEQUENCE: 55
tcagatcgcc tggagaggcc atccacgctg ttttgacctc catagtggac accgggaccg 60
atccagcctc cgcggccggg aacggtgcat tggaacgcgg attccccgtg ccaagagtga 120
c 121

<210> SEQ ID NO 56
<211> LENGTH: 512
<212> TYPE: DNA
<213> ORGANISM: Artificial Sequence
<220> FEATURE:
<223> OTHER INFORMATION: Made in Lab - adenovirus derived enhancer
element

<400> SEQUENCE: 56
ctcactctct tccgcatcgc tgtctgcgag ggccagctgt tgggctcgcg gttgaggaca 60
aactcttcgc ggtctttcca gtactcttgg atcggaaacc cgtcggcctc cgaacggtac 120
tccgccaccg agggacctga gcgagtccgc atcgaccgga tcggaaaacc tctcgagaaa 180
ggcgtctaac cagtcacagt cgcaaggtag gctgagcacc gtggcgggcg gcagcgggtg 240
gcggtcgggg ttgtttctgg cggaggtgct gctgatgatg taattaaagt aggcggtctt 300
gagacggcgg atggtcgagg tgaggtgtgg caggcttgag atccagctgt tggggtgagt 360
actccctctc aaaagcgggc attacttctg cgctaagatt gtcagtttcc aaaaacgagg 420
aggatttgat attcacctgg cccgatctgg ccatacactt gagtgacaat gacatccact 480
ttgcctttct ctccacaggt gtccactccc ag 512

<210> SEQ ID NO 57
<211> LENGTH: 956
<212> TYPE: DNA
<213> ORGANISM: Homo sapiens

<400> SEQUENCE: 57

```
cttttcgca acgggtttgc cgccagaaca caggtaagtg ccgtgtgtgg ttcccgcggg     60

cctggcctct ttacgggtta tggcccttgc gtgccttgaa ttacttccac ctggctccag    120

tacgtgattc ttgatcccga gctggagcca ggggcgggcc ttgcgcttta ggagcccctt    180

cgcctcgtgc ttgagttgag gcctggcctg ggcgctgggg ccgccgcgtg cgaatctggt    240

ggcaccttcg cgcctgtctc gctgctttcg ataagtctct agccatttaa aatttttgat    300

gacgtgctgc gacgcttttt ttctggcaag atagtcttgt aaatgcgggc caggatctgc    360

acactggtat ttcggttttt gggcccgcgg ccggcgacgg ggcccgtgcg tcccagcgca    420

catgttcggc gaggcggggc ctgcgagcgc ggccaccgag aatcggacgg gggtagtctc    480

aagctggccg gcctgctctg gtgcctggcc tcgcgccgcc gtgtatcgcc ccgccctggg    540

cggcaaggct ggcccggtcg gcaccagttg cgtgagcgga aagatggccg cttcccggcc    600

ctgctccagg gggctcaaaa tggaggacgc ggcgctcggg agagcgggcg ggtgagtcac    660

ccacacaaag gaaaagggcc tttccgtcct cagccgtcgc ttcatgtgac tccacggagt    720

accgggcgcc gtccaggcac ctcgattagt tctggagctt ttggagtacg tcgtctttag    780

gttgggggga ggggttttat gcgatggagt ttccccacac tgagtgggtg gagactgaag    840

ttaggccagc ttggcacttg atgtaattct ccttggaatt tggccttttt gagtttggat    900

cttggttcat tctcaagcct cagacagtgg ttcaaagttt ttttcttcca tttcag        956
```

<210> SEQ ID NO 58
<211> LENGTH: 939
<212> TYPE: DNA
<213> ORGANISM: Homo sapiens

<400> SEQUENCE: 58

```
gtaagtgccg tgtgtggttc ccgcgggcct ggcctcttta cgggttatgg cccttgcgtg     60

ccttgaatta cttccacctg gctgcagtac gtgattcttg atcccgagct tcgggttgga    120

agtgggtggg agagttcgag gccttgcgct taaggagccc cttcgcctcg tgcttgagtt    180

gaggcctggc ctgggcgctg gggccgccgc gtgcgaatct ggtggcacct tcgcgcctgt    240

ctcgctgctt tcgataagtc tctagccatt taaaattttt gatgacctgc tgcgacgctt    300

tttttctggc aagatagtct tgtaaatgcg ggccaagatc tgcacactgg tatttcggtt    360

tttggggccg cgggcggcga cggggcccgt gcgtcccagc gcacatgttc ggcgaggcgg    420

ggcctgcgag cgcggccacc gagaatcgga cgggggtagt ctcaagctgg ccggcctgct    480

ctggtgcctg gcctcgcgcc gccgtgtatc gccccgccct gggcggcaag gctggcccgg    540

tcggcaccag ttgcgtgagc ggaaagatgg ccgcttcccg gccctgctgc agggagctca    600

aaatggagga cgcggcgctc gggagagcgg gcgggtgagt cacccacaca aaggaaaagg    660

gcctttccgt cctcagccgt cgcttcatgt gactccacgg agtaccgggc gccgtccagg    720

cacctcgatt agttctcgag cttttggagt acgtcgtctt taggttgggg ggaggggttt    780

tatgcgatgg agtttcccca cactgagtgg gtggagactg aagttaggcc agcttggcac    840

ttgatgtaat tctccttgga atttgccctt tttgagtttg gatcttggtt cattctcaag    900

cctcagacag tggttcaaag ttttttttctt ccatttcag                            939
```

<210> SEQ ID NO 59
<211> LENGTH: 83
<212> TYPE: DNA
<213> ORGANISM: Homo sapiens

<400> SEQUENCE: 59
tcagaagccc cgggctcgtc agtcaaaccg gttctctgtt tgcactcggc agcacgggca 60
ggcaagtggt ccctaggttc ggg 83

<210> SEQ ID NO 60
<211> LENGTH: 476
<212> TYPE: DNA
<213> ORGANISM: Homo sapiens

<400> SEQUENCE: 60
gtgagtctat gggacccttg atgttttctt tccccttctt ttctatggtt aagttcatgt 60
cataggaagg ggagaagtaa cagggtacac atattgacca aatcagggta attttgcatt 120
tgtaatttta aaaaatgctt tcttctttta atatactttt ttgtttatct tatttctaat 180
actttcccta atctctttct ttcagggcaa taatgataca atgtatcatg cctctttgca 240
ccattctaaa gaataacagt gataatttct gggttaaggc aatagcaata tttctgcata 300
taaatatttc tgcatataaa ttgtaactga tgtaagaggt ttcatattgc taatagcagc 360
tacaatccag ctaccattct gcttttattt tatggttggg ataaggctgg attattctga 420
gtccaagcta ggcccttttg ctaatcatgt tcatacctct tatcttcctc ccacag 476

<210> SEQ ID NO 61
<211> LENGTH: 196
<212> TYPE: DNA
<213> ORGANISM: simian virus 40

<400> SEQUENCE: 61
tctagaggat ccggtactcg aggaactgaa aaaccagaaa gttaactggt aagtttagtc 60
tttttgtctt ttatttcagg tcccggatcc ggtggtggtg caaatcaaag aactgctcct 120
cagtggatgt tgcctttact tctaggcctg tacggaagtg ttacttctgc tctaaaagct 180
gcggaattgt acccgc 196

<210> SEQ ID NO 62
<211> LENGTH: 589
<212> TYPE: DNA
<213> ORGANISM: Artificial Sequence
<220> FEATURE:
<223> OTHER INFORMATION: Made in Lab - mutated woodchuck hepatitis
regulatory element

<400> SEQUENCE: 62
aatcaacctc tggattacaa aatttgtgaa agattgactg gtattcttaa ctatgttgct 60
ccttttacgc tatgtggata cgctgcttta atgcctttgt atcatgctat tgcttcccgt 120
atggctttca ttttctcctc cttgtataaa tcctggttgc tgtctcttta tgaggagttg 180
tggcccgttg tcaggcaacg tggcgtggtg tgcactgtgt ttgctgacgc aacccccact 240
ggttggggca ttgccaccac ctgtcagctc ctttccggga ctttcgcttt ccccctccct 300
attgccacgg cggaactcat cgccgcctgc cttgcccgct gctggacagg ggctcggctg 360
ttgggcactg acaattccgt ggtgttgtcg gggaaatcat cgtcctttcc ttggctgctc 420
gcctgtgttg ccacctggat tctgcgcggg acgtccttct gctacgtccc ttcggccctc 480

```
aatccagcgg accttccttc ccgcggcctg ctgccggctc tgcggcctct tccgcgtctt    540

cgccttcgcc ctcagacgag tcggatctcc ctttgggccg cctccccgc                589


<210> SEQ ID NO 63
<211> LENGTH: 588
<212> TYPE: DNA
<213> ORGANISM: Artificial Sequence
<220> FEATURE:
<223> OTHER INFORMATION: Made in Lab - mutated woodchuck hepatitis
      regulatory element

<400> SEQUENCE: 63

tcaacctctg gattacaaaa tttgtgaaag attgactggt attcttaact atgttgctcc     60

ttttacgcta tgtggatacg ctgctttaat gcctttgtat catgctattg cttcccgtat    120

ggctttcatt ttctcctcct tgtataaatc ctggttgctg tctctttatg aggagttgtg    180

gcccgttgtc aggcaacgtg gcgtggtgtg cactgtgttt gctgacgcaa cccccactgg    240

ttggggcatt gccaccacct gtcagctcct ttccgggact ttcgctttcc ccctccctat    300

tgccacggcg gaactcatcg ccgcctgcct tgcccgctgc tggacagggg ctcggctgtt    360

gggcactgac aattccgtgg tgttgtcggg gaaatcatcg tcctttcctt ggctgctcgc    420

ctgtgttgcc acctggattc tgcgcgggac gtccttctgc tacgtccctt cggccctcaa    480

tccagcggac cttccttccc gcggcctgct gccggctctg cggcctcttc cgcgtcttcg    540

ccttcgccct cagacgagtc ggatctccct ttgggccgcc tccccgca                 588


<210> SEQ ID NO 64
<211> LENGTH: 755
<212> TYPE: DNA
<213> ORGANISM: Artificial Sequence
<220> FEATURE:
<223> OTHER INFORMATION: Made in Lab - mutated woodchuck hepatitis
      regulatory element

<400> SEQUENCE: 64

ttcctgttaa tcaacctctg gattacaaaa tttgtgaaag attgactggt attcttaact     60

atgttgctcc ttttacgcta tgtggatacg ctgctttaat gcctttgtat catgctattg    120

cttcccgtat ggctttcatt ttctcctcct tgtataaatc ctggttgctg tctctttatg    180

aggagttgtg gcccgttgtc aggcaacgtg gcgtggtgtg cactgtgttt gctgacgcaa    240

cccccactgg ttggggcatt gccaccacct gtcagctcct ttccgggact ttcgctttcc    300

ccctccctat tgccacggcg gaactcatcg ccgcctgcct tgcccgctgc tggacagggg    360

ctcggctgtt gggcactgac aattccgtgg tgttgtcggg gaagctgacg tcctttccgc    420

ggctgctcgc ctgtgttgcc acctggattc tgcgcgggac gtccttctgc tacgtccctt    480

cggccctcaa tccagcggac cttccttccc gcggcctgct gccggctctg cggcctcttc    540

cgcctcttcg ccttcgccct cagacgagtc ggatctccct ttgggccgcc tccccgccca    600

tgtatctttt tcacctgtgc cttgtttttg cctgtgttcc gcgtcctact tttcaagcct    660

ccaagctgtg ccttgggcgg ctttggggca tggacataga tccctataaa gaatttggtt    720

catcttatca gttgttgaat tttcttcctt tggac                               755


<210> SEQ ID NO 65
<211> LENGTH: 12
<212> TYPE: DNA
<213> ORGANISM: Artificial Sequence
<220> FEATURE:
<223> OTHER INFORMATION: CAAX motif
```

<400> SEQUENCE: 65
tgtgtgataa tg 12

<210> SEQ ID NO 66
<211> LENGTH: 810
<212> TYPE: DNA
<213> ORGANISM: Homo sapiens

<400> SEQUENCE: 66
ctgttctcat cacatcatat caaggttata taccatcaat attgccacag atgttactta 60
gccttttaat atttctctaa tttagtgtat atgcaatgat agttctctga tttctgagat 120
tgagtttctc atgtgtaatg attatttaga gtttctcttt catctgttca aatttttgtc 180
tagttttatt ttttactgat ttgtaagact tctttttata atctgcatat tacaattctc 240
tttactgggg tgttgcaaat attttctgtc attctatggc ctgacttttc ttaatggttt 300
tttaatttta aaaataagtc ttaatattca tgcaatctaa ttaacaatct tttctttgtg 360
gttaggactt tgagtcataa gaaatttttc tctacactga agtcatgatg gcatgcttct 420
atattatttt ctaaaagatt taaagttttg ccttctccat ttagacttat aattcactgg 480
aatttttttg tgtgtatggt atgacatatg ggttcccttt tattttttac atataaatat 540
atttccctgt ttttctaaaa aagaaaaaga tcatcatttt cccattgtaa aatgccatat 600
ttttttcata ggtcacttac atatatcaat gggtctgttt ctgagctcta ctctatttta 660
tcagcctcac tgtctatccc cacacatctc atgctttgct ctaaatcttg atatttagtg 720
gaacattctt tcccattttg ttctacaaga atatttttgt tattgtcttt gggctttcta 780
tatacatttt gaaatgaggt tgacaagtta 810

<210> SEQ ID NO 67
<211> LENGTH: 726
<212> TYPE: DNA
<213> ORGANISM: Hepatitis B virus

<400> SEQUENCE: 67
ataacaggcc tattgattgg aaagtttgtc aacgaattgt gggtcttttg ggggtttgctg 60 cccctttac gcaatgtgga tatcctgctt taatgccttt atatgcatgt atacaagcaa 120
aacaggcttt tactttctcg ccaacttaca aggcctttct cagtaaacag tatatgaccc 180
tttaccccgt tgctcggcaa cggcctggtc tgtgccaagt gtttgctgac gcaaccccca 240
ctggttgggg cttggccata ggccatcagc gcatgcgtgg aacctttgtg tctcctctgc 300
cgatccatac tgcggaactc ctagccgctt gttttgctcg cagcaggtct ggagcaaacc 360
tcatcgggac cgacaattct gtcgtactct cccgcaagta tacatcgttt ccatggctgc 420
taggctgtgc tgccaactgg atcctgcgcg ggacgtcctt tgtttacgtc ccgtcggcgc 480
tgaatcccgc ggacgacccc tcccggggcc gcttggggct ctaccgcccg cttctccgtc 540
tgccgtaccg tccgaccacg gggcgcacct ctctttacgc ggactccccg tctgtgcctt 600
ctcatctgcc ggaccgtgtg cacttcgctt cacctctgca cgtcgcatgg aggccaccgt 660
gaacgcccac cggaacctgc ccaaggtctt gcataagagg actcttggac tttcagcaat 720
gtcatc 726

<210> SEQ ID NO 68
<211> LENGTH: 755
<212> TYPE: DNA

<213> ORGANISM: Artificial Sequence
<220> FEATURE:
<223> OTHER INFORMATION: Made in Lab - HepB derived enhancer element

<400> SEQUENCE: 68
ttcctgtaaa caggcctatt gattggaaag tttgtcaacg aattgtgggt cttttggggt 60
ttgctgcccc ttttacgcaa tgtggatatc ctgctttaat gcctttatat gcatgtatac 120
aagcaaaaca ggcttttact ttctcgccaa cttacaaggc ctttctcagt aaacagtata 180
tgacccttta ccccgttgct cggcaacggc ctggtctgtg ccaagtgttt gctgacgcaa 240
cccccactgg ttggggcttg gccataggcc atcagcgcat gcgtggaacc tttgtgtctc 300
ctctgccgat ccatactgcg gaactcctag ccgcttgttt tgctcgcagc tggactggag 360
caaacctcat cgggaccgac aattctgtcg tactctcccg caagcactca ccgtttccgc 420
ggctgctcgc ctgtgttgcc acctggattc tgcgcgggac gtccttctgc tacgtccctt 480
cggccctcaa tccagcggac cttccttccc gcggcctgct gccggctctg cggcctcttc 540
cgcctcttcg ccttcgccct cagacgagtc ggatctccct ttgggccgcc tccccgccca 600
tgtatctttt tcacctgtgc cttgtttttg cctgtgttcc gcgtcctact tttcaagcct 660
ccaagctgtg ccttgggcgg ctttggggca tggacataga tccctataaa gaatttggtt 720
catcttatca gttgttgaat ttcttccttt tggac 755

<210> SEQ ID NO 69
<211> LENGTH: 94
<212> TYPE: DNA
<213> ORGANISM: Homo sapiens

<400> SEQUENCE: 69
gctggagcct cggtagccgt tcctcctgcc cgctgggcct cccaacgggc cctcctcccc 60
tccttgcacc ggcccttcct ggtctttgaa taaa 94

<210> SEQ ID NO 70
<211> LENGTH: 596
<212> TYPE: DNA
<213> ORGANISM: Woodchuck hepatitis virus

<400> SEQUENCE: 70
attcgagcat cttaccgcca tttattccca tatttgttct gtttttcttg atttgggtat 60
acatttaaat gttaataaaa caaaatggtg gggcaatcat ttacattttt agggatatgt 120
aattactagt tcaggtgtat tgccacaaga caaacatgtt aagaaacttt cccgttattt 180
acgctctgtt cctgttaatc aacctctgga ttacaaaatt tgtgaaagat tgactgatat 240
tcttaactat gttgctcctt ttacgctgtg tggatatgct gctttaatgc ctctgtatca 300
tgctattgct tcccgtacgg ctttcgtttt ctcctccttg tataaatcct ggttgctgtc 360
tctttatgag gagttgtggc ccgttgtccg tcaacgtggc gtggtgtgct ctgtgtttgc 420
tgacgcaacc cccactggct ggggcattgc caccacctgt caactccttt ctgggacttt 480
cgctttcccc ctcccgatcg ccacggcaga actcatcgcc gcctgccttg cccgctgctg 540
gacaggggct aggttgctgg gcactgataa ttccgtggtg ttgtcgggga agggcc 596

<210> SEQ ID NO 71
<211> LENGTH: 387
<212> TYPE: DNA
<213> ORGANISM: Oryctolagus cuniculus

<400> SEQUENCE: 71

-continued tggctaataa aggaaattta ttttcattgc aatagtgtgt tggaattttt tgtgtctctc 60
actcggaaga acatatggga gggcaaatca tttaaaacat cagaatgagt atttggttta 120
gagtttggca acatatgccc atatgctggc tgccatgaac aaaggttggc tataaagagg 180
tcatcagtat atgaaacagc cccctgctgt ccattcctta ttccatagaa aagccttgac 240
ttgaggttag atttttttta tattttgttt tgtgttattt ttttctttaa catccctaaa 300
attttcctta catgttttac tagccagatt tttcctcctc tcctgactac tcccagtcat 360
agctgtccct cttctcttat ggagatc 387

<210> SEQ ID NO 72
<211> LENGTH: 251
<212> TYPE: DNA
<213> ORGANISM: Bos taurus

<400> SEQUENCE: 72
ttgccagcca tctgttgttt gcccctcccc cgtgccttcc ttgaccctgg aaggtgccac 60
tcccactgtc ctttcctaat aaaatgagga aattgcatcg cattgtctga gtaggtgtca 120
ttctattctg gggggtgggg tggggcagga cagcaagggg gaggattggg aatacaatag 180
caggcatgct ggggatgcgg tgggctctat gggtacccag gtgctgaaga attgacccgg 240
ttcctcctgg g 251

<210> SEQ ID NO 73
<211> LENGTH: 251
<212> TYPE: DNA
<213> ORGANISM: Bos taurus

<400> SEQUENCE: 73
ttgccagcca tctgttgttt gcccctcccc cgtgccttcc ttgaccctgg aaggtgccac 60
tcccactgtc ctttcctaat aaaatgagga aattgcatcg cattgtctga gtaggtgtca 120
ttctattctg gggggtgggg tggggcagga cagcaagggg gaggattggg aagacaatag 180
caggcatgct ggggatgcgg tgggctctat gggtacccag gtgctgaaga attgacccgg 240
ttcctcctgg g 251

<210> SEQ ID NO 74
<211> LENGTH: 225
<212> TYPE: DNA
<213> ORGANISM: Bos taurus

<400> SEQUENCE: 74
ctgtgccttc tagttgccag ccatctgttg tttgcccctc ccccgtgcct tccttgaccc 60
tggaaggtgc cactcccact gtcctttcct aataaaatga ggaaattgca tcgcattgtc 120
tgagtaggtg tcattctatt ctggggggtg gggtggggca ggacagcaag gggaggatt 180 gggaagacaa tagcaggcat gctggggatg cggtgggctc tatgg 225

<210> SEQ ID NO 75
<211> LENGTH: 202
<212> TYPE: DNA
<213> ORGANISM: Homo sapiens

<400> SEQUENCE: 75
ctgcccgggt ggcatccctg tgacccctcc ccagtgcctc tcctggccct ggaagttgcc 60
actccagtgc ccaccagcct tgtcctaata aaattaagtt gcatcatttt gtctgactag 120

-continued

```
gtgtccttct ataatattat ggggtggagg ggggtggtat ggagcaaggg gcccaagttg    180

ggaagaaacc tgtagggcct gc                                             202


<210> SEQ ID NO 76
<211> LENGTH: 735
<212> TYPE: PRT
<213> ORGANISM: Adeno-associated virus 2

<400> SEQUENCE: 76

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
```

-continued

```
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735
```

<210> SEQ ID NO 77
<211> LENGTH: 736
<212> TYPE: PRT
<213> ORGANISM: Adeno-associated virus 9

<400> SEQUENCE: 77

-continued

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
```

```
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735


<210> SEQ ID NO 78
<211> LENGTH: 736
<212> TYPE: PRT
<213> ORGANISM: Adeno-associated virus 6

<400> SEQUENCE: 78

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60
```

-continued

```
Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
```

```
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Lys Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
            580                 585                 590

Thr Gly Asp Val His Val Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735


<210> SEQ ID NO 79
<211> LENGTH: 738
<212> TYPE: PRT
<213> ORGANISM: Non-human primate Adeno-associated virus

<400> SEQUENCE: 79

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125
```

```
Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Ala Gly Thr Gln Gln Leu Leu
    450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
    530                 535                 540

Phe Gly Lys Gln Gly Ala Gly Lys Asp Asn Val Asp Tyr Ser Ser Val
```

-continued 545 550 555 560

Met Leu Thr Ser Glu Glu Glu Ile Lys Thr Thr Asn Pro Val Ala Thr
565 570 575

Glu Gln Tyr Gly Val Val Ala Asp Asn Leu Gln Gln Gln Asn Ala Ala
580 585 590

Pro Ile Val Gly Ala Val Asn Ser Gln Gly Ala Leu Pro Gly Met Val
595 600 605

Trp Gln Asn Arg Asp Val Tyr Leu Gln Gly Pro Ile Trp Ala Lys Ile
610 615 620

Pro His Thr Asp Gly Asn Phe His Pro Ser Pro Leu Met Gly Gly Phe
625 630 635 640

Gly Leu Lys His Pro Pro Pro Gln Ile Leu Ile Lys Asn Thr Pro Val
645 650 655

Pro Ala Asp Pro Pro Thr Thr Phe Ser Gln Ala Lys Leu Ala Ser Phe
660 665 670

Ile Thr Gln Tyr Ser Thr Gly Gln Val Ser Val Glu Ile Glu Trp Glu
675 680 685

Leu Gln Lys Glu Asn Ser Lys Arg Trp Asn Pro Glu Ile Gln Tyr Thr
690 695 700

Ser Asn Tyr Tyr Lys Ser Thr Asn Val Asp Phe Ala Val Asn Thr Asp
705 710 715 720

Gly Thr Tyr Ser Glu Pro Arg Pro Ile Gly Thr Arg Tyr Leu Thr Arg
725 730 735

Asn Leu

<210> SEQ ID NO 80
<211> LENGTH: 2217
<212> TYPE: DNA
<213> ORGANISM: Non-human primate adeno-associated virus

<400> SEQUENCE: 80
atggctgccg atggttatct tccagattgg ctcgaggaca acctctctga gggcattcgc 60
gagtggtggg acctgaaacc tggagccccg aaacccaaag ccaaccagca aaagcaggac 120
aacggccggg gtctggtgct tcctggctac aagtacctcg gacccttcaa cggactcgac 180
aagggggagc ccgtcaacgc ggcggacgca gcggccctcg agcacgacaa ggcctacgac 240
cagcagctcc aagcgggtga caatccgtac ctgcggtata atcacgccga cgccgagttt 300
caggagcgtc tgcaagaaga tacgtctttt gggggcaacc tcgggcgcgc agtcttccag 360
gccaaaaagc gggttctcga acctctgggc ctggttgaat cgccggttaa gacggctcct 420
ggaaagaaga gaccggtaga gccatcaccc cagcgctctc cagactcctc tacgggcatc 480
ggcaagaaag gccagcagcc cgcaaaaaag agactcaatt ttgggcagac tggcgactca 540
gagtcagtcc ccgaccctca accaatcgga gaaccaccag caggcccctc tggtctggga 600
tctggtacaa tggctgcagg cggtggcgct ccaatggcag acaataacga aggcgccgac 660
ggagtgggta gttcctcagg aaattggcat tgcgattcca catggctggg cgacagagtc 720
atcaccacca gcacccgcac ctgggccctg cccacctaca acaaccacct ctacaagcaa 780
atctccaacg ggacctcggg aggaagcacc aacgacaaca cctacttcgg ctacagcacc 840
ccctgggggt attttgactt caacagattc cactgccact tttcaccacg tgactggcag 900
cgactcatca acaacaactg gggattccgg cccaagaggc tcaacttcaa gctcttcaac 960
atccaagtca aggaggtcac gcagaatgaa ggcaccaaga ccatcgccaa taaccttacc 1020

```
agcacgattc aggtctttac ggactcggaa taccagctcc cgtacgtgct cggctcggcg   1080

caccagggct gcctgcctcc gttcccggcg gacgtcttca tgattcctca gtacgggtac   1140

ctgactctga acaatggcag tcaggctgtg ggccggtcgt ccttctactg cctggagtac   1200

tttccttctc aaatgctgag aacgggcaac aactttgaat tcagctacaa cttcgaggac   1260

gtgcccttcc acagcagcta cgcgcacagc cagagcctgg accggctgat gaaccctctc   1320

atcgaccagt acttgtacta cctgtcccgg actcaaagca cgggcggtac tgcaggaact   1380

cagcagttgc tattttctca ggccgggcct aacaacatgt cggctcaggc caagaactgg   1440

ctacccggtc cctgctaccg gcagcaacgc gtctccacga cactgtcgca gaacaacaac   1500

agcaactttg cctggacggg tgccaccaag tatcatctga atggcagaga ctctctggtg   1560

aatcctggcg ttgccatggc tacccacaag gacgacgaag agcgattttt tccatccagc   1620

ggagtcttaa tgtttgggaa acagggagct ggaaaagaca acgtggacta tagcagcgtg   1680

atgctaacca gcgaggaaga aataaagacc accaacccag tggccacaga acagtacggc   1740

gtggtggccg ataacctgca acagcaaaac gccgctccta ttgtaggggc cgtcaatagt   1800

caaggagcct tacctggcat ggtgtggcag aaccgggacg tgtacctgca gggtcccatc   1860

tgggccaaga ttcctcatac ggacggcaac tttcatccct cgccgctgat gggaggcttt   1920

ggactgaagc atccgcctcc tcagatcctg attaaaaaca cacctgttcc cgcggatcct   1980

ccgaccacct tcaatcaggc caagctggct tctttcatca cgcagtacag taccggccag   2040

gtcagcgtgg agatcgagtg ggagctgcag aaggagaaca gcaaacgctg gaacccagag   2100

attcagtaca cttccaacta ctacaaatct acaaatgtgg actttgctgt caatactgag   2160

ggtacttatt ccgagcctcg ccccattggc acccgttacc tcacccgtaa tctgtaa      2217
```

<210> SEQ ID NO 81
<211> LENGTH: 535
<212> TYPE: PRT
<213> ORGANISM: Non-human primate adeno-associated virus

<400> SEQUENCE: 81

```
Met Ala Ala Gly Gly Gly Ala Pro Met Ala Asp Asn Asn Glu Gly Ala
1               5                   10                  15

Asp Gly Val Gly Ser Ser Ser Gly Asn Trp His Cys Asp Ser Thr Trp
            20                  25                  30

Leu Gly Asp Arg Val Ile Thr Thr Ser Thr Arg Thr Trp Ala Leu Pro
        35                  40                  45

Thr Tyr Asn Asn His Leu Tyr Lys Gln Ile Ser Asn Gly Thr Ser Gly
    50                  55                  60

Gly Ser Thr Asn Asp Asn Thr Tyr Phe Gly Tyr Ser Thr Pro Trp Gly
65                  70                  75                  80

Tyr Phe Asp Phe Asn Arg Phe His Cys His Phe Ser Pro Arg Asp Trp
                85                  90                  95

Gln Arg Leu Ile Asn Asn Asn Trp Gly Phe Arg Pro Lys Arg Leu Asn
            100                 105                 110

Phe Lys Leu Phe Asn Ile Gln Val Lys Glu Val Thr Gln Asn Glu Gly
        115                 120                 125

Thr Lys Thr Ile Ala Asn Asn Leu Thr Ser Thr Ile Gln Val Phe Thr
    130                 135                 140

Asp Ser Glu Tyr Gln Leu Pro Tyr Val Leu Gly Ser Ala His Gln Gly
145                 150                 155                 160

Cys Leu Pro Pro Phe Pro Ala Asp Val Phe Met Ile Pro Gln Tyr Gly
```

```
                165                 170                 175

Tyr Leu Thr Leu Asn Asn Gly Ser Gln Ala Val Gly Arg Ser Ser Phe
            180                 185                 190

Tyr Cys Leu Glu Tyr Phe Pro Ser Gln Met Leu Arg Thr Gly Asn Asn
        195                 200                 205

Phe Glu Phe Ser Tyr Asn Phe Glu Asp Val Pro Phe His Ser Ser Tyr
    210                 215                 220

Ala His Ser Gln Ser Leu Asp Arg Leu Met Asn Pro Leu Ile Asp Gln
225                 230                 235                 240

Tyr Leu Tyr Tyr Leu Ser Arg Thr Gln Ser Thr Gly Gly Thr Ala Gly
                245                 250                 255

Thr Gln Gln Leu Leu Phe Ser Gln Ala Gly Pro Asn Asn Met Ser Ala
            260                 265                 270

Gln Ala Lys Asn Trp Leu Pro Gly Pro Cys Tyr Arg Gln Gln Arg Val
        275                 280                 285

Ser Thr Thr Leu Ser Gln Asn Asn Asn Ser Asn Phe Ala Trp Thr Gly
    290                 295                 300

Ala Thr Lys Tyr His Leu Asn Gly Arg Asp Ser Leu Val Asn Pro Gly
305                 310                 315                 320

Val Ala Met Ala Thr His Lys Asp Asp Glu Glu Arg Phe Phe Pro Ser
                325                 330                 335

Ser Gly Val Leu Met Phe Gly Lys Gln Gly Ala Gly Lys Asp Asn Val
            340                 345                 350

Asp Tyr Ser Ser Val Met Leu Thr Ser Glu Glu Glu Ile Lys Thr Thr
        355                 360                 365

Asn Pro Val Ala Thr Glu Gln Tyr Gly Val Val Ala Asp Asn Leu Gln
    370                 375                 380

Gln Gln Asn Ala Ala Pro Ile Val Gly Ala Val Asn Ser Gln Gly Ala
385                 390                 395                 400

Leu Pro Gly Met Val Trp Gln Asn Arg Asp Val Tyr Leu Gln Gly Pro
                405                 410                 415

Ile Trp Ala Lys Ile Pro His Thr Asp Gly Asn Phe His Pro Ser Pro
            420                 425                 430

Leu Met Gly Gly Phe Gly Leu Lys His Pro Pro Pro Gln Ile Leu Ile
        435                 440                 445

Lys Asn Thr Pro Val Pro Ala Asp Pro Pro Thr Thr Phe Asn Gln Ala
    450                 455                 460

Lys Leu Ala Ser Phe Ile Thr Gln Tyr Ser Thr Gly Gln Val Ser Val
465                 470                 475                 480

Glu Ile Glu Trp Glu Leu Gln Lys Glu Asn Ser Lys Arg Trp Asn Pro
                485                 490                 495

Glu Ile Gln Tyr Thr Ser Asn Tyr Tyr Lys Ser Thr Asn Val Asp Phe
            500                 505                 510

Ala Val Asn Thr Glu Gly Thr Tyr Ser Glu Pro Arg Pro Ile Gly Thr
        515                 520                 525

Arg Tyr Leu Thr Arg Asn Leu
    530                 535
```

<210> SEQ ID NO 82
<211> LENGTH: 398
<212> TYPE: PRT
<213> ORGANISM: Non-human primate adeno-associated virus

<400> SEQUENCE: 82

-continued

```
Ser Thr Ile Gln Val Phe Thr Asp Ser Glu Tyr Gln Leu Pro Tyr Val
1               5                   10                  15

Leu Gly Ser Ala His Gln Gly Cys Leu Pro Pro Phe Pro Ala Asp Val
            20                  25                  30

Phe Met Ile Pro Gln Tyr Gly Tyr Leu Thr Leu Asn Asn Gly Ser Gln
        35                  40                  45

Ala Val Gly Arg Ser Ser Phe Tyr Cys Leu Glu Tyr Phe Pro Ser Gln
    50                  55                  60

Met Leu Arg Thr Gly Asn Asn Phe Glu Phe Ser Tyr Asn Phe Glu Asp
65                  70                  75                  80

Val Pro Phe His Ser Ser Tyr Ala His Ser Gln Ser Leu Asp Arg Leu
                85                  90                  95

Met Asn Pro Leu Ile Asp Gln Tyr Leu Tyr Tyr Leu Ser Arg Thr Gln
            100                 105                 110

Ser Thr Gly Gly Thr Ala Gly Thr Gln Gln Leu Leu Phe Ser Gln Ala
        115                 120                 125

Gly Pro Asn Asn Met Ser Ala Gln Ala Lys Asn Trp Leu Pro Gly Pro
    130                 135                 140

Cys Tyr Arg Gln Gln Arg Val Ser Thr Thr Leu Ser Gln Asn Asn Asn
145                 150                 155                 160

Ser Asn Phe Ala Trp Thr Gly Ala Thr Lys Tyr His Leu Asn Gly Arg
                165                 170                 175

Asp Ser Leu Val Asn Pro Gly Val Ala Met Ala Thr His Lys Asp Asp
            180                 185                 190

Glu Glu Arg Phe Phe Pro Ser Ser Gly Val Leu Met Phe Gly Lys Gln
        195                 200                 205

Gly Ala Gly Lys Asp Asn Val Asp Tyr Ser Ser Val Met Leu Thr Ser
    210                 215                 220

Glu Glu Glu Ile Lys Thr Thr Asn Pro Val Ala Thr Glu Gln Tyr Gly
225                 230                 235                 240

Val Val Ala Asp Asn Leu Gln Gln Gln Asn Ala Ala Pro Ile Val Gly
                245                 250                 255

Ala Val Asn Ser Gln Gly Ala Leu Pro Gly Met Val Trp Gln Asn Arg
            260                 265                 270

Asp Val Tyr Leu Gln Gly Pro Ile Trp Ala Lys Ile Pro His Thr Asp
        275                 280                 285

Gly Asn Phe His Pro Ser Pro Leu Met Gly Gly Phe Gly Leu Lys His
    290                 295                 300

Pro Pro Pro Gln Ile Leu Ile Lys Asn Thr Pro Val Pro Ala Asp Pro
305                 310                 315                 320

Pro Thr Thr Phe Asn Gln Ala Lys Leu Ala Ser Phe Ile Thr Gln Tyr
                325                 330                 335

Ser Thr Gly Gln Val Ser Val Glu Ile Glu Trp Glu Leu Gln Lys Glu
            340                 345                 350

Asn Ser Lys Arg Trp Asn Pro Glu Ile Gln Tyr Thr Ser Asn Tyr Tyr
        355                 360                 365

Lys Ser Thr Asn Val Asp Phe Ala Val Asn Thr Glu Gly Thr Tyr Ser
    370                 375                 380

Glu Pro Arg Pro Ile Gly Thr Arg Tyr Leu Thr Arg Asn Leu
385                 390                 395
```

<210> SEQ ID NO 83
<211> LENGTH: 332
<212> TYPE: PRT

<213> ORGANISM: Non-human primate adeno-associated virus

<400> SEQUENCE: 83

Arg Thr Gly Asn Asn Phe Glu Phe Ser Tyr Asn Phe Glu Asp Val Pro
1 5 10 15

Phe His Ser Ser Tyr Ala His Ser Gln Ser Leu Asp Arg Leu Met Asn
20 25 30

Pro Leu Ile Asp Gln Tyr Leu Tyr Tyr Leu Ser Arg Thr Gln Ser Thr
35 40 45

Gly Gly Thr Ala Gly Thr Gln Gln Leu Leu Phe Ser Gln Ala Gly Pro
50 55 60

Asn Asn Met Ser Ala Gln Ala Lys Asn Trp Leu Pro Gly Pro Cys Tyr
65 70 75 80

Arg Gln Gln Arg Val Ser Thr Thr Leu Ser Gln Asn Asn Asn Ser Asn
85 90 95

Phe Ala Trp Thr Gly Ala Thr Lys Tyr His Leu Asn Gly Arg Asp Ser
100 105 110

Leu Val Asn Pro Gly Val Ala Met Ala Thr His Lys Asp Asp Glu Glu
115 120 125

Arg Phe Phe Pro Ser Ser Gly Val Leu Met Phe Gly Lys Gln Gly Ala
130 135 140

Gly Lys Asp Asn Val Asp Tyr Ser Ser Val Met Leu Thr Ser Glu Glu
145 150 155 160

Glu Ile Lys Thr Thr Asn Pro Val Ala Thr Glu Gln Tyr Gly Val Val
165 170 175

Ala Asp Asn Leu Gln Gln Gln Asn Ala Ala Pro Ile Val Gly Ala Val
180 185 190

Asn Ser Gln Gly Ala Leu Pro Gly Met Val Trp Gln Asn Arg Asp Val
195 200 205

Tyr Leu Gln Gly Pro Ile Trp Ala Lys Ile Pro His Thr Asp Gly Asn
210 215 220

Phe His Pro Ser Pro Leu Met Gly Gly Phe Gly Leu Lys His Pro Pro
225 230 235 240

Pro Gln Ile Leu Ile Lys Asn Thr Pro Val Pro Ala Asp Pro Pro Thr
245 250 255

Thr Phe Asn Gln Ala Lys Leu Ala Ser Phe Ile Thr Gln Tyr Ser Thr
260 265 270

Gly Gln Val Ser Val Glu Ile Glu Trp Glu Leu Gln Lys Glu Asn Ser
275 280 285

Lys Arg Trp Asn Pro Glu Ile Gln Tyr Thr Ser Asn Tyr Tyr Lys Ser
290 295 300

Thr Asn Val Asp Phe Ala Val Asn Thr Glu Gly Thr Tyr Ser Glu Pro
305 310 315 320

Arg Pro Ile Gly Thr Arg Tyr Leu Thr Arg Asn Leu
325 330

<210> SEQ ID NO 84
<211> LENGTH: 743
<212> TYPE: PRT
<213> ORGANISM: Artificial Sequence
<220> FEATURE:
<223> OTHER INFORMATION: Synthetic construct - AAV9 variant

<400> SEQUENCE: 84

Met Ala Ala Asp Gly Tyr Leu Pro Asp Trp Leu Glu Asp Asn Leu Ser
1 5 10 15

-continued

```
Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430
```

```
Asp Arg Leu Met Asn Pro Leu Ile Asp Gln Tyr Leu Tyr Tyr Leu Ser
        435                 440                 445

Arg Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Thr Leu Ala Val
            580                 585                 590

Pro Phe Lys Ala Gln Ala Gln Thr Gly Trp Val Gln Asn Gln Gly Ile
        595                 600                 605

Leu Pro Gly Met Val Trp Gln Asp Arg Asp Val Tyr Leu Gln Gly Pro
    610                 615                 620

Ile Trp Ala Lys Ile Pro His Thr Asp Gly Asn Phe His Pro Ser Pro
625                 630                 635                 640

Leu Met Gly Gly Phe Gly Met Lys His Pro Pro Pro Gln Ile Leu Ile
                645                 650                 655

Lys Asn Thr Pro Val Pro Ala Asp Pro Pro Thr Ala Phe Asn Lys Asp
            660                 665                 670

Lys Leu Asn Ser Phe Ile Thr Gln Tyr Ser Thr Gly Gln Val Ser Val
        675                 680                 685

Glu Ile Glu Trp Glu Leu Gln Lys Glu Asn Ser Lys Arg Trp Asn Pro
    690                 695                 700

Glu Ile Gln Tyr Thr Ser Asn Tyr Tyr Lys Ser Asn Asn Val Glu Phe
705                 710                 715                 720

Ala Val Asn Thr Glu Gly Val Tyr Ser Glu Pro Arg Pro Ile Gly Thr
                725                 730                 735

Arg Tyr Leu Thr Arg Asn Leu
            740
```

<210> SEQ ID NO 85
<211> LENGTH: 7
<212> TYPE: PRT
<213> ORGANISM: Artificial Sequence
<220> FEATURE:
<223> OTHER INFORMATION: Peptide insert

<400> SEQUENCE: 85

```
Thr Leu Ala Val Pro Phe Lys
1               5
```

<210> SEQ ID NO 86
<211> LENGTH: 7
<212> TYPE: PRT
<213> ORGANISM: Artificial Sequence
<220> FEATURE:

<223> OTHER INFORMATION: Peptide insert

<400> SEQUENCE: 86

Lys Phe Pro Val Ala Leu Thr
1 5

<210> SEQ ID NO 87
<211> LENGTH: 2514
<212> TYPE: DNA
<213> ORGANISM: Artificial Sequence
<220> FEATURE:
<223> OTHER INFORMATION: Made in Lab - codon optimized PKP2a polynucleotide

<400> SEQUENCE: 87

```
atggctgcac ctggtgcgcc tgccgaatat ggttatataa ggacagtttt gggtcaacag     60
atacttggac aacttgattc ctcttctttg gcgctccctt cagaagcaaa gttgaaattg    120
gcaggttcat caggtagagg aggacaaact gtgaaatctc tgcggattca ggaacaagta    180
caacagactt tggctagaaa gggaagatct tccgttggca atggaaattt gcatagaacg    240
agcagcgtac ctgaatacgt atacaatctc catcttgttg aaaacgattt tgtaggaggt    300
cggtctccag ttccgaaaac atatgatatg cttaaagcag gtactacagc tacatacgaa    360
ggtagatggg gaagaggaac tgcacaatat tcatctcaaa aatctgttga agaaaggtca    420
ttgcgacatc ctctcagaag gctcgaaatt tccccggatt catcacctga aagggctcat    480
tatacacaca gtgattatca atatagccaa cgatctcaag caggtcatac acttcatcat    540
caggaaagta ggcgggcggc attgcttgta ccccctcgat atgccaggtc agaaattgta    600
ggagtttcca gagcaggtac tactagtcga caaagacact ttgacacata tcataggcaa    660
tatcaacacg gtagtgtctc agacactgtt tttgattcaa taccagcaaa tccggcattg    720
ctgacgtatc ctcgacctgg tacgtcaagg agcatgggaa atcttctgga gaaagaaaat    780
tatttgactg ctgggcttac agttggacag gtacggccat tggttcctct tcaaccagtt    840
actcagaatc gagcttccag aagctcttgg catcaatcaa gctttcattc cacaaggaca    900
ctgagagaag caggaccttc tgttgccgtt gattccagtg ggcggagagc ccaccttaca    960
gtaggtcaag cagctgccgg aggatcaggt aatttgctta cagaaaggag tacttttaca   1020
gatagccaac tcgggaatgc ggatatggaa atgacattgg agagagctgt atcaatgctg   1080
gaagcggatc atatgcttcc ttctagaatt tccgctgcgg caacttttat acagcacgaa   1140
tgttttcaaa aatccgaagc gcgaaagcgg gttaatcagc tgagaggtat tctgaaactg   1200
ttgcaacttt tgaaagtgca aaatgaagat gttcaaagag ctgtttgtgg agctcttaga   1260
aatcttgttt ttgaagataa tgataataaa ttggaagttg ctgaacttaa tggtgtacct   1320
agattgcttc aagttttgaa acaaacaaga gatttggaaa caaaaaaaca aataacagga   1380
cttttgtgga atctttcttc taatgataaa cttaaaaatt tgatgataac agaagctttg   1440
ttgacactta cagaaaatat tattatacct ttttctggat ggcctgaagg ggattatcca   1500
aaagctaatg ggttgctgga ttttgatatt ttttataatg tgacaggatg tttgaggaat   1560
atgtcctcag ctggtgctga cggtcggaaa gcaatgaggc gatgtgacgg tttgatcgat   1620
tcccttgttc attacgttag gggaacaata gctgattatc aaccagatga taaagcaaca   1680
gaaaattgtg tttgtattct tcataatctg tcttatcaat tggaagccga acttcctgaa   1740
aaatactctc aaaatatcta tattcagaat cggaacatac aaactgataa taacaaatct   1800
ataggatgtt ttggatcaag aagcagaaaa gttaaggaac aatatcaaga cgttcctatg   1860
```

```
cccgaagaaa aatcaaatcc aaagggtgta gaatggctgt ggcattctat tgttattaga   1920

atgtatttgt cactcatagc aaaatctgta cgaaattata cacaagaagc ttctttggga   1980

gcccttcaga atcttacagc aggaagtggt cctatgccta caagtgtagc gcaaacagtt   2040

gtacagaaag aatctggatt gcaacatact agaaagatgc tgcatgtagg agatccttct   2100

gttaaaaaga cagctataag cctcctgagg aacttgagtc gcaacttgtc tctccagaat   2160

gagattgcta aggaaacgct tcctgacctt gtatctatta tacctgacac ggtgccttcc   2220

acagatcttt tgattgaaac aactgcatct gcttgttata cattgaataa tatcattcaa   2280

aatagttatc agaacgcaag agatcttctg aatacaggag gtattcaaaa aataatggct   2340

atttcagcag gtgatgcata tgcttctaat aaagcgtcta aagctgcatc tgttcttttg   2400

tattctcttt gggcacatac agaacttcac catgcctaca agaaagctca attcaagaaa   2460

acagattttg ttaatagtcg cactgcaaaa gcgtatcatt cccttaagga ttaa         2514
```

<210> SEQ ID NO 88
<211> LENGTH: 2646
<212> TYPE: DNA
<213> ORGANISM: Artificial Sequence
<220> FEATURE:
<223> OTHER INFORMATION: Made in Lab - codon optimized PKP2b polynucleotide

<400> SEQUENCE: 88

```
atggccgcac ctggagctcc agctgaatat ggatatatca ggactgtctt gggtcagcag     60

attctgggcc aactggattc ttcaagtctg gccctcccga gtgaggcaaa actgaaactc    120

gcaggatcta gtggaagggg cggacagaca gtgaagtcac tcaggattca ggagcaggtc    180

caacagacac tggcaagaaa agggaggtcc agcgtcggca atggtaactt gcatagaacc    240

tcttcagtgc ctgagtacgt gtacaacctg cacctggtgg aaaacgattt tgtgggcggc    300

agatccccgg tccctaaaac ttatgacatg ctgaaagctg gcacgacagc tacatatgaa    360

ggtagatggg gccggggcac cgcacaatat agttctcaga agtccgtgga agaaagatct    420

cttaggcacc cacttcggcg actggagata agtccagaca gcagccccga aagggcgcat    480

tatacacatt ctgactacca atacagccaa agatctcagg ctggccacac tctgcatcat    540

caggaaagta gaagggccgc ccttctcgtc cccccaagat acgcacggtc agaaatcgtg    600

ggagtgagca gagcaggtac cacctctcga cagaggcatt tcgacacata ccaccgacaa    660

taccaacatg gatcagtgtc agatactgtt tttgactcca taccagcaaa tccagcactc    720

ctgacatatc ctagaccggg gactagtcgc tccatgggga atctgctcga aaaagaaaac    780

tatctcaccg caggtctgac tgtggggcag gtaaggccgt tggtgcccct tcagcctgta    840

acgcagaata gggcttccag gtcatcctgg caccagagta gcttccactc cacaaggact    900

ctgagagagg caggccctag tgttgcagtt gatagttccg gtcgcagggc ccatcttaca    960

gttggtcaag ccgctgcagg gggtagcggt aatctgctga ccgaaagaag cacattcacg   1020

gattcccagc tcggaaatgc agacatggag atgacacttg aacgagccgt gagcatgctg   1080

gaagctgacc atatgctccc ttctagaatc tccgctgcgg ccactttcat ccagcacgag   1140

tgctttcaga aatccgaagc taggaaacgc gtgaaccagc tgaggggcat cctgaagctg   1200

ctgcagctgc ttaaggtgca gaatgaggat gtccaacgcg cagtgtgcgg tgctctgagg   1260

aacctcgtgt ttgaagataa cgataataag ttggaagtcg cagaacttaa cggggtacct   1320

cgactgctcc aggtgttgaa acagacacgg gacctggaaa cgaaaaaaca aattaccgac   1380
```

cacactgtga atctcagaag tcggaatggg tggcctgggg cagtagctca tgcctgtaac 1440
ccttctacat tgggtggcca aggcgggagg attaccagat caggggtacg ggatcaacct 1500
gatcagcacg ggctcctgtg gaacttgtcc tctaatgaca aactgaaaaa cctgatgata 1560
accgaggctc tgctgaccct gacagaaaac attatcatcc ccttctccgg atggccagaa 1620
ggagactatc ctaaagctaa cggcttgctg gacttcgata tcttttataa tgtcacaggg 1680
tgccttagaa atatgagtag cgccggtgcc gatggaagga aggcaatgcg ccggtgtgat 1740
ggtcttatcg attccctggt acattacgtg aggggcacca ttgccgacta ccaaccagac 1800
gataaagcaa ccgagaattg cgtgtgcatc ctgcacaatt tgagctacca actcgaagct 1860
gaactgcctg agaaatattc ccaaaatatt tatatccaga atcggaatat ccagaccgat 1920
aataacaaga gcataggatg ctttggttct agaagccgca aggtcaagga acagtaccag 1980
gatgtaccta tgccagagga aaaatcaaac cccaaaggag tggaatggct gtggcattcc 2040
atcgtgatca ggatgtacct gagtctgatt gctaagagcg tgaggaacta tacacaggag 2100
gcttcccttg gcgcactgca aaatctgacc gccggatctg ggccaatgcc aacaagcgtt 2160
gctcaaacag tagtgcaaaa ggaatctggc cttcagcaca ctaggaaaat gcttcatgtg 2220
ggagatcctt ctgtgaagaa gacggctatt agcctgctcc gcaacttgag cagaaacctt 2280
tctttgcaga atgagattgc gaaagagacg ctccctgacc tggtgtccat tataccagac 2340
acggtccctt ccacagatct tctgattgaa acgaccgctt ccgcatgtta caccctgaat 2400
aatattattc aaaactcata ccaaaatgct agagacctgc tgaacactgg ggggatccag 2460
aagattatgg caatttcagc cggcgatgcc tatgctagta ataaagcctc caaggccgcc 2520
agtgtattgc tgtatagtct gtgggcacat acagaactgc accacgcata taagaaggcc 2580
cagtttaaaa aaaccgattt cgtaaactct cggactgcaa aagcctacca ttcactgaaa 2640
gattga 2646

<210> SEQ ID NO 89
<211> LENGTH: 4650
<212> TYPE: DNA
<213> ORGANISM: Artificial Sequence
<220> FEATURE:
<223> OTHER INFORMATION: Made in Lab - polynucleotide sequence of vector genome

<400> SEQUENCE: 89
gcgcgctcgc tcgctcactg aggccgcccg ggcaaagccc gggcgtcggg cgacctttgg 60
tcgcccggcc tcagtgagcg agcgagcgcg cagagaggga gtggccaact ccatcactag 120
gggttccttg tagttaatga ttaacccgcc atgctactta tctacgtact ctggagacgc 180
gtacccttca gattaaaaat aactgaggta agggcctggg taggggaggt ggtgtgagac 240
gctcctgtct ctcctctatc tgcccatcgg ccctttgggg aggaggaatg tgcccaagga 300
ctaaaaaaag gccatggagc cagaggggcg agggcaacag acctttcatg ggcaaacctt 360
ggggccctgc tgtctagcat gccccactac gggtctaggc tgcccatgta aggaggcaag 420
gcctggggac acccgagatg cctggttata attaacccag acatgtggct gccccccccc 480
ccccaacacc tgctgcctct aaaaataacc ctgtccctgg tggatcccct gcatgcgaag 540
atcttcgaac aaggctgtgg gggactgagg gcaggctgta acaggcttgg gggccagggc 600
ttatacgtgc ctgggactcc caaagtatta ctgttccatg ttcccggcga agggccagct 660
gtcccccgcc agctagactc agcacttagt ttaggaacca gtgagcaagt cagcccttgg 720

-continued

```
ggcagcccat acaaggccat ggggctgggc aagctgcacg cctgggtccg gggtgggcac    780
ggtgcccggg caacgagctg aaagctcatc tgctctcagg ggcccctccc tggggacagc    840
ccctcctggc tagtcacacc ctgtaggctc ctctatataa cccaggggca caggggctgc    900
cctcattcta ccaccacctc cacagcacag acagacactc aggagccagc cagggtaagt    960
ttagtctttt tgtcttttat ttcaggtccc ggatccggtg gtggtgcaaa tcaaagaact   1020
gctcctcagt ggatgttgcc tttacttcta ggcctgtacg gaagtgttac ttctgctcta   1080
aaagctgcgg aattgtaccc gcgccaccat ggcagccccc ggcgccccag ctgagtacgg   1140
ctacatccgg accgtcctgg gccagcagat cctgggacaa ctggacagct ccagcctggc   1200
gctgccctcc gaggccaagc tgaagctggc ggggagcagc ggccgcggcg gccagacagt   1260
caagagcctg cggatccagg agcaggtgca gcagaccctc gcccggaagg gccgcagctc   1320
cgtgggcaac ggaaatcttc accgaaccag cagtgttcct gagtatgtct acaacctaca   1380
cttggttgaa aatgattttg ttggaggccg ttcccctgtt cctaaaacct atgacatgct   1440
aaaggctggc acaactgcca cttatgaagg tcgctgggga agaggaacag cacagtacag   1500
ctcccagaag tccgtggaag aaaggtcctt gaggcatcct ctgaggagac tggagatttc   1560
tcctgacagc agcccggaga gggctcacta cacgcacagc gattaccagt acagccagag   1620
aagccaggct gggcacaccc tgcaccacca agaaagcagg cgggccgccc tcctagtgcc   1680
accgagatat gctcgttccg agatcgtggg ggtcagccgt gctggcacca caagcaggca   1740
gcgccacttt gacacatacc acagacagta ccagcatggc tctgttagcg acaccgtttt   1800
tgacagcatc cctgccaacc cggccctgct cacgtacccc aggccaggga ccagccgcag   1860
catgggcaac ctcttggaga aggagaacta cctgacggca gggctcactg tcgggcaggt   1920
caggccgctg gtgcccctgc agcccgtcac tcagaacagg gcttccaggt cctcctggca   1980
tcagagctcc ttccacagca cccgcacgct gagggaagct gggcccagtg tcgccgtgga   2040
ttccagcggg aggagagcgc acttgactgt cggccaggcg gccgcagggg gaagtgggaa   2100
tctgctcact gagagaagca ctttcactga ctcccagctg gggaatgcag acatggagat   2160
gactctggag cgagcagtga gtatgctcga ggcagaccac atgctgccat ccaggatttc   2220
tgctgcagct actttcatac agcacgagtg cttccagaaa tctgaagctc ggaagagggt   2280
taaccagctt cgtggcatcc tcaagcttct gcagctccta aaagttcaga atgaagacgt   2340
tcagcgagct gtgtgtgggg ccttgagaaa cttagtattt gaagacaatg acaacaaatt   2400
ggaggtggct gaactaaatg ggtacctcg gctgctccag gtgctgaagc aaaccagaga    2460
cttggagact aaaaaacaaa taacaggttt gctgtggaat ttgtcatcta atgacaaact   2520
caagaatctc atgataacag aagcattgct tacgctgacg gagaatatca tcatcccctt   2580
ttctgggtgg cctgaaggag actacccaaa agcaaatggt ttgctcgatt ttgacatatt   2640
ctacaacgtc actggatgcc taagaaacat gagttctgct ggcgctgatg ggagaaaagc   2700
gatgagaaga tgtgacggac tcattgactc actggtccat tatgtcagag gaaccattgc   2760
agattaccag ccagatgaca aggccacgga gaattgtgtg tgcattcttc ataacctctc   2820
ctaccagctg gaggcagagc tcccagagaa atattcccag aatatctata ttcaaaaccg   2880
gaatatccag actgacaaca acaaaagtat tggatgtttt ggcagtcgaa gcaggaaagt   2940
aaaagagcaa taccaggacg tgccgatgcc ggaggaaaag agcaacccca agggcgtgga   3000
gtggctgtgg cattccattg ttataaggat gtatctgtcc ttgatcgcca aaagtgtccg   3060
```

caactacaca caagaagcat ccttaggagc tctgcagaac ctcacggccg gaagtggacc 3120
aatgccgaca tcagtggctc agacagttgt ccagaaggaa agtggcctgc agcacacccg 3180
aaagatgctg catgttggtg acccaagtgt gaaaaagaca gccatctcgc tgctgaggaa 3240
tctgtcccgg aatctttctc tgcagaatga aattgccaaa gaaactctcc ctgatttggt 3300
ttccatcatt cctgacacag tcccgagtac tgaccttctc attgaaacta cagcctctgc 3360
ctgttacaca ttgaacaaca taatccaaaa cagttaccag aatgcacgcg accttctaaa 3420
caccgggggc atccagaaaa ttatggccat tagtgcaggc gatgcctatg cctccaacaa 3480
agcaagtaaa gctgcttccg tccttctgta ttctctgtgg gcacacacgg aactgcatca 3540
tgcctacaag aaggctcagt ttaagaagac agattttgtc aacagccgga ctgccaaagc 3600
ctaccactcc cttaaagact gatcaacctc tggattacaa aatttgtgaa agattgactg 3660
gtattcttaa ctatgttgct ccttttacgc tatgtggata cgctgcttta atgcctttgt 3720
atcatgctat tgcttcccgt atggctttca ttttctcctc cttgtataaa tcctggttgc 3780
tgtctcttta tgaggagttg tggcccgttg tcaggcaacg tggcgtggtg tgcactgtgt 3840
ttgctgacgc aacccccact ggttggggca ttgccaccac ctgtcagctc ctttccggga 3900
ctttcgcttt ccccctccct attgccacgg cggaactcat cgccgcctgc cttgcccgct 3960
gctggacagg ggctcggctg ttgggcactg acaattccgt ggtgttgtcg gggaaatcat 4020
cgtcctttcc ttggctgctc gcctgtgttg ccacctggat tctgcgcggg acgtccttct 4080
gctacgtccc ttcggccctc aatccagcgg accttccttc ccgcggcctg ctgccggctc 4140
tgcggcctct tccgcgtctt cgccttcgcc ctcagacgag tcggatctcc ctttgggccg 4200
cctccccgca tcattgcctg cccgggtggc atccctgtga cccctcccca gtgcctctcc 4260
tggccctgga agttgccact ccagtgccca ccagccttgt cctaataaaa ttaagttgca 4320
tcattttgtc tgactaggtg tccttctata atattatggg gtggaggggg gtggtatgga 4380
gcaaggggcc caagttggga agaaacctgt agggcctgcg ttacccaggc tggagtgcag 4440
tggcacattt ctgctcactg caacctcctc ctccctgggt tctacgtaga taagtagcat 4500
ggcgggttaa tcattaacta caaggaaccc ctagtgatgg agttggccac tccctctctg 4560
cgcgctcgct cgctcactga ggccgggcga ccaaaggtcg cccgacgccc gggctttgcc 4620
cgggcggcct cagtgagcga gcgagcgcgc 4650

<210> SEQ ID NO 90
<211> LENGTH: 4274
<212> TYPE: DNA
<213> ORGANISM: Artificial Sequence
<220> FEATURE:
<223> OTHER INFORMATION: Made in Lab - polynucleotide sequence of vector genome

<400> SEQUENCE: 90
gcgcgctcgc tcgctcactg aggccgcccg ggcaaagccc gggcgtcggg cgacctttgg 60
tcgcccggcc tcagtgagcg agcgagcgcg cagagaggga gtggccaact ccatcactag 120
gggttccttg tagttaatga ttaacccgcc atgctactta tctacgtact ctggagacgc 180
gtctcagtcc attaggagcc agtagcctgg aagatgtctt taccccccagc atcagttcaa 240 gtggagcagc acataactct tgccctctgc cttccaagat tctggtgctg agacttatgg 300
agtgtcttgg aggttgcctt ctgcccccca accctgctcc cagctggccc tcccaggcct 360
gggttgctgg cctctgcttt atcaggattc tcaagaggga cagctggttt atgttgcatg 420

-continued

```
actgttccct gcatatctgc tctggtttta aatagcttat ctgagcagct ggaggaccac    480
atgggcttat atggcgtggg gtacatgttc ctgtagcctt gtccctggca cctgccaaaa    540
tagcagccaa caccccccac ccccaccgcc atccccctgc cccacccgtc ccctgtcgca    600
cattcctccc tccgcagggc tggctcacca ggccccagcc cacatgcctg cttaaagccc    660
tctccatcct ctgcctcacc cagtccccgc tgagactgag cagacgcctc caggatctgt    720
cggcaggcca ccatggcagc ccccggcgcc ccagctgagt acggctacat ccggaccgtc    780
ctgggccagc agatcctggg acaactggac agctccagcc tggcgctgcc ctccgaggcc    840
aagctgaagc tggcggggag cagcggccgc ggcggccaga cagtcaagag cctgcggatc    900
caggagcagg tgcagcagac cctcgcccgg aagggccgca gctccgtggg caacggaaat    960
cttcaccgaa ccagcagtgt tcctgagtat gtctacaacc tacacttggt tgaaaatgat   1020
tttgttggag gccgttcccc tgttcctaaa acctatgaca tgctaaaggc tggcacaact   1080
gccacttatg aaggtcgctg ggaagagga acagcacagt acagctccca gaagtccgtg   1140
gaagaaaggt ccttgaggca tcctctgagg agactggaga tttctcctga cagcagcccg   1200
gagagggctc actacacgca cagcgattac cagtacagcc agagaagcca ggctgggcac   1260
accctgcacc accaagaaag caggcgggcc gccctcctag tgccaccgag atatgctcgt   1320
tccgagatcg tgggggtcag ccgtgctggc accacaagca ggcagcgcca ctttgacaca   1380
taccacagac agtaccagca tggctctgtt agcgacaccg tttttgacag catccctgcc   1440
aacccggccc tgctcacgta ccccaggcca gggaccagcc gcagcatggg caacctcttg   1500
gagaaggaga actacctgac ggcagggctc actgtcgggc aggtcaggcc gctggtgccc   1560
ctgcagcccg tcactcagaa cagggcttcc aggtcctcct ggcatcagag ctccttccac   1620
agcacccgca cgctgaggga agctgggccc agtgtcgccg tggattccag cgggaggaga   1680
gcgcacttga ctgtcggcca ggcggccgca gggggaagtg ggaatctgct cactgagaga   1740
agcactttca ctgactccca gctggggaat gcagacatgg agatgactct ggagcgagca   1800
gtgagtatgc tcgaggcaga ccacatgctg ccatccagga tttctgctgc agctactttc   1860
atacagcacg agtgcttcca gaaatctgaa gctcggaaga gggttaacca gcttcgtggc   1920
atcctcaagc ttctgcagct cctaaaagtt cagaatgaag acgttcagcg agctgtgtgt   1980
ggggccttga gaaacttagt atttgaagac aatgacaaca aattggaggt ggctgaacta   2040
aatggggtac ctcggctgct ccaggtgctg aagcaaacca gagacttgga gactaaaaaa   2100
caaataacag gtttgctgtg gaatttgtca tctaatgaca aactcaagaa tctcatgata   2160
acagaagcat tgcttacgct gacggagaat atcatcatcc ccttttctgg gtggcctgaa   2220
ggagactacc caaaagcaaa tggtttgctc gattttgaca tattctacaa cgtcactgga   2280
tgcctaagaa acatgagttc tgctggcgct gatgggagaa aagcgatgag aagatgtgac   2340
ggactcattg actcactggt ccattatgtc agaggaacca ttgcagatta ccagccagat   2400
gacaaggcca cggagaattg tgtgtgcatt cttcataacc tctcctacca gctggaggca   2460
gagctcccag agaaatattc ccagaatatc tatattcaaa accggaatat ccagactgac   2520
aacaacaaaa gtattggatg ttttggcagt cgaagcagga aagtaaaaga gcaataccag   2580
gacgtgccga tgccggagga aaagagcaac cccaagggcg tggagtggct gtggcattcc   2640
attgttataa ggatgtatct gtccttgatc gccaaaagtg tccgcaacta cacacaagaa   2700
gcatccttag gagctctgca gaacctcacg gccggaagtg gaccaatgcc gacatcagtg   2760
gctcagacag ttgtccagaa ggaaagtggc ctgcagcaca cccgaaagat gctgcatgtt   2820
```

ggtgacccaa gtgtgaaaaa gacagccatc tcgctgctga ggaatctgtc ccggaatctt 2880
tctctgcaga atgaaattgc caaagaaact ctccctgatt tggtttccat cattcctgac 2940
acagtcccga gtactgacct tctcattgaa actacagcct ctgcctgtta cacattgaac 3000
aacataatcc aaaacagtta ccagaatgca cgcgaccttc taaacaccgg gggcatccag 3060
aaaattatgg ccattagtgc aggcgatgcc tatgcctcca acaaagcaag taaagctgct 3120
tccgtccttc tgtattctct gtgggcacac acggaactgc atcatgccta caagaaggct 3180
cagtttaaga agacagattt tgtcaacagc cggactgcca aagcctacca ctcccttaaa 3240
gactgatcaa cctctggatt acaaaatttg tgaaagattg actggtattc ttaactatgt 3300
tgctcctttt acgctatgtg gatacgctgc tttaatgcct ttgtatcatg ctattgcttc 3360
ccgtatggct ttcattttct cctccttgta taaatcctgg ttgctgtctc tttatgagga 3420
gttgtggccc gttgtcaggc aacgtggcgt ggtgtgcact gtgtttgctg acgcaacccc 3480
cactggttgg ggcattgcca ccacctgtca gctcctttcc gggactttcg ctttccccct 3540
ccctattgcc acggcggaac tcatcgccgc ctgccttgcc cgctgctgga caggggctcg 3600
gctgttgggc actgacaatt ccgtggtgtt gtcggggaaa tcatcgtcct ttccttggct 3660
gctcgcctgt gttgccacct ggattctgcg cgggacgtcc ttctgctacg tcccttcggc 3720
cctcaatcca gcggaccttc cttcccgcgg cctgctgccg gctctgcggc ctcttccgcg 3780
tcttcgcctt cgccctcaga cgagtcggat ctccctttgg gccgcctccc cgcatcattg 3840
cctgcccggg tggcatccct gtgacccctc cccagtgcct ctcctggccc tggaagttgc 3900
cactccagtg cccaccagcc ttgtcctaat aaaattaagt tgcatcattt tgtctgacta 3960
ggtgtccttc tataatatta tggggtggag gggggtggta tggagcaagg ggcccaagtt 4020
gggaagaaac ctgtagggcc tgcgttaccc aggctggagt gcagtggcac atttctgctc 4080
actgcaacct cctcctccct gggttctacg tagataagta gcatggcggg ttaatcatta 4140
actacaagga acccctagtg atggagttgg ccactccctc tctgcgcgct cgctcgctca 4200
ctgaggccgg gcgaccaaag gtcgcccgac gcccgggctt tgcccgggcg gcctcagtga 4260
gcgagcgagc gcgc 4274

<210> SEQ ID NO 91
<211> LENGTH: 4782
<212> TYPE: DNA
<213> ORGANISM: Artificial Sequence
<220> FEATURE:
<223> OTHER INFORMATION: Made in Lab - polynucleotide sequence of vector genome

<400> SEQUENCE: 91
gcgcgctcgc tcgctcactg aggccgcccg ggcaaagccc gggcgtcggg cgacctttgg 60
tcgcccggcc tcagtgagcg agcgagcgcg cagagaggga gtggccaact ccatcactag 120
gggttccttg tagttaatga ttaacccgcc atgctactta tctacgtact ctggagacgc 180
gtacccttca gattaaaaat aactgaggta agggcctggg taggggaggt ggtgtgagac 240
gctcctgtct ctcctctatc tgcccatcgg ccctttgggg aggaggaatg tgcccaagga 300
ctaaaaaaag gccatggagc cagaggggcg agggcaacag acctttcatg ggcaaacctt 360
ggggccctgc tgtctagcat gccccactac gggtctaggc tgcccatgta aggaggcaag 420
gcctggggac acccgagatg cctggttata attaacccag acatgtggct gccccccccc 480
ccccaacacc tgctgcctct aaaaataacc ctgtccctgg tggatcccct gcatgcgaag 540

```
atcttcgaac aaggctgtgg gggactgagg gcaggctgta acaggcttgg gggccagggc    600
ttatacgtgc ctgggactcc caaagtatta ctgttccatg ttcccggcga agggccagct    660
gtcccccgcc agctagactc agcacttagt ttaggaacca gtgagcaagt cagcccttgg    720
ggcagcccat acaaggccat ggggctgggc aagctgcacg cctgggtccg gggtgggcac    780
ggtgcccggg caacgagctg aaagctcatc tgctctcagg ggcccctccc tggggacagc    840
ccctcctggc tagtcacacc ctgtaggctc ctctatataa cccaggggca caggggctgc    900
cctcattcta ccaccacctc cacagcacag acagacactc aggagccagc cagggtaagt    960
ttagtctttt tgtcttttat ttcaggtccc ggatccggtg gtggtgcaaa tcaaagaact   1020
gctcctcagt ggatgttgcc tttacttcta ggcctgtacg gaagtgttac ttctgctcta   1080
aaagctgcgg aattgtaccc gcgccaccat ggcagccccc ggcgccccag ctgagtacgg   1140
ctacatccgg accgtcctgg gccagcagat cctgggacaa ctggacagct ccagcctggc   1200
gctgccctcc gaggccaagc tgaagctggc ggggagcagc ggccgcggcg gccagacagt   1260
caagagcctg cggatccagg agcaggtgca gcagaccctc gcccggaagg gccgcagctc   1320
cgtgggcaac ggaaatcttc accgaaccag cagtgttcct gagtatgtct acaacctaca   1380
cttggttgaa aatgattttg ttggaggccg ttcccctgtt cctaaaacct atgacatgct   1440
aaaggctggc acaactgcca cttatgaagg tcgctgggga agaggaacag cacagtacag   1500
ctcccagaag tccgtggaag aaaggtcctt gaggcatcct ctgaggagac tggagatttc   1560
tcctgacagc agcccggaga gggctcacta cacgcacagc gattaccagt acagccagag   1620
aagccaggct gggcacaccc tgcaccacca agaaagcagg cgggccgccc tcctagtgcc   1680
accgagatat gctcgttccg agatcgtggg ggtcagccgt gctggcacca caagcaggca   1740
gcgccacttt gacacatacc acagacagta ccagcatggc tctgttagcg acaccgtttt   1800
tgacagcatc cctgccaacc cggccctgct cacgtacccc aggccaggga ccagccgcag   1860
catgggcaac ctcttggaga aggagaacta cctgacggca gggctcactg tcgggcaggt   1920
caggccgctg gtgcccctgc agcccgtcac tcagaacagg gcttccaggt cctcctggca   1980
tcagagctcc ttccacagca cccgcacgct gagggaagct gggcccagtg tcgccgtgga   2040
ttccagcggg aggagagcgc acttgactgt cggccaggcg gccgcagggg gaagtgggaa   2100
tctgctcact gagagaagca ctttcactga ctcccagctg gggaatgcag acatggagat   2160
gactctggag cgagcagtga gtatgctcga ggcagaccac atgctgccat ccaggatttc   2220
tgctgcagct actttcatac agcacgagtg cttccagaaa tctgaagctc ggaagagggt   2280
taaccagctt cgtggcatcc tcaagcttct gcagctccta aaagttcaga atgaagacgt   2340
tcagcgagct gtgtgtgggg ccttgagaaa cttagtattt gaagacaatg acaacaaatt   2400
ggaggtggct gaactaaatg ggtacctcg gctgctccag gtgctgaagc aaaccagaga   2460
cttggagact aaaaaacaaa taacagacca tacagtcaat ttaagaagta ggaatggctg   2520
gccgggcgcg gtggctcacg cctgtaatcc cagcactttg ggaggccaag gcgggcggat   2580
cacgaggtca ggagttcgag accagcctga ccaacatggt ttgctgtgga atttgtcatc   2640
taatgacaaa ctcaagaatc tcatgataac agaagcattg cttacgctga cggagaatat   2700
catcatcccc ttttctgggt ggcctgaagg agactaccca aaagcaaatg gtttgctcga   2760
ttttgacata ttctacaacg tcactggatg cctaagaaac atgagttctg ctggcgctga   2820
tgggagaaaa gcgatgagaa gatgtgacgg actcattgac tcactggtcc attatgtcag   2880
```

```
aggaaccatt gcagattacc agccagatga caaggccacg gagaattgtg tgtgcattct   2940

tcataacctc tcctaccagc tggaggcaga gctcccagag aaatattccc agaatatcta   3000

tattcaaaac cggaatatcc agactgacaa caacaaaagt attggatgtt ttggcagtcg   3060

aagcaggaaa gtaaaagagc aataccagga cgtgccgatg ccggaggaaa agagcaaccc   3120

caagggcgtg gagtggctgt ggcattccat tgttataagg atgtatctgt ccttgatcgc   3180

caaaagtgtc cgcaactaca cacaagaagc atccttagga gctctgcaga acctcacggc   3240

cggaagtgga ccaatgccga catcagtggc tcagacagtt gtccagaagg aaagtggcct   3300

gcagcacacc cgaaagatgc tgcatgttgg tgacccaagt gtgaaaaaga cagccatctc   3360

gctgctgagg aatctgtccc ggaatctttc tctgcagaat gaaattgcca aagaaactct   3420

ccctgatttg gtttccatca ttcctgacac agtcccgagt actgaccttc tcattgaaac   3480

tacagcctct gcctgttaca cattgaacaa cataatccaa aacagttacc agaatgcacg   3540

cgaccttcta aacaccgggg gcatccagaa aattatggcc attagtgcag gcgatgccta   3600

tgcctccaac aaagcaagta aagctgcttc cgtccttctg tattctctgt gggcacacac   3660

ggaactgcat catgcctaca agaaggctca gtttaagaag acagattttg tcaacagccg   3720

gactgccaaa gcctaccact cccttaaaga ctgatcaacc tctggattac aaaatttgtg   3780

aaagattgac tggtattctt aactatgttg ctccttttac gctatgtgga tacgctgctt   3840

taatgccttt gtatcatgct attgcttccc gtatggcttt cattttctcc tccttgtata   3900

aatcctggtt gctgtctctt tatgaggagt tgtggcccgt tgtcaggcaa cgtggcgtgg   3960

tgtgcactgt gtttgctgac gcaaccccca ctggttgggg cattgccacc acctgtcagc   4020

tcctttccgg gactttcgct ttccccctcc ctattgccac ggcggaactc atcgccgcct   4080

gccttgcccg ctgctggaca ggggctcggc tgttgggcac tgacaattcc gtggtgttgt   4140

cggggaaatc atcgtccttt ccttggctgc tcgcctgtgt tgccacctgg attctgcgcg   4200

ggacgtcctt ctgctacgtc ccttcggccc tcaatccagc ggaccttcct tcccgcggcc   4260

tgctgccggc tctgcggcct cttccgcgtc ttcgccttcg ccctcagacg agtcggatct   4320

ccctttgggc cgcctccccg catcattgcc tgcccgggtg gcatccctgt gacccctccc   4380

cagtgcctct cctggccctg gaagttgcca ctccagtgcc caccagcctt gtcctaataa   4440

aattaagttg catcattttg tctgactagg tgtccttcta taatattatg gggtggaggg   4500

gggtggtatg gagcaagggg cccaagttgg gaagaaacct gtagggcctg cgttacccag   4560

gctggagtgc agtggcacat ttctgctcac tgcaacctcc tcctccctgg gttctacgta   4620

gataagtagc atggcgggtt aatcattaac tacaaggaac ccctagtgat ggagttggcc   4680

actccctctc tgcgcgctcg ctcgctcact gaggccgggc gaccaaaggt cgcccgacgc   4740

ccgggctttg cccgggcggc ctcagtgagc gagcgagcgc gc                      4782
```

<210> SEQ ID NO 92
<211> LENGTH: 4406
<212> TYPE: DNA
<213> ORGANISM: Artificial Sequence
<220> FEATURE:
<223> OTHER INFORMATION: Made in Lab - polynucleotide sequence of vector genome

<400> SEQUENCE: 92

```
gcgcgctcgc tcgctcactg aggccgcccg ggcaaagccc gggcgtcggg cgacctttgg     60

tcgcccggcc tcagtgagcg agcgagcgcg cagagaggga gtggccaact ccatcactag    120
```

-continued

```
gggttccttg tagttaatga ttaacccgcc atgctactta tctacgtact ctggagacgc    180
gtctcagtcc attaggagcc agtagcctgg aagatgtctt tacccccagc atcagttcaa    240
gtggagcagc acataactct tgccctctgc cttccaagat tctggtgctg agacttatgg    300
agtgtcttgg aggttgcctt ctgcccccca accctgctcc cagctggccc tcccaggcct    360
gggttgctgg cctctgcttt atcaggattc tcaagaggga cagctggttt atgttgcatg    420
actgttccct gcatatctgc tctggtttta aatagcttat ctgagcagct ggaggaccac    480
atgggcttat atggcgtggg gtacatgttc ctgtagcctt gtccctggca cctgccaaaa    540
tagcagccaa cacccccac ccccaccgcc atcccccctgc cccacccgtc ccctgtcgca    600
cattcctccc tccgcagggc tggctcacca ggccccagcc cacatgcctg cttaaagccc    660
tctccatcct ctgcctcacc cagtccccgc tgagactgag cagacgcctc caggatctgt    720
cggcaggcca ccatggcagc ccccggcgcc ccagctgagt acggctacat ccggaccgtc    780
ctgggccagc agatcctggg acaactggac agctccagcc tggcgctgcc ctccgaggcc    840
aagctgaagc tggcggggag cagcggccgc ggcggccaga cagtcaagag cctgcggatc    900
caggagcagg tgcagcagac cctcgcccgg aagggccgca gctccgtggg caacggaaat    960
cttcaccgaa ccagcagtgt tcctgagtat gtctacaacc tacacttggt tgaaaatgat   1020
tttgttggag gccgttcccc tgttcctaaa acctatgaca tgctaaaggc tggcacaact   1080
gccacttatg aaggtcgctg gggaagagga acagcacagt acagctccca gaagtccgtg   1140
gaagaaaggt ccttgaggca tcctctgagg agactggaga tttctcctga cagcagcccg   1200
gagagggctc actacacgca cagcgattac cagtacagcc agagaagcca ggctgggcac   1260
accctgcacc accaagaaag caggcgggcc gccctcctag tgccaccgag atatgctcgt   1320
tccgagatcg tgggggtcag ccgtgctggc accacaagca ggcagcgcca ctttgacaca   1380
taccacagac agtaccagca tggctctgtt agcgacaccg tttttgacag catccctgcc   1440
aacccggccc tgctcacgta ccccaggcca gggaccagcc gcagcatggg caacctcttg   1500
gagaaggaga actacctgac ggcagggctc actgtcgggc aggtcaggcc gctggtgccc   1560
ctgcagcccg tcactcagaa cagggcttcc aggtcctcct ggcatcagag ctccttccac   1620
agcacccgca cgctgaggga agctgggccc agtgtcgccg tggattccag cgggaggaga   1680
gcgcacttga ctgtcggcca ggcggccgca gggggaagtg ggaatctgct cactgagaga   1740
agcactttca ctgactccca gctggggaat gcagacatgg agatgactct ggagcgagca   1800
gtgagtatgc tcgaggcaga ccacatgctg ccatccagga tttctgctgc agctactttc   1860
atacagcacg agtgcttcca gaaatctgaa gctcggaaga gggttaacca gcttcgtggc   1920
atcctcaagc ttctgcagct cctaaaagtt cagaatgaag acgttcagcg agctgtgtgt   1980
ggggccttga gaaacttagt atttgaagac aatgacaaca aattggaggt ggctgaacta   2040
aatggggtac ctcggctgct ccaggtgctg aagcaaacca gagacttgga gactaaaaaa   2100
caaataacag accatacagt caatttaaga agtaggaatg gctggccggg cgcggtggct   2160
cacgcctgta atcccagcac tttgggaggc caaggcgggc ggatcacgag gtcaggagtt   2220
cgagaccagc ctgaccaaca tggtttgctg tggaatttgt catctaatga caaactcaag   2280
aatctcatga taacagaagc attgcttacg ctgacggaga atatcatcat cccctttttct   2340
gggtggcctg aaggagacta cccaaaagca aatggtttgc tcgattttga catattctac   2400
aacgtcactg gatgcctaag aaacatgagt tctgctggcg ctgatgggag aaaagcgatg   2460
agaagatgtg acggactcat tgactcactg gtccattatg tcagaggaac cattgcagat   2520
```

taccagccag atgacaaggc cacggagaat tgtgtgtgca ttcttcataa cctctcctac 2580
cagctggagg cagagctccc agagaaatat tcccagaata tctatattca aaaccggaat 2640
atccagactg acaacaacaa aagtattgga tgttttggca gtcgaagcag gaaagtaaaa 2700
gagcaatacc aggacgtgcc gatgccggag gaaaagagca accccaaggg cgtggagtgg 2760
ctgtggcatt ccattgttat aaggatgtat ctgtccttga tcgccaaaag tgtccgcaac 2820
tacacacaag aagcatcctt aggagctctg cagaacctca cggccggaag tggaccaatg 2880
ccgacatcag tggctcagac agttgtccag aaggaaagtg gcctgcagca cacccgaaag 2940
atgctgcatg ttggtgaccc aagtgtgaaa aagacagcca tctcgctgct gaggaatctg 3000
tcccggaatc tttctctgca gaatgaaatt gccaaagaaa ctctccctga tttggtttcc 3060
atcattcctg acacagtccc gagtactgac cttctcattg aaactacagc ctctgcctgt 3120
tacacattga acaacataat ccaaaacagt taccagaatg cacgcgacct tctaaacacc 3180
gggggcatcc agaaaattat ggccattagt gcaggcgatg cctatgcctc caacaaagca 3240
agtaaagctg cttccgtcct tctgtattct ctgtgggcac acacggaact gcatcatgcc 3300
tacaagaagg ctcagtttaa gaagacagat tttgtcaaca gccggactgc caaagcctac 3360
cactccctta aagactgatc aacctctgga ttacaaaatt tgtgaaagat tgactggtat 3420
tcttaactat gttgctcctt ttacgctatg tggatacgct gctttaatgc ctttgtatca 3480
tgctattgct tcccgtatgg ctttcatttt ctcctccttg tataaatcct ggttgctgtc 3540
tctttatgag gagttgtggc ccgttgtcag gcaacgtggc gtggtgtgca ctgtgtttgc 3600
tgacgcaacc cccactggtt ggggcattgc caccacctgt cagctccttt ccgggacttt 3660
cgctttcccc ctccctattg ccacggcgga actcatcgcc gcctgccttg cccgctgctg 3720
gacaggggct cggctgttgg gcactgacaa ttccgtggtg ttgtcgggga aatcatcgtc 3780
ctttccttgg ctgctcgcct gtgttgccac ctggattctg cgcgggacgt ccttctgcta 3840
cgtcccttcg gccctcaatc cagcggacct tccttcccgc ggcctgctgc cggctctgcg 3900
gcctcttccg cgtcttcgcc ttcgccctca gacgagtcgg atctcccttt gggccgcctc 3960
cccgcatcat tgcctgcccg ggtggcatcc ctgtgacccc tccccagtgc ctctcctggc 4020
cctggaagtt gccactccag tgcccaccag ccttgtccta ataaaattaa gttgcatcat 4080
tttgtctgac taggtgtcct tctataatat tatggggtgg aggggggtgg tatggagcaa 4140
ggggcccaag ttgggaagaa acctgtaggg cctgcgttac ccaggctgga gtgcagtggc 4200
acatttctgc tcactgcaac ctcctcctcc ctgggttcta cgtagataag tagcatggcg 4260
ggttaatcat taactacaag gaacccctag tgatggagtt ggccactccc tctctgcgcg 4320
ctcgctcgct cactgaggcc gggcgaccaa aggtcgcccg acgcccgggc tttgcccggg 4380
cggcctcagt gagcgagcga gcgcgc 4406

<210> SEQ ID NO 93
<211> LENGTH: 4237
<212> TYPE: DNA
<213> ORGANISM: Artificial Sequence
<220> FEATURE:
<223> OTHER INFORMATION: Made in Lab - expression cassette
polynucleotide

<400> SEQUENCE: 93
acccttcaga ttaaaaataa ctgaggtaag ggcctgggta ggggaggtgg tgtgagacgc 60
tcctgtctct cctctatctg cccatcggcc ctttggggag gaggaatgtg cccaaggact 120

```
aaaaaaaggc catggagcca gaggggcgag ggcaacagac ctttcatggg caaaccttgg    180
ggccctgctg tctagcatgc cccactacgg gtctaggctg cccatgtaag gaggcaaggc    240
ctggggacac ccgagatgcc tggttataat taacccagac atgtggctgc cccccccccc    300
ccaacacctg ctgcctctaa aaataaccct gtccctggtg gatcccctgc atgcgaagat    360
cttcgaacaa ggctgtgggg gactgagggc aggctgtaac aggcttgggg gccagggctt    420
atacgtgcct gggactccca aagtattact gttccatgtt cccggcgaag ggccagctgt    480
cccccgccag ctagactcag cacttagttt aggaaccagt gagcaagtca gcccttgggg    540
cagcccatac aaggccatgg ggctgggcaa gctgcacgcc tgggtccggg gtgggcacgg    600
tgcccgggca acgagctgaa agctcatctg ctctcagggg cccctccctg gggacagccc    660
ctcctggcta gtcacaccct gtaggctcct ctatataacc caggggcaca ggggctgccc    720
tcattctacc accacctcca cagcacagac agacactcag gagccagcca gggtaagttt    780
agtctttttg tcttttattt caggtcccgg atccggtggt ggtgcaaatc aaagaactgc    840
tcctcagtgg atgttgcctt tacttctagg cctgtacgga agtgttactt ctgctctaaa    900
agctgcggaa ttgtacccgc gccaccatgg cagcccccgg cgccccagct gagtacggct    960
acatccggac cgtcctgggc cagcagatcc tgggacaact ggacagctcc agcctggcgc   1020
tgccctccga ggccaagctg aagctggcgg ggagcagcgg ccgcggcggc cagacagtca   1080
agagcctgcg gatccaggag caggtgcagc agaccctcgc ccggaagggc cgcagctccg   1140
tgggcaacgg aaatcttcac cgaaccagca gtgttcctga gtatgtctac aacctacact   1200
tggttgaaaa tgattttgtt ggaggccgtt cccctgttcc taaaacctat gacatgctaa   1260
aggctggcac aactgccact tatgaaggtc gctggggaag aggaacagca cagtacagct   1320
cccagaagtc cgtggaagaa aggtccttga ggcatcctct gaggagactg gagatttctc   1380
ctgacagcag cccggagagg gctcactaca cgcacagcga ttaccagtac agccagagaa   1440
gccaggctgg gcacaccctg caccaccaag aaagcaggcg ggccgccctc ctagtgccac   1500
cgagatatgc tcgttccgag atcgtggggg tcagccgtgc tggcaccaca agcaggcagc   1560
gccactttga cacataccac agacagtacc agcatggctc tgttagcgac accgtttttg   1620
acagcatccc tgccaacccg gccctgctca cgtaccccag gccagggacc agccgcagca   1680
tgggcaacct cttggagaag gagaactacc tgacggcagg gctcactgtc gggcaggtca   1740
ggccgctggt gcccctgcag cccgtcactc agaacagggc ttccaggtcc tcctggcatc   1800
agagctcctt ccacagcacc cgcacgctga gggaagctgg gcccagtgtc gccgtggatt   1860
ccagcgggag gagagcgcac ttgactgtcg gccaggcggc cgcaggggga agtgggaatc   1920
tgctcactga gagaagcact ttcactgact cccagctggg gaatgcagac atggagatga   1980
ctctggagcg agcagtgagt atgctcgagg cagaccacat gctgccatcc aggatttctg   2040
ctgcagctac tttcatacag cacgagtgct tccagaaatc tgaagctcgg aagagggtta   2100
accagcttcg tggcatcctc aagcttctgc agctcctaaa agttcagaat gaagacgttc   2160
agcgagctgt gtgtggggcc ttgagaaact tagtatttga agacaatgac aacaaattgg   2220
aggtggctga actaaatggg gtacctcggc tgctccaggt gctgaagcaa accagagact   2280
tggagactaa aaaacaaata acaggtttgc tgtggaattt gtcatctaat gacaaactca   2340
agaatctcat gataacagaa gcattgctta cgctgacgga gaatatcatc atcccctttt   2400
ctgggtggcc tgaaggagac tacccaaaag caaatggttt gctcgatttt gacatattct   2460
```

```
acaacgtcac tggatgccta agaaacatga gttctgctgg cgctgatggg agaaaagcga   2520

tgagaagatg tgacggactc attgactcac tggtccatta tgtcagagga accattgcag   2580

attaccagcc agatgacaag gccacggaga attgtgtgtg cattcttcat aacctctcct   2640

accagctgga ggcagagctc ccagagaaat attcccagaa tatctatatt caaaaccgga   2700

atatccagac tgacaacaac aaaagtattg gatgttttgg cagtcgaagc aggaaagtaa   2760

aagagcaata ccaggacgtg ccgatgccgg aggaaaagag caaccccaag ggcgtggagt   2820

ggctgtggca ttccattgtt ataaggatgt atctgtcctt gatcgccaaa agtgtccgca   2880

actacacaca agaagcatcc ttaggagctc tgcagaacct cacggccgga agtggaccaa   2940

tgccgacatc agtggctcag acagttgtcc agaaggaaag tggcctgcag cacacccgaa   3000

agatgctgca tgttggtgac ccaagtgtga aaaagacagc catctcgctg ctgaggaatc   3060

tgtcccggaa tctttctctg cagaatgaaa ttgccaaaga aactctccct gatttggttt   3120

ccatcattcc tgacacagtc ccgagtactg accttctcat tgaaactaca gcctctgcct   3180

gttacacatt gaacaacata atccaaaaca gttaccagaa tgcacgcgac cttctaaaca   3240

ccgggggcat ccagaaaatt atggccatta gtgcaggcga tgcctatgcc tccaacaaag   3300

caagtaaagc tgcttccgtc cttctgtatt ctctgtgggc acacacggaa ctgcatcatg   3360

cctacaagaa ggctcagttt aagaagacag attttgtcaa cagccggact gccaaagcct   3420

accactccct taaagactga tcaacctctg gattacaaaa tttgtgaaag attgactggt   3480

attcttaact atgttgctcc ttttacgcta tgtggatacg ctgctttaat gcctttgtat   3540

catgctattg cttcccgtat ggctttcatt ttctcctcct tgtataaatc ctggttgctg   3600

tctctttatg aggagttgtg gcccgttgtc aggcaacgtg gcgtggtgtg cactgtgttt   3660

gctgacgcaa cccccactgg ttggggcatt gccaccacct gtcagctcct ttccgggact   3720

ttcgctttcc ccctccctat tgccacggcg gaactcatcg ccgcctgcct tgcccgctgc   3780

tggacagggg ctcggctgtt gggcactgac aattccgtgg tgttgtcggg gaaatcatcg   3840

tcctttcctt ggctgctcgc ctgtgttgcc acctggattc tgcgcgggac gtccttctgc   3900

tacgtccctt cggccctcaa tccagcggac cttccttccc gcggcctgct gccggctctg   3960

cggcctcttc cgcgtcttcg ccttcgccct cagacgagtc ggatctccct ttgggccgcc   4020

tccccgcatc attgcctgcc cgggtggcat ccctgtgacc cctccccagt gcctctcctg   4080

gccctggaag ttgccactcc agtgcccacc agccttgtcc taataaaatt aagttgcatc   4140

attttgtctg actaggtgtc cttctataat attatggggt ggaggggggt ggtatggagc   4200

aaggggccca agttgggaag aaacctgtag ggcctgc                            4237
```

<210> SEQ ID NO 94
<211> LENGTH: 3861
<212> TYPE: DNA
<213> ORGANISM: Artificial Sequence
<220> FEATURE:
<223> OTHER INFORMATION: Made in Lab - expression cassette polynucleotide

<400> SEQUENCE: 94

```
ctcagtccat taggagccag tagcctggaa gatgtcttta cccccagcat cagttcaagt     60

ggagcagcac ataactcttg ccctctgcct tccaagattc tggtgctgag acttatggag    120

tgtcttggag gttgccttct gccccccaac cctgctccca gctggccctc ccaggcctgg    180

gttgctggcc tctgctttat caggattctc aagagggaca gctggtttat gttgcatgac    240
```

-continued

```
tgttccctgc atatctgctc tggttttaaa tagcttatct gagcagctgg aggaccacat    300
gggcttatat ggcgtggggt acatgttcct gtagccttgt ccctggcacc tgccaaaata    360
gcagccaaca ccccccaccc ccaccgccat ccccctgccc cacccgtccc ctgtcgcaca    420
ttcctccctc cgcagggctg gctcaccagg ccccagccca catgcctgct taaagccctc    480
tccatcctct gcctcaccca gtccccgctg agactgagca gacgcctcca ggatctgtcg    540
gcaggccacc atggcagccc ccggcgcccc agctgagtac ggctacatcc ggaccgtcct    600
gggccagcag atcctgggac aactggacag ctccagcctg gcgctgccct ccgaggccaa    660
gctgaagctg gcggggagca gcggccgcgg cggccagaca gtcaagagcc tgcggatcca    720
ggagcaggtg cagcagaccc tcgcccggaa gggccgcagc tccgtgggca acggaaatct    780
tcaccgaacc agcagtgttc ctgagtatgt ctacaaccta cacttggttg aaaatgattt    840
tgttggaggc cgttcccctg ttcctaaaac ctatgacatg ctaaaggctg gcacaactgc    900
cacttatgaa ggtcgctggg gaagaggaac agcacagtac agctcccaga agtccgtgga    960
agaaaggtcc ttgaggcatc ctctgaggag actggagatt tctcctgaca gcagcccgga   1020
gagggctcac tacacgcaca gcgattacca gtacagccag agaagccagg ctgggcacac   1080
cctgcaccac caagaaagca ggcgggccgc cctcctagtg ccaccgagat atgctcgttc   1140
cgagatcgtg gggggtcagcc gtgctggcac cacaagcagg cagcgccact ttgacacata   1200
ccacagacag taccagcatg gctctgttag cgacaccgtt tttgacagca tccctgccaa   1260
cccggccctg ctcacgtacc ccaggccagg gaccagccgc agcatgggca acctcttgga   1320
gaaggagaac tacctgacgg cagggctcac tgtcgggcag gtcaggccgc tggtgcccct   1380
gcagcccgtc actcagaaca gggcttccag gtcctcctgg catcagagct ccttccacag   1440
cacccgcacg ctgagggaag ctgggcccag tgtcgccgtg gattccagcg ggaggagagc   1500
gcacttgact gtcggccagg cggccgcagg gggaagtggg aatctgctca ctgagagaag   1560
cactttcact gactcccagc tggggaatgc agacatggag atgactctgg agcgagcagt   1620
gagtatgctc gaggcagacc acatgctgcc atccaggatt tctgctgcag ctactttcat   1680
acagcacgag tgcttccaga aatctgaagc tcggaagagg gttaaccagc ttcgtggcat   1740
cctcaagctt ctgcagctcc taaaagttca gaatgaagac gttcagcgag ctgtgtgtgg   1800
ggccttgaga aacttagtat ttgaagacaa tgacaacaaa ttggaggtgg ctgaactaaa   1860
tggggtacct cggctgctcc aggtgctgaa gcaaaccaga gacttggaga ctaaaaaaca   1920
aataacaggt ttgctgtgga atttgtcatc taatgacaaa ctcaagaatc tcatgataac   1980
agaagcattg cttacgctga cggagaatat catcatcccc ttttctgggt ggcctgaagg   2040
agactaccca aaagcaaatg gtttgctcga ttttgacata ttctacaacg tcactggatg   2100
cctaagaaac atgagttctg ctggcgctga tgggagaaaa gcgatgagaa gatgtgacgg   2160
actcattgac tcactggtcc attatgtcag aggaaccatt gcagattacc agccagatga   2220
caaggccacg gagaattgtg tgtgcattct tcataacctc tcctaccagc tggaggcaga   2280
gctcccagag aaatattccc agaatatcta tattcaaaac cggaatatcc agactgacaa   2340
caacaaaagt attggatgtt ttggcagtcg aagcaggaaa gtaaaagagc aataccagga   2400
cgtgccgatg ccggaggaaa agagcaaccc caagggcgtg gagtggctgt ggcattccat   2460
tgttataagg atgtatctgt ccttgatcgc caaaagtgtc cgcaactaca cacaagaagc   2520
atccttagga gctctgcaga acctcacggc cggaagtgga ccaatgccga catcagtggc   2580
tcagacagtt gtccagaagg aaagtggcct gcagcacacc cgaaagatgc tgcatgttgg   2640
```

tgacccaagt gtgaaaaaga cagccatctc gctgctgagg aatctgtccc ggaatctttc 2700
tctgcagaat gaaattgcca aagaaactct ccctgatttg gtttccatca ttcctgacac 2760
agtcccgagt actgaccttc tcattgaaac tacagcctct gcctgttaca cattgaacaa 2820
cataatccaa aacagttacc agaatgcacg cgaccttcta aacaccgggg gcatccagaa 2880
aattatggcc attagtgcag gcgatgccta tgcctccaac aaagcaagta aagctgcttc 2940
cgtccttctg tattctctgt gggcacacac ggaactgcat catgcctaca agaaggctca 3000
gtttaagaag acagattttg tcaacagccg gactgccaaa gcctaccact cccttaaaga 3060
ctgatcaacc tctggattac aaaatttgtg aaagattgac tggtattctt aactatgttg 3120
ctccttttac gctatgtgga tacgctgctt taatgccttt gtatcatgct attgcttccc 3180
gtatggcttt cattttctcc tccttgtata aatcctggtt gctgtctctt tatgaggagt 3240
tgtggcccgt tgtcaggcaa cgtggcgtgg tgtgcactgt gtttgctgac gcaaccccca 3300
ctggttgggg cattgccacc acctgtcagc tcctttccgg gactttcgct ttccccctcc 3360
ctattgccac ggcggaactc atcgccgcct gccttgcccg ctgctggaca ggggctcggc 3420
tgttgggcac tgacaattcc gtggtgttgt cggggaaatc atcgtccttt ccttggctgc 3480
tcgcctgtgt tgccacctgg attctgcgcg ggacgtcctt ctgctacgtc ccttcggccc 3540
tcaatccagc ggaccttcct tcccgcggcc tgctgccggc tctgcggcct cttccgcgtc 3600
ttcgccttcg ccctcagacg agtcggatct ccctttgggc cgcctccccg catcattgcc 3660
tgcccgggtg gcatccctgt gacccctccc cagtgcctct cctggccctg gaagttgcca 3720
ctccagtgcc caccagcctt gtcctaataa aattaagttg catcattttg tctgactagg 3780
tgtccttcta taatattatg gggtggaggg gggtggtatg gagcaagggg cccaagttgg 3840
gaagaaacct gtagggcctg c 3861

<210> SEQ ID NO 95
<211> LENGTH: 4369
<212> TYPE: DNA
<213> ORGANISM: Artificial Sequence
<220> FEATURE:
<223> OTHER INFORMATION: Made in Lab - expression cassette
polynucleotide

<400> SEQUENCE: 95
acccttcaga ttaaaaataa ctgaggtaag ggcctgggta ggggaggtgg tgtgagacgc 60
tcctgtctct cctctatctg cccatcggcc ctttggggag gaggaatgtg cccaaggact 120
aaaaaaaggc catggagcca gaggggcgag ggcaacagac ctttcatggg caaaccttgg 180
ggccctgctg tctagcatgc cccactacgg gtctaggctg cccatgtaag gaggcaaggc 240
ctggggacac ccgagatgcc tggttataat taacccagac atgtggctgc cccccccccc 300
ccaacacctg ctgcctctaa aaataaccct gtccctggtg gatcccctgc atgcgaagat 360
cttcgaacaa ggctgtgggg gactgagggc aggctgtaac aggcttgggg gccagggctt 420
atacgtgcct gggactccca aagtattact gttccatgtt cccggcgaag ggccagctgt 480
cccccgccag ctagactcag cacttagttt aggaaccagt gagcaagtca gcccttgggg 540
cagcccatac aaggccatgg ggctgggcaa gctgcacgcc tgggtccggg gtgggcacgg 600
tgcccgggca acgagctgaa agctcatctg ctctcagggg cccctccctg ggacagcccc 660
ctcctggcta gtcacaccct gtaggctcct ctatataacc caggggcaca ggggctgccc 720
tcattctacc accacctcca cagcacagac agacactcag gagccagcca gggtaagttt 780

```
agtctttttg tcttttattt caggtcccgg atccggtggt ggtgcaaatc aaagaactgc    840
tcctcagtgg atgttgcctt tacttctagg cctgtacgga agtgttactt ctgctctaaa    900
agctgcggaa ttgtacccgc gccaccatgg cagcccccgg cgccccagct gagtacggct    960
acatccggac cgtcctgggc cagcagatcc tgggacaact ggacagctcc agcctggcgc   1020
tgccctccga ggccaagctg aagctggcgg ggagcagcgg ccgcggcggc cagacagtca   1080
agagcctgcg gatccaggag caggtgcagc agaccctcgc ccggaagggc cgcagctccg   1140
tgggcaacgg aaatcttcac cgaaccagca gtgttcctga gtatgtctac aacctacact   1200
tggttgaaaa tgattttgtt ggaggccgtt cccctgttcc taaaacctat gacatgctaa   1260
aggctggcac aactgccact tatgaaggtc gctggggaag aggaacagca cagtacagct   1320
cccagaagtc cgtggaagaa aggtccttga ggcatcctct gaggagactg gagatttctc   1380
ctgacagcag cccggagagg gctcactaca cgcacagcga ttaccagtac agccagagaa   1440
gccaggctgg gcacaccctg caccaccaag aaagcaggcg ggccgccctc ctagtgccac   1500
cgagatatgc tcgttccgag atcgtggggg tcagccgtgc tggcaccaca agcaggcagc   1560
gccactttga cacataccac agacagtacc agcatggctc tgttagcgac accgtttttg   1620
acagcatccc tgccaacccg gccctgctca cgtaccccag gccagggacc agccgcagca   1680
tgggcaacct cttggagaag gagaactacc tgacggcagg gctcactgtc gggcaggtca   1740
ggccgctggt gcccctgcag cccgtcactc agaacagggc ttccaggtcc tcctggcatc   1800
agagctcctt ccacagcacc cgcacgctga gggaagctgg gcccagtgtc gccgtggatt   1860
ccagcgggag gagagcgcac ttgactgtcg gccaggcggc cgcaggggga agtgggaatc   1920
tgctcactga gagaagcact ttcactgact cccagctggg gaatgcagac atggagatga   1980
ctctggagcg agcagtgagt atgctcgagg cagaccacat gctgccatcc aggatttctg   2040
ctgcagctac tttcatacag cacgagtgct tccagaaatc tgaagctcgg aagagggtta   2100
accagcttcg tggcatcctc aagcttctgc agctcctaaa agttcagaat gaagacgttc   2160
agcgagctgt gtgtggggcc ttgagaaact tagtatttga agacaatgac aacaaattgg   2220
aggtggctga actaaatggg gtacctcggc tgctccaggt gctgaagcaa accagagact   2280
tggagactaa aaaacaaata acagaccata cagtcaattt aagaagtagg aatggctggc   2340
cgggcgcggt ggctcacgcc tgtaatccca gcactttggg aggccaaggc gggcggatca   2400
cgaggtcagg agttcgagac cagcctgacc aacatggttt gctgtggaat ttgtcatcta   2460
atgacaaact caagaatctc atgataacag aagcattgct tacgctgacg gagaatatca   2520
tcatcccctt ttctgggtgg cctgaaggag actacccaaa agcaaatggt ttgctcgatt   2580
ttgacatatt ctacaacgtc actggatgcc taagaaacat gagttctgct ggcgctgatg   2640
ggagaaaagc gatgagaaga tgtgacggac tcattgactc actggtccat tatgtcagag   2700
gaaccattgc agattaccag ccagatgaca aggccacgga gaattgtgtg tgcattcttc   2760
ataacctctc ctaccagctg gaggcagagc tcccagagaa atattcccag aatatctata   2820
ttcaaaaccg gaatatccag actgacaaca acaaaagtat tggatgtttt ggcagtcgaa   2880
gcaggaaagt aaaagagcaa taccaggacg tgccgatgcc ggaggaaaag agcaacccca   2940
agggcgtgga gtggctgtgg cattccattg ttataaggat gtatctgtcc ttgatcgcca   3000
aaagtgtccg caactacaca caagaagcat ccttaggagc tctgcagaac ctcacggccg   3060
gaagtggacc aatgccgaca tcagtggctc agacagttgt ccagaaggaa agtggcctgc   3120
```

-continued agcacacccg aaagatgctg catgttggtg acccaagtgt gaaaaagaca gccatctcgc 3180
tgctgaggaa tctgtcccgg aatctttctc tgcagaatga aattgccaaa gaaactctcc 3240
ctgatttggt ttccatcatt cctgacacag tcccgagtac tgaccttctc attgaaacta 3300
cagcctctgc ctgttacaca ttgaacaaca taatccaaaa cagttaccag aatgcacgcg 3360
accttctaaa caccgggggc atccagaaaa ttatggccat tagtgcaggc gatgcctatg 3420
cctccaacaa agcaagtaaa gctgcttccg tccttctgta ttctctgtgg gcacacacgg 3480
aactgcatca tgcctacaag aaggctcagt ttaagaagac agattttgtc aacagccgga 3540
ctgccaaagc ctaccactcc cttaaagact gatcaacctc tggattacaa aatttgtgaa 3600
agattgactg gtattcttaa ctatgttgct ccttttacgc tatgtggata cgctgcttta 3660
atgcctttgt atcatgctat tgcttcccgt atggctttca ttttctcctc cttgtataaa 3720
tcctggttgc tgtctcttta tgaggagttg tggcccgttg tcaggcaacg tggcgtggtg 3780
tgcactgtgt ttgctgacgc aacccccact ggttggggca ttgccaccac ctgtcagctc 3840
ctttccggga ctttcgcttt ccccctccct attgccacgg cggaactcat cgccgcctgc 3900
cttgcccgct gctggacagg ggctcggctg ttgggcactg acaattccgt ggtgttgtcg 3960
gggaaatcat cgtcctttcc ttggctgctc gcctgtgttg ccacctggat tctgcgcggg 4020
acgtccttct gctacgtccc ttcggccctc aatccagcgg accttccttc ccgcggcctg 4080
ctgccggctc tgcggcctct tccgcgtctt cgccttcgcc ctcagacgag tcggatctcc 4140
ctttgggccg cctccccgca tcattgcctg cccgggtggc atccctgtga cccctcccca 4200
gtgcctctcc tggccctgga agttgccact ccagtgccca ccagccttgt cctaataaaa 4260
ttaagttgca tcattttgtc tgactaggtg tccttctata atattatggg gtggaggggg 4320
gtggtatgga gcaaggggcc caagttggga agaaacctgt agggcctgc 4369

<210> SEQ ID NO 96
<211> LENGTH: 3993
<212> TYPE: DNA
<213> ORGANISM: Artificial Sequence
<220> FEATURE:
<223> OTHER INFORMATION: Made in Lab - expression cassette polynucleotide

<400> SEQUENCE: 96
ctcagtccat taggagccag tagcctggaa gatgtcttta cccccagcat cagttcaagt 60
ggagcagcac ataactcttg ccctctgcct tccaagattc tggtgctgag acttatggag 120
tgtcttggag gttgccttct gccccccaac cctgctccca gctggccctc ccaggcctgg 180
gttgctggcc tctgctttat caggattctc aagagggaca gctggtttat gttgcatgac 240
tgttccctgc atatctgctc tggttttaaa tagcttatct gagcagctgg aggaccacat 300
gggcttatat ggcgtggggt acatgttcct gtagccttgt ccctggcacc tgccaaaata 360
gcagccaaca ccccccaccc ccaccgccat cccccctgccc cacccgtccc ctgtcgcaca 420
ttcctccctc cgcagggctg gctcaccagg ccccagccca catgcctgct taaagccctc 480
tccatcctct gcctcaccca gtccccgctg agactgagca gacgcctcca ggatctgtcg 540
gcaggccacc atggcagccc ccggcgcccc agctgagtac ggctacatcc ggaccgtcct 600
gggccagcag atcctgggac aactggacag ctccagcctg gcgctgccct ccgaggccaa 660
gctgaagctg gcggggagca gcggccgcgg cggccagaca gtcaagagcc tgcggatcca 720
ggagcaggtg cagcagaccc tcgcccggaa gggccgcagc tccgtgggca acggaaatct 780

-continued

```
tcaccgaacc agcagtgttc ctgagtatgt ctacaaccta cacttggttg aaaatgattt    840
tgttggaggc cgttcccctg ttcctaaaac ctatgacatg ctaaaggctg gcacaactgc    900
cacttatgaa ggtcgctggg gaagaggaac agcacagtac agctcccaga agtccgtgga    960
agaaaggtcc ttgaggcatc ctctgaggag actggagatt tctcctgaca gcagcccgga   1020
gagggctcac tacacgcaca gcgattacca gtacagccag agaagccagg ctgggcacac   1080
cctgcaccac caagaaagca ggcgggccgc cctcctagtg ccaccgagat atgctcgttc   1140
cgagatcgtg gggtcagcc gtgctggcac cacaagcagg cagcgccact ttgacacata    1200
ccacagacag taccagcatg gctctgttag cgacaccgtt tttgacagca tccctgccaa   1260
cccggccctg ctcacgtacc ccaggccagg gaccagccgc agcatgggca acctcttgga   1320
gaaggagaac tacctgacgg cagggctcac tgtcgggcag gtcaggccgc tggtgcccct   1380
gcagcccgtc actcagaaca gggcttccag gtcctcctgg catcagagct ccttccacag   1440
cacccgcacg ctgagggaag ctgggcccag tgtcgccgtg gattccagcg ggaggagagc   1500
gcacttgact gtcggccagg cggccgcagg gggaagtggg aatctgctca ctgagagaag   1560
cactttcact gactcccagc tggggaatgc agacatggag atgactctgg agcgagcagt   1620
gagtatgctc gaggcagacc acatgctgcc atccaggatt tctgctgcag ctactttcat   1680
acagcacgag tgcttccaga aatctgaagc tcggaagagg gttaaccagc ttcgtggcat   1740
cctcaagctt ctgcagctcc taaaagttca gaatgaagac gttcagcgag ctgtgtgtgg   1800
ggccttgaga aacttagtat ttgaagacaa tgacaacaaa ttggaggtgg ctgaactaaa   1860
tggggtacct cggctgctcc aggtgctgaa gcaaaccaga gacttggaga ctaaaaaaca   1920
aataacagac catacagtca atttaagaag taggaatggc tggccgggcg cggtggctca   1980
cgcctgtaat cccagcactt tgggaggcca aggcgggcgg atcacgaggt caggagttcg   2040
agaccagcct gaccaacatg gtttgctgtg gaatttgtca tctaatgaca aactcaagaa   2100
tctcatgata acagaagcat tgcttacgct gacggagaat atcatcatcc ccttttctgg   2160
gtggcctgaa ggagactacc caaaagcaaa tggtttgctc gattttgaca tattctacaa   2220
cgtcactgga tgcctaagaa acatgagttc tgctggcgct gatgggagaa aagcgatgag   2280
aagatgtgac ggactcattg actcactggt ccattatgtc agaggaacca ttgcagatta   2340
ccagccagat gacaaggcca cggagaattg tgtgtgcatt cttcataacc tctcctacca   2400
gctggaggca gagctcccag agaaatattc ccagaatatc tatattcaaa accggaatat   2460
ccagactgac aacaacaaaa gtattggatg ttttggcagt cgaagcagga aagtaaaaga   2520
gcaataccag gacgtgccga tgccggagga aaagagcaac cccaagggcg tggagtggct   2580
gtggcattcc attgttataa ggatgtatct gtccttgatc gccaaaagtg tccgcaacta   2640
cacacaagaa gcatccttag gagctctgca gaacctcacg gccggaagtg gaccaatgcc   2700
gacatcagtg gctcagacag ttgtccagaa ggaaagtggc ctgcagcaca cccgaaagat   2760
gctgcatgtt ggtgacccaa gtgtgaaaaa gacagccatc tcgctgctga ggaatctgtc   2820
ccggaatctt tctctgcaga atgaaattgc caaagaaact ctccctgatt tggtttccat   2880
cattcctgac acagtcccga gtactgacct tctcattgaa actacagcct ctgcctgtta   2940
cacattgaac aacataatcc aaaacagtta ccagaatgca cgcgaccttc taaacaccgg   3000
gggcatccag aaaattatgg ccattagtgc aggcgatgcc tatgcctcca acaaagcaag   3060
taaagctgct tccgtccttc tgtattctct gtgggcacac acggaactgc atcatgccta   3120
caagaaggct cagtttaaga agacagattt tgtcaacagc cggactgcca aagcctacca   3180
```

-continued

```
ctcccttaaa gactgatcaa cctctggatt acaaaatttg tgaaagattg actggtattc   3240

ttaactatgt tgctcctttt acgctatgtg gatacgctgc tttaatgcct ttgtatcatg   3300

ctattgcttc ccgtatggct ttcattttct cctccttgta taaatcctgg ttgctgtctc   3360

tttatgagga gttgtggccc gttgtcaggc aacgtggcgt ggtgtgcact gtgtttgctg   3420

acgcaacccc cactggttgg ggcattgcca ccacctgtca gctcctttcc gggactttcg   3480

ctttccccct ccctattgcc acggcggaac tcatcgccgc ctgccttgcc cgctgctgga   3540

caggggctcg gctgttgggc actgacaatt ccgtggtgtt gtcggggaaa tcatcgtcct   3600

ttccttggct gctcgcctgt gttgccacct ggattctgcg cgggacgtcc ttctgctacg   3660

tcccttcggc cctcaatcca gcggaccttc cttcccgcgg cctgctgccg gctctgcggc   3720

ctcttccgcg tcttcgcctt cgccctcaga cgagtcggat ctccctttgg gccgcctccc   3780

cgcatcattg cctgcccggg tggcatccct gtgacccctc cccagtgcct ctcctggccc   3840

tggaagttgc cactccagtg cccaccagcc ttgtcctaat aaaattaagt tgcatcattt   3900

tgtctgacta ggtgtccttc tataatatta tggggtggag gggggtggta tggagcaagg   3960

ggcccaagtt gggaagaaac ctgtagggcc tgc                                 3993
```